United States Patent
Danishefsky et al.

(10) Patent No.: US 8,957,056 B2
(45) Date of Patent: Feb. 17, 2015

(54) MIGRASTATIN ANALOGS IN THE TREATMENT OF CANCER

(75) Inventors: Samuel J. Danishefsky, Englewood, NJ (US); Christoph Gaul, Aesch (CH); Jón T. Njardarson, Ithaca, NY (US); Malcolm A. S. Moore, New York, NY (US); Kaida Wu, Newton, MA (US); David C. Dorn, New York, NY (US); Mihirbaran Mandal, Scotch Plains, NJ (US)

(73) Assignee: Sloan-Kettering Instiute for Cancer Research, New York, NY (US)

(*) Notice: Subject to any disclaimer, the term of this patent is extended or adjusted under 35 U.S.C. 154(b) by 2280 days.

(21) Appl. No.: 11/597,678

(22) PCT Filed: May 25, 2005

(86) PCT No.: PCT/US2005/018603
§ 371 (c)(1),
(2), (4) Date: Jun. 10, 2008

(87) PCT Pub. No.: WO2006/001967
PCT Pub. Date: Jan. 5, 2006

(65) Prior Publication Data
US 2009/0124662 A1  May 14, 2009

Related U.S. Application Data

(60) Provisional application No. 60/574,114, filed on May 25, 2004.

(51) Int. Cl.
*A61K 31/395* (2006.01)
*A61K 31/335* (2006.01)
*C07D 313/00* (2006.01)
*C07D 225/02* (2006.01)
*A61K 31/365* (2006.01)
*A61K 31/435* (2006.01)

(52) U.S. Cl.
CPC ............ *A61K 31/395* (2013.01); *A61K 31/365* (2013.01); *A61K 31/435* (2013.01)
USPC ............ 514/183; 514/450; 540/463; 549/346

(58) Field of Classification Search
USPC ................. 514/183, 450; 540/463; 549/346
See application file for complete search history.

(56) References Cited

U.S. PATENT DOCUMENTS

| | | | |
|---|---|---|---|
| 2,529,825 A | 11/1950 | Stoll | |
| 3,227,742 A | 1/1966 | Lafont et al. | |
| 4,472,435 A | 9/1984 | Branca et al. | |
| 4,938,949 A | 7/1990 | Borch et al. | |
| 6,326,349 B1 | 12/2001 | Helmlinger et al. | |
| 7,943,800 B2 * | 5/2011 | Danishefsky et al. | 568/375 |
| 8,188,141 B2 * | 5/2012 | Danishefsky et al. | 514/431 |
| 2002/0119937 A1 | 8/2002 | Khosla et al. | |
| 2002/0128480 A1 | 9/2002 | Haneda et al. | |
| 2004/0062817 A1 | 4/2004 | Peshoff | |
| 2006/0173205 A1 | 8/2006 | Fukuda et al. | |
| 2007/0037783 A1 | 2/2007 | Huang et al. | |
| 2009/0054488 A1 | 2/2009 | Danishefsky et al. | |

FOREIGN PATENT DOCUMENTS

| | | |
|---|---|---|
| EP | 374445 | 6/1990 |
| EP | 1264594 | 12/2002 |
| EP | 1380579 | 1/2004 |
| GB | 989476 | 4/1965 |
| GB | 1036084 | 7/1966 |
| JP | 56-34655 | 4/1981 |
| JP | 56-34656 | 4/1981 |
| JP | 61-56146 | 3/1986 |
| JP | 7-138257 | 5/1995 |
| JP | 2000-178223 | 6/2000 |
| JP | 2001 078793 A | 3/2001 |
| JP | 2001 081088 A | 3/2001 |

(Continued)

OTHER PUBLICATIONS

Freshney. Culture of Animal Cells: A manual of basic technique. Alan R. Liss, 1983, New York, p. 4.*
Dermer (Bio/Technology, 1994, 12:230).*
Gura (Science, v278, 1997, pp. 1041-1042).*
Stella et al. (Prodrugs: Challenges and Rewards, Part 1, 2007).*
U.S. Appl. No. 13/106,625, Danishefsky, et al.
U.S. Appl. No. 13/053,161, Danishefsky, et al.
Abiko, A.; Liu, J. F.; Masamune, S. *J. Am. Chem. Soc.* 1997, 119, 2586.
Ahmar, M.; Duyck, C.; Fleming I. *J. Chem. Soc., Perkin Trans. 1* 1998, 2721.
Asami, Y.; Kakeya, H.; Onose, R.; Yoshida, A.; Matsuzaki, H.; Osada, H. *Org. Lett.* 2002, 4, 2845.

(Continued)

*Primary Examiner* — Samantha Shterengarts
(74) *Attorney, Agent, or Firm* — Choate, Hall & Stewart, LLP; Brenda Herschbach Jarrell; John P. Rearick

(57) ABSTRACT

In one aspect, the present invention provides a method for treating colon and/or ovarian cancer in a subject comprising administering to a subject in need thereof a compound of general formula (I): wherein R1-R6, R, -R, Q, Y1, Y2 and n are as defined herein, wherein the compound is present in an amount effective to inhibit colon and/or ovarian tumor metastasis.

(I)

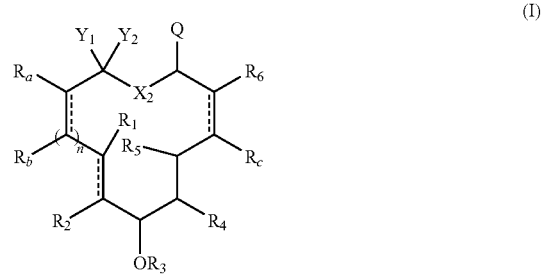

39 Claims, 18 Drawing Sheets

(56) References Cited

FOREIGN PATENT DOCUMENTS

| | | |
|---|---|---|
| JP | 2002-519396 | 7/2002 |
| JP | 2003-104967 | 4/2003 |
| JP | 2003-171335 | 6/2003 |
| WO | WO99/22722 | 5/1999 |
| WO | WO00/01648 | 1/2000 |
| WO | WO01/46451 | 6/2001 |
| WO | WO02/088176 | 11/2002 |
| WO | WO2004/009380 | 1/2004 |
| WO | WO2004/052359 | 6/2004 |
| WO | WO2004/083164 | 9/2004 |
| WO | WO2004/087672 | 10/2004 |
| WO | WO2004/087673 | 10/2004 |
| WO | WO2005/019181 | 3/2005 |
| WO | WO2006/001967 | 1/2006 |
| WO | WO2006/034478 | 3/2006 |
| WO | WO2009/070244 | 6/2009 |

OTHER PUBLICATIONS

Aslakson, C. J., and Miller, F. R. 1992. Selective events in the metastatic process defined by analysis of the sequential dissemination of subpopulations of a mouse mammary tumor. Cancer Research 52: 1399-1405.
Berge, et al., J. Pharmaceutical Sciences, 1977, 66: 1-19.
Biswas, K.; Lin, H.; Njardarson, J. T.; Chappell, M. D.; Chou, T. C.; Guan, Y.; Tong, W. P.; He, L.; Horwitz, S. B.; Danishefsky, S. J. *J. Am. Chem. Soc.* 2002, 124, 9825.
Blanchette et al., *Tet. Lett.*, 1984, 25, 2183.
Boden, E. P.; Keck, G. E. *J. Org. Chem.* 1985, 50, 2394.
Brower, V. *Nat. Biotechnol.* 1999, 17, 963.
Bundgaard, Design and application of prodrugs, In *A textbook of Drug Design and Development* 1991, 113-191.
Capitosti, S. M.; Hansen, T. P.; Brown, M. L. *Bioorg. Med. Chem.* 2004, 12, 327.
Carmeliet, P. *Nat. Med.* 2003, 9, 653.
Chan, J.; Jamison, T. F. *J. Am. Chem. Soc.* 2003, 125, 11514.
Li, C.; Bardhan, S.; Pace, E. A.; Liang, M. C.; Gilmore, T. D.; Porco Jr., J. A. *Org. Lett.* 2002, 4, 3267.
Chun, J.; Li, G.; Byun, H. S.; Bittman, R. *J. Org. Chem.* 2002, 67, 2600.
Cristofanilli, et al. *Nat. Rev. Drug Discovery* 2002, 1, 415.
Crystallographic data (excluding structural data) for compound 24 have been deposited with the Cambridge Crystallographic Data Centre (CCDC) as Deposition No. CCDC 230121.
D'Amato, R. J.; Loughnan, M. S.; Flynn, E.; Folkman, *J. Proc. Natl. Acad. Sci.* 1994, 91, 4082.
Danishefsky, S. J. *Aldrichimica Acta* 1986, 19, 59.
Danishefsky, S.J. *Chemtracts* 1989, 2, 273 (Part I).
Danishefsky, S.J. *Chemtracts* 1989, 2, 273 (Part II).
Danishefsky, S. J., Kitahara, T. *J. Am. Chem. Soc.* 1974, 96, 7807.
Danishefsky, S. J. et al.; *J. J Am. Chem. Soc.* 1979, 101, 7001.
Danishefsky, S. J.; Kato, N.; Askin, D.; Kerwin Jr., J. F. *J. Am. Chem. Soc.* 1982, 104, 360.
Danishefsky et al., *J. Am. Chem. Soc.*, 1985, 107, 1256.
Danishefsky et al., *J. Am. Chem. Soc.* 1996, 118, 2843.
Deplanque, G; Harris, A. L. *Eur. J Cancer* 2000, 36, 1713.
Dermer, *Bio/Technology* 1994, 12, 320.
Dess, D. B.; Martin, J. C. *J. Am. Chem. Soc.* 1991, 113, 7277.
Dixon, D. J.; Krause, L.; Ley, S. V. *J. Chem. Soc., Perkin Trans. 1*, 2001, 2516.
Dredge, K.; Dalgleish, A. G.; Marriott, J. B. *Anti-Cancer Drugs* 2003, 14, 331.
Duffey, M. O.; LeTiran, A.; Morken, J. P. *J. Am. Chem. Soc.* 2003, 125, 1458.
Edmonds, M. K.; Abell, A. D. *J. Org. Chem.* 2001, 66, 3747.
Egawa, Y. et al.; *Chem. Pharm. Bull.* 1963, 11, 589.
Eng, H. M.; Myles, D. C. *Tetrahedron Lett.* 1999, 40, 2279.
Evans, D.A., *Aldrichimica Acta*, 1982, 15, 23-32.
Evans et al., *J. Am. Chem. Soc.*, 2002, 124, 392.
Fenteany, G.; Zhu, S. *Curr. Top. Med. Chem.* 2003, 3, 593.
Ferrier, *J Chem. Soc.*, 1964, 5443.
Freshney, Culture of Animal Cells: A manual of basic technique. Alan R. Liss, 1983, New York, p. 4.
Garbaccio, R. M.; Stachel, S. J.; Baeschlin, D. K.; Danishefsky, S. J. *J. Am. Chem. Soc.* 2001, 123, 10903.
Gaul, C. et al.; *J. Am. Chem. Soc.* 2003, 125, 6042.
Gaul et al.; *J. Amer. Chem. Soc.* 2004, 126(36):11326-11337.
Gaul, C., et al., Tetrahedron Lett., 2002, 43, 9039-9042.
Geho et al, *Physiology*, 2005, 20, 194-200.
Gura, *Science* 1997, 278, 1041-1042.
Harris, C. R.; Danishefsky, S. J. *J. Org. Chem.* 1999, 64, 8434.
Hayashi, Y.; Shoji, M.; Yamaguchi, J.; Sato, K.; Yamaguchi, S.; Mukaiyama, T.; Sakai, K.; Asami, Y.; Kakeya, H.; Osada, H. *J. Am. Chem. Soc.* 2002, 124, 12078.
Hirai, K.; Ooi, H.; Esumi, T.; Iwabuchi, Y.; Hatakeyama, S. *Org. Lett.* 2003, 5, 857.
Hochlowski, J. E.; Whittern, D. N.; Hill, P.; McAlpine, J. B. *J. Antibiot.* 1994, 47, 870.
Inanaga et al., *Bull. Chem. Soc. Jpn.*, 1979, 52, 1989.
Inoue et al., J. Saitama Med. School, 1998, 25(4), 225-238.
International Search Report for PCT/US2004/009380, mailed Sep. 21, 2004.
International Search Report for PCT/US2004/009571, mailed Sep. 22, 2004.
International Search Report for PCT/US2005/018603, mailed Apr. 10, 2006.
International Search Report for PCT/US2005/034305, mailed Sep. 5, 2006.
Jantzen and Robinson, *Modern Pharmaceutics* 1996, 596.
Jorgensen et al., *J. Org. Chem.*, 2001, 66, 4630.
Jung, H. J.; Lee, H. B.; Kim, C. J.; Rho, J. R.; Shin, J.; Kwon, H. J. *J. Antibiot.* 2003, 56, 492.
Kadam, S.; McAlpine, J.B. *J. Antibiot.* 1994, 47, 875.
Kakeya, H.; Onose, R.; Koshino, H.; Yoshida, A.; Kobayashi, K.; Kageyama, S. I.; Osada, H. *J. Am. Chem. Soc.* 2002, 124, 3496.
Kakeya, H.; Onose, R.; Yoshida, A.; Koshino, H.; Osada, H. *J. Antibiot.* 2002, 55, 829.
Karwowski, J. P.; Jackson, M.; Sunga, G.; Sheldon, P.; Poddig, J. B.; Kohl, W. L.; Adam, S. *J. Antibiot.* 1994, 47, 862.
Katzenellenbogen, J.A., et al., J. Am. Chem. Soc., 1976, 98, 4925.
Kerbel, R.; Folkman, *J. Nat. Rev. Cancer* 2002, 2, 727.
Kitaori, K., Furukawa, Y., Yoshimoto, H.; Otera, *J. Tetrahedron* 1999, 55, 14381.
Klohs, W. D.; Hamby, J. M. *Curr. Opin. Biotechnol.* 1999, 10, 544.
Kondo, H.; Oritani, T.; Kiyota, H. *Eur. J. Org. Chem.* 2000, 3459.
Lauffenburger, D. A.; Horwitz, A. F. *Cell* 1996, 84, 359.
Lee, W. W.; Chang, S. *Tetrahedron: Asymmetry* 1999, 10, 4473.
Li, D. R.; Xia, W. J.; Shi, L.; Tu, Y. Q. *Synthesis* 2003, 41.
Lin, S.; Danishefsky, S.J. *Angew. Chem. Int. Ed.* 2002, 41(3), 512-5.
Lin, S.; Danishefsky, S. J. *Angew. Chem. Int. Ed.* 2001, 40(10), 1967-1970.
Luche et al., *J. Am. Chem. Soc.*, 1979, 101, 5848.
Mahoney et al., *J. Am. Chem. Soc.*, 1988, 110, 291.
Mattson, M. P.; Furukawa, K. *Apoptosis* 1997, 2, 257.
"Metabolite-Encyclopedia.com", http://www.encyclopedia.com/doc/1e1-metabolit.html, accessed Jan. 25, 2008.
Mehta, G.; Islam, K. *Tetrahedron Lett.* 2003, 44, 3569.
Miller, F. R., Miller, B. E., and Heppner, G. H. 1983. Invasion Metastasis 3: 22-31.
Mukaiyama, T. *Agnew. Chem. Int. Ed.* 1979, 18, 707.
Mukaiyama, T., Usui, M.; Shimada, E.; Saigo, K. *Chem. Lett.* 1975, 1045.
Myers, A. G.; Siu, M.; Ren, F. *J. Am. Chem. Soc.* 2002, 124, 4230.
Nakae et al., *J. Antibiot.*, 2000, 53, 1228-1230.
Nakae K.; Yoshimoto, Y.; Sawa, T.; Homma, Y.; Hamada, M.; Takeuchi, T.; Imoto, M. *J Antibiotics* 2000, 53, 1130-1136.
Nakamura, H., et al., J. Antibiot., 2002, 55, 442-444.
Njardarson, J.T., et al., J. Am. Chem. Soc., 2004, 126, 1038-1040.
Ogasawara, M.; Matsubara, T.; Suzuki, H. *Biol. Pharm. Bull.* 2001, 24, 720.
Ogasawara, M.; Matsubara, T.; Suzuki, H. *Biol. Pharm. Bull.* 2001, 24, 917.
Ogasawara, M.; Matsunaga, T.; Takahashi, S.; Saiki, I.; Suzuki, H. *Biol. Pharm. Bull.* 2002, 25, 1491.

(56) References Cited

OTHER PUBLICATIONS

Prakash, G. K. S.; Krishnamurti, R.; Olah, G. A. *J. Am. Chem. Soc.* 1989, 111, 393.
Pulaski, B. A., and Ostrand-Rosenberg, S. 1998. Cancer Res 58: 1486-1493.
Raje, N.; Anderson, K. C. *Curr. Opin. Oncol.* 2002, 14, 635.
Reetz, M. T.; Kessler, K. *J. Org. Chem.* 1985, 50, 5434.
Rice, et al., Anal. Biochem. 1996, 241: 254-259.
Rivkin, A.; Yoshimura, F.; Gabarda, A. E.; Chou, T. C.; Dong, H.; Tong, W. P.; Danishefsky, S. J. *J. Am. Chem. Soc.* 2003, 125, 2899.
Roskelley, C. D.; Williams, D. E.; McHardy, L. M.; Leong, K. G.; Troussard, A.; Karsan, A.; Andersen, R. J.; Dedhar, S.; Roberge, M. *Cancer Res.* 2001, 61, 6788.
Scappaticci, F. A. *J Clin. Oncol.* 2002, 20, 3906.
Scholl et al., *Org. Lett.*, 1999, 1, 953.
Scholl, M.; Trnka, T. M.; Morgan, J. P.; Grubbs, R. H *Tetrahedron Lett.* 1999, 40, 2247.
Seco, J. M.; Latypov, S. K.; Quinoa, E.; Riguera, R. *Tetrahedron* 1997, 53, 8541.
Seco, J. M.; Quinoa, E.; Riguera, R. *Tetrahedron: Asymmetry* 2000, 11, 2781.
Shan et al.; *PNAS* 2005, 102(10):3772-3776.
Shin et al, *Journal of Biological Chemistry* 2005, 280(50), 41439-41448.
Shiozawa, H.; Takahashi, M.; Takatsu, T.; Kinoshita, T.; Tanzawa, K.; Hosoya, T.; Furuya, K.; Furihata, K.; Seto, H. *J. Antibiot.* 1995, 48, 357.
Shoji, M.; Yamaguchi, J.; Kakeya, H.; Osada, H.; Hayashi, Y. *Angew. Chem. Int. Ed.* 2002, 41, 3192.
Singh et al.; *Indian Journal of Chemistry* 2002, 41B:423-426.
Smith III, A. B.; Frohn, M. *Org. Lett.* 2001, 3, 3979.
Song et al., *Org. Lett.*, 2002, 4, 647.
Stachel, S. J.; Biswas, K.; Danishefsky, S. J. *Curr. Pharm. Des.* 2001, 7, 1277.
Stachel, S.J.; Lee, C.B.; Spassova, M.; Chappell, M.D.; Bornmann, W.G.; Danishefsky, S.J.*J. Org. Chem.* 2001, 66, 4369.
Stella et al.; *Advanced Drug Delivery Reviews*, 2007, 677-694.
Sugawara, K.; Nishiyama, Y.; Toda, S.; Komiyama, N.; Hatori, M.; Moriyama, T.; Sawada, Y.; Kamei, H. ; Konishi, M.; Oki, T. *J. Antibiot.* 1992, 45, 1433.
Takayasu, Y.; Tsuchiya, K.; Aoyama, T.; Sukenaga, Y. *J. Antibiot.* 2001, 54, 1111.
Takayasu, Y.; Tsuchiya, K.; Sukenaga, Y. *J. Antibiot.* 2002, 55, 337.
Takemoto, Y., et al., J. Antibiot., 2001, 54, 1104-1107.
Tatsuta, K.; Masuda, N. *J. Antibiot.* 1998, 51, 602.
Tebbe, F. N.; Parshall, G. W.; Reddy, G. S. *J. Am. Chem. Soc.* 1978, 100, 3611.
Thomas et al., *Curr. Opin. Oncol.* 2000, 12(6), 564-573.
Trost, B. M.; Bunt, R. C.; Pulley, S. R. *J. Org. Chem.* 1994, 59, 4202.
Van't Veer et al.; *Nature Medicine* 2003, 9(8):999-1000.
Wakabayashi, T.; Kageyama, R.; Naruse, N.; Tsukahara, N.; Funahashi, Y.; Kitoh, K.; Watanabe, Y. *J. Antibiot.* 1997, 50, 671.
Williams, D. E.; Craig, K. S.; Patrick, B.; McHardy, L. M.; van Soest, R.; Roberge, M.; Andersen, R. J. *J. Org. Chem.* 2002, 67, 245.
Williams, D. E.; Lassota, P.; Andersen, R. J. *J. Org. Chem.* 1998, 63, 4838.
Woo et al., J. Antibiot., 2002, 55, 141-146.
Woodhouse, E. C.; Chuaqui, R. F.; Liotta, L. A. *Cancer* 1997, 80(S8), 1529.
Xiang, G.; McLaughlin, L. W. *Tetrahedron* 1998, 54, 375.
Yamamoto, K.; Garbaccio, R. M.; Stachel, S. J.; Solit, D. B.; Chiosis, G. ; Rosen, N.; Danishefsky, S. J. *Angew. Chem. Int. Ed.* 2003, 42, 1280.
Yamamoto, K.; Biswas, K.; Gaul, C.; Danishefsky, S. J. *Tetrahedron Lett.* 2003, 44, 3297.
Yang, Z. Q.; Kwok, B. Ho ; Lin, S.; Koldobskiy, M. A.; Crews, C. M.; Danishefsky, S. J. *Chembiochem* 2003, 4, 508.
Yang, Z. Q.; Danishefsky, S. J. *J. Am. Chem. Soc.* 2003, 125, 9602.
Yoshimura, F.; Rivkin, A.; Gabarda, A. E.; Chou, T. C.; Dong, H.; Sukenick, G.; Morel, F. F.; Taylor, R. E.; Danishefsky, S. J. *Angew. Chem. Int. Ed.* 2003, 42, 2518.

\* cited by examiner

FIG. 5
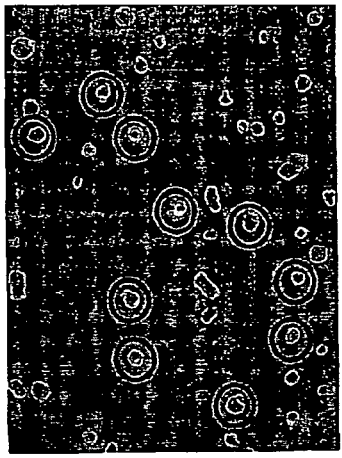
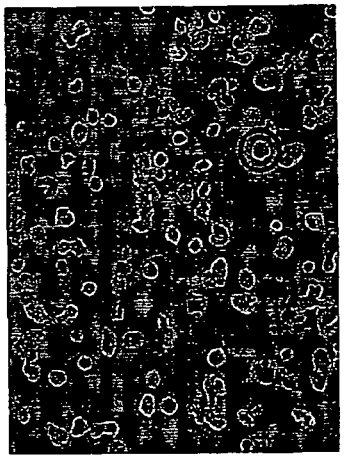
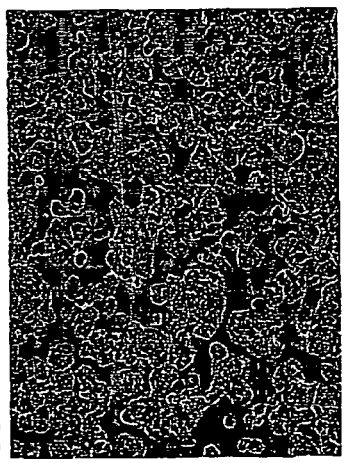
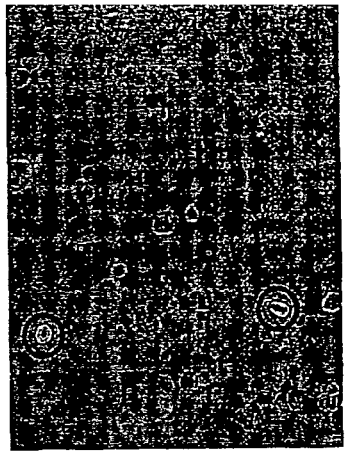
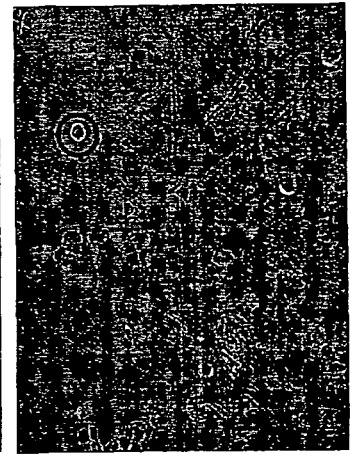
HT 29
IGROV
A  DMSO control (0.1%)
B  DMC 100nM
C  DMC 10.000nM
D  DMSO control (0.1%)
E  DMC 100nM
F  DMC 10.000nM
○ Cells with loss of pseudopodia FIG. 5
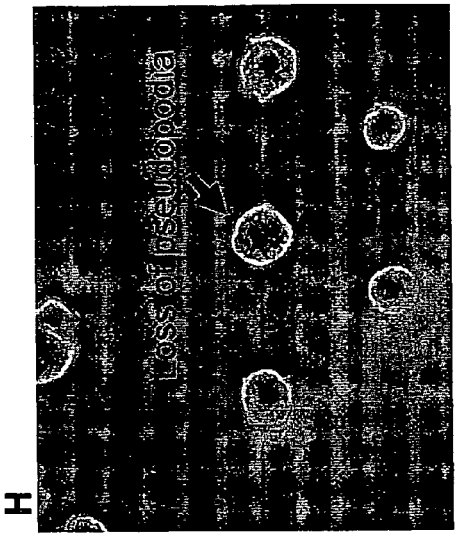 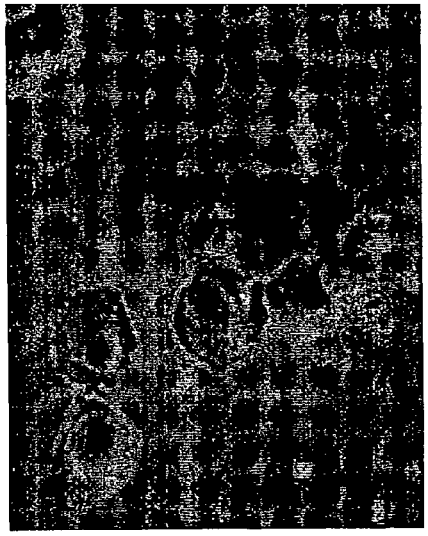
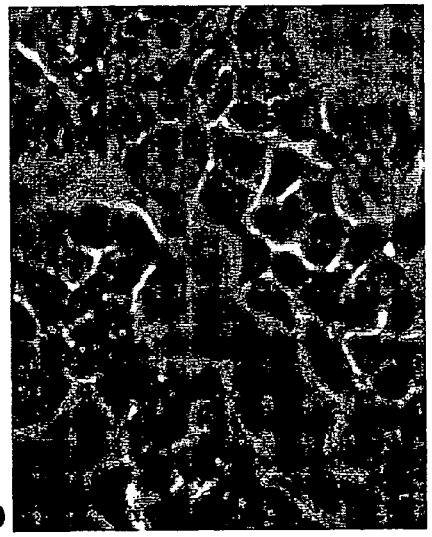 
HT 29
IGROV
DMSO control (0.1%)
DMC 10.000nM

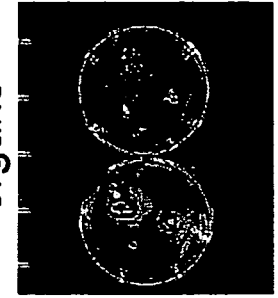
FIG. 7B organs
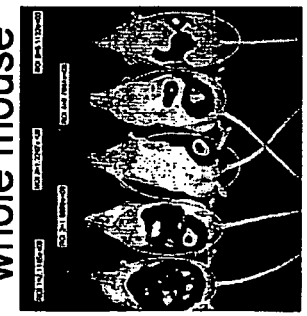
FIG. 7A whole mouse

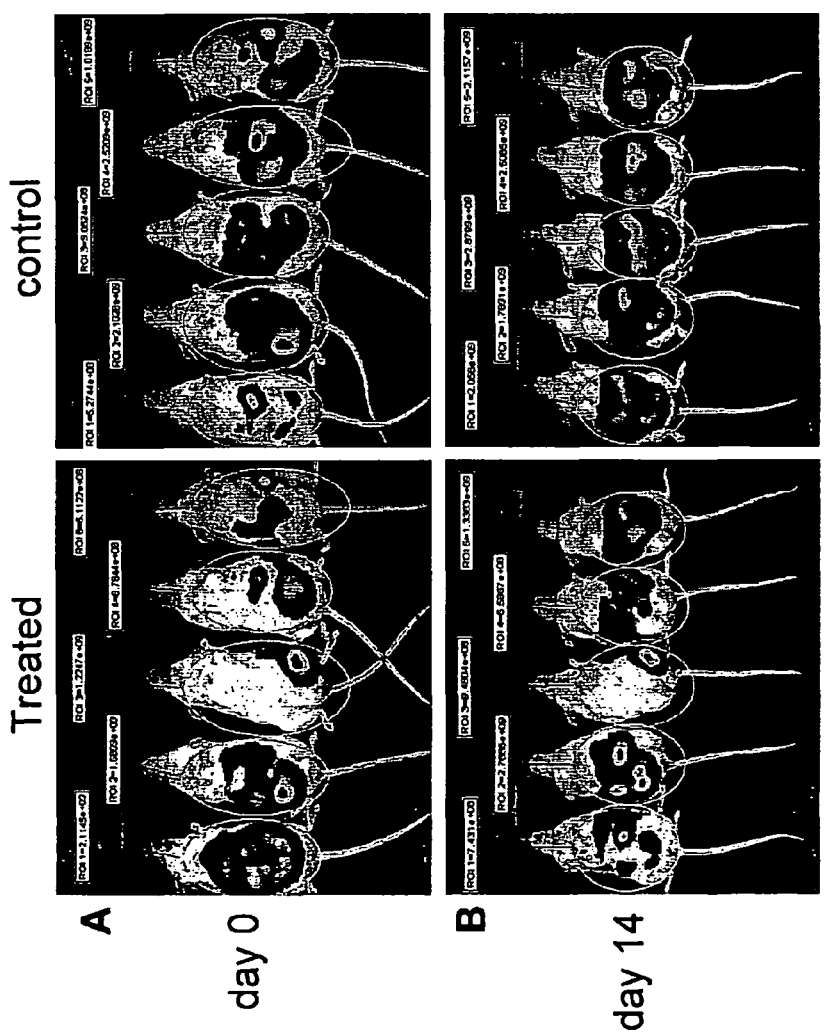
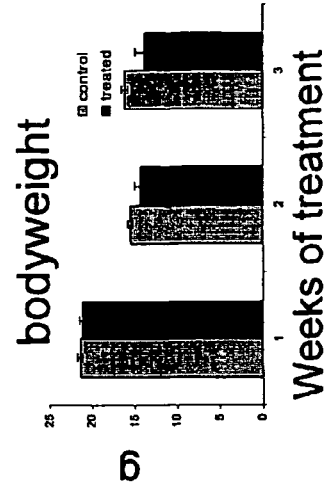
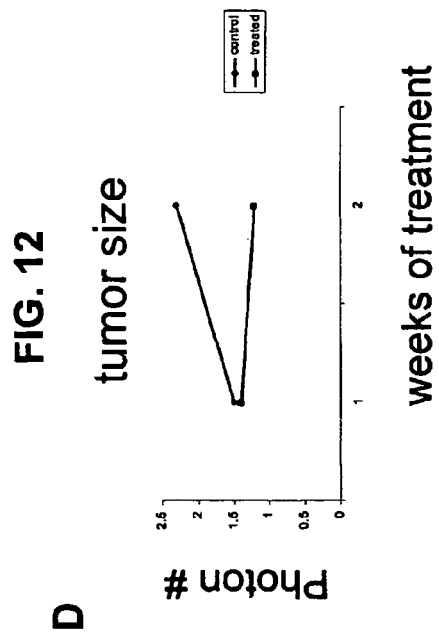
FIG. 10
FIG. 11
FIG. 12

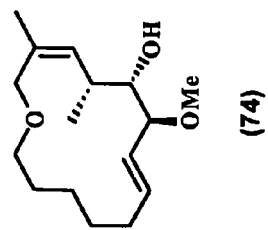
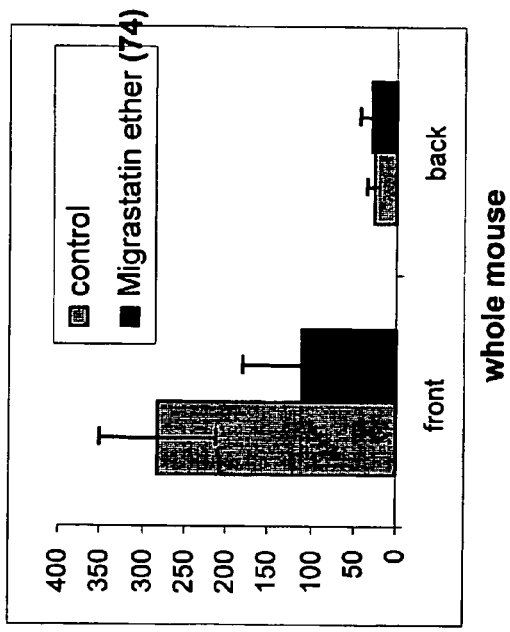
FIG. 15A
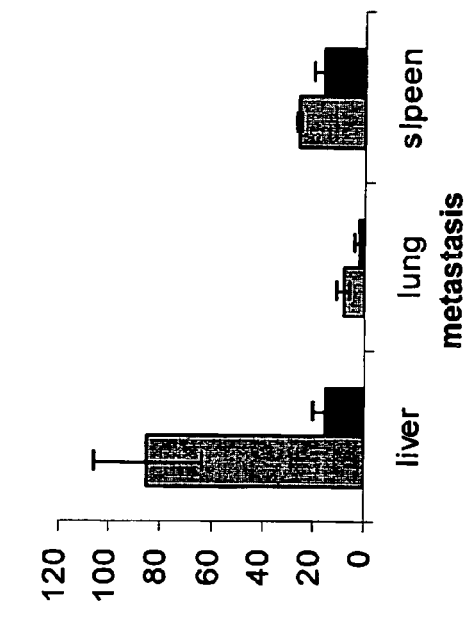
FIG. 15B

FIG. 17

| Fold Change | Gene Title | Gene Symbol | Biological Process Description | Molecular Function Description |
|---|---|---|---|---|
| 3 | CD44 antigen (homing function) | CD44 | --- | Xlink;hyaluronic acid binding;3.6e-44 |
| 2.6 | sciellin | SCEL | cell shape and cell size control | --- |
| 2.4 | thrombospondin 1 | THBS1 | cell motility /// cell adhesion /// blood coagulation | cell adhesion /// calcium ion binding /// heparin binding |
| 2.4 | microtubule-associated protein 2 | MAP2 | microtubule stabilization | structural molecule activity |
| 2.2 | integrin, alpha 2 (CD49B) | ITGA2 | cell-matrix adhesion /// integrin-mediated signaling pathway /// blood coagulation | cell adhesion receptor activity /// collagen binding |
| 2.10 | claudin 1 | CLDN1 | cell adhesion | structural molecule activity |
| 2 | spectrin, beta, non-erythrocytic 5 | SPTBN5 | actin cytoskeleton organization and biogenesis | actin binding |
| 2 | laminin, gamma 2 | LAMC2 | cell adhesion /// epidermal differentiation | cell adhesion molecule activity /// structural molecule activity /// heparin binding |
| 2 | keratin 4 | KRT4 | cytoskeleton organization and biogenesis | structural molecule activity |
| 2 | KIAA0527 protein | KIAA0527 | cell adhesion | hyaluronic acid binding |
| -2 | tumor necrosis factor, alpha-induced protein 6 | TNFAIP6 | inflammatory response /// cell adhesion | cell adhesion receptor activity /// hyaluronic acid binding |
| -2.00 | integrin beta 3 binding protein | ITGB3BP | cell adhesion /// signal transduction | |
| -2 | chemokine (C-X-C motif) ligand 2 | CXCL2 | chemotaxis /// inflammatory response | chemokine activity |
| -2.1 | hyaluronan-mediated motility receptor (RHAMM) | HMMR | cell motility | hyaluronic acid binding |
| -2.2 | laminin, alpha 1 | LAMA1 | cell-matrix adhesion /// cell proliferation | structural molecule activity /// extracellular matrix glycoprotein |
| -2.6 | discoidin domain receptor family, member 2 | DDR2 | cell adhesion | transmembrane receptor protein tyrosine kinase activity |

MIGRASTATIN ANALOGS IN THE TREATMENT OF CANCER

The present application claims the benefit under 35 U.S.C. §371 of International Application No.: PCT/US2005/018603 (published PCT application No. WO 2006/001967), filed May 25, 2005, which claims priority to U.S. Provisional Application Ser. No. 60/574,114 filed May 25, 2004; the entire contents of each of the above-referenced applications are incorporated herein by reference.

GOVERNMENT SUPPORT

The invention was supported in part by Grant No. 08748 from the National Cancer Institute, Grant AI-16943 from the National Institutes of Health and by Postdoctoral Fellowships for Christoph Gaul (Deutscher Akademischer Austauschdienst, DAAD) and Jon Tryggvi Njardarson (General Motors Cancer Research Program). The U.S. government may have certain rights in this invention.

BACKGROUND OF THE INVENTION

Migrastatin (1) is a novel 14-membered ring macrolide natural product, that was first isolated from a cultured broth of *Steptomyces* sp. MK929-43F1 by Imoto et al. (see, Nakae et al., *J. Antibiot.*, 2000, 53, 1130-1136; and Nakae et al., *J. Antibiot.*, 2000, 53, 1228-1230). It was recently reported that cultures of *Steptomyces platensis* also produce Migrastatin (see, Woo et al., *J. Antibiot.*, 2002, 55, 141-146).

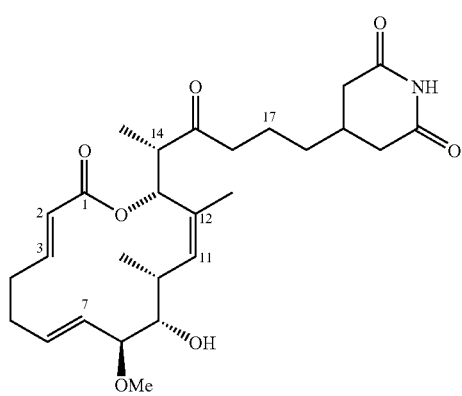

(1)

Migrastatin has been shown to inhibit both migration and anchorage-independent growth of human tumor cells (see, Nakae et al., *J. Antibiot.*, 2001, 54, 1104-1107), and has sparked interest in the area of cancer research. Specifically, migration of tumor cells is part of the complex process of metastasis, which is the leading cause of death in cancer patients. Therefore, Migrastatin and derivatives thereof hold great potential as therapeutic agents for the treatment of cancer.

After initial isolation and reporting of this compound, several groups explored the possibility of preparing derivatives and/or further exploring their biological activity. Each of these groups, however, was only able to obtain Migrastatin and derivatives thereof by fermentation techniques and/or by modifications to the natural product, and thus was limited in the number and types of derivatives that could be prepared and/or evaluated for biological activity.

Clearly, there remains a need for compounds related to Migrastatin. Therefore, there is a need to develop synthetic methodologies to access a variety of novel analogues of Migrastatin, particularly those that are inaccessible by making modifications to the natural product. It would also be of particular interest to develop novel compounds that exhibit a favorable therapeutic profile in vivo (e.g., are safe and effective).

SUMMARY OF THE INVENTION

In one aspect, the present invention provides a method for treating or preventing metastatic colon and/or ovarian cancer in a subject comprising administering to a subject in need thereof a therapeutically effective amount of a compound having the structure:

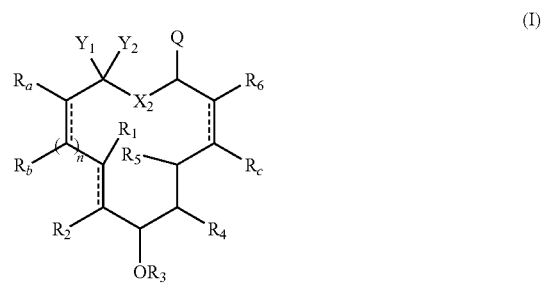

(I)

or pharmaceutically acceptable salt thereof;
wherein n, $R_1$-$R_6$, $R_a$, $R_b$, Q, $Y_1$, $Y_2$ and $X_1$ are as defined in classes and subclasses herein;
wherein the compound is present in an amount effective to inhibit colon and/or ovarian tumor metastasis.

In another aspect, the present invention provides a method for treating or preventing colon and/or ovarian cancer in a subject comprising administering to a subject in need thereof a therapeutically effective amount of a compound of formula I, wherein the compound is present in an amount effective to inhibit colon and/or ovarian tumor cell proliferation.

In another aspect, the present invention provides a method for treating or preventing colon and/or ovarian cancer in a subject comprising administering to a subject in need thereof a therapeutically effective amount of a pharmaceutical composition comprising:
a pharmaceutically acceptable carrier, adjuvant or vehicle; and
a therapeutically effective amount of a compound of formula I, whereby the composition is formulated for administration to a subject at a dosage between about 0.01 mg/kg to about 200 mg/kg of body weight.

In another aspect, the present invention provides a method for treating a wound of facilitating wound healing in a subject comprising administering to a subject in need thereof a therapeutically effective amount of a compound of formula I, wherein the compound is present in an amount effective to enhance cell migration.

In another aspect, the present invention provides a method for treating or preventing ascites in a subject comprising administering to a subject in need thereof a therapeutically effective amount of a compound of formula I, wherein the compound is present in an amount effective to treat or prevent ascites.

In another aspect, the present invention provides a pharmaceutical composition for treating or preventing colon and/or ovarian cancer in a subject comprising:

a pharmaceutically acceptable carrier, adjuvant or vehicle; and a therapeutically effective amount of a compound of formula I, whereby the composition is formulated for administration to a subject at a dosage between about 0.01 mg/kg to about 200 mg/kg of body weight.

DEFINITIONS

It is understood that the compounds, as described herein, may be substituted with any number of substituents or functional moieties. In general, the term "substituted" whether preceded by the term "optionally" or not, and substituents contained in formulas of this invention, refer to the replacement of hydrogen radicals in a given structure with the radical of a specified substituent. When more than one position in any given structure may be substituted with more than one substituent selected from a specified group, the substituent may be either the same or different at every position. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic, carbon and heteroatom substituents of organic compounds. For purposes of this invention, heteroatoms such as nitrogen may have hydrogen substituents and/or any permissible substituents of organic compounds described herein which satisfy the valencies of the heteroatoms. Furthermore, this invention is not intended to be limited in any manner by the permissible substituents of organic compounds. Combinations of substituents and variables envisioned by this invention are preferably those that result in the formation of stable compounds useful in the treatment and prevention, for example of disorders, as described generally above. Examples of substituents include, but are not limited to aliphatic; heteroaliphatic; alicyclic; heterocyclic; aromatic, heteroaromatic; aryl; heteroaryl; alkylaryl; alkylheteroaryl; alkoxy; aryloxy; heteroalkoxy; heteroaryloxy; alkylthio; arylthio; heteroalkylthio; heteroarylthio; F; Cl; Br; I; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$;— or -GR$^{G1}$ wherein G is —O—, —S—, —NR$^{G2}$, —C(=O)—, —S(=O), —SO$_2$—, —C(=O)O—, —C(=O)NR$^{G2}$—, —OC(=O)—, —NR$^{G2}$C(=O)—, —OC(=O)—, —OC(=O)NR$^{G2}$, —NR$^{G2}$C(=O)O—, —NR$^{G2}$C(=O)NR$^{G2}$, —C(—S—, —C(=S)S—, —SC(=S)—, —SC(=S)S—, —C(=NR$^{G2}$)—, —C(=NR$^{G2}$)O—, —C(=NR$^{G2}$)NR$^{G3}$—, —OC(=NR$^{G2}$), —NR$^{G2}$C(=NR$^{G3}$)—, —NR$^{G2}$SO$_2$—, —NR$^{G2}$SO$_2$NR$^{G3}$—, or —SO$_2$NR$^{G2}$—, wherein each occurrence of R$^{G1}$, R$^{G2}$ and R$^{G3}$ independently includes, but is not limited to, hydrogen, halogen, or an optionally substituted aliphatic, heteroaliphatic, alicyclic, heterocyclic, aromatic, heteroaromatic, aryl, heteroaryl, alkylaryl, or alkylheteroaryl moiety. Additional examples of generally applicable substituents are illustrated by the specific embodiments shown in the Examples that are described herein.

The term "stable", as used herein, preferably refers to compounds which possess stability sufficient to allow manufacture and which maintain the integrity of the compound for a sufficient period of time to be detected and preferably for a sufficient period of time to be useful for the purposes detailed herein.

The term "aliphatic", as used herein, includes both saturated and unsatrated, straight chain (i.e., unbranched) or branched aliphatic hydrocarbons, which are optionally substituted with one or more functional groups. As will be appreciated by one of ordinary skill in the art, "aliphatic" is intended herein to include, but is not limited to, alkyl, alkenyl, alkynyl moieties. Thus, as used herein, the term "alkyl" includes straight and branched alkyl groups. An analogous convention applies to other generic terms such as "alkenyl", "alkynyl" and the like. Furthermore, as used herein, the terms "alkyl", "alkenyl", "alkynyl" and the like encompass both substituted and unsubstituted groups. In certain embodiments, as used herein, "lower alkyl" is used to indicate those alkyl groups (substituted, unsubstituted, branched or unbranched) having about 1-6 carbon atoms.

In certain embodiments, the alkyl, alkenyl and alkynyl groups employed in the invention contain about 1-20 aliphatic carbon atoms. In certain other embodiments, the alkyl, alkenyl, and alkynyl groups employed in the invention contain about 1-10 aliphatic carbon atoms. In yet other embodiments, the alkyl, alkenyl, and alkynyl groups employed in the invention contain about 1-8 aliphatic carbon atoms. In still other embodiments, the alkyl, alkenyl, and alkynyl groups employed in the invention contain about 1-6 aliphatic carbon atoms. In yet other embodiments, the alkyl, alkenyl, and alkynyl groups employed in the invention contain about 1-4 carbon atoms. Illustrative aliphatic groups thus include, but are not limited to, for example, methyl, ethyl, n-propyl, iso-propyl, allyl, n-butyl, sec-butyl, isobutyl, tert-butyl, n-pentyl, sec-pentyl, isopentyl, tert-pentyl, n-hexyl, sec-hexyl, moieties and the like, which again, may bear one or more substituents. Alkenyl groups include, but are not limited to, for example, ethenyl, propenyl, butenyl, 1-methyl-2-buten-1-yl, and the like. Representative alkynyl groups include, but are not limited to, ethynyl, 2-propynyl (propargyl), 1-propynyl and the like.

The term "alicyclic", as used herein, refers to compounds which combine the properties of aliphatic and cyclic compounds and include but are not limited to cyclic, or polycyclic aliphatic hydrocarbons and bridged cycloalkyl compounds, which are optionally substituted with one or more functional groups. As will be appreciated by one of ordinary skill in the art, "alicyclic" is intended herein to include, but is not limited to, cycloalkyl, cycloalkenyl, and cycloalkynyl moieties, which are optionally substituted with one or more functional groups. Illustrative alicyclic groups thus include, but are not limited to, for example, cyclopropyl, —CH$_2$-cyclopropyl, cyclobutyl, —CH$_2$-cyclobutyl, cyclopentyl, —CH$_2$-cyclopentyl-n, cyclohexyl, —CH$_2$-cyclohexyl, cyclohexenylethyl, cyclohexanylethyl, norborbyl moieties and the like, which again, may bear one or more substituents.

The term "cycloalkyl", as used herein, refers specifically to groups having three to seven, preferably three to ten carbon atoms. Suitable cycloalkyls include, but are not limited to cyclopropyl, cyclobutyl, cyclopentyl, cyclohexyl, cycloheptyl and the like, which, as in the case of aliphatic, heteroaliphatic or heterocyclic moieties, may optionally be substituted. An analogous convention applies to other generic terms such as "cycloalkenyl", "cycloalkynyl" and the like.

The term "heteroaliphatic", as used herein, refers to aliphatic moieties in which one or more carbon atoms in the main chain have been substituted with a heteroatom. Thus, a heteroaliphatic group refers to an aliphatic chain which contains one or more oxygen, sulfur, nitrogen, phosphorus or silicon atoms, e.g., in place of carbon atoms. Heteroaliphatic moieties may be branched or linear unbranched. In certain embodiments, heteroaliphatic moieties are substituted by independent replacement of one or more of the hydrogen atoms thereon with one or more moieties including, but not limited to aliphatic; heteroaliphatic; alicyclic; heterocyclic; aromatic, heteroaromatic; aryl; heteroaryl; alkylaryl; alkylheteroaryl; alkoxy; aryloxy; heteroalkoxy; heteroaryloxy; alkylthio; arylthio; heteroalkylthio; heteroarylthio; F; Cl; Br; I; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$;— or -GR$^{G1}$ wherein G is —O—, —S—, —NR$^{G2}$—, —C(=O), —S(=O)—, —SO$_2$—, —C(=O)O—, —C(=O)NR$^{G2}$—, —OC(=O)—, —NR$^{G2}$C(=O)—, —C(=O)—, —OC(=O)NR$^{G2}$, —NR$^{G2}$C(=O)O—, —NR$^{G2}$C(=O)NR$^{G2}$—, —C(=S)—, —C(=S)S—, —SC(=S)—, —SC(=S)S—, —C(=NR$^{G2}$)—, —C(=NR$^{G2}$)O—, —C(=NR$^{G2}$)NR$^{G3}$—, —C(=NR$^{G2}$)—, —NR$^{G2}$C(=NR$^{G3}$)—, —NR$^{G2}$SO$_2$—, —NR$^{G2}$SO$_2$NR$^{G3}$—, or —SO$_2$NR$^{G2}$—, wherein each occurrence of R$^{G1}$, R$^{G2}$ and R$^{G3}$ independently includes, but is not limited to, hydrogen, halogen, or an optionally substituted aliphatic, heteroaliphatic, alicyclic, heterocyclic, aromatic, heteroaromatic, aryl, heteroaryl, alkylaryl, or alkylheteroaryl moiety. Additional examples of generally applicable substituents are illustrated by the specific embodiments shown in the Examples that are described herein.

The term "heteroalicyclic", "heterocycloalkyl" or "heterocyclic", as used herein, refers to compounds which combine the properties of heteroaliphatic and cyclic compounds and include but are not limited to saturated and unsaturated mono- or polycyclic heterocycles such as morpholino, pyrrolidinyl, furanyl, thiofuranyl, pyrrolyl etc., which are optionally substituted with one or more functional groups, as defined herein. In certain embodiments, the term "heterocyclic" refers to a non-aromatic 5-, 6- or 7-membered ring or a polycyclic group, including, but not limited to a bi- or tricyclic group comprising fused six-membered rings having between one and three heteroatoms independently selected from oxygen, sulfur and nitrogen, wherein (i) each 5-membered ring has 0 to 2 double bonds and each 6-membered ring has 0 to 2 double bonds, (ii) the nitrogen and sulfur heteroatoms may optionally be oxidized, (iii) the nitrogen heteroatom may optionally be quaternized, and (iv) any of the above heterocyclic rings may be fused to an aryl or heteroaryl ring. Representative heterocycles include, but are not limited to, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl. In certain embodiments, a "substituted heterocycloalkyl or heterocycle" group is utilized and as used herein, refers to a heterocycloalkyl or heterocycle group, as defined above, substituted by the independent replacement of one, two or three of the hydrogen atoms thereon with but are not limited to aliphatic; heteroaliphatic; alicyclic; heterocyclic; aromatic, heteroaromatic; aryl; heteroaryl; alkylaryl; alkylheteroaryl; alkoxy; aryloxy; heteroalkoxy; heteroaryloxy; alkylthio; arylthio; heteroalkylthio; heteroarylthio; F; Cl; Br; I; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$;— or —GR$^{G1}$ wherein G is —O—, —S—, —NR$^{G2}$—, —C(=O)—, —S(=O)—, —SO$_2$—, —C(=O)O—, —C(=O)NR$^{G2}$, —OC(=O)—, —NR$^{G2}$C(=O)—, —OC(=O)O—, —OC(=O)NR$^{G2}$—, —NR$^{G2}$C(=O)O—, —NR$^{G2}$C(=O)NR$^{G2}$—, —C(=S)—, —C(=S)S—, —SC(=S)—, —SC(=S)S—, —C(=NR$^{G2}$)—, —C(=NR$^{G2}$)O—, —C(=NR$^{G2}$)NR$^{G3}$—, —OC(=NR$^{G2}$)—, —NR$^{G2}$C(=NR$^{G3}$)—, —NR$^{G2}$SO$_2$—, —NR$^{G2}$SO$_2$NR$^{G3}$—, or —SO$_2$NR$^{G2}$—, wherein each occurrence of R$^{G1}$, R$^{G2}$ and R$^{G3}$ independently includes, but is not limited to, hydrogen, halogen, or an optionally substituted aliphatic, heteroaliphatic, alicyclic, heterocyclic, aromatic, heteroaromatic, aryl, heteroaryl, alkylaryl, or alkylheteroaryl moiety. Additional examples or generally applicable substituents are illustrated by the specific embodiments shown in the Examples, which are described herein.

Additionally, it will be appreciated that any of the alicyclic or heterocyclic moieties described above and herein may comprise an aryl or heteroaryl moiety fused thereto. Additional examples of generally applicable substituents are illustrated by the specific embodiments shown in the Examples that are described herein.

In general, the term "aromatic moiety", as used herein, refers to stable substituted or unsubstituted unsaturated mono- or polycyclic hydrocarbon moieties having preferably 3-14 carbon atoms, comprising at least one ring satisfying the Huckel rule for aromaticity. Examples of aromatic moieties include, but are not limited to, phenyl, indanyl, indenyl, naphthyl, phenanthryl and anthracyl.

In general, the term "heteroaromatic moiety", as used herein, refers to stable substituted or unsubstituted unsaturated mono-heterocyclic or polyheterocyclic moieties having preferably 3-14 carbon atoms, comprising at least one ring satisfying the Huckel rule for aromaticity. Examples of heteroaromatic moieties include, but are not limited to, pyridyl, quinolinyl, dihydroquinolinyl, isoquinolinyl, quinazolinyl, dihydroquinazolyl, and tetrahydroquinazolyl.

It will also be appreciated that aromatic and heteroaromatic moieties, as defined herein, may be attached via an aliphatic (e.g., alkyl) or heteroaliphatic (e.g., heteroalkyl) moiety and thus also include moieties such as -(aliphatic)aromatic, -(heteroaliphatic)aromatic, -(aliphatic)heteroaromatic, -(heteroaliphatic)heteroaromatic, -(alkyl)aromatic, -(heteroalkyl)aromatic, -(alkyl)heteroaromatic, and -(heteroalkyl)heteroaromatic moieties. Thus, as used herein, the phrases "aromatic or heteroaromatic moieties" and "aromatic, heteroaromatic, -(alkyl)aromatic, -(heteroalkyl)aromatic, -(heteroalkyl)heteroaromatic, and -(heteroalkyl)heteroaromatic" are interchangeable. Substituents include, but are not limited to, any of the previously mentioned substituents, i.e., the substituents recited for aliphatic moieties, or for other moieties as disclosed herein, resulting in the formation of a stable compound.

In general, the term "aryl" refers to aromatic moieties, as described above, excluding those attached via an aliphatic (e.g., alkyl) or heteroaliphatic (e.g., heteroalkyl) moiety. In certain embodiments of the present invention, "aryl" refers to a mono- or bicyclic carbocyclic ring system having one or two rings satisfying the Huckel rule for aromaticity, including, but not limited to, phenyl, naphthyl, tetrahydronaphthyl, indanyl, indenyl and the like.

Similarly, the term "heteroaryl" refers to heteroaromatic moieties, as described above, excluding those attached via an aliphatic (e.g., alkyl) or heteroaliphatic (e.g., heteroalkyl) moiety. In certain embodiments of the present invention, the term "heteroaryl", as used herein, refers to a cyclic unsaturated radical having from about five to about ten ring atoms of which one ring atom is selected from S, O and N; zero, one or two ring atoms are additional heteroatoms independently selected from S, O and N; and the remaining ring atoms are carbon, the radical being joined to the rest of the molecule via any of the ring atoms, such as, for example, pyridyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quiolinyl, isoquinolinyl, and the like.

Substituents for aryl and heteroaryl moieties include, but are not limited to, any of the previously mentioned substitutents, i.e., the substituents recited for aliphatic moieties, or for other moieties as disclosed herein, resulting in the formation of a stable compound. For example, aryl and heteroaryl groups (including bicyclic aryl groups) can be unsubstituted or substituted, wherein substitution includes replacement of one, two or three of the hydrogen atoms thereon independently with any one or more of the following moieties including, but not limited to: aliphatic; heteroaliphatic; alicyclic; heterocyclic; aromatic, heteroaromatic; aryl; heteroaryl; alkylaryl; alkylheteroaryl; alkoxy; aryloxy; heteroalkoxy; heteroaryloxy; alkylthio; arylthio; heteroalkylthio; heteroarylthio; F; Cl; Br; I; —$NO_2$; —CN; —$CF_3$; —$CH_2CF_3$; —$CHCl_2$; —$CH_2OH$; —$CH_2CH_2OH$; —$CH_2NH_2$; —$CH_2SO_2CH_3$;— or —$GR^{G1}$ wherein G is —O—, —S—, —$NR^{G2}$—, —C(=O)—, —S(=O)—, —$SO_2$—, —C(=O)O—, —C(=O)$NR^{G2}$—, —OC(=O)—, —$NR^{G2}$C(=O)—, —OC(=O)O—, —OC(=O)$NR^{G2}$—, —$NR^{G2}$C(=O)O—, —$NR^{G2}$C(=O)$NR^{G2}$—, —C(=S)—, —C(=S)S—, —SC(=S)—, —SC(=S)S—, —C(=$NR^{G2}$)—, —C(=$NR^{G2}$)O—, —C(=$NR^{G2}$)$NR^{G3}$—, —OC(=$NR^{G2}$)—, —$NR^{G2}$C(=$NR^{G3}$)—, —$NR^{G2}SO_2$—, —$NR^{G2}SO_2NR^{G3}$—, or —$SO_2NR^{G2}$—, wherein each occurrence of $R^{G1}$, $R^{G2}$ and $R^{G3}$ independently includes, but is not limited to, hydrogen, halogen, or an optionally substituted aliphatic, heteroaliphatic, alicyclic, heterocyclic, aromatic, heteroaromatic, aryl, heteroaryl, alkylaryl, or alkylheteroaryl moiety. Additional examples of generally applicable substituents are illustrated by the specific embodiments shown in the Examples that are described herein.

The terms "alkoxy" (or "alkyloxy"), and "thioalkyl" as used herein refers to an alkyl group, as previously defined, attached to the parent molecular moiety through an oxygen atom ("alkoxy") or through a sulfur atom ("thioalkyl"). In certain embodiments, the alkyl group contains about 1-20 aliphatic carbon atoms. In certain other embodiments, the alkyl group contains about 1-10 aliphatic carbon atoms. In yet other embodiments, the alkyl group contains about 1-8 aliphatic carbon atoms. In still other embodiments, the alkyl group contains about 1-6 aliphatic carbon atoms. In yet other embodiments, the alkyl group contains about 1-4 aliphatic carbon atoms. Examples of alkoxy groups, include but are not limited to, methoxy, ethoxy, propoxy, isopropoxy, n-butoxy, tert-butoxy, neopentoxy and n-hexoxy. Examples of thioalkyl groups include, but are not limited to, methylthio, ethylthio, propylthio, isopropylthio, n-butylthio, and the like.

The term "amine" refers to a group having the structure —N(R)$_2$ wherein each occurrence of R is independently hydrogen, or an aliphatic, heteroaliphatic, aromatic or heteroaromatic moiety, or the R groups, taken together, may form a heterocyclic moiety.

The term "alkylamino" refers to a group having the structure —NHR' wherein R' is alkyl, as defined herein. The term "aminoalkyl" refers to a group having the structure $NH_2R'$—, wherein R' is alkyl, as defined herein. In certain embodiments, the alkyl group contains about 1-20 aliphatic carbon atoms. In certain other embodiments, the alkyl group contains about 1-10 aliphatic carbon atoms. In yet other embodiments, the alkyl, alkenyl, and alkynyl groups employed in the invention contain about 1-8 aliphatic carbon atoms. In still other embodiments, the alkyl group contains about 1-6 aliphatic carbon atoms. In yet other embodiments, the alkyl group contains about 1-4 aliphatic carbon atoms. Examples of alkylamino include, but are not limited to, methylamino, ethylamino, iso-propylamino and the like.

The terms "halo" and "halogen" as used herein refer to an atom selected from fluorine, chlorine, bromine and iodine.

The term "halogenated" denotes a moiety having one, two, or three halogen atoms attached thereto.

The term "haloalkyl" denotes an alkyl group, as defined above, having one, two, or three halogen atoms attached thereto and is exemplified by such groups as chloromethyl, bromoethyl, trifluoromethyl, and the like.

The term "acyloxy", as used herein, does not substantially differ from the common meaning of this term in the art, and refers to a moiety of structure —OC(O)$R_X$, wherein $R_X$ is a substituted or unsubstituted aliphatic, alicyclic, heteroaliphatic, heterocyclic, aryl or heteroaryl moiety.

The term "acyl", as used herein, does not substantially differ from the common meaning of this term in the art, and refers to a moiety of structure —C(O)$R_X$, wherein $R_X$ is a substituted or unsubstituted, aliphatic, alicyclic, heteroaliphatic, heterocyclic, aryl or heteroaryl moiety.

The term "imino", as used herein, does not substantially differ from the common meaning of this term in the art, and refers to a moiety of structure —C(=$NR_X$)$R_Y$, wherein $R_X$ is hydrogen or an optionally substituted aliphatic, alicyclic, heteroaliphatic, heterocyclic, aryl or heteroaryl moiety; and $R_Y$ is an optionally substituted aliphatic, alicyclic, heteroaliphatic, heterocyclic, aryl or heteroaryl moiety.

The term "$C_{1-6}$alkylidene", as used herein, refers to a substituted or unsubstituted, linear or branched saturated divalent radical consisting solely of carbon and hydrogen atoms, having from one to six carbon atoms, having a free valence "-" at both ends of the radical.

The term "$C_{2-6}$alkenylidene", as used herein, refers to a substituted or unsubstituted, linear or branched unsaturated divalent radical consisting solely of carbon and hydrogen atoms, having from two to six carbon atoms, having a free valence "-" at both ends of the radical, and wherein the unsaturation is present only as double bonds and wherein a double bond can exist between the first carbon of the chain and the rest of the molecule.

As used herein, the terms "aliphatic", "heteroaliphatic", "alkyl", "alkenyl", "alkynyl", "heteroalkyl", "heteroalkenyl", "heteroalkynyl", and the like encompass substituted and unsubstituted, saturated and unsaturated, and linear and branched groups. Similarly, the terms "alicyclic", "heteroalicyclic", "heterocycloalkyl", "heterocycle" and the like encompass substituted and unsubstituted, and saturated and unsaturated groups. Additionally, the terms "cycloalkyl", "cycloalkenyl", "cycloalkynyl", "heterocycloalkyl", "heterocycloalkenyl", "heterocycloalkynyl", "aryl", "heteroaryl" and the like encompass both substituted and unsubstituted groups.

The phrase, "pharmaceutically acceptable derivative", as used herein, denotes any pharmaceutically acceptable salt, ester, or salt of such ester, of such compound, or any other adduct or derivative which, upon administration to a patient, is capable of providing (directly or indirectly) a compound as otherwise described herein, or a metabolite or residue thereof. Pharmaceutically acceptable derivatives thus include among others pro-drugs. A pro-drug is a derivative of a compound, usually with significantly reduced pharmacological activity, which contains an additional moiety, which is susceptible to removal in vivo yielding the parent molecule as the pharmacologically active species. An example of a pro-drug is an ester, which is cleaved in vivo to yield a compound of interest. Pro-drugs of a variety of compounds, and materials and methods for derivatizing the parent compounds to create the pro-drugs, are known and may be adapted to the present invention. Certain exemplary pharmaceutical compositions and pharmaceutically acceptable derivatives will be discussed in more detail herein below.

By the term "protecting group", has used herein, it is meant that a particular functional moiety, e.g., O, S, or N, is temporarily blocked so that a reaction can be carried out selectively at another reactive site in a multifunctional compound. In preferred embodiments, a protecting group reacts selectively in good yield to give a protected substrate that is stable to the projected reactions; the protecting group must be selectively removed in good yield by readily available, preferably non-toxic reagents that do not attack the other functional groups; the protecting group forms an easily separable derivative (more preferably without the generation of new stereogenic centers); and the protecting group has a minimum of additional functionality to avoid further sites of reaction. As detailed herein, oxygen, sulfur, nitrogen and carbon protecting groups may be utilized. For example, in certain embodiments, as detailed herein, certain exemplary oxygen protecting groups are utilized. These oxygen protecting groups include, but are not limited to methyl ethers, substituted methyl ethers (e.g., MOM (methoxymethyl ether), MTM (methylthiomethyl ether), BOM (benzyloxymethyl ether), PMBM or MPM (p-methoxybenzyloxymethyl ether), to name a few), substituted ethyl ethers, substituted benzyl ethers, silyl ethers (e.g., TMS (trimethylsilyl ether), TES (triethylsilylether), TIPS (triisopropylsilyl ether), TBDMS (t-butyldimethylsilyl ether), tribenzyl silyl ether, TBDPS (t-butyldiphenyl silyl ether), to name a few), esters (e.g., formate, acetate, benzoate (Bz), trifluoroacetate, dichloroacetate, to name a few), carbonates, cyclic acetals and ketals. In certain other exemplary embodiments, nitrogen protecting groups are utilized. These nitrogen protecting groups include, but are not limited to, carbamates (including methyl, ethyl and substituted ethyl carbamates (e.g., Troc), to name a few) amides, cyclic imide derivatives, N-Alkyl and N-Aryl amines, imine derivatives, and enamine derivatives, to name a few. Certain other exemplary protecting groups are detailed herein, however, it will be appreciated that the present invention is not intended to be limited to these protecting groups; rather, a variety of additional equivalent protecting groups can be readily identified using the above criteria and utilized in the present invention. Additionally, a variety of protecting groups are described in "Protective Groups in Organic Synthesis" Third Ed. Greene, T. W. and Wuts, P. G., Eds., John Wiley & Sons, New York: 1999, the entire contents of which are hereby incorporated by reference.

As used herein, the term "reaction vessel" denotes any container that can contain a reacting solution. For example, test tubes, petri dishes, and wells can all constitute reaction vessels. Preferably, a reaction vessel is a well in a multiwell plate or other multivessel format.

BRIEF DESCRIPTION OF THE DRAWING

FIG. 5 depicts cell morphology of human colon cancer cell line HT 29 and human ovarian cancer cell line IGROV after treatment with various concentrations of migrastatin analog (48) after 72 hours of incubation.

FIG. 7 depicts bioluminescence imaging (BLI) of intraperitoneally injected Ovcar3 ovarian cancer cell. (A) whole mouse ventral image. (B) preparation of mouse organs (spleen liver and lung) to measure individual tumor burden.

FIG. 10 depicts effects of migrastatin analog (48) in an ovarian in vivo xenograph experiment.

FIG. 11 depicts effects of treatment migrastatin analog (48) on body weight in an ovarian in vivo xenograph experiment.

FIG. 12 depicts effects of treatment migrastatin analog (48) on tumor size in an ovarian in vivo xenograph experiment.

FIG. 15 depicts metastasis inhibition experiments for migrastatin analog (74) in an ovarian xenograph model.

FIG. 17 depicts a micro array experiment with human ovarian cancer cells Ovcar3 treated with 500 nM migrastatin analog (48).

DESCRIPTION OF CERTAIN PREFERRED EMBODIMENTS OF THE INVENTION

Figure 1A:
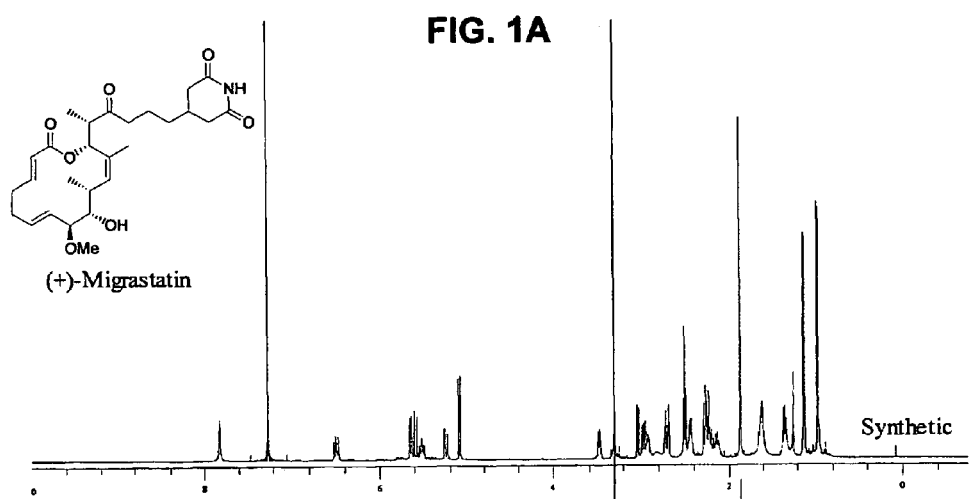
FIG. 1A depicts a $^1$H NMR spectrum of synthetic Migrastatin.
Figure 1B:
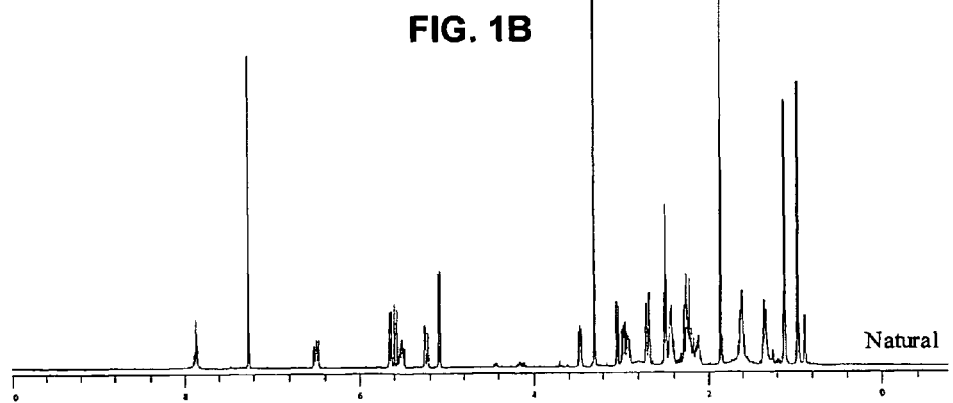
FIG. 1B depicts a $^1$H NMR spectrum of naturally occurring Migrastatin.

In recognition of the need to access novel Migrastatin analogs, and this class of macrocycles in general, the present invention provides novel macrocyclic compounds, as described in more detail herein, which exhibit the ability to inhibit cell migration. Therefore, the compounds may be useful as angiogenesis inhibitors. The invention also provides information regarding structural elements that participate in or contribute to this activity, and therefore provides insight into the biological activity of this class of compounds. Thus, the compounds of the invention, and pharmaceutical compositions thereof, are useful as antiangiogenesis agents for the treatment of cancer and/or abnormal cell proliferation. In certain embodiments, the compounds of the present invention can be used for the treatment of diseases and disorders including, but not limited to solid tumor cancers, metastasis, ocular angiogenic diseases, diabetic retinopathy, retinopathy of prematurity, corneal graft rejection, neovascular glaucoma, retrolental fibroplasias, rubeosis, solid tumors, blood born tumors, leukemias, tumor metastases, benign tumors, acoustic neuromas, neurofibromas, trachomas, pyogenic granulomas, rheumatoid arthritis, psoriasis, Osler-Webber Syndrome, myocardial angiogenesis, plaque neovascularization, telangiectasia, hemophiliac joints, angiofibroma, or wound granulation, to name a few.

General Description of Compounds of the Invention

In certain embodiments, the compounds of the invention include compounds of the general formula (I) as further defined below:

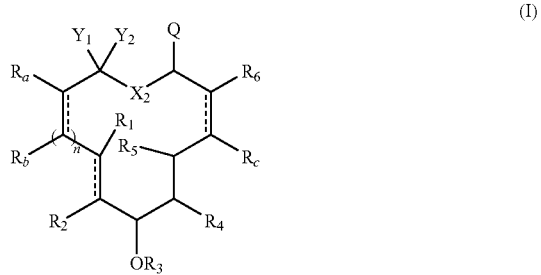

(I)

pharmaceutically acceptable derivatives thereof;

wherein $R_1$ and $R_2$ are each independently hydrogen, halogen, —CN, —S(O)$_{1-2}$R$^{1A}$, —NO$_2$, —COR$^{1A}$, —CO$_2$R$^{1A}$, —NR$^{1A}$C(=O)R$^{1B}$, —NR$^{1A}$C(=O)OR$^{1B}$, —CONR$^{1A}$R$^{1B}$, an aliphatic, heteroaliphatic, alicyclic, heterocyclic, aryl or heteroaryl moiety, or —WR$^{1A}$; wherein W is independently —O—, —S— or —NR$^{1C}$—, wherein each occurrence of R$^{1A}$, R$^{1B}$ and R$^{1C}$ is independently hydrogen, or an aliphatic, heteroaliphatic, alicyclic, heterocyclic, aryl or heteroaryl moiety; or $R_1$ and $R_2$, taken together with the carbon atoms to which they are attached, form an alicyclic, heterocyclic, aryl or heteroaryl moiety;

$R_3$ is hydrogen, an aliphatic, heteroaliphatic, alicyclic, heterocyclic, aryl or heteroaryl moiety; or a prodrug moiety or an oxygen protecting group;

$R_4$ is halogen, —OR$^{4A}$, —OC(=O)R$^{4A}$ or NR$^{4A}$R$^{4B}$; wherein R$^{4A}$ and R$^{4B}$ are independently hydrogen, an aliphatic, heteroaliphatic, alicyclic, heterocyclic, aryl or heteroaryl moiety; a prodrug moiety, a nitrogen protecting group or an oxygen protecting group; or R$^{4A}$ and R$^{4B}$, taken together with the nitrogen atom to which they are attached, form a heterocyclic or heteroaryl moiety; or $R_4$, taken together with the carbon atom to which it is attached forms a moiety having the structure:

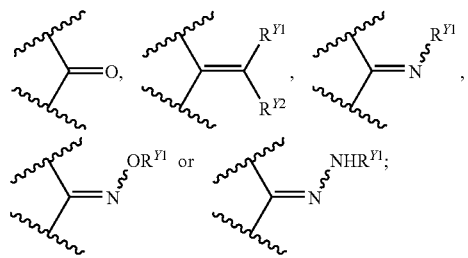

$R_5$ is hydrogen, an aliphatic, heteroaliphatic, alicyclic, heterocyclic, aryl or heteroaryl moiety;

$R_6$ is hydrogen, halogen, —CN, —S(O)$_{1-2}$R$^{6A}$, —NO$_2$, —COR$^{6A}$, —CO$_2$R$^{6A}$, —NR$^{6A}$C(=O)R$^{6B}$, —NR$^{6A}$C(=O)OR$_{6B}$, —CONR$^{6A}$R$^{6B}$, an aliphatic, heteroaliphatic, alicyclic, heterocyclic, aryl or heteroaryl moiety, or —WR$^{6A}$; wherein W is independently —O—, —S— or —NR$^{6C}$—, wherein each occurrence of R$^{6A}$, R$^{6B}$ and R$^{6C}$ is independently hydrogen, or an aliphatic, heteroaliphatic, alicyclic, heterocyclic, aryl or heteroaryl moiety; or $R_6$ and $R_c$, taken together with the carbon atoms to which they are attached, form an alicyclic, heterocyclic, aryl or heteroaryl moiety;

$R_a$ and each occurrence of $R_b$ are independently hydrogen, halogen, —CN, —S(O)$_{1-2}$R$^{a1}$, —NO$_2$, —COR$^{a1}$, —CO$_2$R$^{a1}$, —NR$^{a1}$C(=O)R$^{a2}$, —NR$^{a1}$C(=O)OR$^{a2}$, —CONR$^{a1}$R$^{a2}$, an aliphatic, heteroaliphatic, alicyclic, heterocyclic, aryl or heteroaryl moiety, or —WR$^{a1}$; wherein W is independently —O—, —S— or —NR$^{a3}$—, wherein each occurrence of R$^{a1}$, R$^{a2}$ and R$^{a3}$ is independently hydrogen, or an aliphatic, heteroaliphatic, alicyclic, heterocyclic, aryl or heteroaryl moiety; or $R_a$ and the adjacent occurrence of $R_b$, taken together with the carbon atoms to which they are attached, form an alicyclic, heterocyclic, aryl or heteroaryl moiety;

$R_c$ is hydrogen, halogen, —CN, —S(O)$_{1-2}$R$^{c1}$, —NO$_2$, —COR$^{c1}$, —CO$_2$R$^{c1}$, —NR$^{c1}$C(=O)R$^{c2}$, —NR$^{c1}$C(=O)OR$^{c2}$, —CONR$^{c1}$R$^{c2}$; an aliphatic, heteroaliphatic, alicyclic, heterocyclic, aryl or heteroaryl moiety, or —WR$^{c1}$; wherein W is independently —O—, —S— or —NR$^{c3}$—, wherein each occurrence of R$^{c1}$, R$^{c2}$ and R$^{c3}$ is independently hydrogen, or an aliphatic, heteroaliphatic, alicyclic, heterocyclic, aryl or heteroaryl moiety; or $R_c$ and $R_6$, taken together with the carbon atoms to which they are attached, form an alicyclic, heterocyclic, aryl or heteroaryl moiety;

n is an integer from 1 to 5;

$X_1$ is O, S, NR$^{X1}$ or CR$^{X1}$R$^{X2}$; wherein R$^{X1}$ and R$^{X2}$ are independently hydrogen, halogen, an aliphatic, heteroaliphatic, alicyclic, heterocyclic, aryl or heteroaryl moiety, or a nitrogen protecting group;

Q is hydrogen, halogen, —CN, —S(O)$_{1-2}$R$^{Q1}$, —NO$_2$, —COR$^{Q1}$, —CO$_2$R$^{Q1}$, —NR$^{Q1}$C(=O)R$^{Q2}$, —NR$^{Q1}$C(=O)OR$^{Q2}$, —CONR$^{Q1}$R$^{Q2}$, an aliphatic, heteroaliphatic, alicyclic, heterocyclic, aryl or heteroaryl moiety, or —WR$^{Q1}$; wherein W is independently —O—, —S— or —NR$^{Q3}$—, wherein each occurrence of R$^{Q1}$, R$^{Q2}$ and R$^{Q3}$ is independently hydrogen, or an aliphatic, heteroaliphatic, alicyclic, heterocyclic, aryl or heteroaryl moiety;

$Y_1$ and $Y_2$ are independently hydrogen, an aliphatic, heteroaliphatic, alicyclic, heterocyclic, aryl or heteroaryl moiety; or —WR$^{Y1}$; wherein W is independently —O—, —S— or —NR$^{Y2}$—, wherein each occurrence of R$^{Y1}$ and R$^{Y2}$ is independently hydrogen, or an aliphatic, heteroaliphatic, alicyclic, heterocyclic, aryl or heteroaryl moiety; or $Y_1$ and $Y_2$ together with the carbon atom to which they are attached form a moiety having the structure:

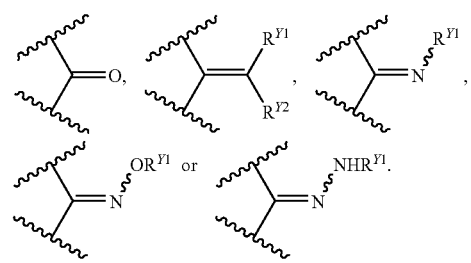

In certain embodiments of compounds described directly above and compounds as described in certain classes and subclasses herein, inventive compounds do not have one of the following structures:

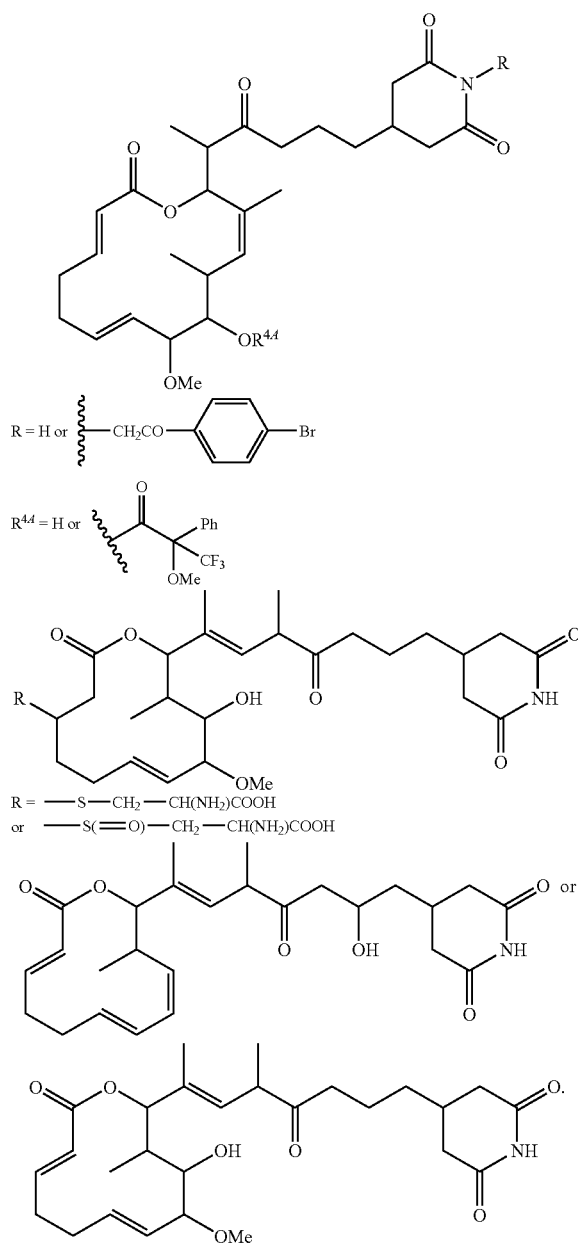

In certain other embodiments, compounds of formula (I) have the following stereochemistry:

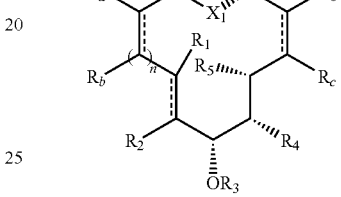

In certain other embodiments, compounds of formula (I) are defined as follows:

$R_1$ and $R_2$ are each independently hydrogen or substituted or unsubstituted lower alkyl; or $R_1$ and $R_2$, taken together with the carbon atoms to which they are attached, form an epoxide, an aziridine or a substituted or unsubstituted cyclopropyl moiety;

$R_3$ is hydrogen, or substituted or unsubstituted lower alkyl or aryl; a prodrug moiety or an oxygen protecting group;

$R_4$ is halogen, $-OR^{4A}$, $-OC(=O)R^{4A}$ or $-NR^{4A}R^{4B}$; wherein $R^{4A}$ and $R^{4B}$ are independently hydrogen, or substituted or unsubstituted lower alkyl; a prodrug moiety, a nitrogen protecting group or an oxygen protecting group; or $R^{4A}$ and $R^{4B}$, taken together with the nitrogen atom to which they are attached, form a heterocyclic or heteroaryl moiety; or $R_4$, taken together with the carbon atom to which it is attached forms a moiety having the structure:

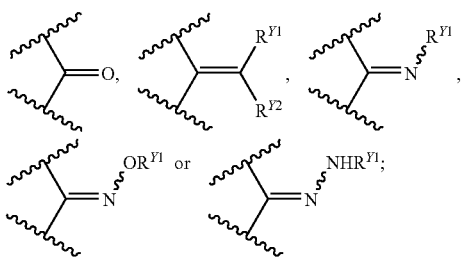

$R_5$ and $R_6$ are each independently hydrogen or substituted or unsubstituted lower alkyl; or $R_6$ and $R_c$, taken together with the carbon atoms to which they are attached, form an epoxide, an aziridine or a substituted or unsubstituted cyclopropyl moiety;

$R_a$ and each occurrence of $R_b$ are independently hydrogen, halogen, alkyl, heteroalkyl, cycloalkyl, heterocycloalkyl, aryl or heteroaryl moiety, or $-WR^{a1}$; wherein W is independently $-O-$, $-S-$ or $-NR^{a3}-$, wherein each occurrence In certain other embodiments, compounds of formula (I) have the following stereochemistry:

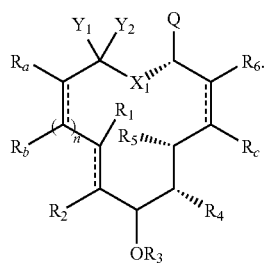

In certain other embodiments, compounds of formula (I) have the following stereochemistry:

of $R^{a1}$, and $R^{a3}$ is independently hydrogen, or an alkyl, heteroalkyl, cycloalkyl, heterocycloalkyl, aryl or heteroaryl moiety; or $R_a$ and the adjacent occurrence of $R_b$, taken together, form an epoxide, an aziridine or a substituted or unsubstituted cyclopropyl moiety;

$R_c$ is hydrogen, halogen, alkyl, heteroalkyl, cycloalkyl, heterocycloalkyl, aryl or heteroaryl moiety, or —$WR^{c1}$; wherein W is independently —O—, —S— or —$NR^{c3}$—, wherein each occurrence of $R^{c1}$ and $R^{c3}$ is independently hydrogen, or an alkyl, heteroalkyl, cycloalkyl, heterocycloalkyl, aryl or heteroaryl moiety; or $R_c$ and $R_6$, taken together with the carbon atoms to which they are attached, form an epoxide, an aziridine or a substituted or unsubstituted cyclopropyl moiety;

n is an integer from 1 to 5;

$X_1$ is O, S, $NR^{X1}$ or $CR^{X1}R^{X2}$; wherein $R^{X1}$ and $R^{X2}$ are independently hydrogen, halogen, substituted or unsubstituted alkyl, heteroalkyl, cycloalkyl, heterocycloalkyl, aryl or heteroaryl, or a nitrogen protecting group;

Q is hydrogen, halogen, —CN, —$S(O)_{1-2}R^{Q1}$, —$NO_2$, —$COR^{Q1}$, —$CO_2R^{Q1}$, —$NR^{Q1}C(=O)R^{Q2}$, —$NR^{Q1}C(=O)OR^{Q2}$, —$CONR^{Q1}R^{Q2}$, an aliphatic, heteroaliphatic, alicyclic, heterocyclic, aryl or heteroaryl moiety, or —$WR^{Q1}$; wherein W is independently —O—, —S— or —$NR^{Q3}$—, wherein each occurrence of $R^{Q1}$, $R^{Q2}$ and $R^{Q3}$ is independently hydrogen, or an aliphatic, heteroaliphatic, alicyclic, heterocyclic, aryl or heteroaryl moiety;

$Y_1$ and $Y_2$ are independently hydrogen, an alkyl, heteroalkyl, cycloalkyl, heterocycloalkyl, aryl or heteroaryl moiety; or —$WR^{Y1}$; wherein W is independently —O—, —S— or —$NR^{Y2}$—, wherein each occurrence of $R^{Y1}$ and $R^{Y2}$ is independently hydrogen, or an alkyl, heteroalkyl, cycloalkyl, heterocycloalkyl, aryl or heteroaryl moiety; or $Y_1$ and $Y_2$ together with the carbon atom to which they are attached form a moiety having the structure:

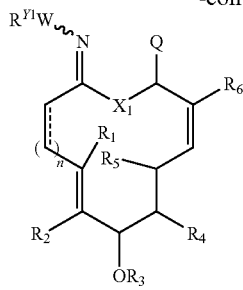

In certain embodiments, the present invention defines certain classes of compounds which are of special interest. For example, one class of compounds of special interest includes those compounds having the structure of formula (I) in which $R_a$, $R_b$ and $R_c$ are each hydrogen, and the compound has one of the following structures:

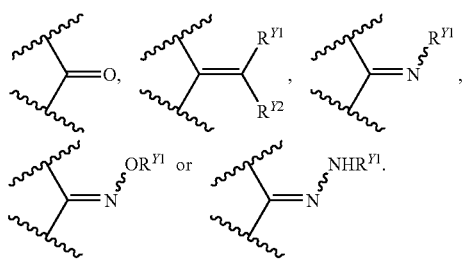

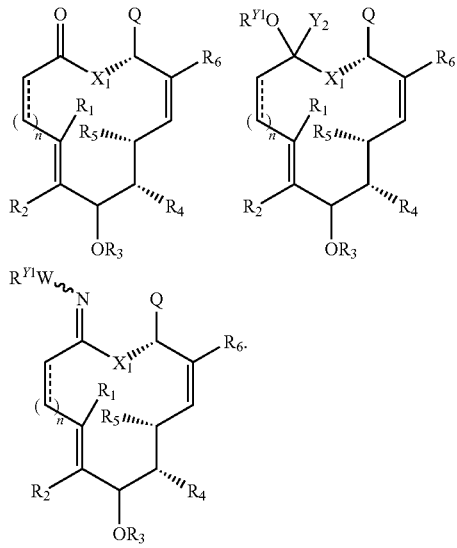

wherein $R_1$-$R_6$, $Y_2$, $X_1$, n and Q are as defined in classes and subclasses herein; W is O or NH; and $R^{Y1}$ is hydrogen, or an aliphatic, heteroaliphatic, alicyclic, heterocyclic, aryl or heteroaryl moiety.

In certain exemplary embodiments, compounds of the invention shown directly above have the following stereochemistry:

Another class of compounds of special interest includes those compounds having the structure of formula (I) in which $R_a$, $R_b$ and $R_c$ are each hydrogen, Q is a carbonyl-containing moiety and the compound has one of the following structures:

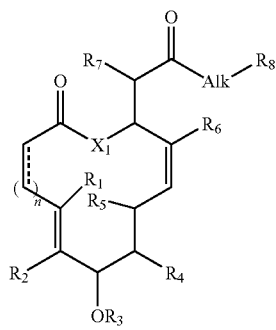

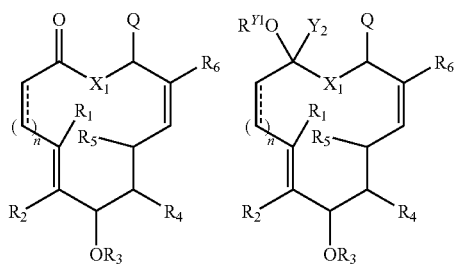

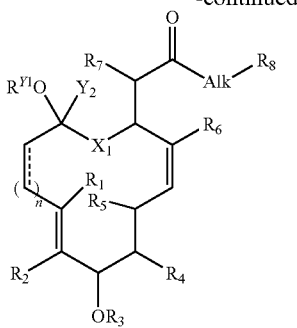

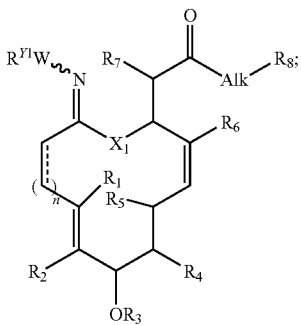

wherein R$_1$-R$_6$, Y$_2$, X$_1$, n and Q are as defined in classes and subclasses herein; W is O or NH; and R$^{Y1}$ is hydrogen, or an aliphatic, heteroaliphatic, alicyclic, heterocyclic, aryl or heteroaryl moiety.

In certain exemplary embodiments, compounds of the invention shown directly above have the following stereochemistry:

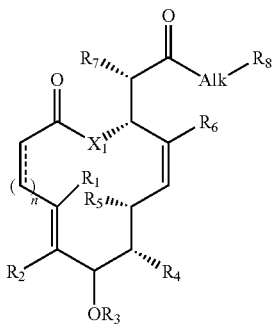

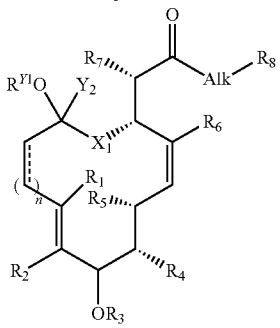

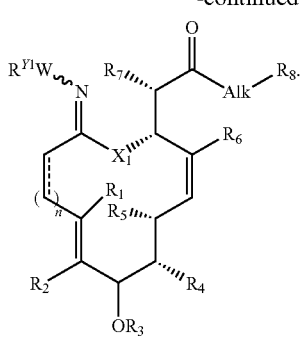

Another class of compounds of special interest includes compounds having the structure of formula (I) in which R$_a$, R$_b$ and R$_c$ are each hydrogen, n is 3 and the compound has one of the following structures:

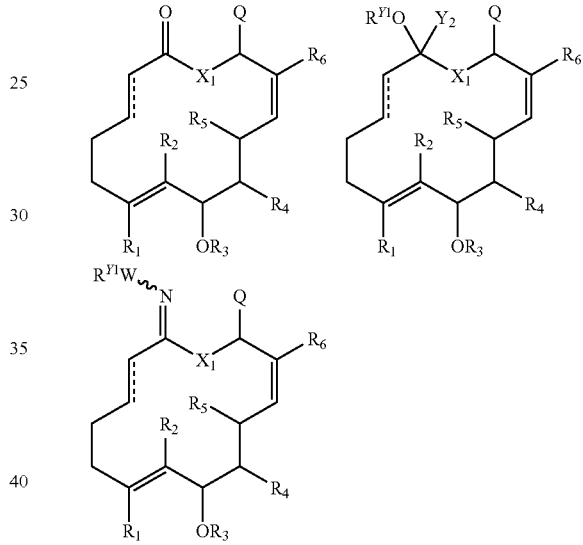

wherein R$_1$-R$_6$, Y$_2$, Q and X$_1$ are as defined in classes and subclasses herein; W is O or NH; and R$^{Y1}$ is hydrogen, or an aliphatic, heteroaliphatic, alicyclic, heterocyclic, aryl or heteroaryl moiety.

In certain exemplary embodiments, compounds of the invention shown directly above have the following stereochemistry:

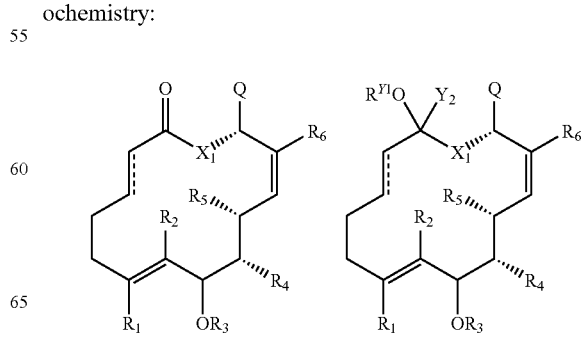

-continued

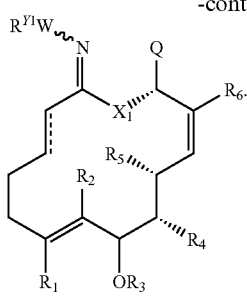

Another class of compounds of special interest includes compounds having the structure of formula (I) in which $R_a$, $R_b$ and $R_c$ are each hydrogen, n is 3, Q is a carbonyl-containing moiety, and the compound has one of the following structures:

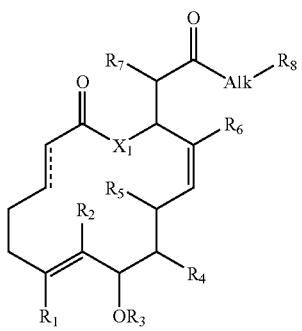

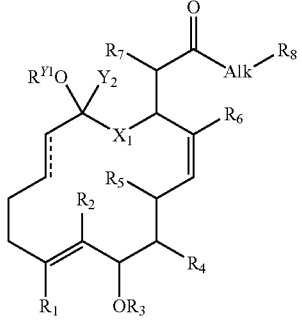

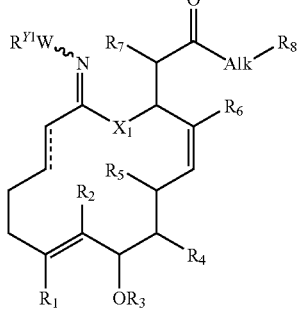

wherein $R_1$-$R_6$, $X_1$ and $Y_2$ are as defined in classes and subclasses herein; W is O or NH; $R^{Y1}$ is hydrogen, or an aliphatic, heteroaliphatic, alicyclic, heterocyclic, aryl or heteroaryl moiety; $R_7$ is a substituted or unsubstituted lower alkyl or heteroalkyl moiety; $R_8$ is a substituted or unsubstituted alkyl, heteroalkyl, cycloalkyl, heterocycloalkyl, aryl or heteroaryl moiety; and Alk is a substituted or unsubstituted $C_{0-6}$alkylidene or $C_{0-6}$alkenylidene chain wherein up to two non-adjacent methylene units are independently optionally replaced by CO, $CO_2$, COCO, $CONR^{Z1}$, $OCONR^{Z1}$, $NR^{Z1}NR^{Z2}$, $NR^{Z1}NR^{Z2}CO$, $NR^{Z1}CO$, $NR^{Z1}CO_2$, $NR^{Z1}CONR^{Z2}$, SO, $SO_2$, $NR^{Z1}SO_2$, $SO_2NR^{Z1}$, $NR^{Z1}SO_2NR^{Z2}$, O, S, or $NR^{Z1}$; wherein each occurrence of $R^{Z1}$ and $R^{Z2}$ is independently hydrogen, alkyl, heteroalkyl, aryl, heteroaryl or acyl.

In certain exemplary embodiments, compounds of the invention shown directly above have the following stereochemistry:

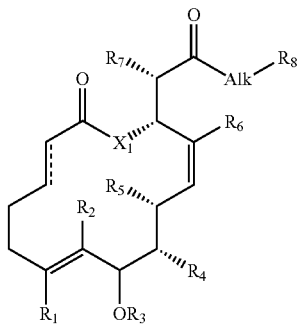

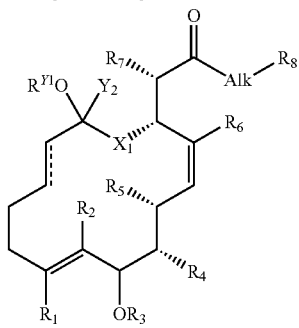

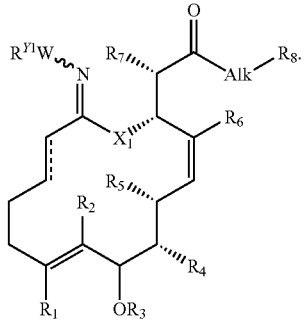

Another class of compounds of special interest includes those compounds having the structure of formula (I) in which $R_a$, $R_b$ and $R_c$ are each hydrogen, Q is hydrogen and the compound has the following structure:

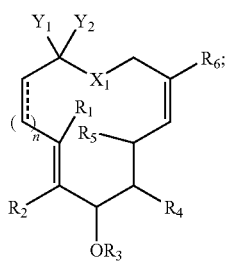

wherein $R_1$-$R_6$, $Y_1$, $Y_2$, $X_1$, and n are as defined in classes and subclasses herein.

In certain exemplary embodiments, compounds of the invention shown directly above have the following stereochemistry:

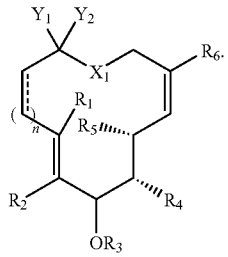

Another class of compounds of special interest includes compounds having the structure of formula (I) in which $R_a$, $R_b$ and $R_c$ are each hydrogen, Q is hydrogen, n is 3 and the compound has the following structure:

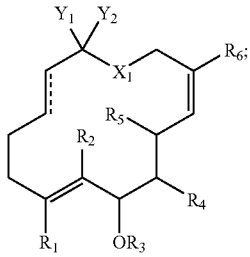

wherein $R_1$-$R_6$, $Y_1$, $Y_2$, and $X_1$ are as defined in classes and subclasses herein.

In certain exemplary embodiments, compounds of the invention shown directly above have the following stereochemistry:

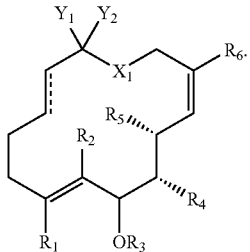

The following structures illustrate several exemplary types of compounds of these classes. Additional compounds are described in the Exemplification herein. Other compounds of the invention will be readily apparent to the reader:

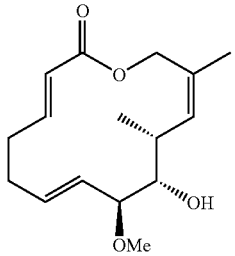

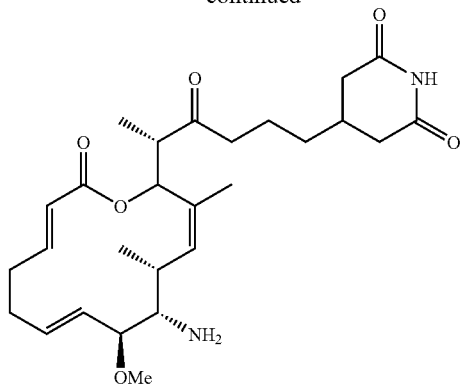

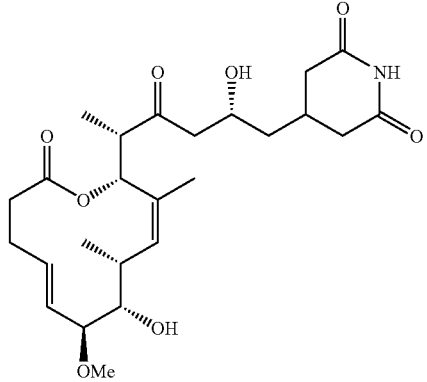

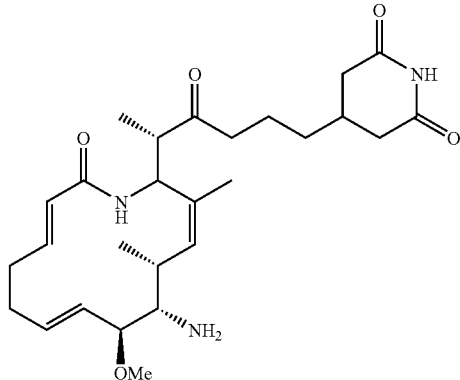

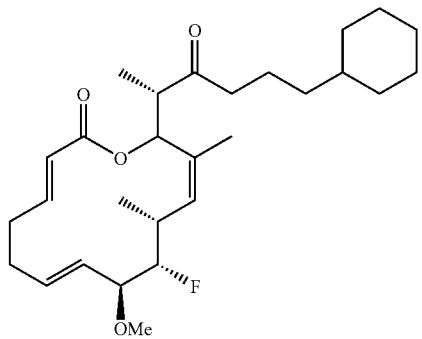 [SMILES: CO[C@H]1/C=C/CC/C=C/C(=O)OC([C@H](C)C(=O)CCCC2CCCCC2)/C(C)=C\[C@@H](C)[C@@H]1F]

A number of important subclasses of each of the foregoing classes deserve separate mention; these subclasses include subclasses of the foregoing classes in which:

i) $R_1$ is hydrogen, halogen, —CN, —S(O)$_{1-2}$R$^{1A}$, —NO$_2$, —COR$^{1A}$, —CO$_2$R$^{1A}$, —NR$^{1A}$C(=O)R$^{1B}$, —NR$^{1A}$C(=O)OR$^{1B}$, —CONR$^{1A}$R$^{1B}$, an aliphatic, heteroaliphatic, alicyclic, heterocyclic, aryl or heteroaryl moiety, or —WR$^{1A}$; wherein W is independently —O—, —S— or —NR$^{1C}$—, wherein each occurrence of R$^{1A}$, R$^{1B}$ and R$^{1C}$ is independently hydrogen, or an aliphatic, heteroaliphatic, alicyclic, heterocyclic, aryl or heteroaryl moiety;

ii) $R_1$ is hydrogen, halogen, —CN, —S(O)$_{1-2}$R$^{1A}$, —NO$_2$, —COR$^{1A}$, —CO$_2$R$^{1A}$, —NR$^{1A}$C(=O)R$^{1B}$, —NR$^{1A}$C(=O)OR$^{1B}$, —CONR$^{1A}$R$^{1B}$, an alkyl, heteroalkyl, cycloalkyl, heterocycloalkyl, aryl or heteroaryl moiety, or —WR$^{1A}$; wherein W is independently —O—, —S— or —NR$^{1C}$—, wherein each occurrence of R$^{1A}$, R$^{1B}$ and R$^{1C}$ is independently hydrogen, or an alkyl, heteroalkyl, cycloalkyl, heterocycloalkyl, aryl or heteroaryl moiety;

iii) $R_1$ is hydrogen or lower alkyl;

iv) $R_1$ is hydrogen;

v) $R_2$ is hydrogen, halogen, —CN, —S(O)$_{1-2}$R$^{1A}$, —NO$_2$, —COR$^{1A}$, —CO$_2$R$^{1A}$, —NR$^{1A}$C(=O)R$^{1B}$, —NR$^{1A}$C(=O)OR$^{1B}$, —CONR$^{1A}$R$^{1B}$, an aliphatic, heteroaliphatic, alicyclic, heterocyclic, aryl or heteroaryl moiety, or —WR$^{1A}$; wherein W is independently —O—, —S— or —NR$^{1C}$—, wherein each occurrence of R$^{1A}$, R$^{1B}$ and R$^{1C}$ is independently hydrogen, or an aliphatic, heteroaliphatic, alicyclic, heterocyclic, aryl or heteroaryl moiety;

vi) $R_2$ is hydrogen, halogen, —CN, —S(O)$_{1-2}$R$^{1A}$, —NO$_2$, —COR$^{1A}$, —CO$_2$R$^{1A}$, —NR$^{1A}$C(=O)R$^{1B}$, —NR$^{1A}$C(=O)OR$^{1B}$, —CONR$^{1A}$R$^{1B}$, an alkyl, heteroalkyl, cycloalkyl, heterocycloalkyl, aryl or heteroaryl moiety, or —WR$^{1A}$; wherein W is independently —O—, —S— or —NR$^{1C}$—, wherein each occurrence of R$^{1A}$, R$^{1B}$ and R$^{1C}$ is independently hydrogen, or an alkyl, heteroalkyl, cycloalkyl, heterocycloalkyl, aryl or heteroaryl moiety;

vii) $R_2$ is hydrogen or lower alkyl;

viii) $R_2$ is hydrogen;

ix) $R_1$ and $R_2$ are each hydrogen;

x) $R_1$ and $R_2$, taken together with the carbon atoms to which they are attached, form an alicyclic, heterocyclic, aryl or heteroaryl moiety;

xi) $R_1$ and $R_2$, taken together with the carbon atoms to which they are attached, form a cycloalkyl, heterocycloalkyl, aryl or heteroaryl moiety;

xii) $R_1$ and $R_2$, taken together with the carbon atoms to which they are attached, form an epoxide;

xiii) $R_1$ and $R_2$, taken together with the carbon atoms to which they are attached, form an aziridine;

xiv) $R_1$ and $R_2$, taken together with the carbon atoms to which they are attached, form a substituted or unsubstituted cyclopropyl;

xv) $R_3$ is hydrogen, alkyl, alkenyl, alkynyl, heteroalkyl, heteroalkenyl, heteroalkynyl, aryl, heteroaryl, silyl, —C(=O)R$^x$, —C(=S)R$^x$, —C(=NR$^x$)R$^y$, —SO$_2$R$^x$, wherein R$^x$ and R$^y$ are each independently hydrogen, alkyl, alkenyl, alkynyl, cycloalkyl, cycloalkenyl, cycloalkynyl, heteroalkyl, heteroalkenyl, heteroalkynyl, heterocycloalkyl, heterocycloalkenyl, heterocycloalkynyl, heteroaliphatic, heterocyclic, aryl, heteroaryl, —C(=O)R$^A$ or —ZR$^A$, wherein Z is —O—, —S—, —NR$^B$, wherein each occurrence of R$^A$ and R$^B$ is independently hydrogen, or an alkyl, alkenyl, alkynyl, cycloalkyl, cycloalkenyl, cycloalkynyl, heteroalkyl, heteroalkenyl, heteroalkynyl, heterocycloalkyl, heterocycloalkenyl, heterocycloalkynyl, heteroaliphatic, heterocyclic, aryl or heteroaryl moiety;

xvi) $R_3$ is hydrogen, an alkyl, heteroalkyl, cycloalkyl, heterocycloalkyl, aryl or heteroaryl moiety; or a prodrug moiety or an oxygen protecting group;

xvii) $R_3$ is hydrogen, lower alkyl, aryl, a prodrug moiety or an oxygen protecting group;

xviii) $R_3$ is hydrogen, lower alkyl, aryl or an oxygen protecting group;

xix) $R_3$ is methyl;

xxi) the carbon atom bearing $R_4$ is of R-configuration;

xxii) the carbon atom bearing $R_4$ is of S-configuration xxiii) $R_4$ is halogen, —OR$^{4A}$, —OC(=O)R$^{4A}$ or —NR$^{4A}$R$^{4B}$; wherein R$^{4A}$ and R$^{4B}$ are independently hydrogen, or substituted or unsubstituted lower alkyl; a prodrug moiety, a nitrogen protecting group or an oxygen protecting group; or R$^{4A}$ and R$^{4B}$, taken together with the nitrogen atom to which they are attached, form a heterocyclic or heteroaryl moiety, or $R_4$, taken together with the carbon atom to which it is attached forms a moiety having the structure:

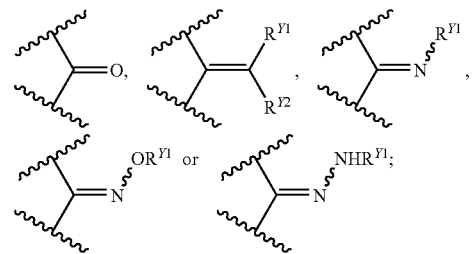

xxiv) $R_4$ is a halogen selected from fluorine, chlorine, bromine, and iodine;

xxv) $R_4$ is fluorine;

xxvi) the carbon atom bearing $R_4$ is of R-configuration, and $R_4$ is a halogen selected from fluorine, chlorine, bromine, and iodine;

xxvii) the carbon atom bearing $R_4$ is of R-configuration, and $R_4$ is fluorine;

xxviii) $R_4$ is OR$^{4A}$, wherein R$^{4A}$ is hydrogen, a substituted or unsubstituted lower alkyl; acyl; a prodrug moiety or an oxygen protecting group;

xxix) $R_4$ is OH;

xxx) $R_4$ is —OC(=O)R$^{4A}$ wherein R$^{4A}$ is hydrogen, lower alkyl, aryl or heteroaryl;

xxxi) $R_4$ is OAc;

xxxii) $R_4$ is NR$^{4A}$R$^{4B}$; wherein R$^{4A}$ and R$^{4B}$ are independently hydrogen, a substituted or unsubstituted lower alkyl; a prodrug moiety or a nitrogen protecting group; or R$^{4A}$ and R$^{4B}$, taken together with the nitrogen atom to which they are attached, form a heterocyclic or heteroaryl moiety;

xxxiii) $R_4$ is NR$^{4A}$R$^{4B}$; wherein R$^{4A}$ and R$^{4B}$ are independently hydrogen, alkyl, alkenyl, —C(=O)R$^x$, —C(=O)OR$^x$, —SR$^x$, SO$_2$R$^x$, or R$^{4A}$ and R$^{4B}$, taken together with the nitrogen atom to which they are attached form a moiety having the structure =CR$^x$R$^y$, wherein R$_{4A}$ and R$^{4B}$ are not simultaneously hydrogen and R$^x$ and R$^y$ are each independently hydrogen, alkyl, alkenyl, alkynyl, cycloalkyl, cycloalkenyl, cycloatyynyl, heteroalkyl, heteroalkenyl, heteroalkynyl, heterocycloalkyl, heterocycloalkenyl, heterocycloalkynyl, heteroaliphatic, heterocyclic, aryl, heteroaryl, —C(=O)R$^A$ or —ZR$^A$, wherein Z is —O—, —S—, —NR$^B$, wherein each occurrence of R$^A$ and R$^B$ is independently hydrogen, or an alkyl, alkenyl, alkynyl, cycloalkyl, cycloalkenyl, cycloalkynyl, heteroalkyl, heteroalkenyl, heteroalkynyl, heterocycloalkyl, heterocycloalkenyl, heterocycloalkynyl, heteroaliphatic, heterocyclic, aryl or heteroaryl moiety;

xxxiv) $R_4$ is NH$_2$;

xxxv) $R_4$ together with the carbon atom to which it is attached forms a moiety having the structure:

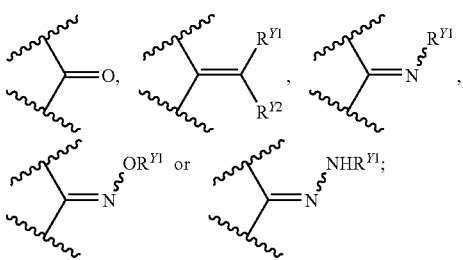

xxxvi) R₄ together with the carbon atom to which it is attached forms a moiety having the structure:

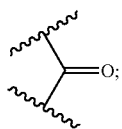

xxxvii) $R_5$ is hydrogen or an alkyl, heteroalkyl, cycloalkyl, heterocycloalkyl, aryl or heteroaryl moiety;

xxxviii) $R_5$ is hydrogen or substituted or unsubstituted lower alkyl;

xxxix) $R_5$ is methyl;

xl) $R_6$ is hydrogen, halogen, —CN, —S(O)$_{1-2}$R$^{6A}$, —NO$_2$, —COR$^{6A}$, —CO$_2$R$^{6A}$, —NR$^{6A}$C(=O)R$^{6B}$, —NR$^{6A}$C(=O)OR$^{6B}$, —CONR$^{6A}$R$^{6B}$, an aliphatic, heteroaliphatic, alicyclic, heterocyclic, aryl or heteroaryl moiety, or —WR$^{6A}$; wherein W is independently —O—, —S— or —NR$^{1C}$—, wherein each occurrence of R$^{6A}$, R$^{6B}$ and R$^{6C}$ is independently hydrogen, or an aliphatic, heteroaliphatic, alicyclic, heterocyclic, aryl or heteroaryl moiety;

xli) $R_6$ is hydrogen, halogen, —CN, —S(O)$_{1-2}$R$^{6A}$, —NO$_2$, —COR$^{6A}$, —CO$_2$R$^{6A}$, —NR$^{6A}$C(=O)R$^{6B}$, —NR$^{6A}$C(=O)OR$^{6B}$, —CONR$^{6A}$R$^{6B}$, an alkyl, heteroalkyl, cycloalkyl, heterocycloalkyl, aryl or heteroaryl moiety, or —WR$^{6A}$; wherein W is independently —O—, —S— or —NR$^{1C}$—, wherein each occurrence of R$^{6A}$, R$^{6B}$ and R$^{6C}$ is independently hydrogen, or an alkyl, heteroalkyl, cycloalkyl, heterocycloalkyl, aryl or heteroaryl moiety;

xlii) $R_6$ is hydrogen or substituted or unsubstituted lower alkyl;

xliii) $R_6$ is methyl;

xxliv) $R_5$ and $R_6$ are each methyl;

xlv) $R_a$ is hydrogen, halogen, —CN, —S(O)$_{1-2}$R$^{a1}$, —NO$_2$, —COR$^{a1}$, —CO$_2$R$^{a1}$, —NR$^{a1}$C(=O)R$^{a2}$, —NR$^{a1}$C(=O)OR$^{a2}$, —CONR$^{a1}$R$^{a2}$, an aliphatic, heteroaliphatic, alicyclic, heterocyclic, aryl or heteroaryl moiety, or —WR$^{a1}$; wherein W is independently —O—, —S— or —NR$^{1C}$—, wherein each occurrence of R$^{a1}$, R$_{a2}$ and R$_{a3}$ is independently hydrogen, or an aliphatic, heteroaliphatic, alicyclic, heterocyclic, aryl or heteroaryl moiety;

xlvi) $R_a$ is hydrogen, halogen, —CN, —S(O)$_{1-2}$R$^{a1}$, —NO$_2$, —COR$^{a1}$, —CO$_2$R$^{a1}$, —NR$^{a1}$C(=O)R$^{a2}$, —NR$^{a1}$C(=O)OR$^{a2}$, —CONR$^{a1}$R$^{a2}$, an alkyl, heteroalkyl, cycloalkyl, heterocycloalkyl, aryl or heteroaryl moiety, or —WR$^{a1}$; wherein W is independently —O—, —S— or —NR$^{1C}$—, wherein each occurrence of R$^{a1}$, R$^{a2}$ and R$^{a3}$ is independently hydrogen, or an alkyl, heteroalkyl, cycloalkyl, heterocycloalkyl, aryl or heteroaryl moiety;

xlvii) $R_a$ is hydrogen or lower alkyl;

xlviii) $R_a$ is hydrogen;

xlix) $R_b$ is hydrogen, halogen, —CN, —S(O)$_{1-2}$R$^{a1}$, —NO$_2$, —COR$^{a1}$, —CO$_2$R$^{a1}$, —NR$^{a1}$C(=O)R$^{a2}$, —NR$^{a1}$C(=O)OR$^{a2}$, —CONR$^{a1}$R$^{a2}$, an aliphatic, heteroaliphatic, alicyclic, heterocyclic, aryl or heteroaryl moiety, or —WR$^{a1}$; wherein W is independently —O—, —S— or —NR$^{1C}$—, wherein each occurrence of R$^{a1}$, R$^{a2}$ and R$^{a3}$ is independently hydrogen, or an aliphatic, heteroaliphatic, alicyclic, heterocyclic, aryl or heteroaryl moiety;

l) $R_b$ is hydrogen, halogen, —CN, —S(O)$_{1-2}$R$^{a1}$, —NO$_2$, —COR$^{a1}$, —CO$_2$R$^{a1}$, —NR$^{a1}$C(=O)R$^{a2}$, —NR$^{a1}$C(=O)OR$^{a2}$, —CONR$^{a1}$R$^{a2}$, an alkyl, heteroalkyl, cycloalkyl, heterocycloalkyl, aryl or heteroaryl moiety, or —WR$^{a1}$; wherein W is independently —O—, —S— or —NR$^{1C}$—, wherein each occurrence of R$^{a1}$, R$^{a2}$ and R$^{a3}$ is independently hydrogen, or an alkyl, heteroalkyl, cycloalkyl, heterocycloalkyl, aryl or heteroaryl moiety;

li) $R_b$ is hydrogen or lower alkyl;

lii) $R_b$ is hydrogen;

liii) $R_a$ and $R_b$ are each hydrogen;

liv) $R_a$ and $R_b$, taken together with the carbon atoms to which they are attached, form a cycloalkyl, heterocycloalkyl, aryl or heteroaryl moiety;

lv) $R_a$ and $R_b$, taken together with the carbon atoms to which they are attached, form an epoxide;

lvi) $R_a$ and $R_b$, taken together with the carbon atoms to which they are attached, form an aziridine;

lvii) $R_a$ and $R_b$, taken together with the carbon atoms to which they are attached, form a substituted or unsubstituted cyclopropyl;

lviii) $R_c$ is hydrogen, halogen, —CN, —S(O)$_{1-2}$R$^{c1}$, —NO$_2$, —COR$^{c1}$, —CO$_2$R$^{c1}$, —NR$^{c1}$C(=O)R$^{c2}$, —NR$^{c1}$C(=O)OR$^{c2}$, —CONR$^{c1}$R$^{c2}$, an aliphatic, heteroaliphatic, alicyclic, heterocyclic, aryl or heteroaryl moiety, or —WR$^{c1}$; wherein W is independently —O—, —S— or —NR$^{1C}$—, wherein each occurrence of R$^{c1}$, R$^{c2}$ and R$^{c3}$ is independently hydrogen, or an aliphatic, heteroaliphatic, alicyclic, heterocyclic, aryl or heteroaryl moiety;

lix) $R_c$ is hydrogen, halogen, —CN, —S(O)$_{1-2}$R$^{c1}$, —NO$_2$, —COR$^{c1}$, —CO$_2$R$^{c1}$, —NR$^{c1}$C(=O)R$^{c2}$, —NR$^{c1}$C(=O)OR$^{c2}$, —CONR$^{c1}$WR$^{c2}$, an alkyl, heteroalkyl, cycloalkyl, heterocycloalkyl, aryl or heteroaryl moiety, or —WR$^{c1}$; wherein W is independently —O—, —S— or —NR$^{1C}$—, wherein each occurrence of R$^{c1}$, R$^{c2}$ and R$^{c3}$ is independently hydrogen, or an alkyl, heteroalkyl, cycloalkyl, heterocycloalkyl, aryl or heteroaryl moiety;

lx) $R_c$ is hydrogen or lower alkyl;

lxi) $R_c$ is hydrogen;

lxii) $R_c$ and $R^6$, taken together with the carbon atoms to which they are attached, form a cycloalkyl, heterocycloalkyl, aryl or heteroaryl moiety;

lxiii) $R_c$ and $R_6$, taken together with the carbon atoms to which they are attached with the carbon atoms to which they are attached, form an epoxide;

lxiv) $R_c$ and $R_6$, taken together with the carbon atoms to which they are attached, form an aziridine;

lxv) $R_c$ and $R_6$, taken together with the carbon atoms to which they are attached, form a substituted or unsubstituted cyclopropyl;

lxvi) $X_1$ is O, S, NR$^{X1}$ or CR$^{X1}$R$^{X2}$; wherein R$^{X1}$ and R$^{X2}$ are independently hydrogen, halogen, substituted or unsubstituted alkyl, heteroalkyl, cycloalkyl, heterocycloalkyl, aryl or heteroaryl, or a nitrogen protecting group;

lxvii) $X_1$ is O, NR$^{X1}$ or CR$^{X1}$R$^{X2}$; wherein R$^{X1}$ and R$^{X2}$ are independently hydrogen, halogen, substituted or unsubstituted alkyl, heteroalkyl, cycloalkyl, heterocycloalkyl, aryl or heteroaryl, or a nitrogen protecting group;

lxviii) $X_1$ is O;

lxix) $X_1$ is NH;

lxx) $X_1$ is $CH_2$;

lxxi) n is an integer from 1 to 5;

lxxii) n is 3;

lxxii) Q is hydrogen, halogen, —CN, —S(O)$_{1-2}$R$^{Q1}$, —NO$_2$, —COR$^{Q1}$, —CO$_2$R$^{Q1}$, —NR$^{Q1}$C(=O)R$^{Q2}$, —NR$^{Q1}$C(=O)OR$^{Q2}$, —CONR$^{Q1}$R$^{Q2}$, a substituted or unsubstituted alkyl, heteroalkyl, cycloalkyl, heterocycloalkyl, aryl or heteroaryl; or —WR$^{Q1}$; wherein W is independently —O—, —S— or —NR$^{Q3}$—, wherein each occurrence of R$^{Q1}$, R$^{Q2}$ and R$^{Q3}$ is independently hydrogen, or an alkyl, heteroalkyl, cycloalkyl, heterocycloalkyl, aryl or heteroaryl moiety lxxiv) Q is a substituted or unsubstituted carbonyl-containing alkyl or heteroalkyl moiety;

lxxv) Q comprises a carbonyl linked to a carbocyclic, heterocyclic, aryl or heteroaryl moiety through a $C_{0-6}$alkylidene or $C_{0-6}$alkenylidene chain wherein up to two non-adjacent methylene units are independently optionally replaced by CO, CO$_2$, COCO, CONR$^{Z1}$, OCONR$^{Z1}$, NR$^{Z1}$NR$^{Z2}$, NR$^{Z1}$NR$^{Z2}$CO, NR$^{Z1}$CO, NR$^{Z1}$CO$_2$, NR$^{Z1}$CONR$^{Z2}$, SO, SO$_2$, NR$^{Z1}$SO$_2$, SO$_2$NR$^{Z1}$, NR$^{Z1}$SO$_2$NR$^{Z2}$, O, S, or NR$^{Z1}$; wherein each occurrence of R$^{Z1}$ and R$^{Z2}$ is independently hydrogen, alkyl, heteroalkyl, aryl, heteroaryl or acyl;

lxxvi) Q has the structure:

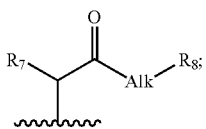

wherein $R_7$ is a substituted or unsubstituted lower alkyl or heteroalkyl moiety; $R_8$ is a substituted or unsubstituted alkyl, heteroalkyl, cycloalkyl, heterocycloalkyl, aryl or heteroaryl moiety; and Alk is a substituted or unsubstituted $C_{0-6}$alkylidene or $C_{0-6}$alkenylidene chain wherein up to two non-adjacent methylene units are independently optionally replaced by CO, CO$_2$, COCO, CONR$^{Z1}$, OCONR$^{Z1}$, NR$^{Z1}$NR$^{Z2}$, NR$^{Z1}$NR$^{Z2}$CO, NR$^{Z1}$CO, NR$^{Z1}$CO$_2$, NR$^{Z1}$CONR$^{Z2}$, SO, SO$_2$, NR$^{Z1}$SO$_2$, SO$_2$NR$^{Z1}$, NR$^{Z1}$SO$_2$NR$^{Z2}$, O, S, or NR$^{Z1}$; wherein each occurrence of R$^{Z1}$ and R$^{Z2}$ is independently hydrogen, alkyl, heteroalkyl, aryl, heteroaryl or acyl;

xxvii) Q has the structure:

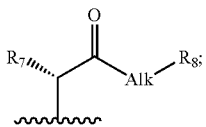

wherein $R_7$ is a substituted or unsubstituted, linear or branched, cyclic or acyclic lower alkyl moiety; $R_8$ is a substituted or unsubstituted carbocyclic, heterocyclic, aryl or heteroaryl moiety; and Alk is a substituted or unsubstituted $C_{0-6}$alkylidene or $C_{0-6}$alkenylidene chain wherein up to two non-adjacent methylene units are independently optionally replaced by CO, CO$_2$, COCO, CONR$^{Z1}$, OCONR$^{Z1}$, NR$^{Z1}$NR$^{Z2}$, NR$^{Z1}$NR$^{Z2}$CO, NR$^{Z1}$CO, NR$^{Z1}$C$_2$, NR$^{Z1}$CONR$^{Z2}$, SO, SO$_2$, NR$^{Z1}$SO$_2$, SO$_2$NR$^{Z1}$, NR$^{Z1}$SO$_2$NR$^{Z2}$, O, S, or NR$^{Z1}$; wherein each occurrence of R$^{Z1}$ and R$^{Z2}$ is independently hydrogen, alkyl, heteroalkyl, aryl, heteroaryl or acyl;

lxxxviii) Q has the structure:

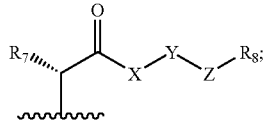

wherein $R_7$ is a substituted or unsubstituted, linear or branched, cyclic or acyclic lower alkyl moiety; $R_8$ is a substituted or unsubstituted carbocyclic, heterocyclic, aryl or heteroaryl moiety; and X, Y and Z are independently a bond, —O—, —S—, —C(=O)—, —NR$^{Z1}$—, —CHOR$^{Z1}$, —CHNR$^{Z1}$R$^{Z2}$, C=S, C=N(R$^{Y1}$) or —CH(Hal); or a substituted or unsubstituted $C_{0-6}$alkylidene or $C_{0-6}$alkenylidene chain wherein up to two non-adjacent methylene units are independently optionally replaced by CO, CO$_2$, COCO, CONR$^{Z1}$, OCONR$^{Z1}$, NR$^{Z1}$NR$^{Z2}$, NR$^{Z1}$NR$^{Z2}$CO, NR$^{Z1}$CO, NR$^{Z1}$CO$_2$, NR$^{Z1}$CONR$^{Z2}$, SO, SO$_2$, NR$^{Z1}$SO$_2$, SO$_2$NR$^{Z1}$, NR$^{Z1}$SO$_2$NR$^{Z2}$, O, S, or NR$^{Z1}$; wherein Hal is a halogen selected from F, Cl, Br and I; and each occurrence of R$^{Z1}$ and R$^{Z2}$ is independently hydrogen, alkyl, heteroalkyl, aryl, heteroaryl or acyl; or R$^{Z1}$ and R$^{Z2}$, taken together with the nitrogen atom to which they are attached, for a heterocyclic or heteroaryl moiety;

lxxix) Q has the structure:

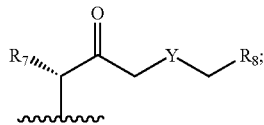

wherein $R_7$ is a substituted or unsubstituted, linear or branched, cyclic or acyclic lower alkyl moiety; $R_8$ is a substituted or unsubstituted carbocyclic, heterocyclic, aryl or heteroaryl moiety; and Y is a bond, —O—, —S—, —C(=O)—, —NR$^{Z1}$, —CHOR$^{Z1}$, —CHNR$^{Z1}$R$^{Z2}$, C=S, C=N(R$^{Y1}$) or —CH(Hal); or a substituted or unsubstituted $C_{0-6}$alkylidene or $C_{0-6}$alkenylidene chain wherein up to two non-adjacent methylene units are independently optionally replaced by CO, CO$_2$, COCO, CONR$^{Z1}$, OCONR$^{Z1}$, NR$^{Z1}$NR$^{Z2}$, NR$^{Z1}$NR$^{Z2}$CO, NR$^{Z1}$CO, NR$^{Z1}$CO$_2$, NR$^{Z1}$CONR$^{Z2}$, SO, SO$_2$, NR$^{Z1}$SO$_2$, SO$_2$NR$^{Z1}$, NR$^{Z1}$SO$_2$NR$^{Z2}$, O, S, or NR$^{Z1}$; wherein Hal is a halogen selected from F, Cl, Br and I; and each occurrence of R$^{Z1}$ and R$^{Z2}$ is independently hydrogen, alkyl, heteroalkyl, aryl, heteroaryl or acyl; or R$^{Z1}$ and R$^{Z2}$, taken together with the nitrogen atom to which they are attached, for a heterocyclic or heteroaryl moiety;

lxxx) Q has the structure:

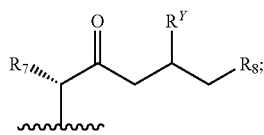

wherein $R_7$ is a substituted or unsubstituted, linear or branched, cyclic or acyclic lower alkyl moiety; $R_8$ is a substituted or unsubstituted carbocyclic, heterocyclic, aryl or heteroaryl moiety; and R$^Y$ is hydrogen, halogen, —OR$^{Y1}$ or —NR$^{Y1}$NR$^{Y2}$; wherein R$^{Y1}$ and R$^{Y2}$ are independently hydrogen, alkyl, heteroalkyl, aryl, heteroaryl or acyl, or $R^{Y1}$ and $R^{Y2}$, taken together with the nitrogen atom to which they are attached, for a heterocyclic or heteroaryl moiety;

lxxxi) Q is hydrogen;

lxxxii) compounds of subsets lxxvi)-lxxx) wherein $R_7$ is substituted or unsubstituted lower alkyl;

lxxxiii) compounds of subsets lxxvi)-lxxx) wherein $R_7$ is methyl;

lxxxiv) compounds of subset lxxx) wherein $R^Y$ is hydrogen;

lxxxv) compounds of subset lxxx) wherein $R^Y$ is a halogen selected from fluorine, chlorine, bromine, and iodine;

lxxxvi) compounds of subset lxxx) wherein $R^Y$ is fluorine;

lxxxvii) compounds of subset lxxx) wherein $R^Y$ is $OR^{Y1}$, wherein $R^{Y1}$ is hydrogen, a substituted or unsubstituted lower alkyl; a prodrug moiety or an oxygen protecting group;

lxxxviii) compounds of subset lxxx) wherein $R^Y$ is OH;

lxxxix) compounds of subset lxxx) wherein $R^Y$ is $NR^{Y1}R^{Y2}$; wherein $R^{Y1}$ and $R^{Y2}$ are independently hydrogen, a substituted or unsubstituted lower alkyl; a prodrug moiety or a nitrogen protecting group; or $R^{Y1}$ and $R^{Y2}$, taken together with the nitrogen atom to which they are attached, form a heterocyclic or heteroaryl moiety;

xc) compounds of subset lxxx) wherein $R^Y$ is $NH_2$;

xci) compounds of subsets lxxvi)-lxxx) wherein $R_8$ is one of:

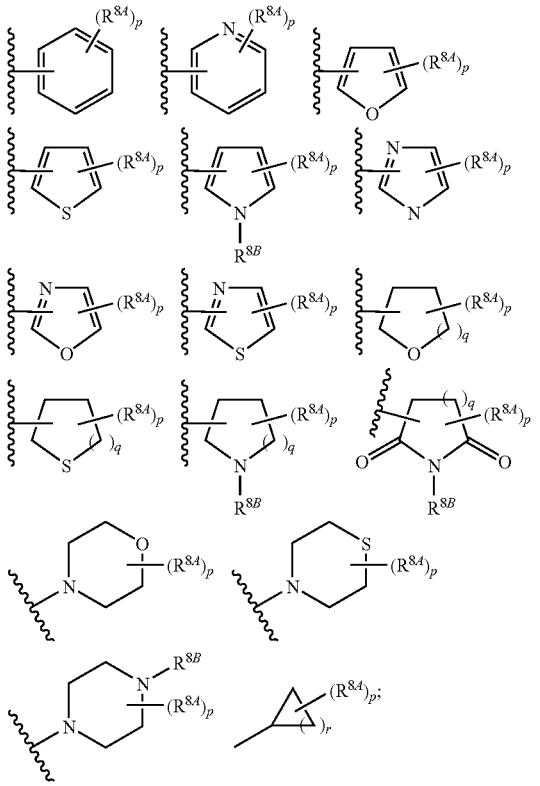

wherein p is an integer from 0 to 5; q is 1 or 2, r is an integer from 1 to 6; each occurrence of $R^{8A}$ is independently hydrogen, alkyl, heteroalkyl, aryl, heteroaryl, -(alkyl)aryl or -(alkyl)heteroaryl, $-OR^{8C}$, $-SR^{8C}$, $-N(R^{8C})_2$, $-SO_2N(R^{8C})_2$, $-(C=O)N(R^{8C})_2$, halogen, $-CN$, $-NO_2$, $-(C=O)OR^{8C}$, $-N(R^{8C})(C=O)R^{8D}$, wherein each occurrence of $R^{8C}$ and $R^{8D}$ is independently hydrogen, lower alkyl, lower heteroalkyl, aryl, heteroaryl, -(alkyl)aryl or -(alkyl)heteroaryl; and each occurrence of $R^{8B}$ is independently hydrogen or lower alkyl;

xcii) compounds of subsets lxxvi)-lxxx) wherein $R_8$ is substituted or unsubstituted cycloalkyl;

xciii) compounds of subsets lxxvi)-lxxx) wherein $R_8$ is substituted or unsubstituted cyclohexyl;

xciv) compounds of subsets lxxvi)-lxxx) wherein $R_8$ has the structure:

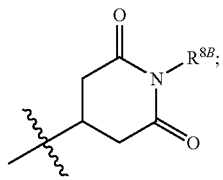

wherein $R^{8B}$ is hydrogen or lower alkyl;

xcv) compounds of subsets lxxvi)-lxxx) wherein $R_8$ has the structure:

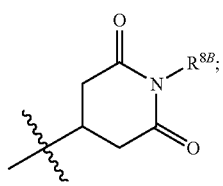

wherein $R^{8B}$ is hydrogen or methyl;

xcvi) compounds of subsets lxxvi)-lxxx) wherein $R_8$ has the structure:

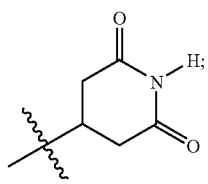

xcvii) $X_1$ is O, $CH_2$ or NH; Q is as described in subsets lxxvi)-lxxx) wherein $R_8$ has the structure:

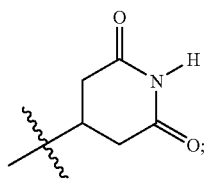 [SMILES: *C1CC(=O)NC(=O)C1]

xcviii) $Y_1$ is $OR^{Y1}$ and $Y_2$ is lower alkyl; wherein $R^{Y1}$ is hydrogen or lower alkyl;

xcix) $Y_1$ is $OR^{Y1}$ and $Y_2$ is lower alkyl substituted with one or more halogen atoms selected from F, Cl, Br and I; wherein $R^{Y1}$ is hydrogen or lower alkyl;

c) $Y_1$ is OH and $Y_2$ is $CF_3$;

ci) $X_1$ is $CH_2$; $Y_1$ is $OR^{Y1}$ and $Y_2$ is lower alkyl; wherein $R^{Y1}$ is hydrogen or lower alkyl;

cii) $X_1$ is $CH_2$; $Y_1$ is $OR^{Y1}$ and $Y_2$ is lower alkyl substituted with one or more halogen atoms selected from F, Cl, Br and I; wherein $R^{Y1}$ is hydrogen or lower alkyl;

ciii) $X_1$ is $CH_2$; $Y_1$ is OH and $Y_2$ is $CF_3$;

civ) $Y_1$ and $Y_2$ together with the carbon atom to which they are attached form a moiety having the structure:

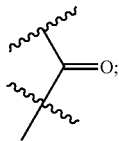 [SMILES: *C(*)=O]

cv) $Y_1$ and $Y_2$ together with the carbon atom to which they are attached form a moiety having the structure:

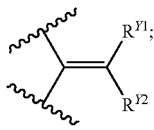

wherein $R^{Y1}$ and $R^{Y2}$ are independently hydrogen or lower alkyl;

cvi) $Y_1$ and $Y_2$ together with the carbon atom to which they are attached form a moiety having the structure:

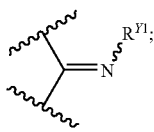

wherein $R^{Y1}$ is hydrogen or lower alkyl;

cvii) $Y_1$ and $Y_2$ together with the carbon atom to which they are attached form a moiety having the structure:

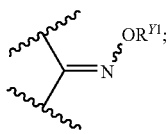

wherein $R^{Y1}$ is hydrogen or lower alkyl;

cviii) $Y_1$ and $Y_2$ together with the carbon atom to which they are attached form a moiety having the structure:

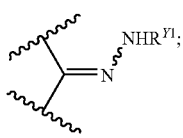

wherein $R^{Y1}$ is hydrogen or lower alkyl;

cix) $X_1$ is O; and $Y_1$ and $Y_2$ together with the carbon atom to which they are attached form a moiety having the structure:

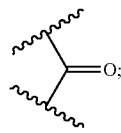 [SMILES: *C(*)=O]

cx) $X_1$ is NH; and $Y_1$ and $Y_2$ together with the carbon atom to which they are attached form a moiety having the structure:

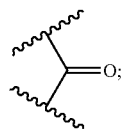 [SMILES: *C(*)=O]

cxi) $X_1$ is $CH_2$; and $Y_1$ and $Y_2$ together with the carbon atom to which they are attached form a moiety having the structure:

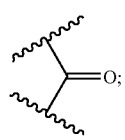

cxii) $X_1$ is $CH_2$; and $Y_1$ and $Y_2$ together with the carbon atom to which they are attached form a moiety having the structure:

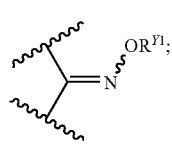

wherein $R^{Y1}$ is hydrogen or lower alkyl;

cxiii) $X_1$ is $CH_2$; and $Y_1$ and $Y_2$ together with the carbon atom to which they are attached form a moiety having the structure:

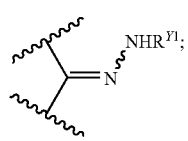

wherein $R^{Y1}$ is hydrogen or lower alkyl;

cxiv) compounds as described in classes and subclasses herein wherein the stereocenter

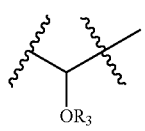

has the following stereochemistry

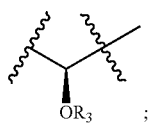
;

cxv) compounds as described in classes and subclasses herein wherein the stereocenter

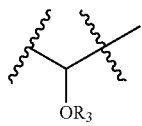

has the following stereochemistry

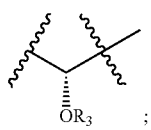
;

cxvi) Q is hydrogen and $Y_1$ and $Y_2$ are independently hydrogen, lower alkyl or lower alkoxy;

cxvii) Q is hydrogen and $Y_1$ and $Y_2$ are each hydrogen;

cxviii) Q is hydrogen; $Y_1$ and $Y_2$ are independently hydrogen, lower alkyl or lower alkoxy; and $X_1$ is O; and/or cxix) Q is hydrogen; $Y_1$ and $Y_2$ are each hydrogen; and $X_1$ is O.

It will be appreciated that for each of the classes and subclasses described above and herein, any one or more occurrences of groups such as aliphatic, heteroaliphatic, alkyl, heteroalkyl may independently be substituted or unsubstituted, linear or branched, saturated or unsaturated; and any one or more occurrences of alicyclic, heterocyclic, cycloalkyl, aryl, heteroaryl, cycloaliphatic, cycloheteroaliphatic may be substituted or unsubstituted.

The reader will also appreciate that all possible combinations of the variables described in i)-through cxix) above (e.g., $R_1$-$R_6$, $R_{a-c}$, n, Q, $X_1$, $Y_1$ and $Y_2$, among others) are considered part of the invention. Thus, the invention encompasses any and all compounds of formula I, and subclasses thereof, generated by taking any possible permutation of variables $R_1$-$R_6$, $R_{a-c}$, n, Q, $X_1$, $Y_1$ and $Y_2$, and other variables/substituents (e.g., X, Y, Z, $R^Y$, etc.) as further defined for $R_1$-$R_6$, $R_{a-c}$, n, Q, $X_1$, $Y_1$ and $Y_2$, described in i)-through cxix) above.

As the reader will appreciate, compounds of particular interest include, among others, those which share the attributes of one or more of the foregoing subclasses. Some of those subclasses are illustrated by the following sorts of compounds:

I) Compounds of the Formula (and Pharmaceutically Acceptable Derivatives Thereof):

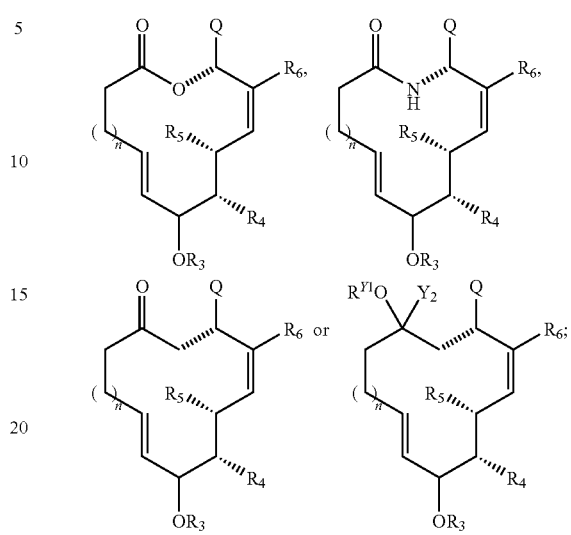

wherein $R_3$-$R_6$, n and Q are as defined in classes and subclasses herein; and $Y_2$ and $R^{Y1}$ are independently hydrogen or lower alkyl. In certain embodiments, $R_3$ is hydrogen, lower alkyl or an oxygen protecting group. In certain exemplary embodiments, $R_3$ is methyl. In certain other embodiments, $R_5$ and $R_6$ are independently lower alkyl. In certain exemplary embodiments, $R_5$ and $R_6$ are each methyl. In certain embodiments, n is 3. In certain embodiments, $R_4$ is halogen, hydroxyl, lower alkoxy, acyloxy or $NR^{4A}R^{4B}$, wherein $R^{4A}$ and $R^{4B}$ are independently hydrogen, lower alky, aryl, acyl or a nitrogen protecting group, or $R^{4A}$ and $R^{4B}$, taken together with the nitrogen atom to which they are attached, form a substituted or unsubstituted heterocyclic or heteroaryl moiety; or $R_4$, taken together with the carbon atom to which it is attached forms a moiety having the structure:

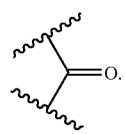 [SMILES: *C(*)=O]

In certain embodiments, $R_4$ is a halogen selected from fluorine, chlorine, bromine and iodine. In certain exemplary embodiments, $R_4$ is fluorine. In certain other embodiments, $R_4$ is F, OH, OAc, $NH_2$ or $R_4$, taken together with the carbon atom to which it is attached forms a moiety having the structure:

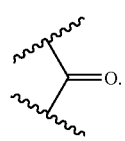

In certain exemplary embodiments, Q is hydrogen or a carbonyl-containing moiety. In certain exemplary embodiments, Q is hydrogen. In certain exemplary embodiments, $Y_2$ is hydrogen or lower alkyl substituted with one or more halogen atoms selected from F, Cl, Br and I. In certain exemplary embodiments, $Y_2$ is hydrogen or methyl substituted with one or more halogen atoms selected from F, Cl, Br and I. In certain exemplary embodiments, $Y_2$ is hydrogen or $CF_3$. In certain exemplary embodiments, $R^{Y1}$ is hydrogen or lower alkyl. In certain exemplary embodiments, $R^{Y1}$ is hydrogen or methyl. In certain exemplary embodiments, $Y_2$ is $CF_3$ and $R^{Y1}$ is methyl.

II) Compounds of the Formula (and Pharmaceutically Acceptable Derivatives Thereof):

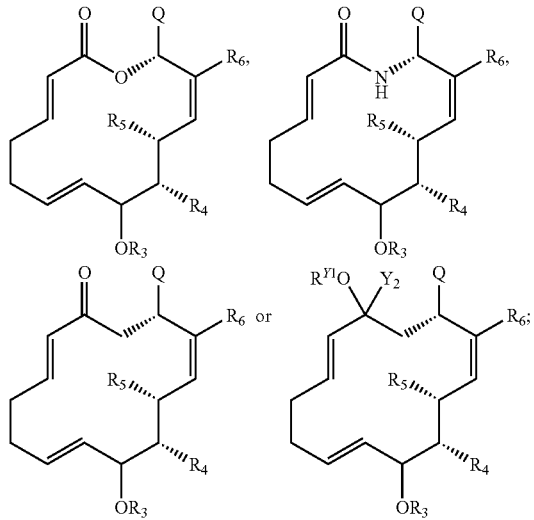

wherein $R_3$-$R_6$ and Q are as defined in classes and subclasses herein; and $Y_2$ and $R^{Y1}$ are independently hydrogen or lower alkyl. In certain embodiments, $R_3$ is hydrogen, lower alkyl or an oxygen protecting group. In certain exemplary embodiments, $R_3$ is methyl. In certain other embodiments, $R_5$ and $R_6$ are independently lower alkyl. In certain exemplary embodiments, $R_5$ and $R_6$ are each methyl. In certain embodiments, $R_4$ is halogen, hydroxyl, lower alkoxy, acyloxy or $NR^{4A}R^{4B}$, wherein $R^{4A}$ and $R^{4B}$ are independently hydrogen, lower alkyl, aryl, acyl or a nitrogen protecting group, or $R^{4A}$ and $R^{4B}$, taken together with the nitrogen atom to which they are attached, form a substituted or unsubstituted heterocyclic or heteroaryl moiety; or $R_4$, taken together with the carbon atom to which it is attached forms a moiety having the structure:

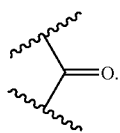 [SMILES: *C(*)=O]

In certain embodiments, $R_4$ is a halogen selected from fluorine, chlorine, bromine and iodine. In certain exemplary embodiments, $R_4$ is fluorine. In certain other embodiments, $R_4$ is F, OH, OAc, $NH_2$ or $R_4$, taken together with the carbon atom to which it is attached forms a moiety having the structure:

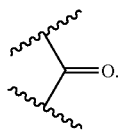 [SMILES: *C(*)=O]

In certain exemplary embodiments, Q is hydrogen or a carbonyl-containing moiety. In certain exemplary embodiments, Q is hydrogen. In certain exemplary embodiments, $Y_2$ is hydrogen or lower alkyl substituted with one or more halogen atoms selected from F, Cl, Br and I. In certain exemplary embodiments, $Y_2$ is hydrogen or methyl substituted with one or more halogen atoms selected from F, Cl, Br and I. In certain exemplary embodiments, $Y_2$ is hydrogen or $CF_3$. In certain exemplary embodiments, $R^{Y1}$ is hydrogen or lower alkyl. In certain exemplary embodiments, $R^{Y1}$ is hydrogen or methyl. In certain exemplary embodiments, $Y_2$ is $CF_3$ and $R^{Y1}$ is methyl.

In certain other embodiments, for compounds of classes I)-II) above, Q is a substituted or unsubstituted carbonyl-containing alkyl or heteroalkyl moiety. In certain exemplary embodiments, Q comprises a carbonyl linked to a carbocyclic, heterocyclic, aryl or heteroaryl moiety through a $C_{0-6}$alkylidene or $C_{0-6}$alkenylidene moiety. In certain embodiments, Q has the structure:

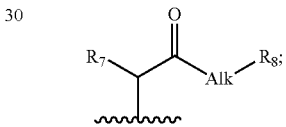

wherein $R_7$ is a substituted or unsubstituted, linear or branched, cyclic or acyclic lower alkyl moiety; $R_8$ is a substituted or unsubstituted carbocyclic, heterocyclic, aryl or heteroaryl moiety; and Alk is a substituted or unsubstituted $C_{0-6}$alkylidene or $C_{0-6}$alkenylidene chain wherein up to two non-adjacent methylene units are independently optionally replaced by CO, $CO_2$, COCO, $CONR^{Z1}$, $OCONR^{Z1}$, $NR^{Z1}NR^{Z2}$, $NR^{Z1}NR^{Z2}CO$, $NR^{Z1}CO$, $NR^{Z1}CO_2$, $NR^{Z1}CONR^{Z2}$, SO, $SO_2$, $NR^{Z1}SO_2$, $SO_2NR^{Z1}$, $NR^{Z1}SO_2NR^{Z2}$, O, S, or $NR^{Z1}$; wherein each occurrence of $R^{Z1}$ and $R^{Z2}$ is independently hydrogen, alkyl, heteroalkyl, aryl, heteroaryl or acyl; and $R_8$ is a substituted or unsubstituted alkyl, heteroalkyl, cycloalkyl, heterocycloalkyl, aryl or heteroaryl moiety. In certain embodiments, $R_7$ is lower alkyl. In certain other embodiments, Alk is a $C_3$ alkylidene moiety. In yet other embodiments, $R_8$ is one of:

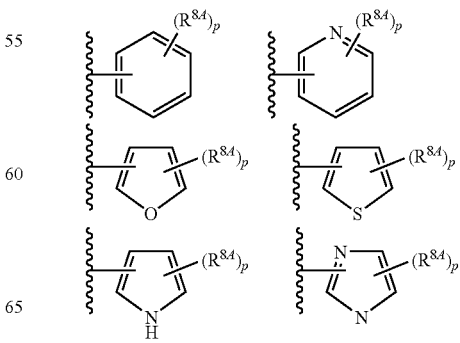

-continued

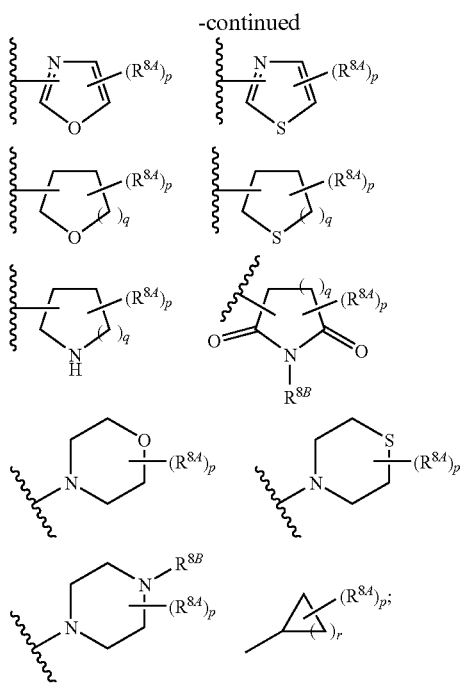

wherein p is an integer from 0 to 5; q is 1 or 2, r is an integer from 1 to 6; each occurrence of $R^{8A}$ is independently hydrogen, alkyl, heteroalkyl, aryl, heteroaryl, -(alkyl)aryl or -(alkyl)heteroaryl, $-OR^{8C}$, $-SR^{8C}$, $-N(R^{8C})_2$, $-SO_2N(R^{8C})_2$, $-(C=O)N(R_{8C})_2$, halogen, $-CN$, $-NO_2$, $-(C=O)OR^{8C}$, $-N(S)(C=O)R^{8D}$, wherein each occurrence of $R^{8C}$ and $R^{8D}$ is independently hydrogen, lower alkyl, lower heteroalkyl, aryl, heteroaryl, -(alkyl)aryl or -(alkyl)heteroaryl; and each occurrence of $R^{8B}$ is independently hydrogen or lower alkyl. In certain exemplary embodiments, $R_8$ has the structure:

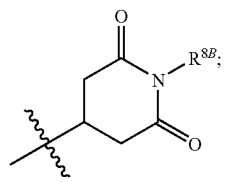

wherein $R^{8B}$ is hydrogen or lower alkyl. In certain exemplary embodiments, $R^{8B}$ is hydrogen. In certain exemplary embodiments, Q has the following stereochemistry:

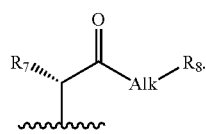

III) Compounds of the Formula (and Pharmaceutically Acceptable Derivatives Thereof):

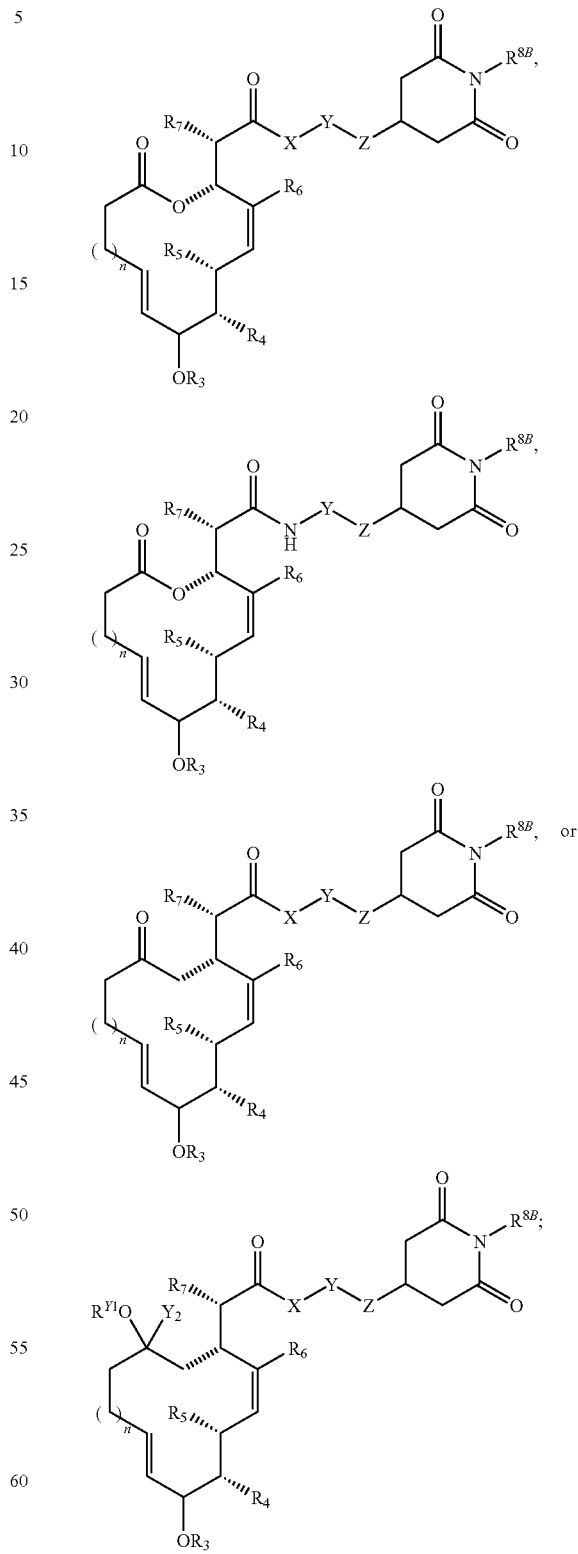

wherein $R_3$-$R_6$ and n are as defined in classes and subclasses herein; $Y_2$ and $R^{Y1}$ are independently hydrogen or lower alkyl; $R_7$ is a substituted or unsubstituted, linear or branched, cyclic or acyclic lower alkyl moiety; $R^{8B}$ is hydrogen or lower alkyl; and X, Y and Z are independently a bond, —O—, —S—, —C(=O)—, —NR$^{Z1}$—, —CHOR$^{Z1}$, —CHNR$^{Z1}$R$^{Z2}$, C=S, C=N(R$^{Y1}$) or —CH(Hal); or a substituted or unsubstituted C$_{0-6}$alkylidene or C$_{0-6}$alkenylidene chain wherein up to two non-adjacent methylene units are independently optionally replaced by CO, CO$_2$, COCO, CONR$^{Z1}$, OCONR$^{Z1}$, NR$^{Z1}$NR$^{Z2}$, NR$^{Z1}$NR$^{Z2}$CO, NR$^{Z1}$CO, NR$^{Z1}$CO$_2$, NR$^{Z1}$CONR$^{Z2}$, SO, SO$_2$, NR$^{Z1}$SO$_2$, SO$_2$NR$^{Z1}$, NR$^{Z1}$SO$_2$NR$^{Z2}$, O, S, or NR$^{Z1}$; wherein Hal is a halogen selected from F, Cl, Br and I; and each occurrence of R$^{Z1}$ and R$^{Z2}$ is independently hydrogen, alkyl, heteroalkyl, aryl, heteroaryl or acyl; or R$^{Z1}$ and R$^{Z2}$, taken together with the nitrogen atom to which they are attached, for a heterocyclic or heteroaryl moiety; and pharmaceutically acceptable derivatives thereof. In certain embodiments, $R_3$ is hydrogen, lower alkyl or an oxygen protecting group. In certain exemplary embodiments, $R_3$ is methyl. In certain other embodiments, $R_5$ and $R_6$ are independently lower alkyl. In certain exemplary embodiments, $R_5$ and $R_6$ are each methyl. In certain embodiments, n is 3. In certain embodiments, $R_4$ is halogen, hydroxyl, lower alkoxy, acyloxy or NR$^{4A}$R$^{4B}$, wherein R$^{4A}$ and R$^{4B}$ are independently hydrogen, lower alkyl, aryl, acyl or a nitrogen protecting group, or R$^{4A}$ and R$_{4B}$, taken together with the nitrogen atom to which they are attached, form a substituted or unsubstituted heterocyclic or heteroaryl moiety; or $R_4$, taken together with the carbon atom to which it is attached forms a moiety having the structure:

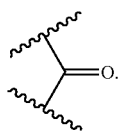 [SMILES: *C(*)=O]

In certain embodiments, $R_4$ is a halogen selected from fluorine, chlorine, bromine and iodine. In certain exemplary embodiments, $R_4$ is fluorine. In certain other embodiments, $R_4$ is F, OH, OAc, NH$_2$ or $R_4$, taken together with the carbon atom to which it is attached forms a moiety having the structure:

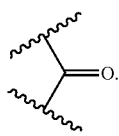 [SMILES: *C(*)=O]

In certain other embodiments, $R_7$ is methyl. In certain other embodiments, X and Z are each CH$_2$ and Y is —CHOH, —CHNH$_2$ or —CHF. In certain other embodiments, $R^{8B}$ is hydrogen, methyl or ethyl. In certain exemplary embodiments, $Y_2$ is hydrogen or lower alkyl substituted with one or more halogen atoms selected from F, Cl, Br and I. In certain exemplary embodiments, $Y_2$ is hydrogen or methyl substituted with one or more halogen atoms selected from F, Cl, Br and I. In certain exemplary embodiments, $Y_2$ is hydrogen or CF$_3$. In certain exemplary embodiments, $R^{Y1}$ is hydrogen or lower alkyl. In certain exemplary embodiments, $R^{Y1}$ is hydrogen or methyl. In certain exemplary embodiments, $Y_2$ is CF$_3$ and $R^{Y1}$ is methyl.

Iv) Compounds of the Formula (and Pharmaceutically Acceptable Derivatives Thereof):

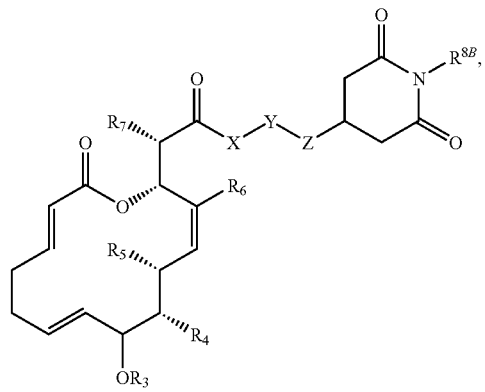

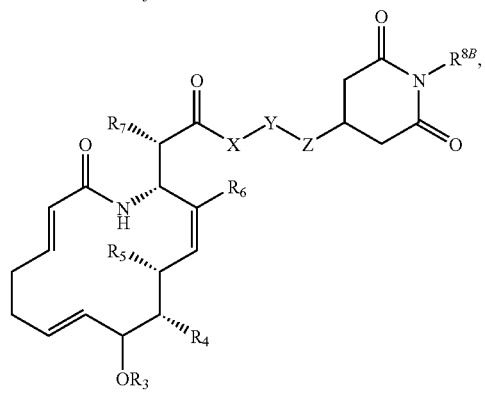

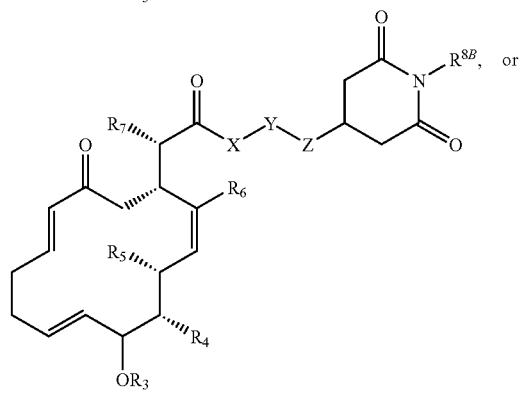

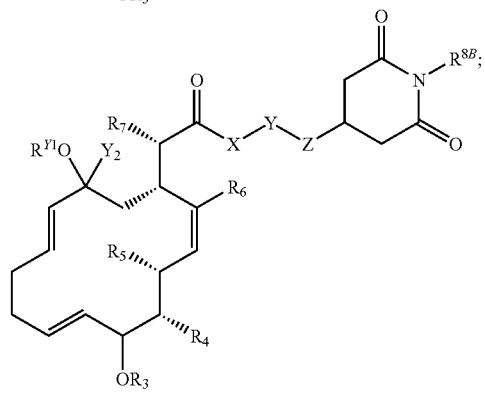

wherein $R_3$-$R_6$ are as defined in classes and subclasses herein; $Y_2$ and $R^{Y1}$ are independently hydrogen or lower alkyl; $R_7$ is a substituted or unsubstituted, linear or branched, cyclic or acyclic lower alkyl moiety; $R^{8B}$ is hydrogen or lower alkyl; and X, Y and Z are independently a bond, —O—, —S—, —C(=O)—, —NR$^{Z1}$—, —CHOR$^{Z1}$, —CHNR$^{Z1}$R$^{Z2}$, C=S, C=N(R$^{Y1}$) or —CH(Hal); or a substituted or unsubstituted $C_{0-6}$alkylidene or $C_{0-6}$alkenylidene chain wherein up to two non-adjacent methylene units are independently optionally replaced by CO, $CO_2$, COCO, CONR$^{Z1}$, OCONR$^{Z1}$, NR$^{Z1}$NR$^{Z2}$, NR$^{Z1}$NR$^{Z1}$CO, NR$^{Z1}$CO, NR$^{Z1}$CO$_2$, NR$^{Z1}$CONR$^{Z2}$, SO, SO$_2$, NR$^{Z1}$SO$_2$, SO$_2$NR$^{Z1}$, NR$^{Z1}$SO$_2$NR$^{Z2}$, O, S, or NR$^{Z1}$; wherein Hal is a halogen selected from F, Cl, Br and I; and each occurrence of R$^{Z1}$ and R$^{Z2}$ is independently hydrogen, alkyl, heteroalkyl, aryl, heteroaryl or acyl; or R$^{Z1}$ and R$^{Z2}$, taken together with the nitrogen atom to which they are attached, for a heterocyclic or heteroaryl moiety; and pharmaceutically acceptable derivatives thereof. In certain embodiments, $R_3$ is hydrogen, lower alkyl or an oxygen protecting group. In certain exemplary embodiments, $R_3$ is methyl. In certain other embodiments, $R_5$ and $R_6$ are independently lower alkyl. In certain exemplary embodiments, $R_5$ and $R_6$ are each methyl. In certain embodiments, $R_4$ is halogen, hydroxyl, lower alkoxy, acyloxy or NR$^{4A}$R$^{4B}$, wherein R$^{4A}$ and R$^{4B}$ are independently hydrogen, lower alkyl, aryl, acyl or a nitrogen protecting group, or R$^{4A}$ and R$^{4B}$, taken together with the nitrogen atom to which they are attached, form a substituted or unsubstituted heterocyclic or heteroaryl moiety; or $R_4$, taken together with the carbon atom to which it is attached forms a moiety having the structure:

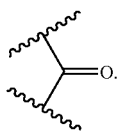 [SMILES: *C(*)=O]

In certain embodiments, $R_4$ is a halogen selected from fluorine, chlorine, bromine and iodine. In certain exemplary embodiments, $R_4$ is fluorine. In certain other embodiments, $R_4$ is F, OH, OAc, NH$_2$ or $R_4$, taken together with the carbon atom to which it is attached forms a moiety having the structure:

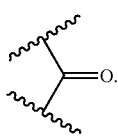 [SMILES: *C(*)=O]

In certain other embodiments, $R_7$ is methyl. In certain other embodiments, X and Z are each CH$_2$ and Y is —CHOH, —CHNH$_2$ or —CHF. In certain other embodiments, $R^{8B}$ is hydrogen, methyl or ethyl. In certain exemplary embodiments, $Y_2$ is hydrogen or lower alkyl substituted with one or more halogen atoms selected from F, Cl, Br and I. In certain exemplary embodiments, $Y_2$ is hydrogen or methyl substituted with one or more halogen atoms selected from F, Cl, Br and I. In certain exemplary embodiments, $Y_2$ is hydrogen or CF$_3$. In certain exemplary embodiments, R$^{Y1}$ is hydrogen or lower alkyl. In certain exemplary embodiments, R$^{Y1}$ is hydrogen or methyl. In certain exemplary embodiments, $Y_2$ is CF$_3$ and R$^{Y1}$ is methyl.

In certain embodiments, for compounds of classes III-IV above, —X—Y—Z together represents the moiety —CH$_2$—Y—CH$_2$—; wherein Y is —CHOR$^{Y1}$, —CHNR$^{Y1}$R$^{Y2}$, C=O, C=S, C=N(R$^{Y1}$) or —CH(Hal); wherein Hal is a halogen selected from F, Cl, Br and I; and R$^{Y1}$ and R$^{Y2}$ are independently hydrogen, alkyl, heteroalkyl, aryl, heteroaryl or acyl, or R$^{Y1}$ and R$^{Y2}$, taken together with the nitrogen atom to which they are attached, for a heterocyclic or heteroaryl moiety.

V) Compounds of the Formula (and Pharmaceutically Acceptable Derivatives Thereof):

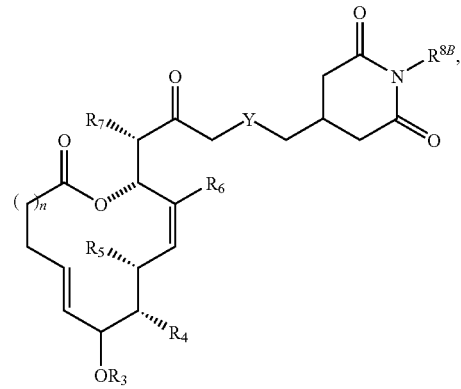

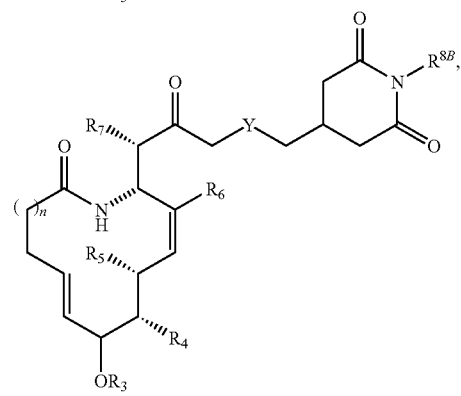

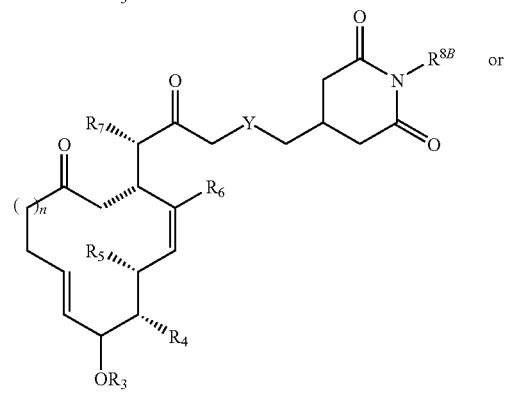

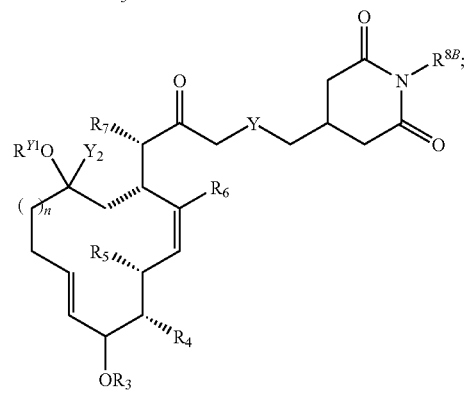

wherein $R_3$-$R_6$ and n are as defined in classes and subclasses herein; $Y_2$ and R$^{Y1}$ are independently hydrogen or lower alkyl; $R_7$ is a substituted or unsubstituted, linear or branched, cyclic or acyclic lower alkyl moiety; $R^{8B}$ is hydrogen or lower alkyl; and Y is —CHOR$^{Y1}$, —CHNR$^{Y1}$R$^{Y2}$, C=O, C=S, C=N(R$^{Y1}$) or —CH(Hal); wherein Hal is a halogen selected from F, Cl, Br and I; and R$^{Y1}$ and R$^{Y2}$ are independently hydrogen, alkyl, heteroalkyl, aryl, heteroaryl or acyl, or R$^{Y1}$ and R$^{Y2}$, taken together with the nitrogen atom to which they are attached, for a heterocyclic or heteroaryl moiety. In certain embodiments, $R_3$ is hydrogen, lower alkyl or an oxygen protecting group. In certain exemplary embodiments, $R_3$ is methyl. In certain other embodiments, $R_5$ and $R_6$ are independently lower alkyl. In certain exemplary embodiments, $R_5$ and $R_6$ are each methyl. In certain embodiments, n is 3. In certain embodiments, $R_4$ is halogen, hydroxyl, lower alkoxy, acyloxy or NR$^{4A}$R$^{4B}$, wherein R$^{4A}$ and R$^{4B}$ are independently hydrogen, lower alkyl, aryl, acyl or a nitrogen protecting group, or R$^{4A}$ and R$^{4B}$, taken together with the nitrogen atom to which they are attached, form a substituted or unsubstituted heterocyclic or heteroaryl moiety; or $R_4$, taken together with the carbon atom to which it is attached forms a moiety having the structure:

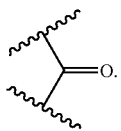 [SMILES: *C(*)=O]

In certain embodiments, $R_4$ is a halogen selected from fluorine, chlorine, bromine and iodine. In certain exemplary embodiments, $R_4$ is fluorine. In certain other embodiments, $R_4$ is F, OH, OAc, NH$_2$ or $R_4$, taken together with the carbon atom to which it is attached forms a moiety having the structure:

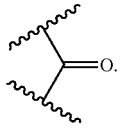 [SMILES: *C(*)=O]

In certain other embodiments, $R_7$ is methyl. In certain other embodiments, Y is —CHOH, —CHNH$_2$ or —CHF. In certain other embodiments, $R^{8B}$ is hydrogen, methyl or ethyl. In certain exemplary embodiments, $Y_2$ is hydrogen or lower alkyl substituted with one or more halogen atoms selected from F, Cl, Br and I. In certain exemplary embodiments, $Y_2$ is hydrogen or methyl substituted with one or more halogen atoms selected from F, Cl, Br and I. In certain exemplary embodiments, $Y_2$ is hydrogen or CF$_3$. In certain exemplary embodiments, R$^{Y1}$ is hydrogen or lower alkyl. In certain exemplary embodiments, R$^{Y1}$ is hydrogen or methyl. In certain exemplary embodiments, $Y_2$ is CF$_3$ and R$^{Y1}$ is methyl.

VI) Compounds of the Formula (and Pharmaceutically Acceptable Derivatives Thereof):

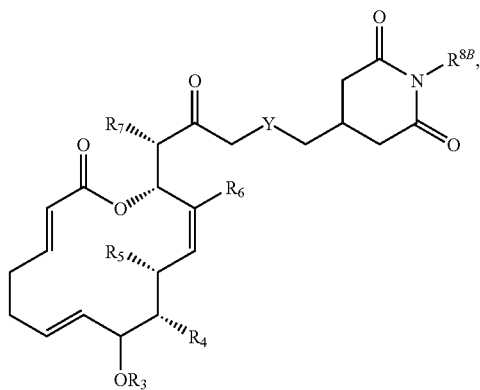

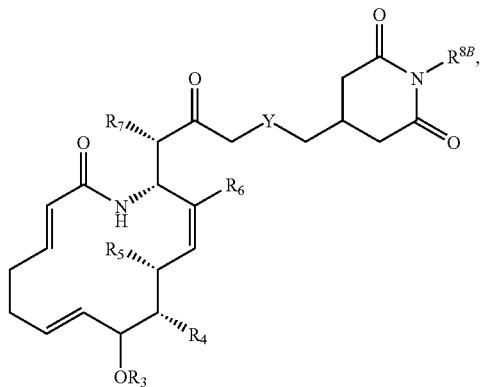

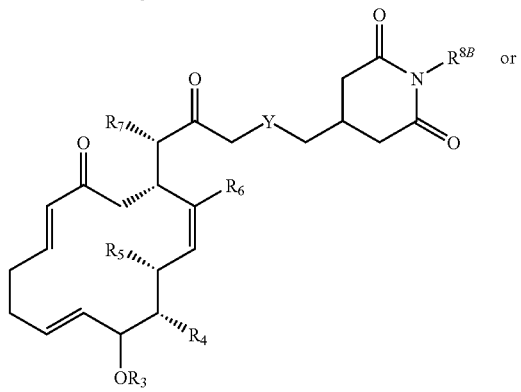

or

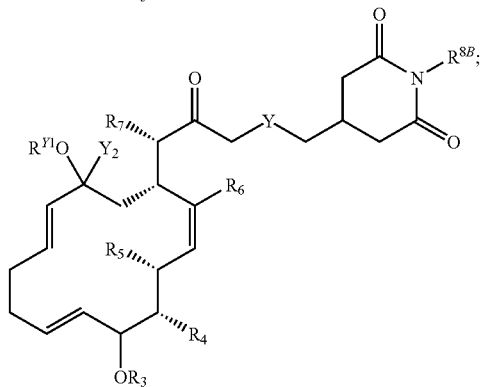

wherein $R_3$-$R_6$ are as defined in classes and subclasses herein; $Y_2$ and R$^{Y1}$ are independently hydrogen or lower alkyl; $R_7$ is a substituted or unsubstituted, linear or branched, cyclic or acyclic lower alkyl moiety; $R^{8B}$ is hydrogen or lower alkyl; and Y is —CHOR$^{Y1}$, —CHNR$^{Y1}$R$^{Y2}$, C=O, C=S, C=N(R$^{Y1}$) or —CH(Hal); wherein Hal is a halogen selected from F, Cl, Br and I; and R$^{Y1}$ and R$^{Y2}$ are independently hydrogen, alkyl, heteroalkyl, aryl, heteroaryl or acyl, or R$^{Y1}$ and R$^{Y2}$, taken together with the nitrogen atom to which they are attached, for a heterocyclic or heteroaryl moiety. In certain embodiments, $R_3$ is hydrogen, lower alkyl or an oxygen protecting group. In certain exemplary embodiments, $R_3$ is methyl. In certain other embodiments, $R_5$ and $R_6$ are independently lower alkyl. In certain exemplary embodiments, $R_5$ and $R_6$ are each methyl. In certain embodiments, $R_4$ is halogen, hydroxyl, lower alkoxy, acyloxy or NR$^{4A}$R$^{4B}$, wherein R$^{4A}$ and R$^{4B}$ are independently hydrogen, lower alkyl, aryl, acyl or a nitrogen protecting group, or R$^{4A}$ and R$^{4B}$, taken together with the nitrogen atom to which they are attached, form a substituted or unsubstituted heterocyclic or heteroaryl moiety; or $R_4$, taken together with the carbon atom to which it is attached forms a moiety having the structure:

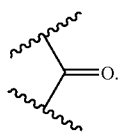 [SMILES: *C(*)=O]

In certain embodiments, $R_4$ is a halogen selected from fluorine, chlorine, bromine and iodine. In certain exemplary embodiments, $R_4$ is fluorine. In certain other embodiments, $R_4$ is F, OH, OAc, NH$_2$ or $R_4$, taken together with the carbon atom to which it is attached forms a moiety having the structure:

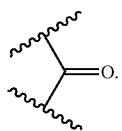 [SMILES: *C(*)=O]

In certain other embodiments, $R_7$ is methyl. In certain other embodiments, Y is —CHOH, —CHNH$_2$ or —CHF. In certain other embodiments, $R^{8B}$ is hydrogen, methyl or ethyl. In certain exemplary embodiments, $Y_2$ is hydrogen or lower alkyl substituted with one or more halogen atoms selected from F, Cl, Br and I. In certain exemplary embodiments, $Y_2$ is hydrogen or methyl substituted with one or more halogen atoms selected from F, Cl, Br and I. In certain exemplary embodiments, $Y_2$ is hydrogen or CF$_3$. In certain exemplary embodiments, R$^{Y1}$ is hydrogen or lower alkyl. In certain exemplary embodiments, R$^{Y1}$ is hydrogen or methyl. In certain exemplary embodiments, $Y_2$ is CF$_3$ and R$^{Y1}$ is methyl.

VII) Compounds of the Formula (and Pharmaceutically Acceptable Derivatives Thereof):

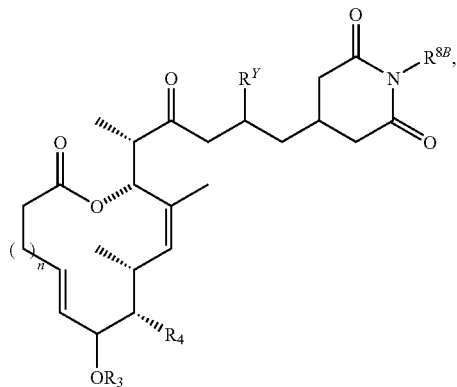

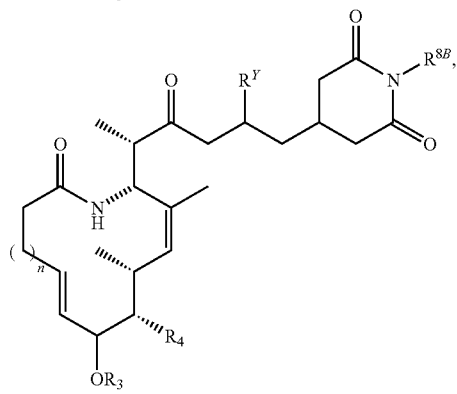

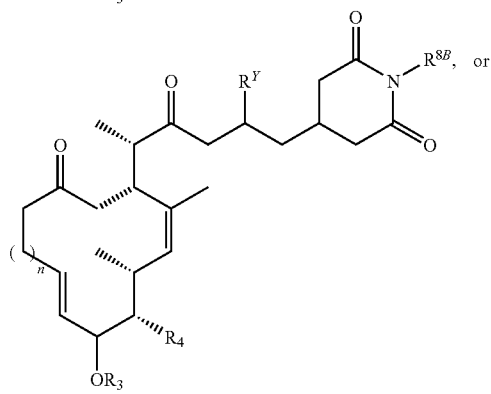

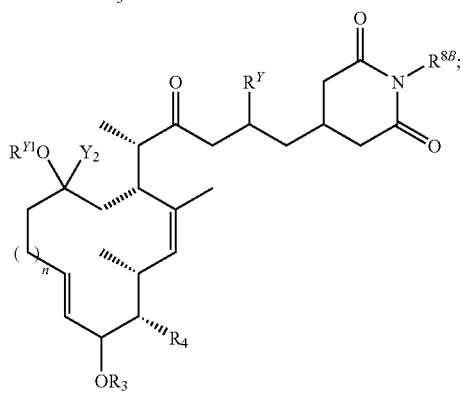

wherein n, $R_3$ and $R_4$ are as defined in classes and subclasses herein; $Y_2$ and R$^{Y1}$ are independently hydrogen or lower alkyl; $R^{8B}$ is hydrogen or lower alkyl; and $R^Y$ is hydrogen, halogen, $-OR^{Y1}$ or $-NR^{Y1}NR^{Y2}$; wherein $R^{Y1}$ and $R^{Y2}$ are independently hydrogen, alkyl, heteroalkyl, aryl, heteroaryl or acyl, or $R^{Y1}$ and $R^{Y2}$, taken together with the nitrogen atom to which they are attached, for a heterocyclic or heteroaryl moiety. In certain embodiments, $R_3$ is hydrogen, lower alkyl or an oxygen protecting group. In certain exemplary embodiments, $R_3$ is methyl. In certain embodiments, n is 3. In certain embodiments, $R_4$ is halogen, hydroxyl, lower alkoxy, acyloxy or $NR^{4A}R^{4B}$, wherein $R^{4A}$ and $R^{4B}$ are independently hydrogen, lower alkyl, aryl, acyl or a nitrogen protecting group, or $R^{4A}$ and $R^{4B}$, taken together with the nitrogen atom to which they are attached, form a substituted or unsubstituted heterocyclic or heteroaryl moiety; or $R_4$, taken together with the carbon atom to which it is attached forms a moiety having the structure:

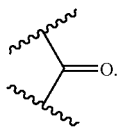

In certain embodiments, $R_4$ is a halogen selected from fluorine, chlorine, bromine and iodine. In certain exemplary embodiments, $R_4$ is fluorine. In certain other embodiments, $R_4$ is F, OH, OAc, $NH_2$ or $R_4$, taken together with the carbon atom to which it is attached forms a moiety having the structure:

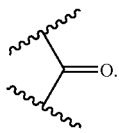 [SMILES: *C(*)=O]

In certain other embodiments, $R^Y$ is OH, $NH_2$ or halogen (e.g., F). In certain other embodiments, $R^{8B}$ is hydrogen, methyl or ethyl. In certain exemplary embodiments, $Y_2$ is hydrogen or lower alkyl substituted with one or more halogen atoms selected from F, Cl, Br and I. In certain exemplary embodiments, $Y_2$ is hydrogen or methyl substituted with one or more halogen atoms selected from F, Cl, Br and I. In certain exemplary embodiments, $Y_2$ is hydrogen or $CF_3$. In certain exemplary embodiments, $R^{Y1}$ is hydrogen or lower alkyl. In certain exemplary embodiments, $R^{Y1}$ is hydrogen or methyl. In certain exemplary embodiments, $Y_2$ is $CF_3$ and $R^{Y1}$ is methyl.

VIII) Compounds of the Formula (and Pharmaceutically Acceptable Derivatives Thereof):

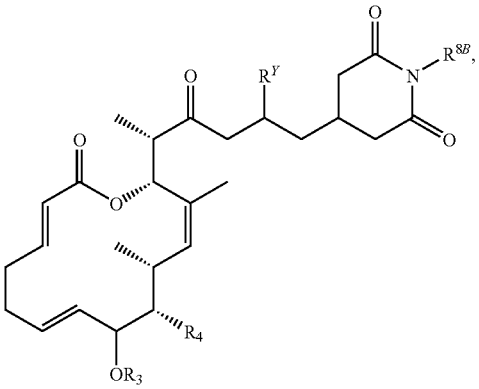

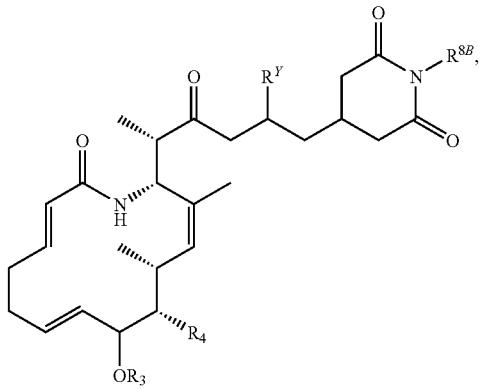

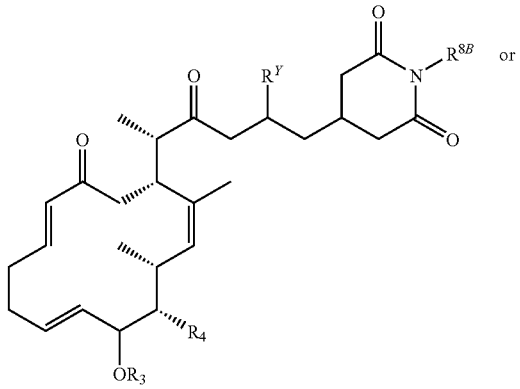

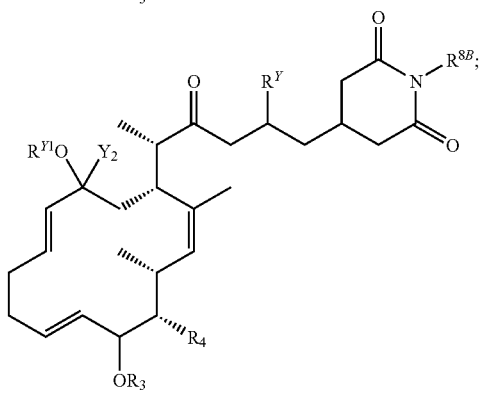

wherein $R_3$ and $R_4$ are as defined in classes and subclasses herein; $Y_2$ and $R^{Y1}$ are independently hydrogen or lower alkyl; $R^{8B}$ is hydrogen or lower alkyl; and $R^Y$ is hydrogen, halogen, $-OR^{Y1}$ or $-NR^{Y1}NR^{Y2}$; wherein $R^{Y1}$ and $R^{Y2}$ are independently hydrogen, alkyl, heteroalkyl, aryl, heteroaryl or acyl, or $R^{Y1}$ and $R^{Y2}$, taken together with the nitrogen atom to which they are attached, for a heterocyclic or heteroaryl moiety. In certain embodiments, $R_3$ is hydrogen, lower alkyl or an oxygen protecting group. In certain exemplary embodiments, $R_3$ is methyl. In certain embodiments, $R_4$ is halogen, hydroxyl, lower alkoxy, acyloxy or $NR^{4A}R^{4B}$, wherein $R^{4A}$ and $R^{4B}$ are independently hydrogen, lower alkyl, aryl, acyl or a nitrogen protecting group, or $R^{4A}$ and $R^{4B}$, taken together with the nitrogen atom to which they are attached, form a substituted or unsubstituted heterocyclic or heteroaryl moiety; or $R_4$, taken together with the carbon atom to which it is attached forms a moiety having the structure:

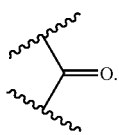 [SMILES: *C(*)=O]

In certain embodiments, $R_4$ is a halogen selected from fluorine, chlorine, bromine and iodine. In certain exemplary embodiments, $R_4$ is fluorine. In certain other embodiments, $R_4$ is F, OH, OAc, $NH_2$ or $R_4$, taken together with the carbon atom to which it is attached forms a moiety having the structure:

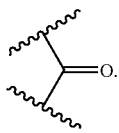 [SMILES: *C(*)=O]

In certain other embodiments, $R^Y$ is OH, $NH_2$ or halogen (e.g., F). In certain other embodiments, $R^{8B}$ is hydrogen, methyl or ethyl. In certain exemplary embodiments, $Y_2$ is hydrogen or lower alkyl substituted with one or more halogen atoms selected from F, Cl, Br and I. In certain exemplary embodiments, $Y_2$ is hydrogen or methyl substituted with one or more halogen atoms selected from F, Cl, Br and I. In certain exemplary embodiments, $Y_2$ is hydrogen or $CF_3$. In certain exemplary embodiments, $R^{Y1}$ is hydrogen or lower alkyl. In certain exemplary embodiments, $R^{Y1}$ is hydrogen or methyl. In certain exemplary embodiments, $Y_2$ is $CF_3$ and $R^{Y1}$ is methyl.

IX) Compounds of the Formula (and Pharmaceutically Acceptable Derivatives Thereof):

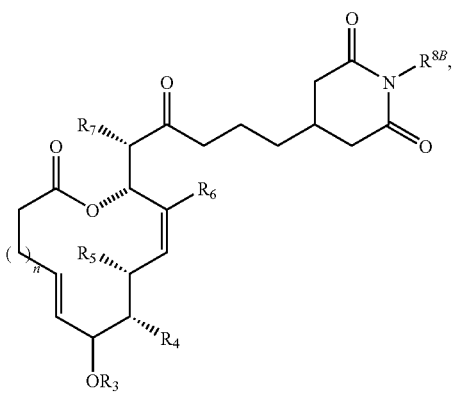

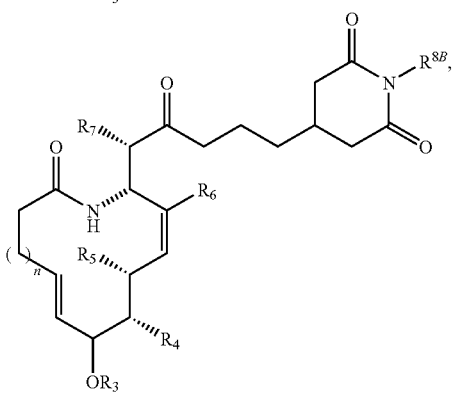

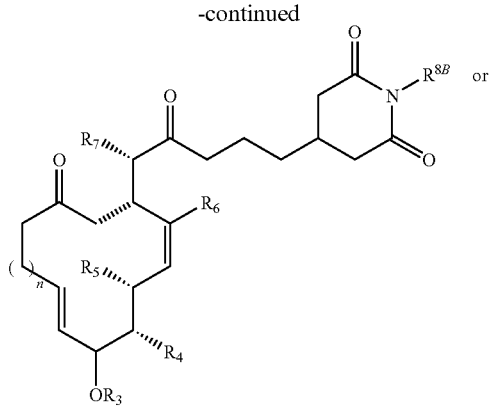

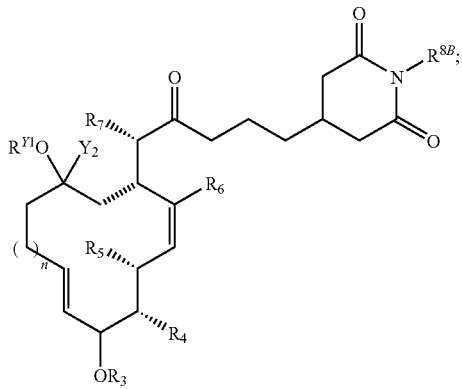

wherein $R_3$-$R_6$ and n are as defined in classes and subclasses herein; $Y_2$ and $R^{Y1}$ are independently hydrogen or lower alkyl; $R_7$ is a substituted or unsubstituted, linear or branched, cyclic or acyclic lower alkyl moiety; and $R^{8B}$ is hydrogen or lower alkyl. In certain embodiments, $R_3$ is hydrogen, lower alkyl or an oxygen protecting group. In certain exemplary embodiments, $R_3$ is methyl. In certain other embodiments, $R_5$ and $R_6$ are independently lower alkyl. In certain exemplary embodiments, $R_5$ and $R_6$ are each methyl. In certain embodiments, n is 3. In certain embodiments, $R_4$ is halogen, hydroxyl, lower alkoxy, acyloxy or $NR^{4A}R^{4B}$, wherein $R^{4A}$ and $R^{4B}$ are independently hydrogen, lower alkyl, aryl, acyl or a nitrogen protecting group, or $R^{4A}$ and $R^{4B}$, taken together with the nitrogen atom to which they are attached, form a substituted or unsubstituted heterocyclic or heteroaryl moiety; or $R_4$, taken together with the carbon atom to which it is attached forms a moiety having the structure:

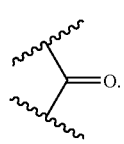 [SMILES: *C(*)=O]

In certain embodiments, $R_4$ is a halogen selected from fluorine, chlorine, bromine and iodine. In certain exemplary embodiments, $R_4$ is fluorine. In certain other embodiments, $R_4$ is F, OH, OAc, $NH_2$ or $R_4$, taken together with the carbon atom to which it is attached forms a moiety having the structure:

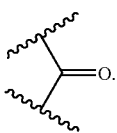 [SMILES: *C(*)=O]

In certain other embodiments, $R_7$ is methyl. In certain other embodiments, $R^{8B}$ is hydrogen, methyl or ethyl. In certain exemplary embodiments, $Y_2$ is hydrogen or lower alkyl substituted with one or more halogen atoms selected from F, Cl, Br and I. In certain exemplary embodiments, $Y_2$ is hydrogen or methyl substituted with one or more halogen atoms selected from F, Cl, Br and I. In certain exemplary embodiments, $Y_2$ is hydrogen or $CF_3$. In certain exemplary embodiments, $R^{Y1}$ is hydrogen or lower alkyl. In certain exemplary embodiments, $R^{Y1}$ is hydrogen or methyl. In certain exemplary embodiments, $Y_2$ is $CF_3$ and $R^{Y1}$ is methyl.

X) Compounds of the Formula (and Pharmaceutically Acceptable Derivatives Thereof):

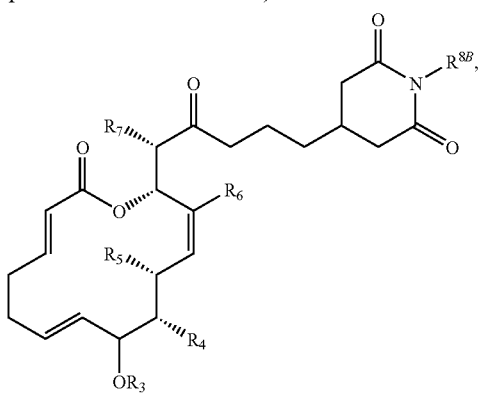

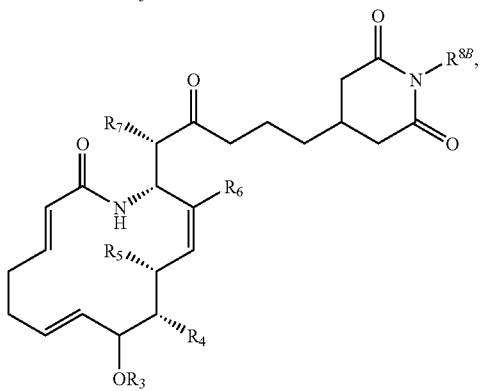

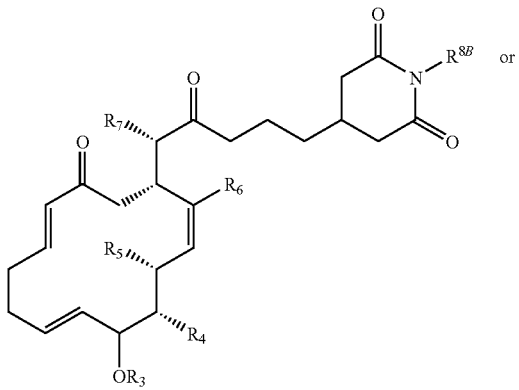

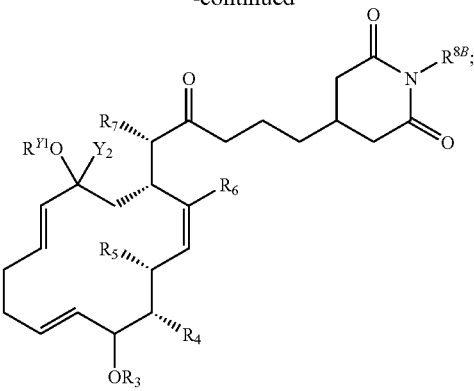

wherein $R_3$-$R_6$ are as defined in classes and subclasses herein; $Y_2$ and $R^{Y1}$ are independently hydrogen or lower alkyl; $R_7$ is a substituted or unsubstituted, linear or branched, cyclic or acyclic lower alkyl moiety; and $R^{8B}$ is hydrogen or lower alkyl. In certain embodiments, $R_3$ is hydrogen, lower alkyl or an oxygen protecting group. In certain exemplary embodiments, $R_3$ is methyl. In certain other embodiments, $R_5$ and $R_6$ are independently lower alkyl. In certain exemplary embodiments, $R_5$ and $R_6$ are each methyl. In certain embodiments, $R_4$ is halogen, hydroxyl, lower alkoxy, acyloxy or $NR^{4A}R^{4B}$, wherein $R^{4A}$ and $R^{4B}$ are independently hydrogen, lower alkyl, aryl, acyl or a nitrogen protecting group, or $R^{4A}$ and $R^{4B}$, taken together with the nitrogen atom to which they are attached, form a substituted or unsubstituted heterocyclic or heteroaryl moiety; or $R_4$, taken together with the carbon atom to which it is attached forms a moiety having the structure:

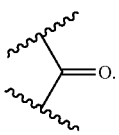 [SMILES: *C(*)=O]

In certain embodiments, $R_4$ is a halogen selected from fluorine, chlorine, bromine and iodine. In certain exemplary embodiments, $R_4$ is fluorine. In certain other embodiments, $R_4$ is F, OH, OAc, $NH_2$ or $R_4$, taken together with the carbon atom to which it is attached forms a moiety having the structure:

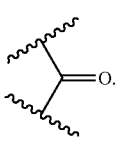 [SMILES: *C(*)=O]

In certain other embodiments, $R_7$ is methyl. In certain other embodiments, $R^{8B}$ is hydrogen, methyl or ethyl. In certain exemplary embodiments, $Y_2$ is hydrogen or lower alkyl substituted with one or more halogen atoms selected from F, Cl, Br and I. In certain exemplary embodiments, $Y_2$ is hydrogen or methyl substituted with one or more halogen atoms selected from F, Cl, Br and I. In certain exemplary embodiments, $Y_2$ is hydrogen or $CF_3$. In certain exemplary embodiments, $R^{Y1}$ is hydrogen or lower alkyl. In certain exemplary embodiments, $R^{Y1}$ is hydrogen or methyl. In certain exemplary embodiments, $Y_2$ is $CF_3$ and $R^{Y1}$ is methyl.

XI) Compounds of the Formula (and Pharmaceutically Acceptable Derivatives Thereof):

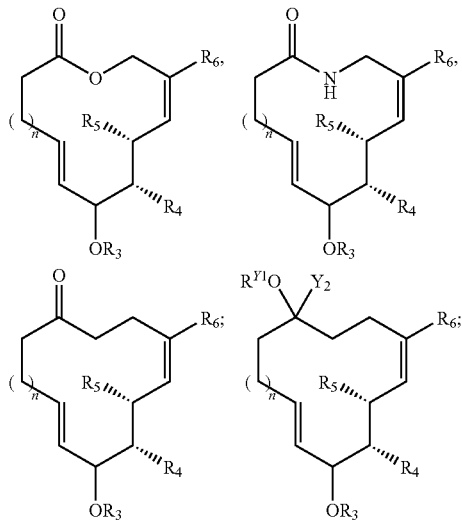

wherein $R_3$-$R_6$ and n are as defined in classes and subclasses herein; and $Y_2$ and $R^{Y1}$ are independently hydrogen or lower alkyl. In certain embodiments, $R_3$ is hydrogen, lower alkyl or an oxygen protecting group. In certain exemplary embodiments, $R_3$ is methyl. In certain other embodiments, $R_5$ and $R_6$ are independently lower alkyl. In certain exemplary embodiments, $R_5$ and $R_6$ are each methyl. In certain embodiments, n is 3. In certain embodiments, $R_4$ is halogen, hydroxyl, lower alkoxy, acyloxy or $NR^{4A}R^{4B}$, wherein $R^{4A}$ and $R^{4B}$ are independently hydrogen, lower alkyl, aryl, acyl or a nitrogen protecting group, or $R^{4A}$ and $R^{4B}$, taken together with the nitrogen atom to which they are attached, form a substituted or unsubstituted heterocyclic or heteroaryl moiety; or $R_4$, taken together with the carbon atom to which it is attached forms a moiety having the structure:

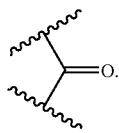 [SMILES: *C(*)=O]

In certain embodiments, $R_4$ is a halogen selected from fluorine, chlorine, bromine and iodine. In certain exemplary embodiments, $R_4$ is fluorine. In certain other embodiments, $R_4$ is F, OH, OAc, $NH_2$ or $R_4$, taken together with the carbon atom to which it is attached forms a moiety having the structure:

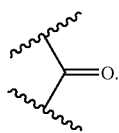 [SMILES: *C(*)=O]

In certain exemplary embodiments, $Y_2$ is hydrogen or lower alkyl substituted with one or more halogen atoms selected from F, Cl, Br and I. In certain exemplary embodiments, $Y_2$ is hydrogen or methyl substituted with one or more halogen atoms selected from F, Cl, Br and I. In certain exemplary embodiments, $Y_2$ is hydrogen or $CF_3$. In certain exemplary embodiments, $R^{Y1}$ is hydrogen or lower alkyl. In certain exemplary embodiments, $R^{Y1}$ is hydrogen or methyl. In certain exemplary embodiments, $Y_2$ is $CF_3$ and $R^{Y1}$ is methyl.

XII) Compounds of the Formula (and Pharmaceutically Acceptable Derivatives Thereof):

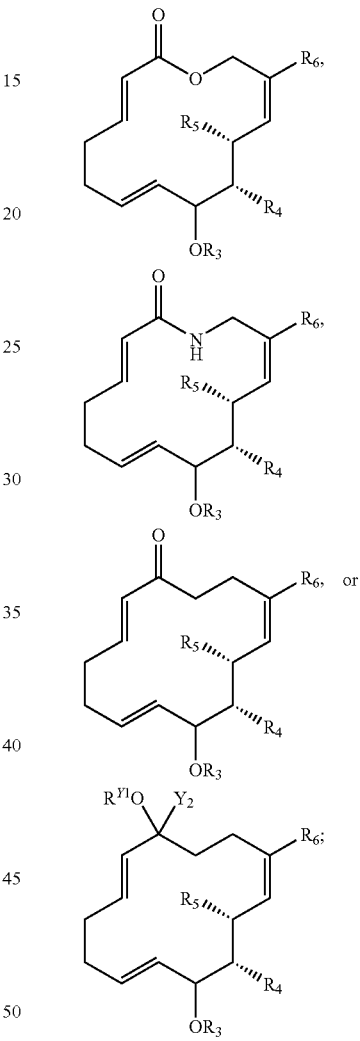

wherein $R_3$-$R_6$ are as defined in classes and subclasses herein; and $Y_2$ and $R^{Y1}$ are independently hydrogen or lower alkyl. In certain embodiments, $R_3$ is hydrogen, lower alkyl or an oxygen protecting group. In certain exemplary embodiments, $R_3$ is methyl. In certain other embodiments, $R_5$ and $R_6$ are independently lower alkyl. In certain exemplary embodiments, $R_5$ and $R_6$ are each methyl. In certain embodiments, $R_4$ is halogen, hydroxyl, lower alkoxy, acyloxy or $NR^{4A}R^{4B}$, wherein $R^{4A}$ and $R^{4B}$ are independently hydrogen, lower alkyl, aryl, acyl or a nitrogen protecting group, or $R^{4A}$ and $R^{4B}$, taken together with the nitrogen atom to which they are attached, form a substituted or unsubstituted heterocyclic or heteroaryl moiety; or $R_4$, taken together with the carbon atom to which it is attached forms a moiety having the structure:

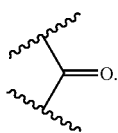 [SMILES: *C(*)=O]

In certain embodiments, $R_4$ is a halogen selected from fluorine, chlorine, bromine and iodine. In certain exemplary embodiments, $R_4$ is fluorine. In certain other embodiments, $R_4$ is F, OH, OAc, $NH_2$ or $R_4$, taken together with the carbon atom to which it is attached forms a moiety having the structure:

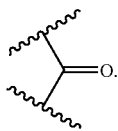 [SMILES: *C(*)=O]

In certain exemplary embodiments, $Y_2$ is hydrogen or lower alkyl substituted with one or more halogen atoms selected from F, Cl, Br and I. In certain exemplary embodiments, $Y_2$ is hydrogen or methyl substituted with one or more halogen atoms selected from F, Cl, Br and I. In certain exemplary embodiments, $Y_2$ is hydrogen or $CF_3$. In certain exemplary embodiments, $R^{Y1}$ is hydrogen or lower alkyl. In certain exemplary embodiments, $R^{Y1}$ is hydrogen or methyl. In certain exemplary embodiments, $Y_2$ is $CF_3$ and $R^{Y1}$ is methyl.

XIII) Compounds of the Formula (and Pharmaceutically Acceptable Derivatives Thereof):

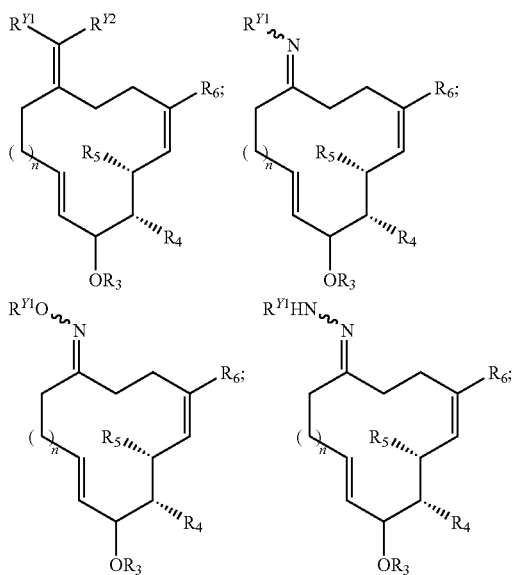

wherein $R_3$-$R_6$ and n are as defined in classes and subclasses herein; and $Y_2$ and $R^{Y1}$ are independently hydrogen or lower alkyl. In certain embodiments, $R_3$ is hydrogen, lower alkyl or an oxygen protecting group. In certain exemplary embodiments, $R_3$ is methyl. In certain other embodiments, $R_5$ and $R_6$ are independently lower alkyl. In certain exemplary embodiments, $R_5$ and $R_6$ are each methyl. In certain embodiments, n is 3. In certain embodiments, $R_4$ is halogen, hydroxyl, lower alkoxy, acyloxy or $NR^{4A}R^{4B}$, wherein $R^{4A}$ and $R^{4B}$ are independently hydrogen, lower alkyl, aryl, acyl or a nitrogen protecting group, or $R^{4A}$ and $R^{4B}$, taken together with the nitrogen atom to which they are attached, form a substituted or unsubstituted heterocyclic or heteroaryl moiety; or $R_4$, taken together with the carbon atom to which it is attached forms a moiety having the structure:

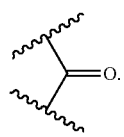

In certain embodiments, $R_4$ is a halogen selected from fluorine, chlorine, bromine and iodine. In certain exemplary embodiments, $R_4$ is fluorine. In certain other embodiments, $R_4$ is F, OH, OAc, $NH_2$ or $R_4$, taken together with the carbon atom to which it is attached forms a moiety having the structure:

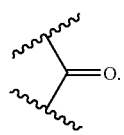 [SMILES: *C(*)=O]

In certain exemplary embodiments, $Y_2$ is hydrogen or lower alkyl substituted with one or more halogen atoms selected from F, Cl, Br and I. In certain exemplary embodiments, $Y_2$ is hydrogen or methyl substituted with one or more halogen atoms selected from F, Cl, Br and I. In certain exemplary embodiments, $Y_2$ is hydrogen or $CF_3$. In certain exemplary embodiments, $R^{Y1}$ is hydrogen, hydroxyl, lower alkoxy or lower alkyl. In certain exemplary embodiments, $R^{Y1}$ is hydrogen, hydroxyl, methoxy or methyl. In certain exemplary embodiments, $Y_2$ is $CF_3$ and $R^{Y1}$ is methyl or methoxy.

XIV) Compounds of the Formula (and Pharmaceutically Acceptable Derivatives Thereof):

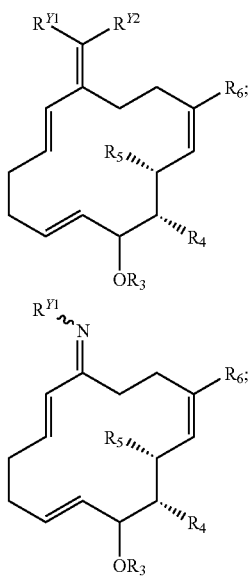

-continued

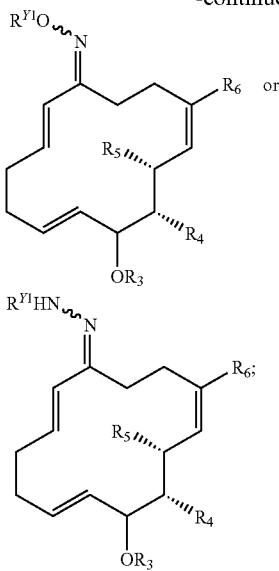

wherein $R_3$-$R_6$ are as defined in classes and subclasses herein; and $Y_2$ and $R^{Y1}$ are independently hydrogen or lower alkyl. In certain embodiments, $R_3$ is hydrogen, lower alkyl or an oxygen protecting group. In certain exemplary embodiments, $R_3$ is methyl. In certain other embodiments, $R_5$ and $R_6$ are independently lower alkyl. In certain exemplary embodiments, $R_5$ and $R_6$ are each methyl. In certain embodiments, $R_4$ is halogen, hydroxyl, lower alkoxy, acyloxy or $NR^{4A}R^{4B}$, wherein $R^{4A}$ and $R^{4B}$ are independently hydrogen, lower alkyl, aryl, acyl or a nitrogen protecting group, or $R^{4A}$ and $R^{4B}$, taken together with the nitrogen atom to which they are attached, form a substituted or unsubstituted heterocyclic or heteroaryl moiety; or $R_4$, taken together with the carbon atom to which it is attached forms a moiety having the structure:

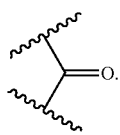 [SMILES: *C(*)=O]

In certain embodiments, $R_4$ is a halogen selected from fluorine, chlorine, bromine and iodine. In certain exemplary embodiments, $R_4$ is fluorine. In certain other embodiments, $R_4$ is F, OH, OAc, $NH_2$ or $R_4$, taken together with the carbon atom to which it is attached forms a moiety having the structure:

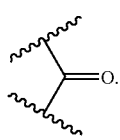

In certain exemplary embodiments, $Y_2$ is hydrogen or lower alkyl substituted with one or more halogen atoms selected from F, Cl, Br and I. In certain exemplary embodiments, $Y_2$ is hydrogen or methyl substituted with one or more halogen atoms selected from F, Cl, Br and I. In certain exemplary embodiments, $Y_2$ is hydrogen or $CF_3$. In certain exemplary embodiments, $R^{Y1}$ is hydrogen, hydroxyl, lower alkyl or lower alkoxy. In certain exemplary embodiments, $R^{Y1}$ is hydrogen, hydroxyl, methyl or methoxy. In certain exemplary embodiments, $Y_2$ is $CF_3$ and $R^{Y1}$ is methyl or methoxy.

XV) Compounds of the Formula (and Pharmaceutically Acceptable Derivatives Thereof):

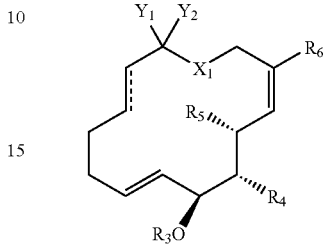

wherein $R_3$-$R_6$ are as defined in classes and subclasses herein; $X_1$ is O, NH or $CH_2$; and $Y_1$ and $Y_2$ are independently OH, $C(R^{Y1})_3$ or $Y_1$ and $Y_2$ taken together with the carbon atom to which they are attached are —C=O; wherein $R^{Y1}$ is halo. In certain embodiments, $R_6$ is H or lower alkyl. In certain other embodiments, $R_5$ is H or lower alkyl. In yet other embodiments, $R_4$ is OH. In other embodiments, $R_3$ is alkyl. In certain exemplary embodiments, $X_1$ is $CH_2$, NH or O; $Y_1$ and $Y_2$ are independently OH, $C(R^{Y1})_3$ or $Y_1$ and $Y_2$ taken together with the carbon atom to which they are attached are —C=O, wherein $R^{Y1}$ is halo; $R_6$ is H or lower alkyl; $R_5$ is H or lower alkyl; $R_4$ is OH; and $R_3$ is alkyl.

XVI) Compounds of the Formula (and Pharmaceutically Acceptable Derivatives Thereof):

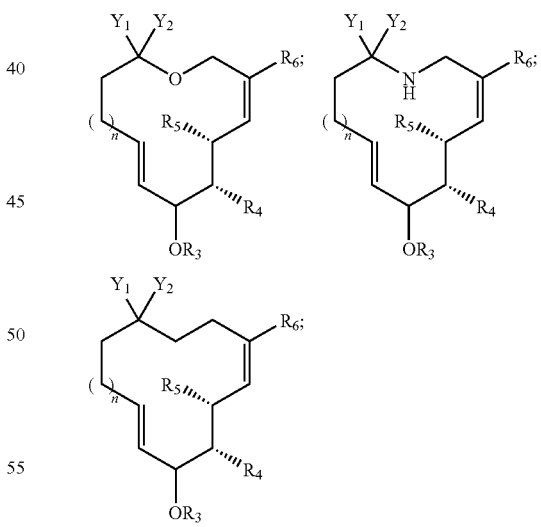

wherein $Y_1$ and $Y_2$ are independently hydrogen, an alkyl, heteroalkyl, cycloalkyl, heterocycloalkyl, aryl or heteroaryl moiety; or —$WR^{Y1}$; wherein W is independently —O—, —S— or —$NR^{Y2}$—, wherein each occurrence of $R^{Y1}$ and $R^{Y2}$ is independently hydrogen, or an alkyl, heteroalkyl, cycloalkyl, heterocycloalkyl, aryl or heteroaryl moiety; or $Y_1$ and $Y_2$ together with the carbon atom to which they are attached form a moiety having the structure:

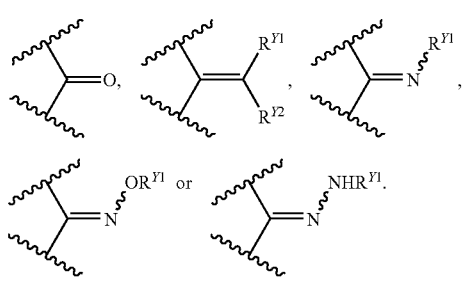

In certain embodiments, the compound has the structure:

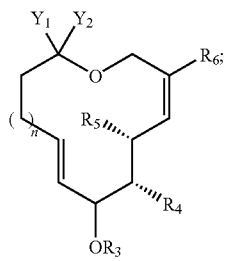

wherein n is 3; and $Y_1$ and $Y_2$ are independently hydrogen, an alkyl, heteroalkyl, cycloalkyl, heterocycloalkyl, aryl or heteroaryl moiety. In certain exemplary embodiments, $Y_1$ and $Y_2$ are each hydrogen. In certain embodiments, the compound has the structure:

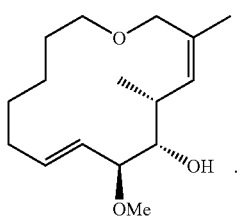 [SMILES: CO[C@H]1/C=C/CCCCCOC/C(C)=C\[C@@H](C)[C@@H]1O ; "."]

XVII) Compounds of the Formula (and Pharmaceutically Acceptable Derivatives Thereof):

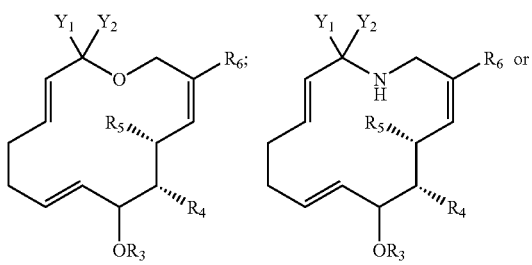

-continued

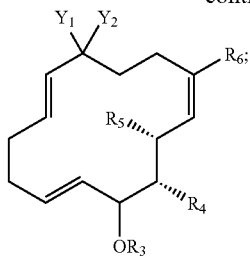

wherein $Y_1$ and $Y_2$ are independently hydrogen, an alkyl, heteroalkyl, cycloalkyl, heterocycloalkyl, aryl or heteroaryl moiety; or —$WR^{Y1}$; wherein W is independently —O—, —S— or —$NR^{Y2}$—, wherein each occurrence of $R^{Y1}$ and $R^{Y2}$ is independently hydrogen, or an alkyl, heteroalkyl, cycloalkyl, heterocycloalkyl, aryl or heteroaryl moiety; or $Y_1$ and $Y_2$ together with the carbon atom to which they are attached form a moiety having the structure:

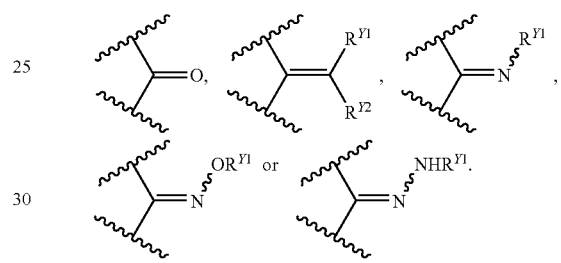

In certain embodiments, the compound has the structure:

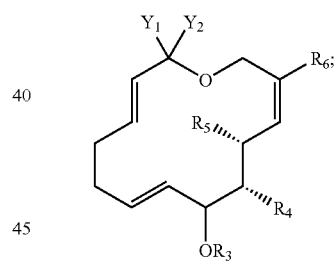

wherein $Y_1$ and $Y_2$ are independently hydrogen, an alkyl, heteroalkyl, cycloalkyl, heterocycloalkyl, aryl or heteroaryl moiety. In certain exemplary embodiments, $Y_1$ and $Y_2$ are each hydrogen. In certain embodiments, the compound has the structure:

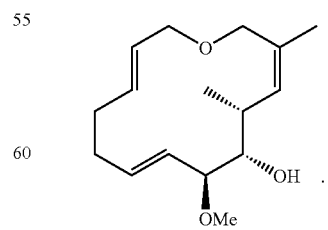

In certain embodiments, for compounds of classes XVI and XVII, $R_5$ and $R_6$ are each methyl. In certain embodiments, $R_3$ is lower alkyl. In certain embodiments, $R_3$ is lower methyl. In certain embodiments, $R_4$ is OH, OAc, $NH_2$ or halogen, or $R_4$ taken together with the carbon atom to which it is attached forms a moiety having the structure:

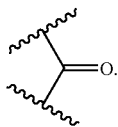 [SMILES: *C(*)=O]

In certain embodiments, for compounds of classes I, III, V, VII, IX, XI, XIII and XVI, n is 3.

It will also be appreciated that for each of the subgroups I-XV described above, a variety of other subclasses are of special interest, including, but not limited to those classes described above i)-cxix) and classes, subclasses and species of compounds described above and in the examples herein.

Some of the foregoing compounds can comprise one or more asymmetric centers, and thus can exist in various isomeric forms, e.g., stereoisomers and/or diastereomers. Thus, inventive compounds and pharmaceutical compositions thereof may be in the form of an individual enantiomer, diastereomer or geometric isomer, or may be in the form of a mixture of stereoisomers. In certain embodiments, the compounds of the invention are enantiopure compounds. In certain other embodiments, mixtures of stereoisomers or diastereomers are provided.

Furthermore, certain compounds, as described herein may have one or more double bonds that can exist as either the Z or E isomer, unless otherwise indicated. The invention additionally encompasses the compounds as individual isomers substantially free of other isomers and alternatively, as mixtures of various isomers, e.g., racemic mixtures of stereoisomers. In addition to the above-mentioned compounds per se, this invention also encompasses pharmaceutically acceptable derivatives of these compounds and compositions comprising one or more compounds of the invention and one or more pharmaceutically acceptable excipients or additives.

Compounds of the invention may be prepared by crystallization of compound of formula (I) under different conditions and may exist as one or a combination of polymorphs of compound of general formula (I) forming part of this invention. For example, different polymorphs may be identified and/or prepared using different solvents, or different mixtures of solvents for recrystallization; by performing crystallizations at different temperatures; or by using various modes of cooling, ranging from very fast to very slow cooling during crystallizations. Polymorphs may also be obtained by heating or melting the compound followed by gradual or fast cooling. The presence of polymorphs may be determined by solid probe NMR spectroscopy, IR spectroscopy, differential scanning calorimetry, powder X-ray diffractogram and/or other techniques. Thus, the present invention encompasses inventive compounds, their derivatives, their tautomeric forms, their stereoisomers, their polymorphs, their pharmaceutically acceptable salts their pharmaceutically acceptable solvates and pharmaceutically acceptable compositions containing them.

As discussed above, this invention provides novel compounds with a range of biological properties. Preferred compounds of this invention have biological activities relevant for the treatment of cancer and angiogenesis-related disorders.

Compounds of this invention include those specifically set forth above and described herein, and are illustrated in part by the various classes, subgenera and species disclosed elsewhere herein.

Additionally, the present invention provides pharmaceutically acceptable derivatives of the inventive compounds, and methods of treating a subject using these compounds, pharmaceutical compositions thereof, or either of these in combination with one or more additional therapeutic agents. Certain compounds of the present invention are described in more detail below. For purposes of this invention, the chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in "Organic Chemistry", Thomas Sorrell, University Science Books, Sausalito: 1999, the entire contents of which are incorporated herein by reference. Furthermore, it will be appreciated by one of ordinary skill in the art that the synthetic methods, as described herein, utilize a variety of protecting groups. It will be appreciated that the compounds, as described herein, may be substituted with any number of substituents or functional moieties. In general, the term "substituted" whether preceded by the term "optionally" or not, and substituents contained in formulas of this invention, refer to the replacement of hydrogen radicals in a given structure with the radical of a specified substituent. When more than one position in any given structure may be substituted with more than one substituent selected from a specified group, the substituent may be either the same or different at every position. As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. For purposes of this invention, heteroatoms such as nitrogen may have hydrogen substituents and/or any permissible substituents of organic compounds described herein which satisfy the valencies of the heteroatoms. Furthermore, this invention is not intended to be limited in any manner by the permissible substituents of organic compounds. Combinations of substituents and variables envisioned by this invention are preferably those that result in the formation of stable compounds useful in the treatment, for example of proliferative disorders, including, but not limited to cancer. The term "stable", as used herein, preferably refers to compounds which possess stability sufficient to allow manufacture and which maintain the integrity of the compound for a sufficient period of time to be detected and preferably for a sufficient period of time to be useful for the purposes detailed herein.

It will also be appreciated that certain of the compounds of present invention can exist in free form for treatment, or where appropriate, as a pharmaceutically acceptable derivative thereof. According to the present invention, a pharmaceutically acceptable derivative includes, but is not limited to, pharmaceutically acceptable salts, esters, salts of such esters, or a prodrug or other adduct or derivative of a compound of this invention which upon administration to a patient in need is capable of providing, directly or indirectly, a compound as otherwise described herein, or a metabolite or residue thereof.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts of amines, carboxylic acids, and other types of compounds, are well known in the art. For example, S. M. Berge, et al. describe pharmaceutically acceptable salts in detail in *J. Pharmaceutical Sciences*, 66: 1-19 (1977), incorporated herein by reference. The salts can be prepared in situ during the final isolation and purification of the compounds of the invention, or separately by reacting a free base or free acid function with a suitable reagent, as described generally below. For example, a free base function can be reacted with a suitable acid. Furthermore, where the compounds of the invention carry an acidic moiety, suitable pharmaceutically acceptable salts thereof may, include metal salts such as alkali metal salts, e.g. sodium or potassium salts; and alkaline earth metal salts, e.g. calcium or magnesium salts. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hernisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

Additionally, as used herein, the term "pharmaceutically acceptable ester" refers to esters that hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moeity advantageously has not more than 6 carbon atoms. Examples of particular esters include formates, acetates, propionates, butyrates, acrylates and ethylsuccinates.

Furthermore, the term "pharmaceutically acceptable prodrugs" as used herein refers to those prodrugs of the compounds of the present invention which are, within the scope of sound medical judgment, suitable for use in contact with the issues of humans and lower animals with undue toxicity, irritation, allergic response, and the like, commensurate with a reasonable benefit/risk ratio, and effective for their intended use, as well as the zwitterionic forms, where possible, of the compounds of the invention. The term "prodrug" refers to compounds that are rapidly transformed in vivo to yield the parent compound of the above formula, for example by hydrolysis in blood. A thorough discussion is provided in T. Higuchi and V. Stella, Pro-drugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987, both of which are incorporated herein by reference.

2) Synthetic Methodology

In another aspect, the present invention provides methods for preparing novel macrocycles having formula (I) a described above and in certain classes and subclasses herein. An overview of exemplary synthetic approaches to the inventive compounds is provided below, as detailed in Schemes 1-15, and in the Exemplification herein. It will be appreciated that the methods as described herein can be applied to each of the compounds as disclosed herein and equivalents thereof. Additionally, the reagents and starting materials are well known to those skilled in the art. Although the following schemes describe certain exemplary compounds, it will be appreciated that the use of alternate starting materials will yield other analogs of the invention. For example, compounds are described below where X is O; however, it will be appreciated that alternate starting materials and/or intermediates can be utilized to generate compounds where X is NH, N-alkyl, S, $CH_2$, etc.

In certain embodiments, compounds as provided herein, for example those where n is 3, X is O, and $R_1$ and $R_2$ are each hydrogen, are prepared from assembly of three segments, as depicted in Scheme 1A below:

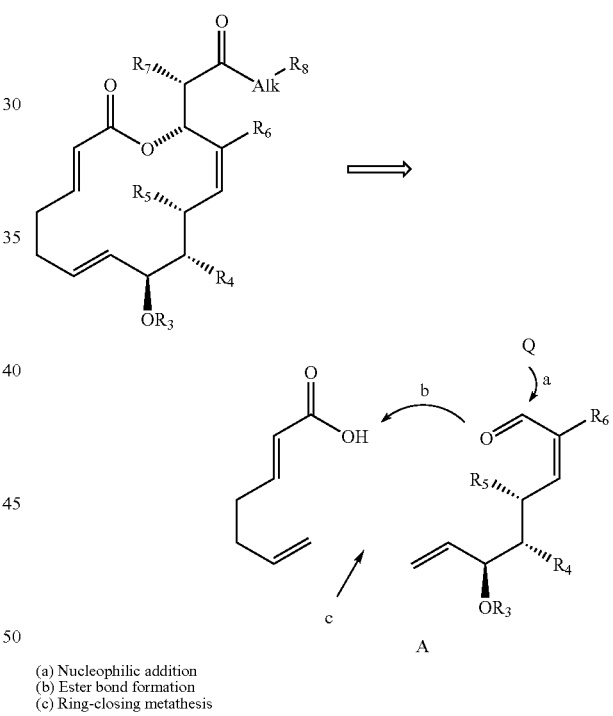

(a) Nucleophilic addition
(b) Ester bond formation
(c) Ring-closing metathesis

In certain other embodiments, compounds as provided herein, for example those where n is 3, X is O, $R_1$ and $R_2$ are each hydrogen, and Q is a moiety having the structure

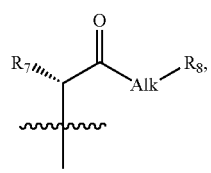

are prepared from assembly of five segments, as depicted in Scheme 1B below:

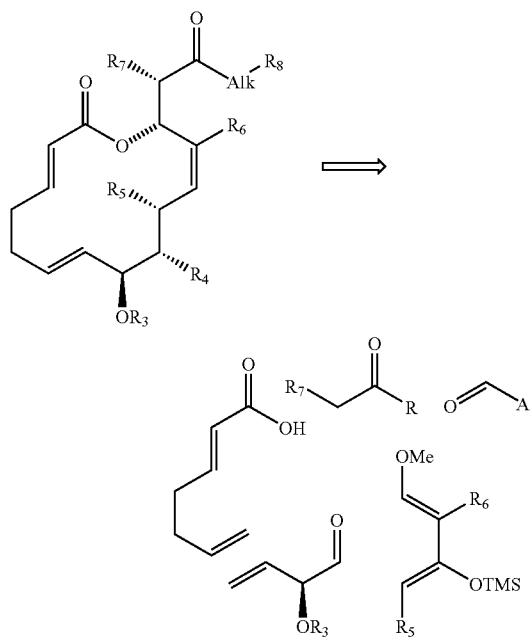

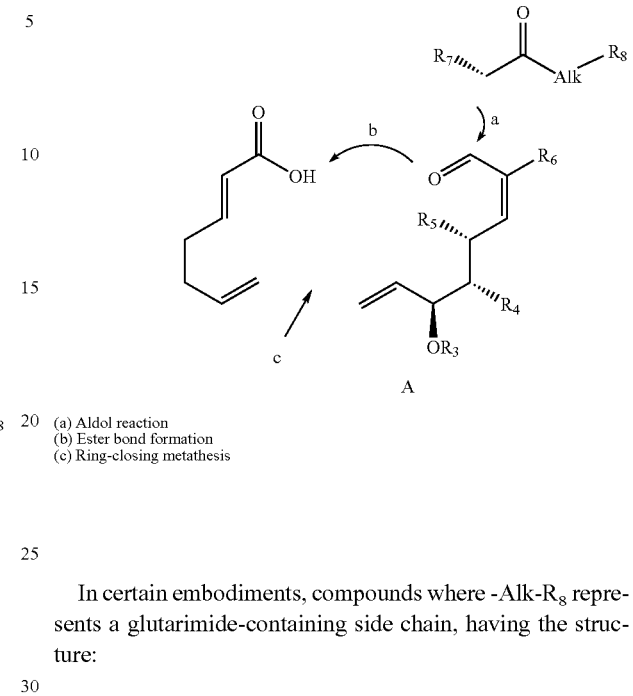

(a) Aldol reaction
(b) Ester bond formation
(c) Ring-closing metathesis

In certain embodiments, compounds where -Alk-$R_8$ represents a glutarimide-containing side chain, having the structure:

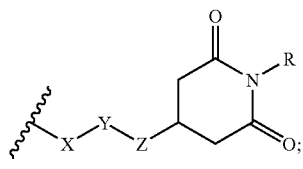

wherein X, Y, Z and R are as defined in classes and subclasses herein;

are prepared from assembly of three segments, as depicted in Scheme 3 below:

In certain embodiments, compounds of the invention where Q is a carbonyl-containing moiety having the structure:

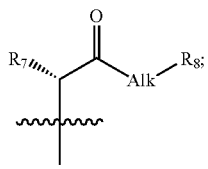

are prepared from assembly of three segments, as depicted in Scheme 2 below:

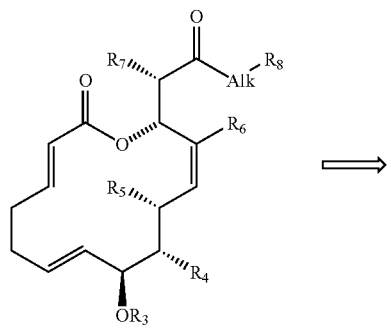

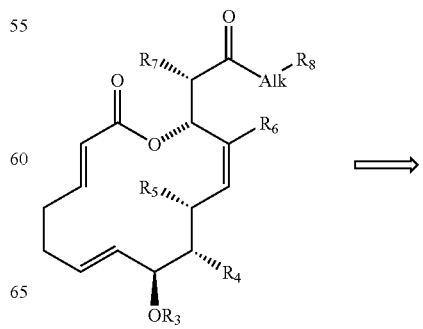

-continued

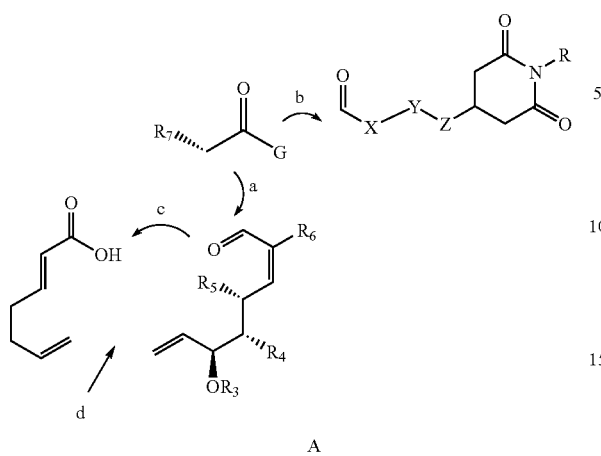

(a) Aldol reaction
(b) Horner-Wadsworth-Emmons reaction
(c) Ester bond formation
(d) Ring-closing metathesis wherein G represents a group suitable for effecting the Horner-Wadsworth-Emmons-type coupling.

In certain embodiments, the preparation of fragment A may be accomplished as depicted in Scheme 4 below:

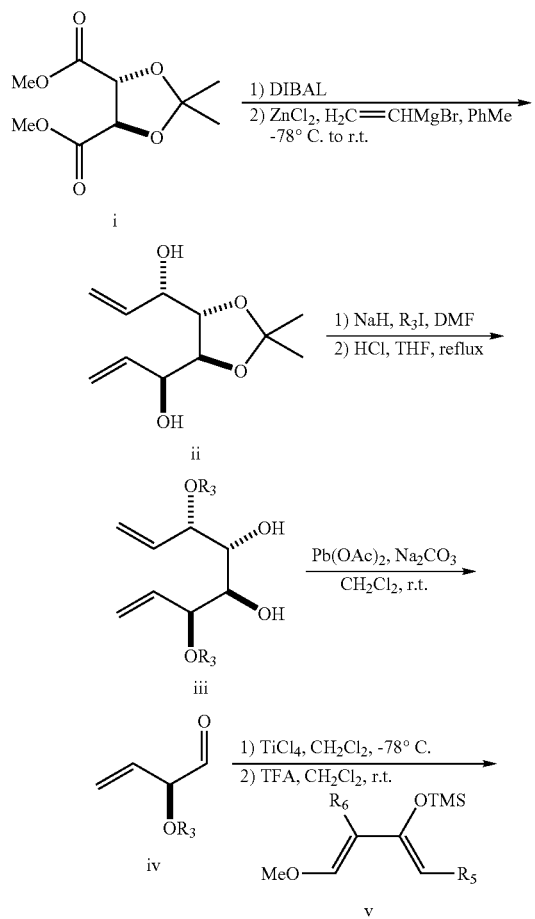

-continued

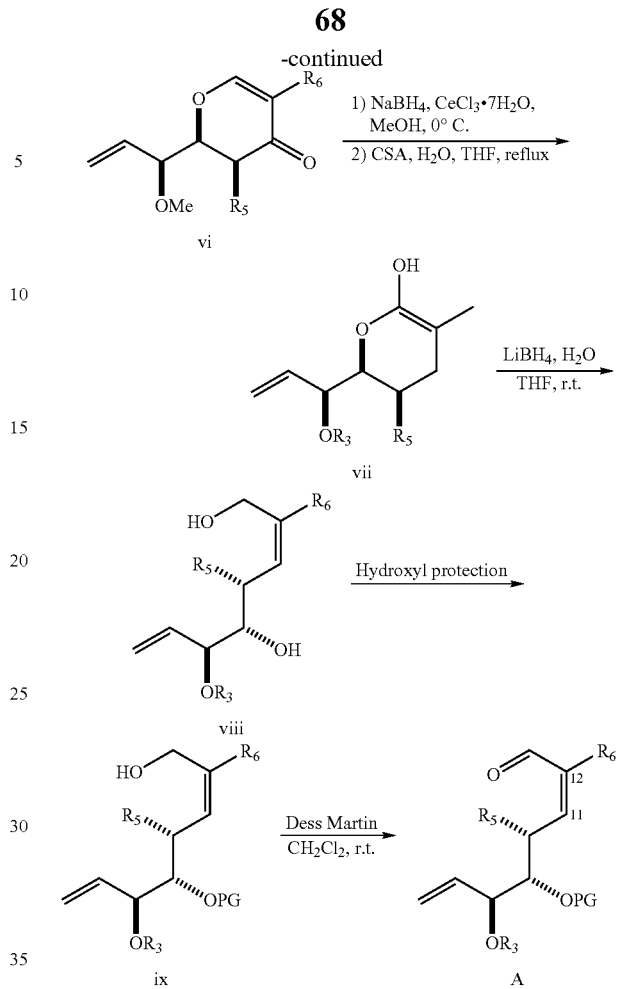

For example, reduction of commercially available dimethyl 2,3-O-isopropylidene-L-tartrate i, followed by diastereoselective divinyzinc addition to the in situ generated dialdehyde produces the desired vinyl carbinol ii (see, Jorgensen et al., *J. Org. Chem.*, 2001, 66, 4630). Alkylation (or arylation) of the two hydroxyl groups and removal of the acetonide protecting group yields diol iii. Glycol cleavage of iii affords α-alkoxy-β-vinyl aldehyde iv. Subjecting iv to a Lewis acid catalyzed diene aldehyde condensation (LACDAC) sequence with the synergistically activated diene v in the presence of $TiCl_4$, yields the α-chelation controlled dihydropyrone vi (for chelation-controlled cyclocondensations of α-alkoxy aldehydes with synergistically activated dienes, see: Danishefsky et al., *J. Am. Chem. Soc.*, 1985, 107, 1256). The cyclocondensation allows the construction of the three contiguous stereocenters of the macrolide and sets the stage for establishing the trisubstituted (Z)-alkene C11-C12. Luche reduction of enone vi affords the corresponding allylic alcohol, which can be made to undergo an aqueous Ferrier rearrangement to give alcohol vii (for a reference on the Luche reduction, see: Luche et al., *J. Am. Chem. Soc.*, 1979, 101, 5848; for a reference on the Ferrier rearrangement, see: Ferrier, *J. Chem. Soc.*, 1964, 5443). Reductive opening of lactol vii, protection of the secondary hydroxyl group, and oxidation of the primary alcohol yields the C7-C13 core fragment A.

One of ordinary skill in the art will recognize that the protected hydroxyl (OPG) may be converted to a variety of functional groups, including, but not limited to OH, $NH_2$ and F, thus allowing access to compounds where $R_4$ is OH, OAc, $NH_2$, F, or $R_4$, taken together with the carbon atom to which it is attached forms a moiety having the structure:

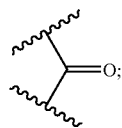

among others.

In certain embodiments, coupling of fragment A with a glutarimide moiety may be accomplished as exemplified in Scheme 5 below:

Scheme 5

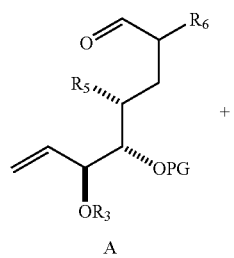

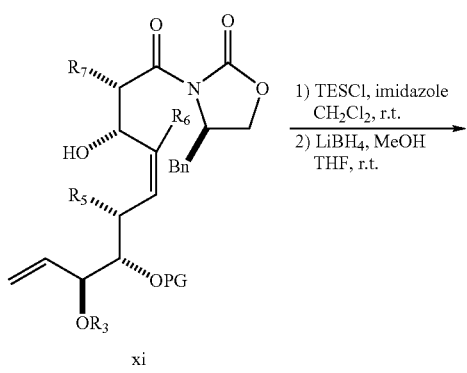

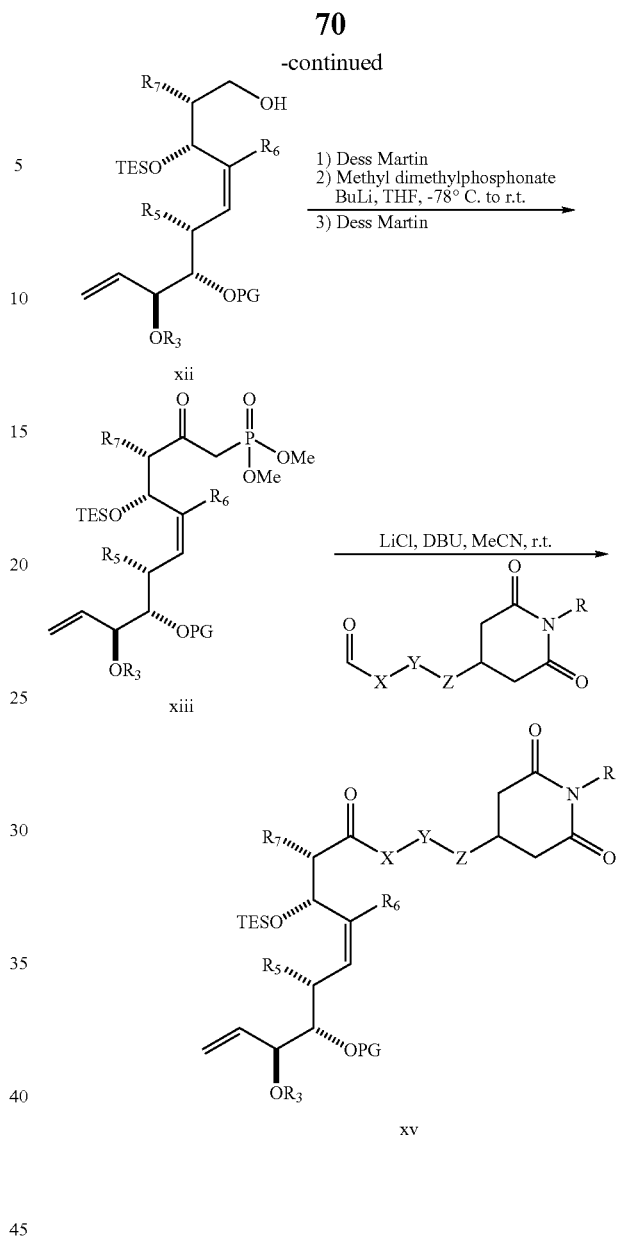

For example, Addition of x to fragment A in the presence of $MgCl_2$ and TMSCl produces alcohol xi (for a reference reporting a suitable protocol for anti-selective aldol coupling, see: Evans et al., *J. Am. Chem. Soc.*, 2002, 124, 392). Protection of the resulting secondary hydroxyl group and reductive cleavage of the chiral auxiliary affords alcohol xii. Coupling of compound xii with the glutarimide side chain may be effected, for example, via a Horner-Wadsworth-Emmons reaction. For example, the Masamune-Roush variant of the Horner-Wadsworth-Emmons reaction may be used (see: Blanchette et al., *Tet. Lett.*, 1984, 25, 2183). Thus, conversion of xii via an oxidation/nucleophilic addition/oxidation sequence gives β-ketophosphonate xiii. Treatment of the phosphonate with LiCl and DBU in the presence of glutarimide aldehyde xiv results in efficient formation of the desired enone xv.

In certain embodiments, formation of the macrolide ring is effected as shown in Scheme 6 below:

Scheme 6
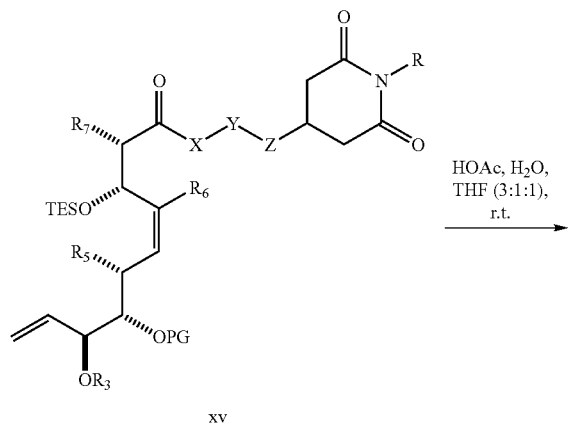
xv
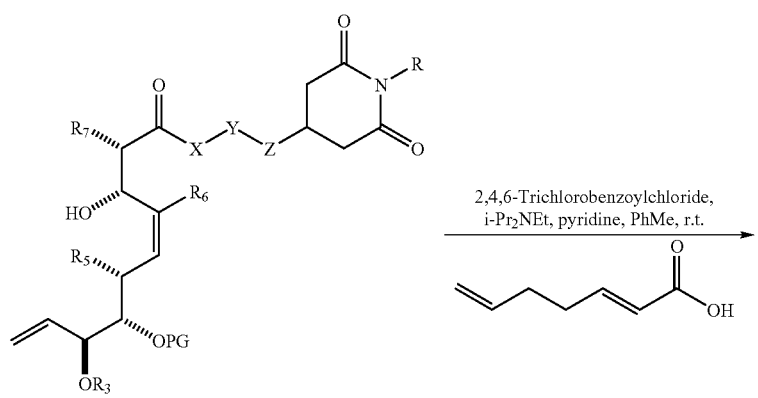
xvi
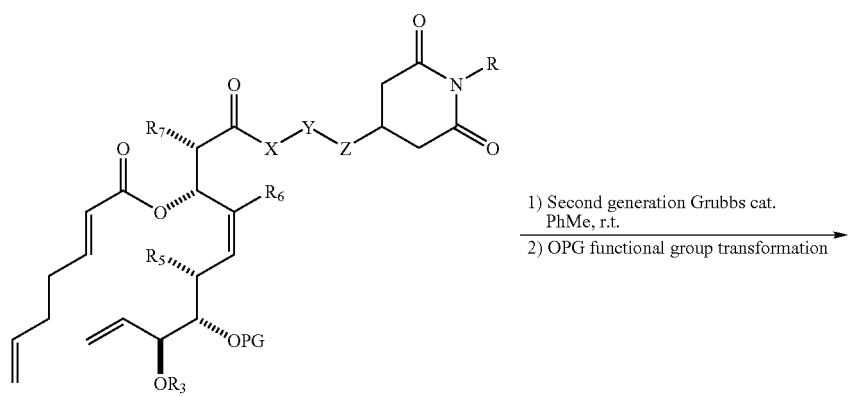
xvii

-continued

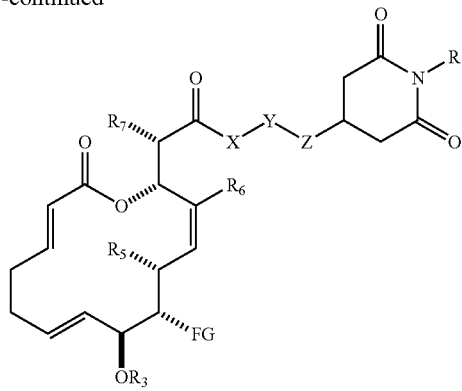

xviii

For example, removal of the TES protecting group of enone xv yields seco-alcohol xvi. A variety of methods for effecting acylation of xvi with dienoic acid may be utilized. For example, a modified Yamaguchi procedure may be used to give the metathesis precursor xvii (see, Inanaga et al., *Bull. Chem. Soc. Jpn.*, 1979, 52, 1989; and Song et al., *Org. Lett.*, 2002, 4, 647). A variety of methods for effecting ring-closure metathesis of xvii to the desired (E)-isomer may be utilized. For example, subjecting tetraene xvii to ring-closure metathesis conditions using the second generation Grubbs catalyst gives the desired macrocyclic (E)-isomer xviii in high yield (see, Scholl et al., *Org. Lett.*, 1999, 1, 953).

Methods for converting the protected hydroxyl group (OPG) into a variety of functionalities are known in the art. The practitioner skilled in the relevant art will know how to select reagents and reaction conditions to effect transformation of the protected hydroxyl group (OPG) into a desired functionality FG. In certain embodiments, FG represents OH, $NH_2$ or halogen (e.g., F).

In certain other embodiments, the conjugate ester group present in compound xviii (i.e., at $C_2$-$C_3$) may be reduced to the corresponding saturated ester xix. The practitioner skilled in the relevant art will know how to select reagents and reaction conditions to effect this transformation. For example, the Stryker copper hydride may be used (see, Mahoney et al., *J. Am. Chem. Soc.*, 1988, 110, 291), as depicted in Scheme 7 below:

Scheme 7

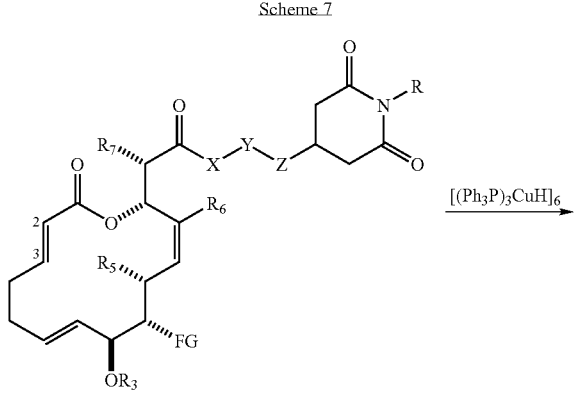

xviii

-continued

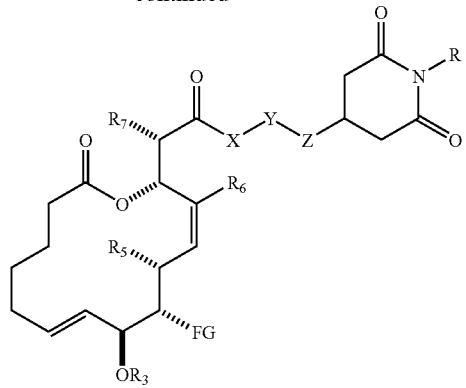

xix

In certain embodiments, in Schemes 5-7 above, —X—Y—Z— represents —CH═CH—$(CH_2)_v$— where v is an integer from 1-4. Thus, compound xv depicted in scheme 5 may have the following structure (xv):

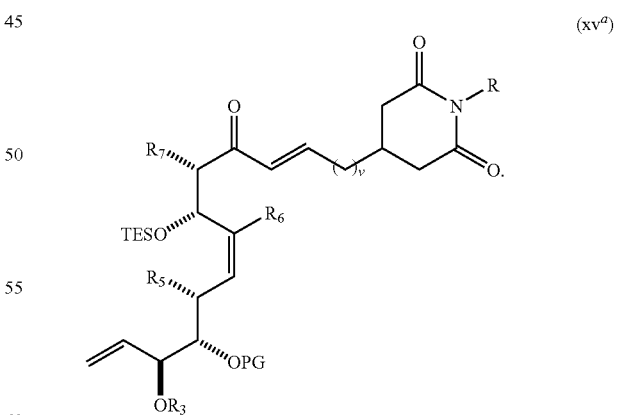

(xv$^a$)

In certain embodiments, conjugate reduction of this intermediate may be effected using the stryker reagent, as shown in scheme 8 below:

Scheme 8

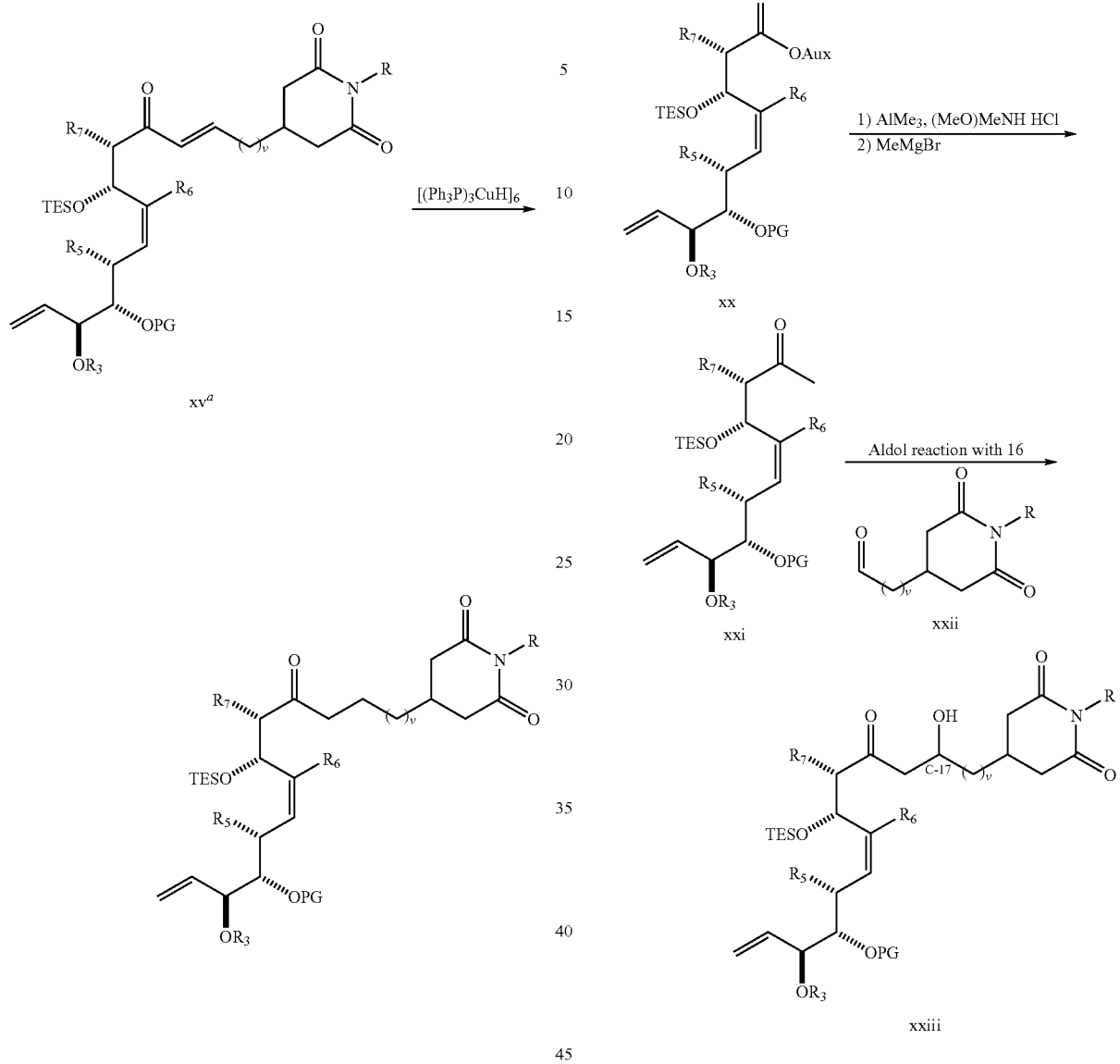

In certain other embodiments, where further functionalization at $C_{17}$ of the alkyl-glutarimide side chain of $xv^a$ is desired, coupling of fragment xii with a glutarimide moiety may be accomplished as shown in Scheme 9 below:

Scheme 9

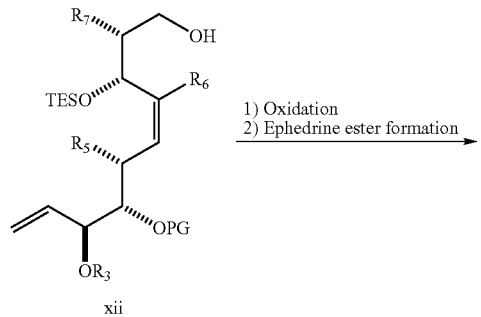

For example, ephedrine ester xx may be converted to the corresponding Weinreb amide, which is then transformed into the corresponding methyl ketone upon treatment with MeMgBr. Aldol reaction of ketone xxi with protected glutarimide aldehyde xxii yields the formation of the $C_{17}$-hydroxylated adduct xxiii. The practitioner skilled in the relevant art will know how to select reagents and reaction conditions to effect transformation of this C-17 hydroxyl group into functionalities of interest (e.g., alkoxyl, aryloxy, $NH_2$ or halogen (e.g., F)).

One of ordinary skill in the art will recognize that the ring closing metathesis coupling may be effected with fragments where at least one of $R_1$ and $R_2$ is not hydrogen, to introduce functionalization at $C_6$ and/or $C_7$, as shown in Scheme 10 below. In addition, metathesis reaction conditions may be adjusted so that the (Z)isomer is predominantly formed, rather than the (E)-isomer.

Scheme 10

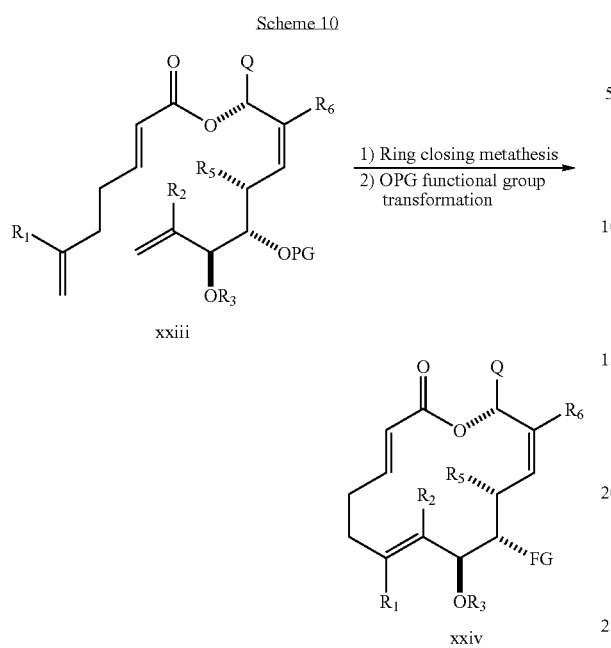

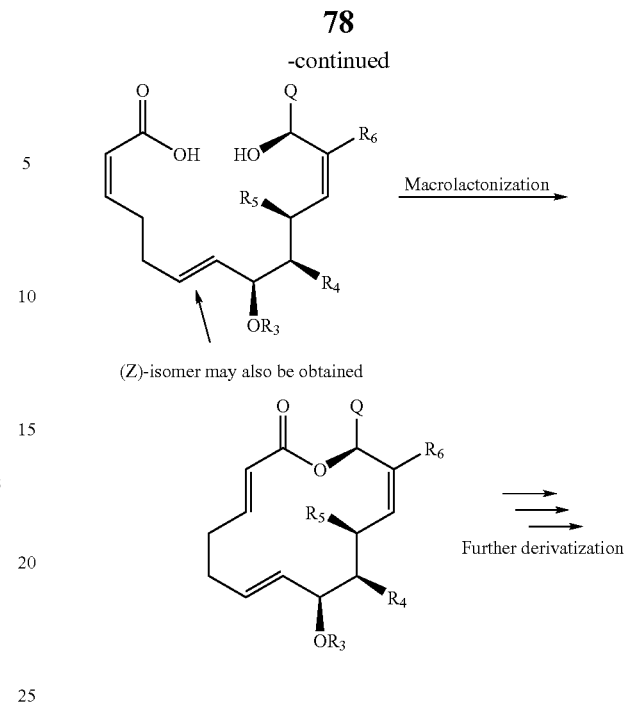

(Z)-isomer may also be obtained

One of ordinary skill in the art will also recognize that the inventive methods for assembling the macrocyclic structure are not limited by the order in which the different fragments may be put together. Exemplary synthetic approaches were described in Schemes 1-10 above, whereby the inventive compounds are prepared by (i) nucleophilic addition of Q on fragment A, followed by (ii) ester bond formation between the A-Q adduct with a suitable dienoic acid and (iii) ring closing ring closure to give the desired macrocyclic scaffold. Other approaches may be used. For example, inventive compounds may be prepared by (i) nucleophilic addition of Q on fragment A, followed by (ii) cross-metathesis reaction of the A-Q adduct obtained in (i) with a suitable dienoic acid and (iii) macrolactonization (i.e., intramolecular ester bond formation) to give the desired macrocyclic scaffold (See Scheme 11).

Alternatively, inventive compounds may be prepared by (i) nucleophilic addition of Q on fragment A, followed by (ii) cross-metathesis reaction of the A-Q adduct obtained in (i) with a suitable enone, (iii) acylation of the adduct obtained in (ii) with a suitable reagent and (iv) intramolecular Horner-Wadsworth-Emmons olefination to give the desired macrocyclic scaffold (See Scheme 12).

Scheme 11

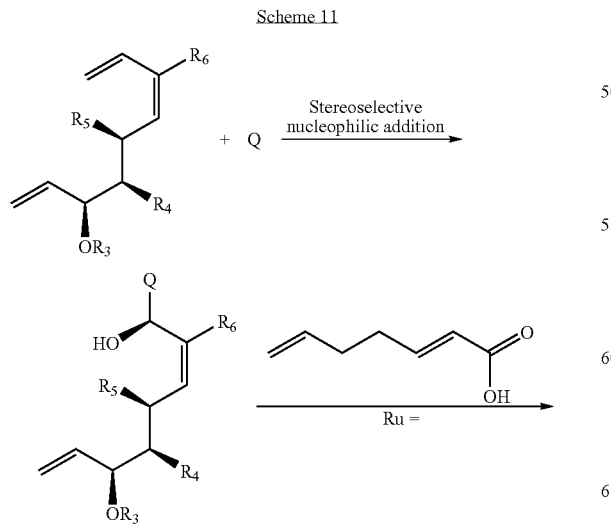

Scheme 12

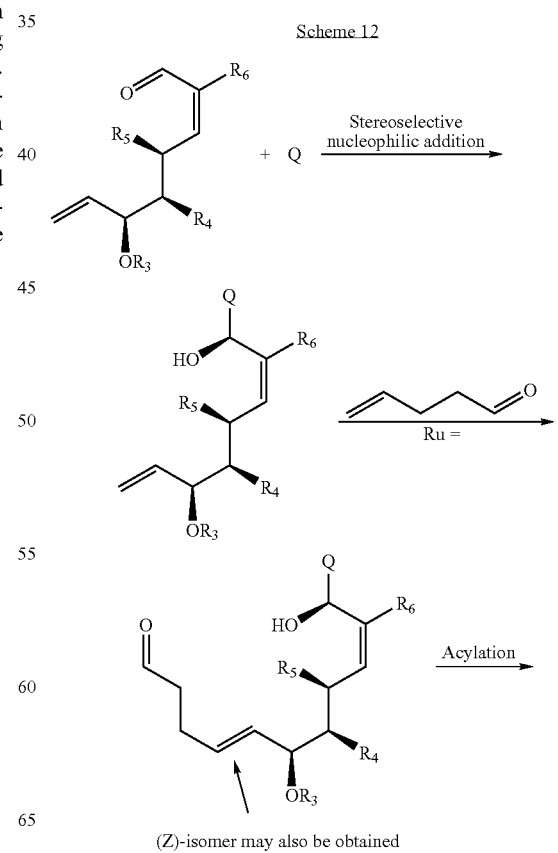

(Z)-isomer may also be obtained

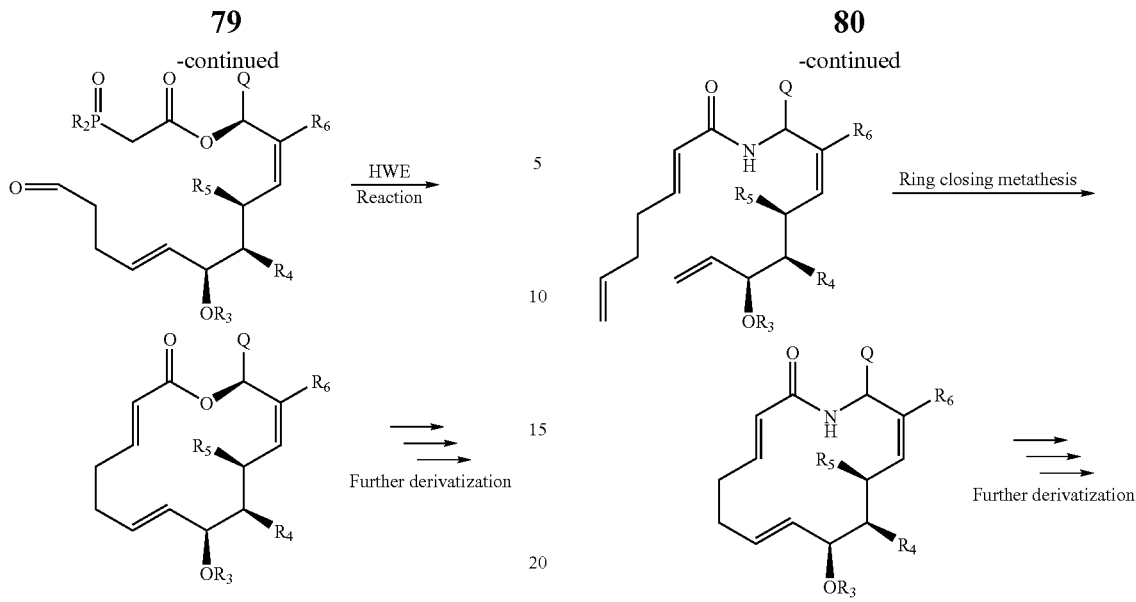

In certain embodiments, the invention provides methods of preparing compounds where $X_1$ is NH. Schemes 1-12 above detail exemplary synthetic approaches for preparing inventive compounds where $X_1$ is O. A similar approach may be used to access compounds where $X_1$ is NH (i.e., macrolactams). For example, inventive compounds may be prepared by (i) nucleophilic addition of Q on fragment A, followed by (ii) conversion of the resulting alcohol to an amine, (iii) amide bond formation between the A-Q adduct formed in (ii) with a suitable dienoic acid and (iv) ring closing metathesis to give the desired macrolactam scaffold (Scheme 13).

In certain embodiments, inventive compounds may be prepared by (i) nucleophilic addition of Q on fragment A, followed by (ii) conversion of the resulting alcohol to the corresponding amine, (iii) cross-metathesis reaction of the A-Q adduct obtained in (ii) with a suitable dienoic acid and (iv) intramolecular amide bond formation to give the desired macrolactam scaffold (See Scheme 14).

Scheme 13

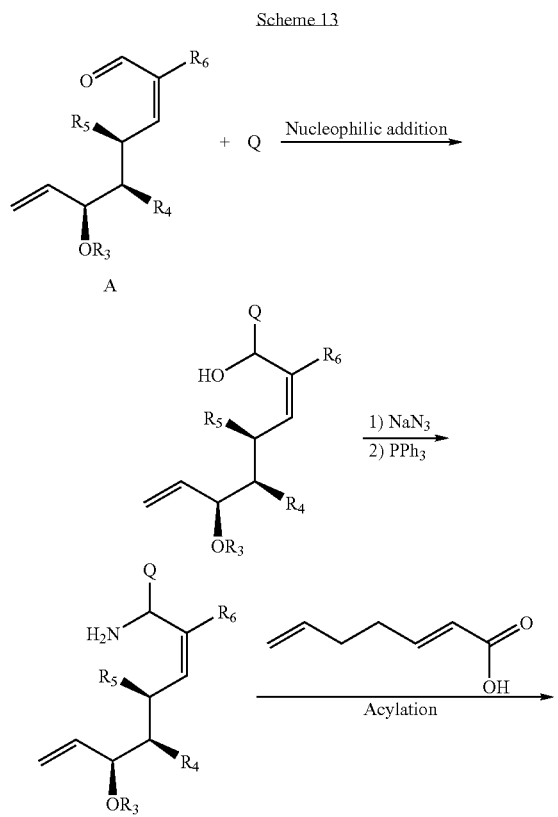

Scheme 14

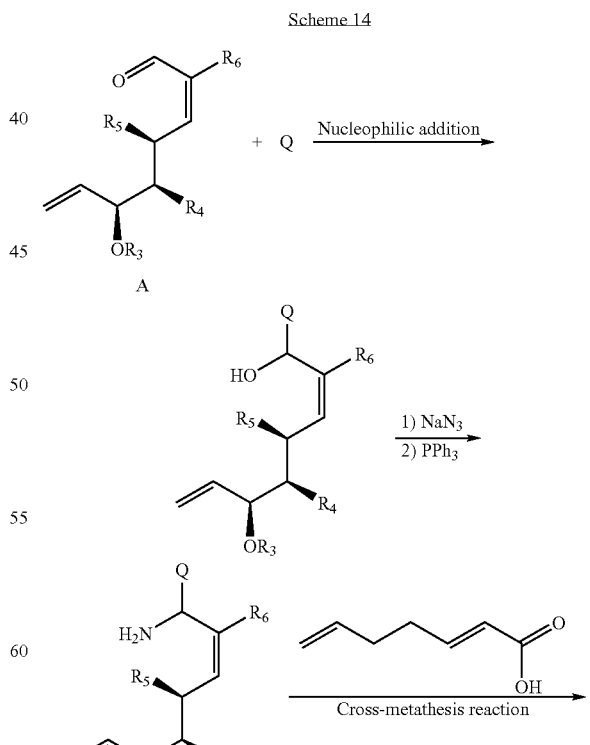

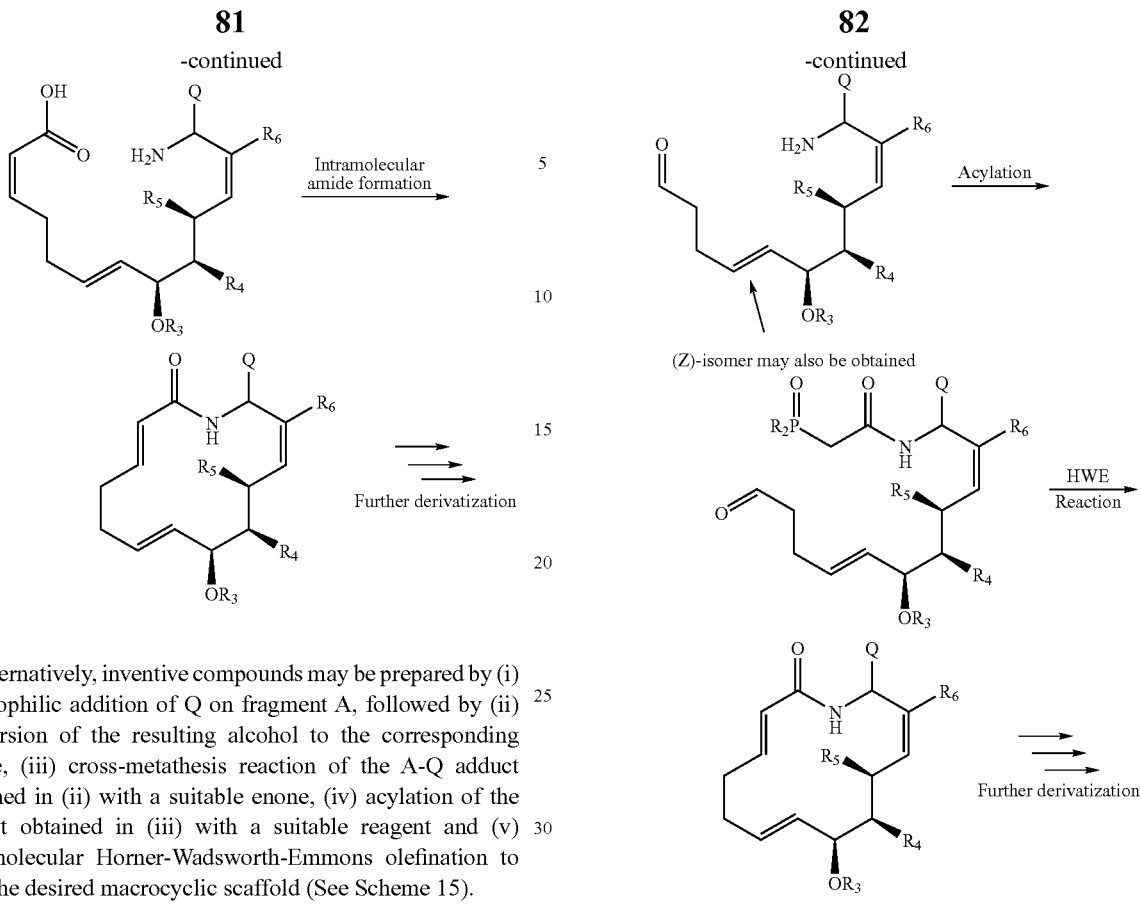

Alternatively, inventive compounds may be prepared by (i) nucleophilic addition of Q on fragment A, followed by (ii) conversion of the resulting alcohol to the corresponding amine, (iii) cross-metathesis reaction of the A-Q adduct obtained in (ii) with a suitable enone, (iv) acylation of the adduct obtained in (iii) with a suitable reagent and (v) intramolecular Horner-Wadsworth-Emmons olefination to give the desired macrocyclic scaffold (See Scheme 15).

Other approaches to prepare inventive compounds will be readily apparent to the practitioner skilled in the relevant art.

Diversification:

It will also be appreciated that each of the components used in the synthesis of Migrastatin analogues can be diversified either before synthesis or alternatively after the construction of the macrocycle. As used herein, the term "diversifying" or "diversify" means reacting an inventive compound (I) or any of the precursor fragments (e.g., (A) etc.) as defined herein (or any classes or subclasses thereof) at one or more reactive sites to modify a functional moiety or to add a functional moiety (e.g., nucleophilic addition of a substrate). Described generally herein are a variety of schemes to assist the reader in the synthesis of a variety of analogues, either by diversification of the intermediate components or by diversification of the macrocyclic structures as described herein, and classes and subclasses thereof. It will also be appreciated that although many of the schemes herein depict 14-membered macrocycles, the reactions described herein may also be applied to other ring structures (for example to 12-, 13- and 15-membered ring structures). It will be appreciated that a variety of diversification reactions can be employed to generate novel analogues. As but a few examples, epoxidation and aziridation can be conducted to generate epoxide and aziridine analogues of compounds described herein. Additionally, addition across either double bond will generate additional diversity. In addition to diversification after macrocyclization, it will be understood that diversification can occur prior to macrocyclization (e.g., epoxidation, aziridation, reduction at a $C_{2-3}$ and/or $C_{12-13}$ double bond(s) could occur prior to metathesis ring-closure, or other means known in the art to effect macrocyclic ring closure, to describe just one example). For additional guidance available in the art, the practitioner is directed to "Advanced Organic Chemistry", March, J. John Wiley & Sons, 2001, 5th ed., the entire contents of which are hereby incorporated by reference.

In certain embodiments, the present invention provides a method for preparing a Migrastatin analog having the structure:

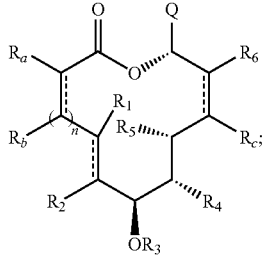

said method comprising steps of:

a. reacting a fragment Q with a compound having the structure:

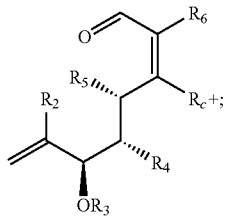

under suitable conditions to effect formation of an A-Q adduct having the structure:

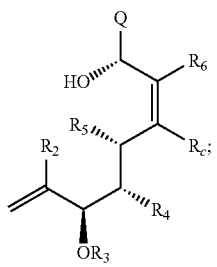

b. reacting A-Q formed in step a with a dienoic acid having the structure:

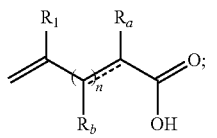

under suitable conditions to effect formation of an ester having the structure:

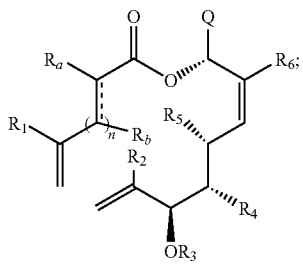

and c. subjecting the ester formed in step b to ring closing metathesis reaction conditions to effect formation of the macrolide having the structure:

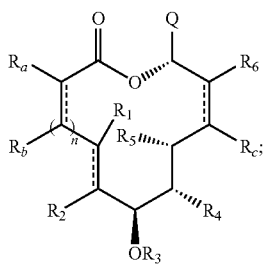

wherein $R_1$ and $R_2$ are each independently hydrogen, halogen, —CN, —S(O)$_{1-2}$R$^{1A}$, —NO$_2$, —COR$^{1A}$, —CO$_2$R$^{1A}$, —NR$^{1A}$C(=O)R$^{1B}$, —NR$^{1A}$C(=O)OR$^{1B}$, —CONR$^{1A}$R$^{1B}$, an aliphatic, heteroaliphatic, alicyclic, heterocyclic, aryl or heteroaryl moiety, or —WR$^{1A}$; wherein W is independently —O—, —S— or —NR$^{1C}$—, wherein each occurrence of R$^{1A}$, R$^{1B}$ and R$^{1C}$ is independently hydrogen, or an aliphatic, heteroaliphatic, alicyclic, heterocyclic, aryl or heteroaryl moiety; or $R_1$ and $R_2$, taken together, form an alicyclic, heterocyclic, aryl or heteroaryl moiety;

$R_3$ is hydrogen, an aliphatic, heteroaliphatic, alicyclic, heterocyclic, aryl or heteroaryl moiety; or a prodrug moiety or an oxygen protecting group;

$R_4$ is, —OR$^{4A}$, —OC(=O)R$^{4A}$ or —NR$^{4A}$R$^{4B}$; wherein R$^{4A}$ and R$^{4B}$ are independently hydrogen, an aliphatic, heteroaliphatic, alicyclic, heterocyclic, aryl or heteroaryl moiety; a prodrug moiety, a nitrogen protecting group or an oxygen protecting group; or R$^{4A}$ and R$^{4B}$, taken together with the nitrogen atom to which they are attached, form a heterocyclic or heteroaryl moiety; or $R_4$, taken together with the carbon atom to which it is attached forms a moiety having the structure:

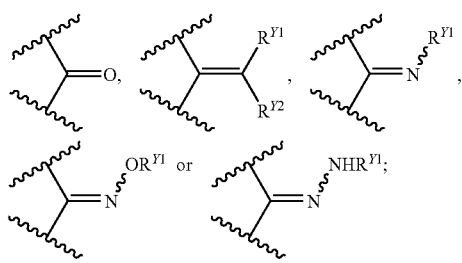

$R_5$ is hydrogen, an aliphatic, heteroaliphatic, alicyclic, heterocyclic, aryl or heteroaryl moiety;

$R_6$ is hydrogen, halogen, —CN, —S(O)$_{1-2}$R$^{6A}$, —NO$_2$, —COR$^{6A}$, —CO$_2$R$^{6A}$, —NR$^{6A}$C(=O)R$^{6B}$, —NR$^{6A}$C(=O)OR$^{6B}$, —CONR$^{6A}$R$^{6B}$, an aliphatic, heteroaliphatic, alicyclic, heterocyclic, aryl or heteroaryl moiety, or —WR$^{6A}$; wherein W is independently —O—, —S— or —NR$^{6C}$—, wherein each occurrence of R$^{6A}$, R$^{6B}$ and R$^{6C}$ is independently hydrogen, or an aliphatic, heteroaliphatic, alicyclic, heterocyclic, aryl or heteroaryl moiety; or $R_6$ and $R_c$ taken together with the carbon atoms to which they are attached, form an alicyclic, heterocyclic, aryl or heteroaryl moiety;

$R_a$ and each occurrence of $R_b$ are independently hydrogen, halogen, —CN, —S(O)$_{1-2}$R$^{a1}$, —NO$_2$, —COR$^{a1}$, —CO$_2$R$^{a1}$, —NR$^{a1}$C(=O)R$^{a2}$, —NR$^{a1}$C(=O)OR$^{a2}$, —CONR$^{a1}$R$^{a2}$, an aliphatic, heteroaliphatic, alicyclic, heterocyclic, aryl or heteroaryl moiety, or —WR$^{a1}$; wherein W is independently —O—, —S— or —NR$^{a3}$—, wherein each occurrence of R$^{a1}$, R$^{a2}$ and R$^{a3}$ is independently hydrogen, or an aliphatic, heteroaliphatic, alicyclic, heterocyclic, aryl or heteroaryl moiety; or $R_a$ and the adjacent occurrence of $R_b$, taken together with the carbon atoms to which they are attached, form an alicyclic, heterocyclic, aryl or heteroaryl moiety;

$R_c$ is hydrogen, halogen, —CN, —S(O)$_{1-2}$R$^{c1}$, —NO$_2$, —COR$^{c1}$, —CO$_2$R$^{c1}$, —NR$^{c1}$C(=O)R$^{c2}$, —NR$^{c1}$C(=O)OR$^{c2}$, —CONR$^{c1}$R$^{c2}$; an aliphatic, heteroaliphatic, alicyclic, heterocyclic, aryl or heteroaryl moiety, or —WR$^{c1}$; wherein W is independently —O—, —S— or —NR$^{c3}$—, wherein each occurrence of R$^{c1}$, R$^{c2}$ and R$^{c3}$ is independently hydrogen, or an aliphatic, heteroaliphatic, alicyclic, heterocyclic, aryl or heteroaryl moiety; or $R_c$ and $R_6$, taken together with the carbon atoms to which they are attached, form an alicyclic, heterocyclic, aryl or heteroaryl moiety;

n is an integer from 1 to 5; and

Q is hydrogen, halogen, —CN, —S(O)$_{1-2}$R$^{Q1}$, —NO$_2$, —COR$^{Q1}$, —CO$_2$R$^{Q1}$, —NR$^{Q1}$C(=O)R$^{Q2}$, —NR$^{Q1}$C(=O)OR$^{Q2}$, —CONR$^{Q1}$R$^{Q2}$, an aliphatic, heteroaliphatic, alicyclic, heterocyclic, aryl or heteroaryl moiety, or —WR$^{Q1}$; wherein W is independently —O—, —S— or —NR$^{Q3}$—, wherein each occurrence of R$^{Q1}$, R$^{Q2}$ and R$^{Q3}$ is independently hydrogen, or an aliphatic, heteroaliphatic, alicyclic, heterocyclic, aryl or heteroaryl moiety; and pharmaceutically acceptable derivatives thereof.

In certain embodiments, the method further comprises steps of diversifying the macrolide obtained in step c to form a Migrastatin analog with the desired functionalization.

In certain embodiments, the present invention provides a method for preparing a Migrastatin analog having the structure:

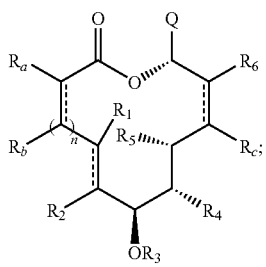

said method comprising steps of:

a. reacting a fragment Q with a compound having the structure:

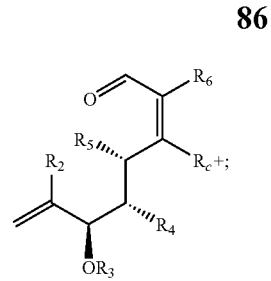

under suitable conditions to effect formation of an A-Q adduct having the structure:

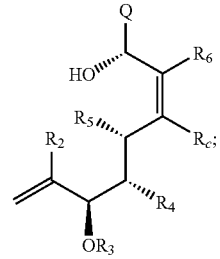

b. reacting A-Q formed in step a with a dienoic acid having the structure:

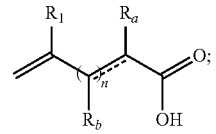

under suitable conditions to effect formation of an olefin having the structure:

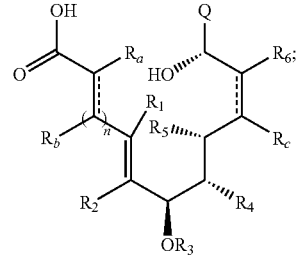

c. subjecting the olefin formed in step b to suitable conditions to effect formation of the macrolide having the structure:

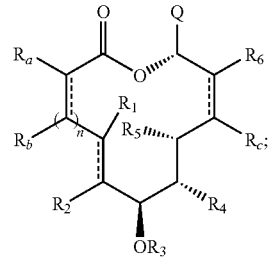

wherein $R_1$ and $R_2$ are each independently hydrogen, halogen, —CN, —S(O)$_{1-2}$R$^{1A}$, —NO$_2$, —COR$^{1A}$, —CO$_2$R$^{1A}$, —NR$^{1A}$C(=O)R$^{1B}$, —NR$^{1A}$C(=O)ORB, —CONR$^{1A}$R$^{1B}$, an aliphatic, heteroaliphatic, alicyclic, heterocyclic, aryl or heteroaryl moiety, or —WR$^{1A}$; wherein W is independently —O—, —S— or —NR$^{1C}$—, wherein each occurrence of R$^{1A}$, R$^{1B}$ and R$^{1C}$ is independently hydrogen, or an aliphatic, heteroaliphatic, alicyclic, heterocyclic, aryl or heteroaryl moiety; or $R_1$ and $R_2$, taken together with the carbon atoms to which they are attached, form an alicyclic, heterocyclic, aryl or heteroaryl moiety;

$R_3$ is hydrogen, an aliphatic, heteroaliphatic, alicyclic, heterocyclic, aryl or heteroaryl moiety; or a prodrug moiety or an oxygen protecting group;

$R_4$ is halogen, —$OR^{4A}$, —$OC(=O)R^A$ or $NR^{4A}R^{4B}$; wherein $R^{4A}$ and $R^{4B}$ are independently hydrogen, an aliphatic, heteroaliphatic, alicyclic, heterocyclic, aryl or heteroaryl moiety; a prodrug moiety, a nitrogen protecting group or an oxygen protecting group; or $R^{4A}$ and $R^{4B}$, taken together with the nitrogen atom to which they are attached, form a heterocyclic or heteroaryl moiety; or $R_4$, taken together with the carbon atom to which it is attached forms a moiety having the structure:

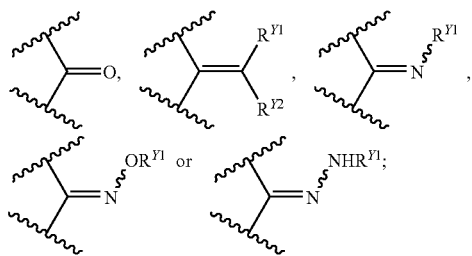

$R_5$ is hydrogen, an aliphatic, heteroaliphatic, alicyclic, heterocyclic, aryl or heteroaryl moiety;

$R_6$ is hydrogen, halogen, —CN, —$S(O)_{1-2}R^{6A}$, —$NO_2$, —$COR^{6A}$, —$CO_2R^{6A}$, —$NR^{6A}C(=O)R^{6B}$, —$NR^{6A}C(=O)OR^{6B}$, —$CONR^{6A}R^{6B}$, an aliphatic, heteroaliphatic, alicyclic, heterocyclic, aryl or heteroaryl moiety, or —$WR^{6A}$; wherein W is independently —O—, —S— or —$NR^{6C}$—, wherein each occurrence of $R^{6A}$, $R^{6B}$ and $R^{6C}$ is independently hydrogen, or an aliphatic, heteroaliphatic, alicyclic, heterocyclic, aryl or heteroaryl moiety; or $R_6$ and $R_c$, taken together with the carbon atoms to which they are attached, form an alicyclic, heterocyclic, aryl or heteroaryl moiety;

$R_a$ and each occurrence of $R_b$ are independently hydrogen, halogen, —CN, —$S(O)_{1-2}R^{a1}$, —$NO_2$, —$COR^{a1}$, —$CO_2R^{a1}$, —$NR^{a1}C(=O)R^{a2}$, —$NR^{a1}C(=O)OR^{a2}$, —$CONR^{a1}R^{a2}$, an aliphatic, heteroaliphatic, alicyclic, heterocyclic, aryl or heteroaryl moiety, or —$WR^{a1}$; wherein W is independently —O—, —S— or —$NR^{a3}$—, wherein each occurrence of $R^{a1}$, $R^{a2}$ and $R^{a3}$ is independently hydrogen, or an aliphatic, heteroaliphatic, alicyclic, heterocyclic, aryl or heteroaryl moiety; or $R_a$ and the adjacent occurrence of $R_b$, taken together with the carbon atoms to which they are attached, form an alicyclic, heterocyclic, aryl or heteroaryl moiety;

$R_c$ is hydrogen, halogen, —CN, —$S(O)_{1-2}R^{c1}$, —$NO_2$, —$COR^{c1}$, —$CO_2R^{c1}$, —$NR^{c1}C(=O)R^{c2}$, —$NR^{c1}C(=O)OR^{c2}$, —$CONR^{c1}R^{c2}$; an aliphatic, heteroaliphatic, alicyclic, heterocyclic, aryl or heteroaryl moiety, or —$WR^{c1}$; wherein W is independently —O—, —S— or —$NR^{c3}$—, wherein each occurrence of $R^{c1}$, $R^{c2}$ and $R^{c3}$ is independently hydrogen, or an aliphatic, heteroaliphatic, alicyclic, heterocyclic, aryl or heteroaryl moiety; or $R_c$ and $R_6$, taken together with the carbon atoms to which they are attached, form an alicyclic, heterocyclic, aryl or heteroaryl moiety;

n is an integer from 1 to 5; and

Q is hydrogen, halogen, —CN, —$S(O)_{1-2}R^{Q1}$, —$NO_2$, —$COR^{Q1}$, —$CO_2R^{Q1}$, —$NR^{Q1}C(=O)R^{Q2}$, —$NR^{Q1}C(=O)OR^{Q2}$, —$CONR^{Q1}R^{Q2}$, an aliphatic, heteroaliphatic, alicyclic, heterocyclic, aryl or heteroaryl moiety, or —$WR^{Q1}$; wherein W is independently —O—, —S— or —$NR^{Q3}$, wherein each occurrence of $R^{Q1}$, $R^{Q2}$ and $R^{Q3}$ is independently hydrogen, or an aliphatic, heteroaliphatic, alicyclic, heterocyclic, aryl or heteroaryl moiety; and pharmaceutically acceptable derivatives thereof.

In certain embodiments, the method further comprises steps of diversifying the macrolide obtained in step c to form a Migrastatin analog with the desired functionalization.

In certain embodiments, the present invention provides a method for preparing a Migrastatin analog having the structure:

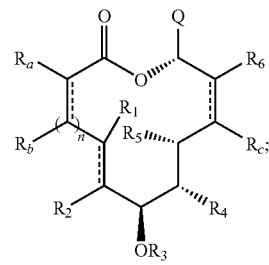

said method comprising steps of:

a. reacting a fragment Q with a compound having the structure:

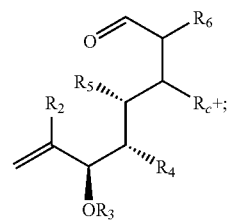

under suitable conditions to effect formation of an A-Q adduct having the structure:

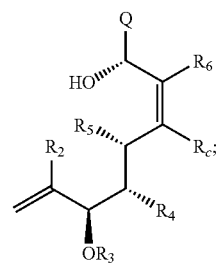

b. reacting A-Q formed in step a with n enone having the structure:

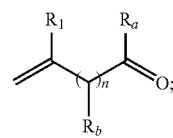

under suitable conditions to effect formation of an olefin having the structure:

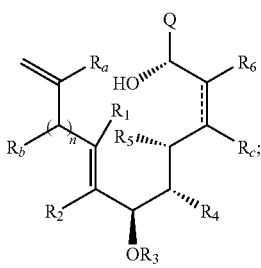

c. acylating the olefin formed in step b with a suitable reagent under suitable conditions to effect formation of an intermediate having the structure:

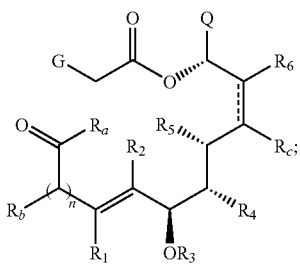

wherein G is a group suitable to effect ring closure; and d. subjecting the intermediate formed in step c to suitable conditions to effect formation of the macrolide having the structure:

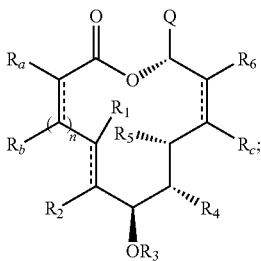

wherein $R_1$ and $R_2$ are each independently hydrogen, halogen, —CN, —S(O)$_{1\text{-}2}$R$^{1A}$, —NO$_2$, —COR$^{1A}$, —CO$_2$R$^{1A}$, —NR$^{1A}$C(=O)R$^{1B}$, —NR$^{1A}$C(=O)OR$^{1B}$, —CONR$^{1A}$R$^{1B}$, an aliphatic, heteroaliphatic, alicyclic, heterocyclic, aryl or heteroaryl moiety, or —WR$^{1A}$; wherein W is independently —O—, —S— or —NR$^{1C}$—, wherein each occurrence of R$^{1A}$, R$^{1B}$ and R$^{1C}$ is independently hydrogen, or an aliphatic, heteroaliphatic, alicyclic, heterocyclic, aryl or heteroaryl moiety; or $R_1$ and $R_2$, taken together with the carbon atoms to which they are attached, form an alicyclic, heterocyclic, aryl or heteroaryl moiety;

$R_3$ is hydrogen, an aliphatic, heteroaliphatic, alicyclic, heterocyclic, aryl or heteroaryl moiety; or a prodrug moiety or an oxygen protecting group;

$R_4$ is halogen, —OR$^{4A}$, —OC(=O)R$^{4A}$ or —NR$^{4A}$R$^{4B}$; wherein R$^{4A}$ and R$_{4B}$ are independently hydrogen, an aliphatic, heteroaliphatic, alicyclic, heterocyclic, aryl or heteroaryl moiety; a prodrug moiety, a nitrogen protecting group or an oxygen protecting group; or R$^{4A}$ and R$^{4B}$, taken together with the nitrogen atom to which they are attached, form a heterocyclic or heteroaryl moiety;

$R_5$ is hydrogen, an aliphatic, heteroaliphatic, alicyclic, heterocyclic, aryl or heteroaryl moiety;

$R^6$ is hydrogen, halogen, —CN, —S(O)$_{1\text{-}2}$R$^{6A}$, —NO$_2$, —COR$^{6A}$, —CO$_2$R$^{6A}$, —NR$^{6A}$C(=O)R$^{6B}$, —NR$^{6A}$C(=O)OR$^{6B}$, —CONR$^{6A}$R$^{6B}$, an aliphatic, heteroaliphatic, alicyclic, heterocyclic, aryl or heteroaryl moiety, or —WR$^{6A}$; wherein W is independently —O—, —S— or —NR$^{6C}$—, wherein each occurrence of R$^{6A}$, R$^{6B}$ and R$^{6C}$ is independently hydrogen, or an aliphatic, heteroaliphatic, alicyclic, heterocyclic, aryl or heteroaryl moiety; or $R_6$ and $R_c$, taken together with the carbon atoms to which they are attached, form an alicyclic, heterocyclic, aryl or heteroaryl moiety;

$R_a$ and each occurrence of $R_b$ are independently hydrogen, halogen, —CN, —S(O)$_{1\text{-}2}$R$^{a1}$, —NO$_2$, —COR$^{a1}$, —CO$_2$R$^{a1}$, —NR$^{a1}$C(=O)R$^{a2}$, —NR$^{a1}$C(=O)OR$^{a2}$, —CONR$^{a1}$R$^{a2}$, an aliphatic, heteroaliphatic, alicyclic, heterocyclic, aryl or heteroaryl moiety, or —WR$^{a1}$; wherein W is independently —O—, —S— or —NR$^{a3}$—, wherein each occurrence of R$^{a1}$, R$^{a2}$ and R$^{a3}$ is independently hydrogen, or an aliphatic, heteroaliphatic, alicyclic, heterocyclic, aryl or heteroaryl moiety; or $R_a$ and the adjacent occurrence of $R_b$, taken together with the carbon atoms to which they are attached, form an alicyclic, heterocyclic, aryl or heteroaryl moiety;

$R_c$ is hydrogen, halogen, —CN, —S(O)$_{1\text{-}2}$R$^{c1}$, —NO$_2$, —COR$^{c1}$, —CO$_2$R$^{c1}$, —NR$^{c1}$C(=O)R$^{c2}$, —NR$^{c1}$C(=O)OR$^{c2}$, —CONR$^{c1}$R$^{c2}$; an aliphatic, heteroaliphatic, alicyclic, heterocyclic, aryl or heteroaryl moiety, or —WR$^{c1}$; wherein W is independently —O—, —S— or —NR$^{c3}$, wherein each occurrence of R$^{c1}$, R$^{c2}$ and R$^{c3}$ is independently hydrogen, or an aliphatic, heteroaliphatic, alicyclic, heterocyclic, aryl or heteroaryl moiety; or $R_c$ and $R_6$, taken together with the carbon atoms to which they are attached, form an alicyclic, heterocyclic, aryl or heteroaryl moiety;

n is an integer from 1 to 5; and

Q is hydrogen, halogen, —CN, —S(O)$_{1\text{-}2}$R$^{Q1}$, —NO$_2$, —COR$^{Q1}$, —CO$_2$R$^{Q1}$, —NR$^{Q1}$C(=O)R$^{Q2}$, —NR$^{Q1}$C(=O)OR$^{Q2}$, —CONR$^{Q1}$R$^{Q2}$, an aliphatic, heteroaliphatic, alicyclic, heterocyclic, aryl or heteroaryl moiety, or —WR$^{Q1}$; wherein W is independently —O—, —S— or —NR$^{Q3}$—, wherein each occurrence of R$^{Q1}$, R$^{Q2}$ and R$^{Q3}$ is independently hydrogen, or an aliphatic, heteroaliphatic, alicyclic, heterocyclic, aryl or heteroaryl moiety, and pharmaceutically acceptable derivatives thereof.

In certain embodiments, G is —P(=O)R'$_2$ and step d involves subjecting the intermediate formed in step c to Horner-Wadsworth-Emmons reaction conditions to effect formation of the macrolide. In certain other embodiments, the method further comprises steps of diversifying the macrolide obtained in step d to form a Migrastatin analog with the desired functionalization.

In certain embodiments, the present invention provides a method for preparing a Migrastatin analog having the structure:

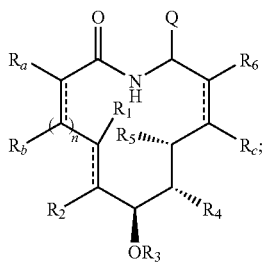

said method comprising steps of:

a. reacting a fragment Q with a compound having the structure:

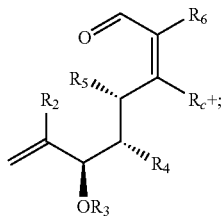

under suitable conditions to effect formation of an alcohol adduct having the structure:

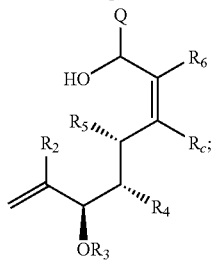

b. converting the alcohol adduct formed in step a under suitable conditions to form an amine having the structure:

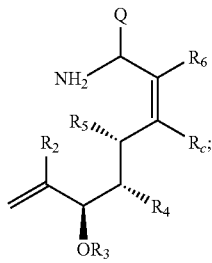

c. reacting the amine formed in step b with a dienoic acid having the structure:

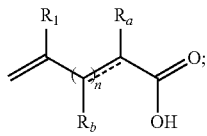

under suitable conditions to effect formation of an amide having the structure:

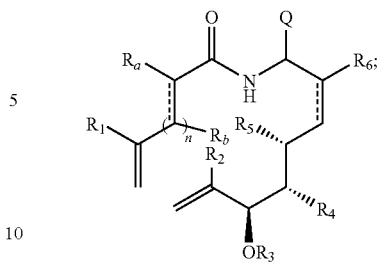

and d. subjecting the amide formed in step c to ring closing metathesis reaction conditions to effect formation of the macrolide having the structure:

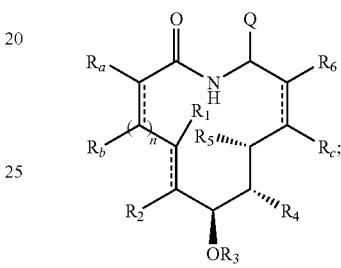

wherein $R_1$ and $R_2$ are each independently hydrogen, halogen, —CN, —S(O)$_{1-2}$R$^{1A}$, —NO$_2$, —COR$^{1A}$, —CO$_2$R$^{1A}$, —NR$^{1A}$C(=O)R$^{1B}$, —NR$^{1A}$C(=O)OR$^{1B}$, —CONR$^{1A}$R$^{1B}$, an aliphatic, heteroaliphatic, alicyclic, heterocyclic, aryl or heteroaryl moiety, or —WR$^{1A}$; wherein W is independently —O—, —S— or —NR$_{1C}$—, wherein each occurrence of R$^{1A}$, R$^{1B}$ and R$^{1C}$ is independently hydrogen, or an aliphatic, heteroaliphatic, alicyclic, heterocyclic, aryl or heteroaryl moiety; or $R_1$ and $R_2$, taken together with the carbon atoms to which they are attached, form an alicyclic, heterocyclic, aryl or heteroaryl moiety;

$R_3$ is hydrogen, an aliphatic, heteroaliphatic, alicyclic, heterocyclic, aryl or heteroaryl moiety; or a prodrug moiety or an oxygen protecting group;

$R_4$ is halogen, —OR$^{4A}$, —C(=O)R$^{4A}$ or —NR$^{4A}$R$^{4B}$; wherein R$^{4A}$ and R$^{4B}$ are independently hydrogen, an aliphatic, heteroaliphatic, alicyclic, heterocyclic, aryl or heteroaryl moiety; a prodrug moiety, a nitrogen protecting group or an oxygen protecting group; or R$^{4A}$ and R$^{4B}$, taken together with the nitrogen atom to which they are attached, form a heterocyclic or heteroaryl moiety;

$R_5$ is hydrogen, an aliphatic, heteroaliphatic, alicyclic, heterocyclic, aryl or heteroaryl moiety;

$R_6$ is hydrogen, halogen, —CN, —S(O)$_{1-2}$R$^{6A}$, —NO$_2$, —COR$^{6A}$, —CO$_2$R$^{6A}$, —NR$^{6A}$C(=O)R$^{6B}$, —NR$^{6A}$C(=O)OR$^{6B}$, —CONR$^{6A}$R$^{6B}$, an aliphatic, heteroaliphatic, alicyclic, heterocyclic, aryl or heteroaryl moiety, or —WR$^{6A}$; wherein W is independently —O—, —S— or —NR$^{6C}$—, wherein each occurrence of R$^{6A}$, R$^{6B}$ and R$^{6C}$ is independently hydrogen, or an aliphatic, heteroaliphatic, alicyclic, heterocyclic, aryl or heteroaryl moiety; or $R_6$ and $R_c$, taken together with the carbon atoms to which they are attached, form an alicyclic, heterocyclic, aryl or heteroaryl moiety;

$R_a$ and each occurrence of $R_b$ are independently hydrogen, halogen, —CN, —S(O)$_{1-2}$R$^{a1}$, —NO$_2$, —COR$^{a1}$, —CO$_2$R$^{a1}$, —NR$^{a1}$C(=O)R$^{a2}$, —NR$^{a1}$C(=O)OR$^{a2}$, —CONR$^{a1}$R$^{a2}$, an aliphatic, heteroaliphatic, alicyclic, heterocyclic, aryl or heteroaryl moiety, or —WR$^{a1}$; wherein W is independently —O—, —S— or —NR$^{a3}$—, wherein each occurrence of R$^{a1}$, R$^{a2}$ and R$^{a3}$ is independently hydrogen, or an aliphatic, heteroaliphatic, alicyclic, heterocyclic, aryl or heteroaryl moiety; or R$_a$ and the adjacent occurrence of R$_b$, taken together with the carbon atoms to which they are attached, form an alicyclic, heterocyclic, aryl or heteroaryl moiety;

R$_c$ is hydrogen, halogen, —CN, —S(O)$_{1-2}$R$^{c1}$, —NO$_2$, —COR$^{c1}$, —CO$_2$R$^{c1}$, —NR$^{c1}$C(=O)R$^{c2}$, —NR$^{c1}$C(=O)OR$^{c2}$, —CONR$^{c1}$R$^{c2}$; an aliphatic, heteroaliphatic, alicyclic, heterocyclic, aryl or heteroaryl moiety, or —WR$^{c1}$; wherein W is independently —O—, —S— or —NR$^{c3}$—, wherein each occurrence of R$^{c1}$, R$^{c2}$ and R$^{c3}$ is independently hydrogen, or an aliphatic, heteroaliphatic, alicyclic, heterocyclic, aryl or heteroaryl moiety; or R$_c$ and R$_6$, taken together with the carbon atoms to which they are attached, form an alicyclic, heterocyclic, aryl or heteroaryl moiety;

n is an integer from 1 to 5;

Q is hydrogen, halogen, —CN, —S(O)$_{1-2}$R$^{Q1}$, —NO$_2$, —COR$^{Q1}$, —CO$_2$R$^{Q1}$, —NR$^{Q1}$C(=O)R$^{Q2}$, —NR$^{Q1}$C(=O)OR$^{Q2}$, —CONR$^{Q1}$R$^{Q2}$, an aliphatic, heteroaliphatic, alicyclic, heterocyclic, aryl or heteroaryl moiety, or —WR$^{Q1}$; wherein W is independently —O—, —S— or —NR$^{Q3}$—, wherein each occurrence of R$^{Q1}$, R$^{Q2}$ and R$^{Q3}$ is independently hydrogen, or an aliphatic, heteroaliphatic, alicyclic, heterocyclic, aryl or heteroaryl moiety; and pharmaceutically acceptable derivatives thereof.

In certain embodiments, the method further comprises steps of diversifying the macrolide obtained in step d to form a macrolactam (i.e., Migrastatin analog) with the desired functionalization.

In certain embodiments, the present invention provides a method for preparing a Migrastatin analog having the structure:

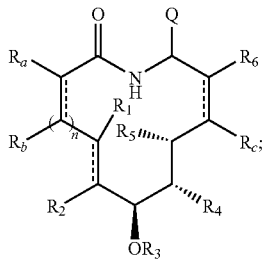

said method comprising steps of:

b. reacting a fragment Q with a compound having the structure:

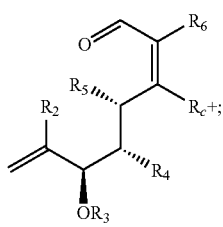

under suitable conditions to effect formation of an alcohol adduct having the structure:

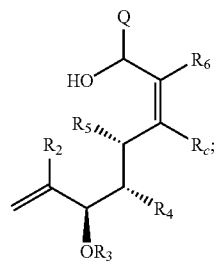

b. converting the alcohol adduct formed in step a under suitable conditions to form an amine having the structure:

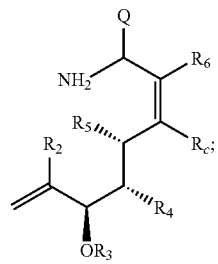

d. reacting the amine formed in step b with a dienoic acid having the structure:

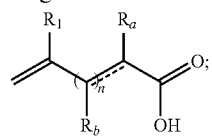

under suitable conditions to effect formation of an olefin having the structure:

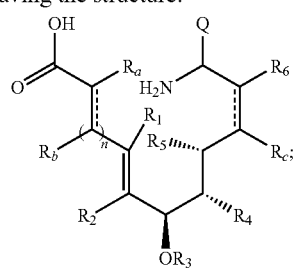

and e. subjecting the olefin formed in step c to suitable conditions to effect formation of the macrolactam having the structure:

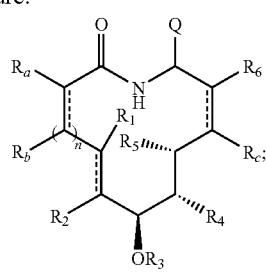

wherein R$_1$ and R$_2$ are each independently hydrogen, halogen, —CN, —S(O)$_{1-2}$R$^{1A}$, —NO$_2$, —COR$^{1A}$, —CO$_2$R$^{1A}$, —NR$^{1A}$C(=O)R$^{1B}$, —NR$^{1A}$C(=O)OR$^{1B}$, —CONR$^{1A}$R$^{1B}$, an aliphatic, heteroaliphatic, alicyclic, heterocyclic, aryl or heteroaryl moiety, or —WR$^{1A}$; wherein W is independently —O—, —S— or —NR$^{1C}$—, wherein each occurrence of R$^{1A}$, R$^{1B}$ and R$^{1C}$ is independently hydrogen, or an aliphatic, heteroaliphatic, alicyclic, heterocyclic, aryl or heteroaryl moiety; or R$_1$ and R$_2$, taken together with the carbon atoms to which they are attached, form an alicyclic, heterocyclic, aryl or heteroaryl moiety;

R$_3$ is hydrogen, an aliphatic, heteroaliphatic, alicyclic, heterocyclic, aryl or heteroaryl moiety; or a prodrug moiety or an oxygen protecting group;

R$_4$ is halogen, —OR$^{4A}$, —C(=O)R$^{4A}$ or —NR$^{4A}$R$^{4B}$; wherein R$^{4A}$ and R$^{4B}$ are independently hydrogen, an aliphatic, heteroaliphatic, alicyclic, heterocyclic, aryl or heteroaryl moiety; a prodrug moiety, a nitrogen protecting group or an oxygen protecting group; or R$^{4A}$ and R$^{4B}$, taken together with the nitrogen atom to which they are attached, form a heterocyclic or heteroaryl moiety;

R$_5$ is hydrogen, an aliphatic, heteroaliphatic, alicyclic, heterocyclic, aryl or heteroaryl moiety;

R$_6$ is hydrogen, halogen, —CN, —S(O)$_{1-2}$R$^{6A}$, —NO$_2$, —COR$^{6A}$, —CO$_2$R$^{6A}$, —NR$^{6A}$C(=O)R$^{6B}$, NR$^{6A}$C(=O)OR$^{6B}$, —CONR$^{6A}$R$^{6B}$, an aliphatic, heteroaliphatic, alicyclic, heterocyclic, aryl or heteroaryl moiety, or —WR$^{6A}$; wherein W is independently —O—, —S— or —NR$^{6C}$—, wherein each occurrence of R$^{6A}$, R$^{6B}$ and R$^{6C}$ is independently hydrogen, or an aliphatic, heteroaliphatic, alicyclic, heterocyclic, aryl or heteroaryl moiety; or R$_6$ and R$_c$, taken together with the carbon atoms to which they are attached, form an alicyclic, heterocyclic, aryl or heteroaryl moiety;

R$_a$ and each occurrence of R$_b$ are independently hydrogen, halogen, —CN, —S(O)$_{1-2}$R$^{a1}$, —NO$_2$, —COR$^{a2}$, —CO$_2$R$^{a1}$, —NR$^{a1}$C(=O)R$^{a2}$, —NR$^{a1}$C(=O)OR$^{a2}$, —CONR$^{a1}$R$^{a2}$, an aliphatic, heteroaliphatic, alicyclic, heterocyclic, aryl or heteroaryl moiety, or —WR$^{a1}$; wherein W is independently —O—, —S— or —NR$^{a3}$—, wherein each occurrence of R$^{a1}$, R$^{a2}$ and R$^{a3}$ is independently hydrogen, or an aliphatic, heteroaliphatic, alicyclic, heterocyclic, aryl or heteroaryl moiety; or R$_a$ and the adjacent occurrence of R$_b$, taken together with the carbon atoms to which they are attached, form an alicyclic, heterocyclic, aryl or heteroaryl moiety;

R$_c$ is hydrogen, halogen, —CN, —S(O)$_{1-2}$R$^{c1}$, —NO$_2$, —COR$^{c1}$, —CO$_2$R$^{c1}$, —NR$^{c1}$C(=O)R$^{c2}$, —NR$^{c1}$C(=O)OR$^{c2}$, —CONR$^{c1}$R$^{c2}$; an aliphatic, heteroaliphatic, alicyclic, heterocyclic, aryl or heteroaryl moiety, or —WR$^{c1}$; wherein W is independently —O—, —S— or —NR$^{c3}$—, wherein each occurrence of R$^{c1}$, R$^{c2}$ and R$^{c3}$ is independently hydrogen, or an aliphatic, heteroaliphatic, alicyclic, heterocyclic, aryl or heteroaryl moiety; or R$_c$ and R$_6$, taken together with the carbon atoms to which they are attached, form an alicyclic, heterocyclic, aryl or heteroaryl moiety;

n is an integer from 1 to 5;

Q is hydrogen, halogen, —CN, —S(O)$_{1-2}$R$^{Q1}$, —NO$_2$, —COR$^{Q1}$, —CO$_2$R$^{Q1}$, —NR$^{Q1}$C(=O)R$^{Q2}$, —NR$^{Q1}$C(=O)OR$^{Q2}$, —CONR$^{Q1}$R$^{Q2}$, an aliphatic, heteroaliphatic, alicyclic, heterocyclic, aryl or heteroaryl moiety, or —WR$^{Q1}$; wherein W is independently —O—, —S— or —NR$^{Q3}$—, wherein each occurrence of R$^{Q1}$, R$^{Q2}$ and R$^{Q3}$ is independently hydrogen, or an aliphatic, heteroaliphatic, alicyclic, heterocyclic, aryl or heteroaryl moiety; and pharmaceutically acceptable derivatives thereof.

In certain embodiments, the method further comprises steps of diversifying the macrolide obtained in step e to form a macrolactam (i.e., Migrastatin analog) with the desired functionalization.

In certain embodiments, the present invention provides a method for preparing a Migrastatin analog having the structure:

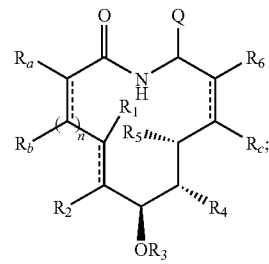

said method comprising steps of:

a. reacting a fragment Q with a compound having the structure:

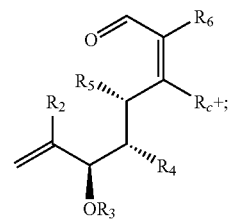

under suitable conditions to effect formation of an A-Q adduct having the structure:

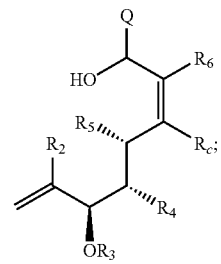

b. converting the alcohol adduct formed in step a under suitable conditions to form an amine having the structure:

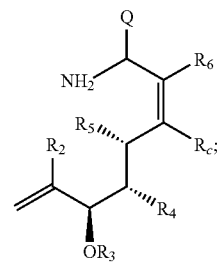

c. reacting the amine formed in step b with an enone having the structure:

[structure shown with $R_1$, $R_a$, $R_b$, n, O]

under suitable conditions to effect formation of an olefin having the structure:

[structure shown with Q, $R_a$, $H_2N$, $R_1$, $R_b$, n, $R_5$, $R_6$, $R_c$, $R_2$, $R_4$, $OR_3$, O]

d. acylating the olefin formed in step c with a suitable reagent under suitable conditions to effect formation of an intermediate having the structure:

[structure shown with G, O, Q, N, H, $R_a$, $R_5$, $R_6$, $R_c$, $R_b$, n, $R_2$, $R_4$, $R_1$, $OR_3$]

wherein G is a group suitable to effect ring closure; and e. subjecting the intermediate formed in step d to suitable conditions to effect formation of the macrolide having the structure:

[structure shown with O, Q, $R_a$, N, H, $R_1$, $R_6$, $R_c$, $R_b$, n, $R_5$, $R_2$, $R_4$, $OR_3$]

wherein $R_1$ and $R_2$ are each independently hydrogen, halogen, —CN, —S(O)$_{1-2}$R$^{1A}$, —NO$_2$, —COR$^{1A}$, —CO$_2$R$^{1A}$, —NR$^{1A}$C(=O)R$^{1B}$, —NR$^{1A}$C(=O)OR$^{1B}$, —CONR$^{1A}$R$^{1B}$, an aliphatic, heteroaliphatic, alicyclic, heterocyclic, aryl or heteroaryl moiety, or —WR$^{1A}$; wherein W is independently —O—, —S— or —NR$^{1C}$—, wherein each occurrence of R$^{1A}$, R$^{1B}$ and R$^{1C}$ is independently hydrogen, or an aliphatic, heteroaliphatic, alicyclic, heterocyclic, aryl or heteroaryl moiety; or $R_1$ and $R_2$, taken together with the carbon atoms to which they are attached, form an alicyclic, heterocyclic, aryl or heteroaryl moiety;

$R_3$ is hydrogen, an aliphatic, heteroaliphatic, alicyclic, heterocyclic, aryl or heteroaryl moiety; or a prodrug moiety or an oxygen protecting group;

$R_4$ is halogen, OR$^{4A}$, —OC(=O)R$^{4A}$ or NR$^{4A}$R$^{4B}$; wherein R$^{4A}$ and R$^{4B}$ are independently hydrogen, an aliphatic, heteroaliphatic, alicyclic, heterocyclic, aryl or heteroaryl moiety; a prodrug moiety, a nitrogen protecting group or an oxygen protecting group; or R$^{4A}$ and R$^{4B}$, taken together with the nitrogen atom to which they are attached, form a heterocyclic or heteroaryl moiety;

$R_5$ is hydrogen, an aliphatic, heteroaliphatic, alicyclic, heterocyclic, aryl or heteroaryl moiety;

$R_6$ is hydrogen, halogen, —CN, —S(O)$_{1-2}$R$^{6A}$, —NO$_2$, —COR$^{6A}$, —CO$_2$R$^{6A}$, —NR$^{6A}$C(=O)R$^{6B}$, —NR$^{6A}$C(=O)OR$^{6B}$, —CONR$^{6A}$R$^{6B}$, an aliphatic, heteroaliphatic, alicyclic, heterocyclic, aryl or heteroaryl moiety, or —WR$^{6A}$; wherein W is independently —O—, —S— or —NR$^{6C}$—, wherein each occurrence of R$^{6A}$, R$^{6B}$ and R$^{6C}$ is independently hydrogen, or an aliphatic, heteroaliphatic, alicyclic, heterocyclic, aryl or heteroaryl moiety; or $R_6$ and $R^c$, taken together with the carbon atoms to which they are attached, form an alicyclic, heterocyclic, aryl or heteroaryl moiety;

$R_a$ and each occurrence of $R_b$ are independently hydrogen, halogen, —CN, —S(O)$_{1-2}$R$^{a1}$, —NO$_2$, —COR$^{a1}$, —CO$_2$R$^{a1}$, —NR$^{a1}$C(=O)R$^{a2}$, —NR$^{a1}$C(=O)OR$^{a2}$, —CONR$^{a1}$R$^{a2}$, an aliphatic, heteroaliphatic, alicyclic, heterocyclic, aryl or heteroaryl moiety, or —WR$^{a1}$; wherein W is independently —O—, —S— or —NR$^{a3}$—, wherein each occurrence of R$^{a1}$, R$^{a2}$ and R$^{a3}$ is independently hydrogen, or an aliphatic, heteroaliphatic, alicyclic, heterocyclic, aryl or heteroaryl moiety; or $R_a$ and the adjacent occurrence of $R_b$, taken together with the carbon atoms to which they are attached, form an alicyclic, heterocyclic, aryl or heteroaryl moiety;

$R_c$ is hydrogen, halogen, —CN, —S(O)$_{1-2}$R$^{c1}$, —NO$_2$, —COR$^{c1}$, —CO$_2$R$^{c1}$, —NR$^{c1}$C(=O)R$^{c2}$, —NR$^{c1}$C(=O)OR$^{c2}$, —CONR$^{c1}$R$^{c2}$; an aliphatic, heteroaliphatic, alicyclic, heterocyclic, aryl or heteroaryl moiety, or —WR$^{c1}$; wherein W is independently —O—, —S— or —NR$^{c3}$—, wherein each occurrence of R$^{c1}$, R$^{c2}$ and R$^{c3}$ is independently hydrogen, or an aliphatic, heteroaliphatic, alicyclic, heterocyclic, aryl or heteroaryl moiety; or $R_c$ and $R_6$, taken together with the carbon atoms to which they are attached, form an alicyclic, heterocyclic, aryl or heteroaryl moiety;

n is an integer from 1 to 5; and

Q is hydrogen, halogen, —CN, —S(O)$_{1-2}$R$^{Q1}$, —NO$_2$, —COR$^{Q1}$, —CO$_2$R$^{Q1}$, —NR$^{Q1}$C(=O)R$^{Q2}$, —NR$^{Q1}$C(=O)OR$^{Q2}$, —CONR$^{Q1}$R$^{Q2}$, an aliphatic, heteroaliphatic, alicyclic, heterocyclic, aryl or heteroaryl moiety, or —WR$^{Q1}$; wherein W is independently —O—, —S— or —NR$^{Q3}$—, wherein each occurrence of R$^{Q1}$, R$^{Q2}$ and R$^{Q3}$ is independently hydrogen, or an aliphatic, heteroaliphatic, alicyclic, heterocyclic, aryl or heteroaryl moiety; and pharmaceutically acceptable derivatives thereof.

In certain embodiments, G is —P(=O)R'$_2$ and step e involves subjecting the intermediate formed in step d to Horner-Wadsworth-Emmons reaction conditions to effect formation of the macrolide. In certain other embodiments, the method further comprises steps of diversifying the macrolide obtained in step e to form a Migrastatin analog with the desired functionalization.

3) Pharmaceutical Compositions

Iin another aspect of the present invention, pharmaceutical compositions are provided, which comprise any one of the compounds described herein (or a prodrug, pharmaceutically acceptable salt or other pharmaceutically acceptable derivative thereof), and optionally comprise a pharmaceutically acceptable carrier, adjuvant or vehicle. In certain other embodiments, the compositions of the invention are useful for the treatment of cancer and disorders associated with metastasis and/or angiogenesis. In certain embodiments, the inventive compositions optionally further comprise one or more additional therapeutic agents. In certain other embodiments, the additional therapeutic agent is a cytotoxic agent, as discussed in more detail herein. In certain other embodiments, the additional therapeutic agent is an anticancer agent. In certain embodiments, the anticancer agent is an epothilone, taxol, radicicol or TMC-95A/B. In certain embodiments, the epothilone is 12,13-desoxyepothilone B, (E)-9,10-dehydro-12,13-desoxyEpoB and 26-$CF_3$-(E)-9,10-dehydro-12,13-desoxyEpoB. Alternatively, a compound of this invention may be administered to a patient in need thereof in combination with the administration of one or more other therapeutic agents. For example, additional therapeutic agents for conjoint administration or inclusion in a pharmaceutical composition with a compound of this invention may be an antiangiogenesis agent or anticancer agent approved for the treatment of cancer, as discussed in more detail herein, or it may be any one of a number of agents undergoing approval in the Food and Drug Administration that ultimately obtain approval for the treatment of cancer.

As described above, the pharmaceutical compositions of the present invention additionally comprise a pharmaceutically acceptable carrier, adjuvant or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutical compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutical composition, its use is contemplated to be within the scope of this invention. Some examples of materials which can serve as pharmaceutically acceptable carriers include, but are not limited to, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatine; talc; excipients such as cocoa butter and suppository waxes; oils such as peanut oil, cottonseed oil; safflower oil, sesame oil; olive oil; corn oil and soybean oil; glycols; such as propylene glycol; esters such as ethyl oleate and ethyl laurate; agar; buffering agents such as magnesium hydroxide and aluminum hydroxide; alginic acid; pyrogenfree water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and penning agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension or crystalline or amorphous material with poor water solubility. The rate of absorption of the drug then depends upon its rate of dissolution that, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include (poly (orthoesters) and poly(anhydrides). Depot injectable formulations are also prepared by entrapping the drug in liposomes or microemulsions, which are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in microencapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose and starch. Such dosage forms may also comprise, as in normal practice, additional substances other than inert diluents, e.g., tableting lubricants and other tableting aids such as magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions, which can be used, include polymeric substances and waxes.

The present invention encompasses pharmaceutically acceptable topical formulations of inventive compounds. The term "pharmaceutically acceptable topical formulation", as used herein, means any formulation which is pharmaceutically acceptable for intradermal administration of a compound of the invention by application of the formulation to the epidermis. In certain embodiments of the invention, the topical formulation comprises a carrier system. Pharmaceutically effective carriers include, but are not limited to, solvents (e.g., alcohols, poly alcohols, water), creams, lotions, ointments, oils, plasters, liposomes, powders, emulsions, microemulsions, and buffered solutions (e.g., hypotonic or buffered saline) or any other carrier known in the art for topically administering pharmaceuticals. A more complete listing of art-known carriers is provided by reference texts that are standard in the art, for example, Remington's Pharmaceutical Sciences, 16th Edition, 1980 and 17th Edition, 1985, both published by Mack Publishing Company, Easton, Pa., the disclosures of which are incorporated herein by reference in their entireties. In certain other embodiments, the topical formulations of the invention may comprise excipients. Any pharmaceutically acceptable excipient known in the art may be used to prepare the inventive pharmaceutically acceptable topical formulations. Examples of excipients that can be included in the topical formulations of the invention include, but are not limited to, preservatives, antioxidants, moisturizers, emollients, buffering agents, solubilizing agents, other penetration agents, skin protectants, surfactants, and propellants, and/or additional therapeutic agents used in combination to the inventive compound. Suitable preservatives include, but are not limited to, alcohols, quaternary amines, organic acids, parabens, and phenols. Suitable antioxidants include, but are not limited to, ascorbic acid and its esters, sodium bisulfite, butylated hydroxytoluene, butylated hydroxyanisole, tocopherols, and chelating agents like EDTA and citric acid. Suitable moisturizers include, but are not limited to, glycerine, sorbitol, polyethylene glycols, urea, and propylene glycol. Suitable buffering agents for use with the invention include, but are not limited to, citric, hydrochloric, and lactic acid buffers. Suitable solubilizing agents include, but are not limited to, quaternary ammonium chlorides, cyclodextrins, benzyl benzoate, lecithin, and polysorbates. Suitable skin protectants that can be used in the topical formulations of the invention include, but are not limited to, vitamin E oil, allatoin, dimethicone, glycerin, petrolatum, and zinc oxide.

In certain embodiments, the pharmaceutically acceptable topical formulations of the invention comprise at least a compound of the invention and a penetration enhancing agent. The choice of topical formulation will depend or several factors, including the condition to be treated, the physicochemical characteristics of the inventive compound and other excipients present, their stability in the formulation, available manufacturing equipment, and costs constraints. As used herein the term "penetration enhancing agent" means an agent capable of transporting a pharmacologically active compound through the stratum corneum and into the epidermis or dermis, preferably, with little or no systemic absorption. A wide variety of compounds have been evaluated as to their effectiveness in enhancing the rate of penetration of drugs through the skin. See, for example, Percutaneous Penetration Enhancers, Maibach H. I. and Smith H. E. (eds.), CRC Press, Inc., Boca Raton, Fla. (1995), which surveys the use and testing of various skin penetration enhancers, and Buyuktimkin et al., Chemical Means of Transdermal Drug Permeation Enhancement in Transdermal and Topical Drug Delivery Systems, Gosh T. K., Pfister W. R., Yum S. I. (Eds.), Interpharm Press Inc., Buffalo Grove, Ill. (1997). In certain exemplary embodiments, penetration agents for use with the invention include, but are not limited to, triglycerides (e.g., soybean oil), aloe compositions (e.g., aloe-vera gel), ethyl alcohol, isopropyl alcohol, octolyphenylpolyethylene glycol, oleic acid, polyethylene glycol 400, propylene glycol, N-decylmethylsulfoxide, fatty acid esters (e.g., isopropyl myristate, methyl laurate, glycerol monooleate, and propylene glycol monooleate) and N-methylpyrrolidone.

In certain embodiments, the compositions may be in the form of ointments, pastes, creams, lotions, gels, powders, solutions, sprays, inhalants or patches. In certain exemplary embodiments, formulations of the compositions according to the invention are creams, which may further contain saturated or unsaturated fatty acids such as stearic acid, palmitic acid, oleic acid, palmito-oleic acid, cetyl or oleyl alcohols, stearic acid being particularly preferred. Creams of the invention may also contain a non-ionic surfactant, for example, polyoxy-40-stearate. In certain embodiments, the active component is admixed under sterile conditions with a pharmaceutically acceptable carrier, adjuvant or vehicle and any needed preservatives or buffers as may be required. Ophthalmic formulation, eardrops, and eye drops are also contemplated as being within the scope of this invention. Additionally, the present invention contemplates the use of transdermal patches, which have the added advantage of providing controlled delivery of a compound to the body. Such dosage forms are made by dissolving or dispensing the compound in the proper medium. As discussed above, penetration enhancing agents can also be used to increase the flux of the compound across the skin. The rate can be controlled by either providing a rate controlling membrane or by dispersing the compound in a polymer matrix or gel.

It will also be appreciated that the compounds and pharmaceutical compositions of the present invention can be formulated and employed in combination therapies, that is, the compounds and pharmaceutical compositions can be formulated with or administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another anticancer agent), or they may achieve different effects (e.g., control of any adverse effects).

For example, other therapies or therapeutic agents that may be used in combination with the inventive compounds of the present invention include surgery, radiotherapy (in but a few examples, γ-radiation, neutron beam radiotherapy, electron beam radiotherapy, proton therapy, brachytherapy, and systemic radioactive isotopes, to name a few), endocrine therapy, biologic response modifiers (interferons, interleukins, and tumor necrosis factor (TNF) to name a few), hyperthermia and cryotherapy, agents to attenuate any adverse effects (e.g., antiemetics), and other approved chemotherapeutic drugs, including, but not limited to, alkylating drugs (mechlorethamine, chlorambucil, Cyclophosphamide, Melphalan, Ifosfamide), antimetabolites (Methotrexate), purine antagonists and pyrimidine antagonists (6-Mercaptopurine, 5-Fluorouracil, Cytarabile, Gemcitabine), spindle poisons (Vinblastine, Vincristine, Vinorelbine, Paclitaxel), podophyllotoxins (Etoposide, Irinotecan, Topotecan), antibiotics (Doxorubicin, Bleomycin, Mitomycin), nitrosoureas (Carmustine, Lomustine), inorganic ions (Cisplatin, Carboplatin), enzymes (Asparaginase), and hormones (Tamoxifen, Leuprolide, Flutamide, and Megestrol), to name a few. For a more comprehensive discussion of updated cancer therapies see, The Merck Manual, Seventeenth Ed. 1999, the entire contents of which are hereby incorporated by reference. See also the National Cancer Institute (CNI) website (www.nci.nih.gov) and the Food and Drug Administration (FDA) website for a list of the FDA approved oncology drugs (www.fda.gov/cder/cancer/druglistframe—See Appendix A).

In certain embodiments, the pharmaceutical compositions of the present invention further comprise one or more additional therapeutically active ingredients (e.g., chemotherapeutic and/or palliative). For purposes of the invention, the term "Palliative" refers to treatment that is focused on the relief of symptoms of a disease and/or side effects of a therapeutic regimen, but is not curative. For example, palliative treatment encompasses painkillers, antinausea medications and anti-sickness drugs. In addition, chemotherapy, radiotherapy and surgery can all be used palliatively (that is, to reduce symptoms without going for cure; e.g., for shrinking tumors and reducing pressure, bleeding, pain and other symptoms of cancer).

4) Research Uses, Pharmaceutical Uses and Methods of Treatment

Research Uses

According to the present invention, the inventive compounds may be assayed in any of the available assays known in the art for identifying compounds having antiangiogenic activity and/or antiproliferative activity. For example, the assay may be cellular or non-cellular, in vivo or in vitro, high- or low-throughput format, etc.

Thus, in one aspect, compounds of this invention which are of particular interest include those which:

exhibit activity as inhibitors of cell migration;

exhibit an antiproliferative and/or an antiangiogenic effect on solid tumors;

facilitate wound healing;

exhibit a favorable therapeutic profile (e.g., safety, efficacy, and stability).

As discussed above, certain of the compounds as described herein exhibit activity generally as inhibitors of cell migration and/or angiogenesis. More specifically, compounds of the invention act as inhibitors of tumor growth and angiogenesis.

As detailed in the exemplification herein, in assays to determine the ability of compounds to inhibit tumor cell migration (e.g., chamber cell migration assay), certain inventive compounds exhibited $IC_{50}$ values≤50 μM. In certain other embodiments, inventive compounds exhibit $IC_{50}$ values≤40 μM. In certain other embodiments, inventive compounds exhibited $IC_{50}$ values≤30 μM. In certain other embodiments, inventive compounds exhibited $IC_{50}$ values≤20 μM. In certain other embodiments, inventive compounds exhibited $IC_{50}$ values≤10 μM. In certain other embodiments, inventive compounds exhibited $IC_{50}$ values≤7.5 μM. In certain embodiments, inventive compounds exhibited $IC_{50}$ values≤5 μM. In certain other embodiments, inventive compounds exhibit $IC_{50}$ values≤2.5 μM. In certain embodiments, inventive compounds exhibited $IC_{50}$ values≤1 μM. In certain other embodiments, inventive compounds exhibited $IC_{50}$ values≤750 nM. In certain other embodiments, inventive compounds exhibited $IC_{50}$ values≤500 nM. In certain other embodiments, inventive compounds exhibited $IC_{50}$ values≤250 nM. In certain other embodiments, inventive compounds exhibited $IC_{50}$ values≤100 nM. In other embodiments, exemplary compounds exhibited $IC_{50}$ values≤75 nM. In other embodiments, exemplary compounds exhibited $IC_{50}$ values≤50 nM. In other embodiments, exemplary compounds exhibit $IC_{50}$ values≤40 nM. In other embodiments, exemplary compounds exhibited $IC_{50}$ values≤30 nM. In other embodiments, exemplary compounds exhibited $IC_{50}$ values≤25 nM.

As detailed in the exemplification herein, in assays to determine the ability of compounds to inhibit tumor cell proliferation, certain inventive compounds exhibit $IC_{50}$ values≤200 μM. In certain other embodiments, inventive compounds exhibit $IC_{50}$ values≤150 μM. In certain other embodiments, inventive compounds exhibit $IC_{50}$ values≤100 μM. In certain other embodiments, inventive compounds exhibit $IC_{50}$ values≤50 μM. In certain other embodiments, inventive compounds exhibit $IC_{50}$ values≤10 μM. In certain other embodiments, inventive compounds exhibit $IC_{50}$ values≤7.5 μM. In certain embodiments, inventive compounds exhibit $IC_{50}$ values≤5 μM. In certain other embodiments, inventive compounds exhibit $IC_{50}$ values≤2.5 μM. In certain embodiments, inventive compounds exhibit $IC_{50}$ values≤1 μM. In certain other embodiments, inventive compounds exhibit $IC_{50}$ values≤750 nM. In certain other embodiments, inventive compounds exhibit $IC_{50}$ values≤500 nM. In certain other embodiments, inventive compounds exhibit $IC_{50}$ values≤250 nM. In certain other embodiments, inventive compounds exhibit IC$_{50}$ values ≤100 nM. In other embodiments, exemplary compounds exhibit IC$_{50}$ values ≤75 nM. In other embodiments, exemplary compounds exhibit IC$_{50}$ values ≤50 nM.

In certain embodiments, the present invention provides methods for identifying Migrastatin analogs useful in the preparation of pharmaceutical compositions for the treatment of various disorders including cancer, metastasis, proliferative disorders and disorders involving increased angiogenesis.

In certain exemplary embodiments, there is provided a method for identifying Migrastatin analogs having anti-angiogenic activity, the method comprising steps of:

a. contacting a compound with a plurality of cells, whereby the compound has the structure:

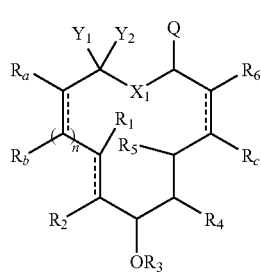

(I)

or pharmaceutically acceptable derivative thereof;

wherein $R_1$ and $R_2$ are each independently hydrogen, halogen, —CN, —S(O)$_{1-2}$R$^{1A}$, —NO$_2$, —COR$^{1A}$, —CO$_2$R$^{1A}$, —NR$^{1A}$C(=O)R$^{1B}$, —NR$^{1A}$C(=O)OR$^{1B}$, —CONR$^{1A}$R$^{1B}$, an aliphatic, heteroaliphatic, alicyclic, heterocyclic, aryl or heteroaryl moiety, or —WR$^{1A}$; wherein W is independently —O—, —S— or —NR$^{1C}$—, wherein each occurrence of R$^{1A}$, R$^{1B}$ and R$^{1C}$ is independently hydrogen, or an aliphatic, heteroaliphatic, alicyclic, heterocyclic, aryl or heteroaryl moiety; or $R_1$ and $R_2$, taken together with the carbon atoms to which they are attached, form an alicyclic, heterocyclic, aryl or heteroaryl moiety;

$R_3$ is hydrogen, an aliphatic, heteroaliphatic, alicyclic, heterocyclic, aryl or heteroaryl moiety; or a prodrug moiety or an oxygen protecting group;

$R_4$ is halogen, —OR$^{4A}$, —OC(=O)R$^{4A}$ or —NR$^{4A}$R$^{4B}$; wherein R$^{4A}$ and R$^{4B}$ are independently hydrogen, an aliphatic, heteroaliphatic, alicyclic, heterocyclic, aryl or heteroaryl moiety; a prodrug moiety, a nitrogen protecting group or an oxygen protecting group; or R$^{4A}$ and R$^{4B}$, taken together with the nitrogen atom to which they are attached, form a heterocyclic or heteroaryl moiety;

$R_5$ is hydrogen, an aliphatic, heteroaliphatic, alicyclic, heterocyclic, aryl or heteroaryl moiety;

$R_6$ is hydrogen, halogen, —CN, —S(O)$_{1-2}$R$^{6A}$, —NO$_2$, —COR$^{6A}$, —CO$_2$R$^{6A}$, —NR$^{6A}$C(O)R$^{6B}$, —NR$^{6A}$C(=O)OR$^{6B}$, —CONR$^{6A}$R$^{6B}$, an aliphatic, heteroaliphatic, alicyclic, heterocyclic, aryl or heteroaryl moiety, or —WR$^{6A}$; wherein W is independently —O—, —S— or —NR$^{6C}$—, wherein each occurrence of R$^{6A}$, R$^{6B}$ and R$^{6C}$ is independently hydrogen, or an aliphatic, heteroaliphatic, alicyclic, heterocyclic, aryl or heteroaryl moiety; or $R_6$ and $R_c$, taken together with the carbon atoms to which they are attached, form an alicyclic, heterocyclic, aryl or heteroaryl moiety;

$R_a$ and each occurrence of $R_b$ are independently hydrogen, halogen, —CN, —S(O)$_{1-2}$R$^{a1}$, —NO$_2$, —COR$^{a1}$, —CO$_2$R$^{a1}$, —NR$^{a1}$C(=O)R$^{a2}$, —NR$^{a1}$C(=O)OR$^{a2}$, —CONR$^{a1}$R$^{a2}$, an aliphatic, heteroaliphatic, alicyclic, heterocyclic, aryl or heteroaryl moiety, or —WR$^{a1}$; wherein W is independently —O—, —S— or —NR$^{a3}$—, wherein each occurrence of R$^{a1}$, R$^{a2}$ and R$^{a3}$ is independently hydrogen, or an aliphatic, heteroaliphatic, alicyclic, heterocyclic, aryl or heteroaryl moiety; or $R_a$ and the adjacent occurrence of $R_b$, taken together with the carbon atoms to which they are attached, form an alicyclic, heterocyclic, aryl or heteroaryl moiety;

$R_c$ is hydrogen, halogen, —CN, —S(O)$_{1-2}$R$^{c1}$, —NO$_2$, —COR$^{c1}$, —CO$_2$R$^{c1}$, —NR$^{c1}$C(=O)R$^{c2}$, —NR$^{c1}$C(=O)OR$^{c2}$, —CONR$^{c1}$R$^{c2}$; an aliphatic, heteroaliphatic, alicyclic, heterocyclic, aryl or heteroaryl moiety, or —WR$^{c1}$; wherein W is independently —O—, —S— or —NR$^{c3}$—, wherein each occurrence of R$^{c1}$, R$^{c2}$ and R$^{c3}$ is independently hydrogen, or an aliphatic, heteroaliphatic, alicyclic, heterocyclic, aryl or heteroaryl moiety; or $R_c$ and $R_6$, taken together with the carbon atoms to which they are attached, form an alicyclic, heterocyclic, aryl or heteroaryl moiety;

n is an integer from 1 to 5;

$X_1$ is O, S, NR$^{X1}$ or CR$^{X1}$R$^{X2}$; wherein R$^{X1}$ and R$^{X2}$ are independently hydrogen, halogen, an aliphatic, heteroaliphatic, alicyclic, heterocyclic, aryl or heteroaryl moiety, or a nitrogen protecting group;

Q is hydrogen, halogen, —CN, —S(O)$_{1-2}$R$^{Q1}$, —NO$_2$, —COR$^{Q1}$, —CO$_2$R$^{Q1}$, —NR$^{Q1}$C(=O)R$^{Q2}$, —NR$^{Q1}$C(=O)OR$^{Q2}$, —CONR$^{Q1}$R$^{Q2}$, an aliphatic, heteroaliphatic, alicyclic, heterocyclic, aryl or heteroaryl moiety, or —WR$^{Q1}$; wherein W is independently —O—, —S— or —NR$^{Q3}$—, wherein each occurrence of R$^{Q1}$, R$^{Q2}$ and R$^{Q3}$ is independently hydrogen, or an aliphatic, heteroaliphatic, alicyclic, heterocyclic, aryl or heteroaryl moiety;

$Y_1$ and $Y_2$ are independently hydrogen, an aliphatic, heteroaliphatic, alicyclic, heterocyclic, aryl or heteroaryl moiety; or —WR$^{Y1}$; wherein W is independently —O—, —S— or —NR$^{Y2}$—, wherein each occurrence of R$^{Y1}$ and R$^{Y2}$ is independently hydrogen, or an aliphatic, heteroaliphatic, alicyclic, heterocyclic, aryl or heteroaryl moiety; or $Y_1$ and $Y_2$ together with the carbon atom to which they are attached form a moiety having the structure:

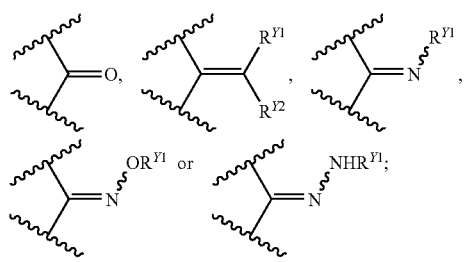

and b. evaluating the effect of the compound on the complexity of the tube network among the cells.

In certain embodiments, the compound being contacted with the plurality of cells is at a concentration ≤200 μM. In certain exemplary embodiments, the compound has the following stereochemistry:

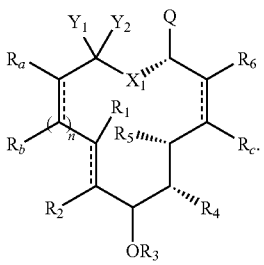

In certain embodiments, in the method described directly above, the step of evaluating comprises comparing the disturbance of the complexity of the tube network with that observed for cells exposed to a reference Migrastatin concentration. In certain exemplary embodiments, the reference Migrastatin concentration is about 100 μM. In certain exemplary embodiments, the reference Migrastatin concentration is about 75 μM. In certain exemplary embodiments, the reference Migrastatin concentration is about 50 μM. In certain exemplary embodiments, the reference Migrastatin concentration is about 30 μM.

In certain embodiments, the method is for identifying Migrastatin analogs useful in the preparation of pharmaceutical compositions for the treatment of angiogenesis-related disorders.

In certain other embodiments, the invention provides a highthroughput method for identifying Migrastatin analogs having anti-angiogenic activity, the method comprising steps of:
a. introducing in each of a plurality of reaction vessels:
   a plurality of cells; and
   one or more test compounds with having the structure (I) as defined generally above and in classes and subclasses herein; or pharmaceutically acceptable derivative thereof; and
b. evaluating in each reaction vessel the effect of the test compound on the complexity of the tube network in the cells.

In certain embodiments, the test compound being contacted with the plurality of cells is at a concentration≤200 μM. In certain exemplary embodiments, the test compound has the following stereochemistry:

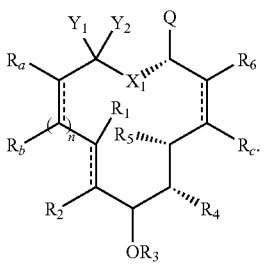

In certain embodiments, in the method described directly above, the step of evaluating comprises comparing the disturbance of the complexity of the tube network in each reaction vessel with that observed for cells exposed to a reference Migrastatin concentration. In certain exemplary embodiments, the reference Migrastatin concentration is about 100 μM. In certain exemplary embodiments, the reference Migrastatin concentration is about 75 μM. In certain exemplary embodiments, the reference Migrastatin concentration is about 50 μM. In certain exemplary embodiments, the reference Migrastatin concentration is about 30 μM.

In certain embodiments, the method is for identifying Migrastatin analogs useful in the preparation of pharmaceutical compositions for the treatment of angiogenesis-related disorders.

In certain exemplary embodiments, there is provided a method for identifying Migrastatin analogs having cell migration inhibitory activity, the method comprising steps of:
a. providing a plurality of cells;
b. applying a scratch to the cell layer surface;
c. contacting the cells with a compound having the structure (I) as defined generally above and in classes and subclasses herein; or pharmaceutically acceptable derivative thereof; and
b. evaluating the wound healing effect of the compound on the cells.

In certain embodiments, the compound being contacted with the plurality of cells is at a concentration≤200 μM. In certain exemplary embodiments, the compound has the following stereochemistry:

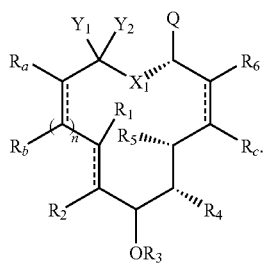

In certain embodiments, in the method described directly above, the step of evaluating comprises comparing the compound wound healing effect with that observed for cells exposed to a reference Migrastatin concentration. In certain exemplary embodiments, the reference Migrastatin concentration is about 100 μM. In certain exemplary embodiments, the reference Migrastatin concentration is about 75 μM. In certain exemplary embodiments, the reference Migrastatin concentration is about 50 μM. In certain exemplary embodiments, the reference Migrastatin concentration is about 30 μM.

In certain embodiments, the method is for identifying Migrastatin analogs useful in the preparation of pharmaceutical compositions for the treatment of metastasis-related disorders In certain embodiments, the method may be adapted to high-throughput format wherein the cells and test compounds are introduced and assayed in each of a plurality of reaction vessels. For example, in certain embodiments, there is provided a highthroughput method for identifying Migrastatin analogs having cell migration inhibitory activity, the method comprising steps of:
a. introducing a plurality of cells in each of a plurality of reaction vessels;
b. in each reaction vessel, applying a scratch to the cell layer surface;
c. contacting the cells, in each reaction vessel, with one or more test compounds having the structure (I) as defined generally above and in classes and subclasses herein; or pharmaceutically acceptable derivative thereof; and
d. evaluating the wound healing effect of the test compound on the cells in each reaction vessel.

In certain embodiments, the test compound being contacted with the plurality of cells is at a concentration ≤200 µM. In certain exemplary embodiments, the test compound has the following stereochemistry:

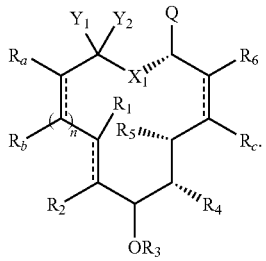

In certain embodiments, in the method described directly above, the step of evaluating comprises comparing the compound wound healing effect in each reaction vessel with that observed for cells exposed to a reference Migrastatin concentration. In certain exemplary embodiments, the reference Migrastatin concentration is about 100 µM. In certain exemplary embodiments, the reference Migrastatin concentration is about 75 µM. In certain exemplary embodiments, the reference Migrastatin concentration is about 50 µM. In certain exemplary embodiments, the reference Migrastatin concentration is about 30 µM.

In certain embodiments, the method is for identifying Migrastatin analogs useful in the preparation of pharmaceutical compositions for the treatment of angiogenesis-related disorders.

In certain other exemplary embodiments, there is provided a method for identifying Migrastatin analogs having cell migration inhibitory activity, comprising steps of:
  a. introducing a plurality of cells into an upper compartment;
  b. introducing a test compound having the structure (I) as defined generally above and in classes and subclasses herein; or pharmaceutically acceptable derivative thereof; into the upper compartment and a lower compartment, whereby the lower compartment is separated from the upper compartment by a cell-permeable membrane; and
  c. assessing cell migration from the upper to the lower compartment after a given period of time.

In certain embodiments, the compound being contacted with the plurality of cells is at a concentration ≤200 µM. In certain exemplary embodiments, the compound has the following stereochemistry:

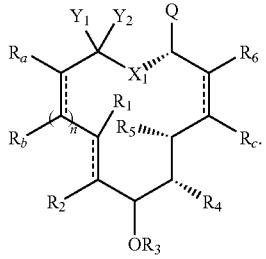

In certain embodiments, in the method described directly above, the step of evaluating comprises comparing cell migration from the upper to the lower compartment with that observed for cells exposed to a reference Migrastatin concentration after about the same period of time. In certain exemplary embodiments, the reference Migrastatin concentration is about 100 µM. In certain exemplary embodiments, the reference Migrastatin concentration is about 75 µM. In certain exemplary embodiments, the reference Migrastatin concentration is about 50 µM. In certain exemplary embodiments, the reference Migrastatin concentration is about 30 µM.

In certain embodiments, the method is for identifying Migrastatin analogs useful in the preparation of pharmaceutical compositions for the treatment of metastasis-related disorders.

In certain embodiments, the method may be adapted to high-throughput format wherein the cells and test compounds are introduced and assayed in each of a plurality of reaction vessels. For example, in certain embodiments, there is provided a highthroughput method for identifying Migrastatin analogs having cell migration inhibitory activity, the method comprising steps of:
  a. providing a plurality of reaction vessels, each comprising an upper and lower compartment separated by a cell-permeable membrane;
  b. introducing a plurality of cells into the upper compartment of each of the plurality of reaction vessels;
  c. introducing a test compound having the structure (I) as defined generally above and in classes and subclasses herein; or pharmaceutically acceptable derivative thereof; into the upper and lower compartment of each of the plurality of reaction vessels; and
  d. in each reaction vessel, assessing cell migration from the upper to the lower compartment after a given period of time.

In certain embodiments of each of the highthroughput methods described above, a different concentration of the same test compound is introduced in each reaction vessel. In certain other embodiments, a different test compound is introduced in each reaction vessel. In certain embodiments, a different concentration of the same test compound is introduced in a subset of the reaction vessels; and a different test compound is introduced in another subset of the reaction vessels.

In certain embodiments, a highthroughput method according to the present invention is practiced with dense arrays of reaction vessels. Preferably, the center-to-center distance between reaction vessels is less than about 8.5 mm. More preferably, the distance is less than 4.5 mm. Even more preferably the distance is less than approximately 2.25 mm. Most preferably, the distance is less than approximately 1 mm. In certain embodiments, the method is performed with a 48-well culture dish.

Conventional high throughput screens are often performed in commercially available 48- or 96-well plates (see, for example, Rice et al. *Anal. Biochem.* 241:254-259. 1996). Such plates may be utilized according to the present invention. However, denser arrays are generally preferred, though it is appreciated that such arrays may desirably have the same external dimensions of a standard 48- or 96-well plate in order to facilitate automation using available equipment. Plates containing 384 (Nalge Nunc International, Naperville, Ill.; Greiner America, Lake Mary, Fla.; Corning Costar, Corning, N.Y.) or 1536 (Greiner America, Lake Mary, Fla.) wells have recently become commercially available and may be used in the practice of the present invention. In certain embodiments, a highthroughput method according to the present invention is compatible with any or all of these array formats.

Pharmaceutical Uses and Methods of Treatment

In yet another aspect, the present invention provides methods of treatment of various disorders, including those associated with metastasis and/or increased angiogenic activity. In certain embodiments, according to the methods of treatment of the present invention, metastasis and/or the growth of tumor cells is inhibited by contacting said tumor cells with an inventive compound or composition, as described herein.

Accordingly, in another aspect of the invention, methods for the treatment of cancer are provided comprising administering a therapeutically effective amount of a compound of formula (I), as described herein, to a subject in need thereof. In certain embodiments, a method for the treatment of cancer is provided comprising administering a therapeutically effective amount of an inventive compound, or a pharmaceutical composition comprising an inventive compound to a subject in need thereof, in such amounts and for such time as is necessary to achieve the desired result.

In certain embodiments, the method involves the administration of a therapeutically effective amount of the compound or a pharmaceutically acceptable derivative thereof to a subject (including, but not limited to a human or animal) in need of it. In certain embodiments, the inventive compounds as useful for the treatment of cancer (including, but not limited to, glioblastoma, retinoblastoma, breast cancer, cervical cancer, colon and rectal cancer, leukemia, lymphoma, lung cancer (including, but not limited to small cell lung cancer), melanoma and/or skin cancer, multiple myeloma, non-Hodgkin's lymphoma, ovarian cancer, pancreatic cancer, prostate cancer and gastric cancer, bladder cancer, uterine cancer, kidney cancer, testicular cancer, stomach cancer, brain cancer, liver cancer, or esophageal cancer). In certain exemplary embodiments, the inventive compounds as useful for the treatment of ovarian and/or cancer. In certain exemplary embodiments, the inventive compounds as useful for the treatment of metastatic ovarian and/or cancer. In certain other embodiments, the compounds are useful for facilitating wound healing. In yet other embodiments, the compounds are useful for treating ascites.

As discussed above, the compounds of the present invention inhibit metastasis of tumor cells and/or inhibiting the growth of tumor cells. In general, the inventive anticancer agents are useful in the treatment of cancers and other proliferative disorders, including, but not limited to breast cancer, cervical cancer, colon and rectal cancer, leukemia, lung cancer, melanoma, multiple myeloma, non-Hodgkin's lymphoma, ovarian cancer, pancreatic cancer, prostate cancer, and gastric cancer, to name a few. In certain embodiments, the inventive anticancer agents are active against leukemia cells and melanoma cells, and thus are useful for the treatment of leukemias (e.g., myeloid, lymphocytic, myelocytic and lymphoblastic leukemias) and malignant melanomas. In still other embodiments, the inventive anticancer agents are active against solid tumors. In certain exemplary embodiments, the inventive compounds as useful for the treatment of ovarian and/or cancer. In certain exemplary embodiments, the inventive compounds as useful for the treatment of metastatic ovarian and/or cancer.

In certain embodiments, the present invention provides a method for treating and/or preventing metastasis and/or proliferation of tumor cells in a subject comprising administering to a subject (including, but not limited to, a human or animal) in need thereof a therapeutically effective amount of a compound of the invention and a pharmaceutically acceptable carrier, adjuvant or vehicle. In certain exemplary embodiments, the method is used to treat and/or prevent metastasis and/or proliferation of prostate, breast, colon, bladder, cervical, skin, testicular, kidney, ovarian, stomach, brain, liver, pancreatic or esophageal cancer or lymphoma, leukemia, or multiple myeloma, to name a few. In preferred embodiments, the inventive method is for treating and/or preventing ovarian and/or colon cancer. In preferred embodiments, the inventive method is for treating and/or preventing metastatic ovarian and/or colon cancer.

In another aspect, the present invention provides methods for decreasing migration of tumor cells. In a further aspect, the present invention provides methods for decreasing anchorage-independent growth of tumor cells. In yet a further aspect, the present invention provides methods for inhibiting angiogenesis.

In yet another aspect, the present invention provides methods for preventing unwanted angiogenesis in a subject (including, but not limited to, a human or animal).

As used herein, the term "angiogenesis" means the generation of new blood vessels into a tissue or organ. Under normal physiological conditions, humans or animals only undergo angiogenesis in very specific restricted situations. For example, angiogenesis is normnally observed in wound healing, fetal and embryonal development and formation of the corpus luteum, endometrium and placenta. The control of angiogenesis is a highly regulated system of angiogenic stimulators and inhibitors. The control of angiogenesis has been found to be altered in certain disease states and, in many cases, the pathological damage associated with the disease is related to the uncontrolled angiogenesis.

Both controlled and uncontrolled angiogenesis are thought to proceed in a similar manner. Endothelial cells and pericytes, surrounded by a basement membrane, form capillary blood vessels. Angiogenesis begins with the erosion of the basement membrane by enzymes released by endothelial cells and leukocytes. The endothelial cells, which line the lumen of blood vessels, then protrude through the basement membrane. Angiogenic stimulants induce the endothelial cells to migrate through the eroded basement membrane. The migrating cells form a "sprout" off the parent blood vessel, where the endothelial cells undergo mitosis and proliferate. The endothelial sprouts merge with each other to form capillary loops, creating the new blood vessel. In the disease state, prevention of angiogenesis could avert the damage caused by the invasion of the new microvascular system.

Persistent, unregulated angiogenesis occurs in a multiplicity of disease states, tumor metastasis and abnormal growth by endothelial cells and supports the pathological damage seen in these conditions. The diverse pathological states created due to unregulated angiogenesis have been grouped together as angiogenic dependent or angiogenic associated diseases. Therapies directed at control of the angiogenic processes could lead to the abrogation or mitigation of these diseases.

One example of a disease involving an angiogenic process is ocular neovascular disease. This disease is characterized by invasion of new blood vessels into the structures of the eye such as the retina or cornea. It is the most common cause of blindness and is involved in approximately twenty eye diseases. In age-related macular degeneration, the associated visual problems are caused by an ingrowth of chorioidal capillaries through defects in Bruch's membrane with proliferation of fibrovascular tissue beneath the retinal pigment epithelium. Angiogenic damage is also associated with diabetic retinopathy, retinopathy of prematurity, corneal graft rejection, neovascular glaucoma and retrolental fibroplasia. Other diseases associated with corneal neovascularization include, but are not limited to, epidemic keratoconjunctivitis, Vitamin A deficiency, contact lens overwear, atopic keratitis, superior limbic keratitis, pterygium keratitis sicca, sjogrens, acne rosacea, phylectenulosis, syphilis, Mycobacteria infections, lipid degeneration, chemical burns, bacterial ulcers, fungal ulcers, Herpes simplex infections, Herpes zoster infections, protozoan infections, Kaposi's sarcoma, Mooren's ulcer, Terrien's marginal degeneration, mariginal keratolysis, rheumatoid arthritis, systemic lupus, polyarteritis, trauma, Wegener's sarcoidosis, scleritis, Stevens-Johnson disease, pemphigoid, radial keratotomy, and corneal graph rejection.

Diseases associated with retinal/choroidal neovascularization include, but are not limited to, diabetic retinopathy, macular degeneration, sickle cell anemia, sarcoid, syphilis, pseudoxanthoma elasticum, Paget's disease, vein occlusion, artery occlusion, carotid obstructive disease, chronic uveitis/vitritis, mycobacterial infections, Lyme's disease, systemic lupus erythematosis, retinopathy of prematurity, Eales' disease, Behcet's disease, infections causing a retinitis or chorioiditis, presumed ocular histoplasmosis, Best's disease, myopia, optic pits, Stargardt's disease, pars planitis, chronic retinal detachment, hyperviscosity syndromes, toxoplasmosis, trauma and post-laser complications. Other diseases include, but are not limited to, diseases associated with rubeosis (neovasculariation of the angle) and diseases caused by the abnormal proliferation of fibrovascular or fibrous tissue including all forms of proliferative vitreoretinopathy.

Another disease in which angiogenesis is believed to be involved is rheumatoid arthritis. The blood vessels in the synovial lining of the joints undergo angiogenesis. In addition to forming new vascular networks, the endothelial cells release factors and reactive oxygen species that lead to pannus growth and cartilage destruction. The factors involved in angiogenesis may actively contribute to, and help maintain, the chronically inflamed state of rheumatoid arthritis.

Factors associated with angiogenesis may also have a role in osteoarthritis. The activation of the chondrocytes by angiogenic-related factors contributes to the destruction of the joint. At a later stage, the angiogenic factors would promote new bone formation. Therapeutic intervention that prevents the bone destruction could halt the progress of the disease and provide relief for persons suffering with arthritis.

Chronic inflammation may also involve pathological angiogenesis. Such disease states as ulcerative colitis and Crohn's disease show histological changes with the ingrowth of new blood vessels into the inflamed tissues. Bartonellosis, a bacterial infection found in South America, can result in a chronic stage that is characterized by proliferation of vascular endothelial cells. Another pathological role associated with angiogenesis is found in atherosclerosis. The plaques formed within the lumen of blood vessels have been shown to have angiogenic stimulatory activity.

One of the most frequent angiogenic diseases of childhood is the hemangioma. In most cases, the tumors are benign and regress without intervention. In more severe cases, the tumors progress to large cavernous and infiltrative forms and create clinical complications. Systemic forms of hemangiomas, the hemangiomatoses, have a high mortality rate. Therapy-resistant hemangiomas exist that cannot be treated with therapeutics currently in use.

Angiogenesis is also responsible for damage found in hereditary diseases such as Osler-Weber-Rendu disease, or hereditary hemorrhagic telangiectasia. This is an inherited disease characterized by multiple small angiomas, tumors of blood or lymph vessels. The angiomas are found in the skin and mucous membranes, often accompanied by epistaxis (nosebleeds) or gastrointestinal bleeding and sometimes with pulmonary or hepatic arteriovenous fistula.

Angiogenesis is prominent in solid tumor formation and metastasis. Angiogenic factors have been found associated with several solid tumors such as rhabdomyosarcomas, retinoblastoma, Ewing sarcoma, neuroblastoma, and osteosarcoma. A tumor cannot expand without a blood supply to provide nutrients and remove cellular wastes. Tumors in which angiogenesis is important include solid tumors, and benign tumors such as acoustic neuroma, neurofibroma, trachoma and pyogenic granulomas. Prevention of angiogenesis could halt the growth of these tumors and the resultant damage to the animal due to the presence of the tumor.

It should be noted that angiogenesis has been associated with blood-born tumors such as leukemias, any of various acute or chronic neoplastic diseases of the bone marrow in which unrestrained proliferation of white blood cells occurs, usually accompanied by anemia, impaired blood clotting, and enlargement of the lymph nodes, liver, and spleen. It is believed that angiogenesis plays a role in the abnormalities in the bone marrow that give rise to leukemia-like tumors.

Angiogenesis is important in two stages of tumor metastasis. The first stage where angiogenesis stimulation is important is in the vascularization of the tumor which allows tumor cells to enter the blood stream and to circulate throughout the body. After the tumor cells have left the primary site, and have settled into the secondary, metastasis site, angiogenesis must occur before the new tumor can grow and expand. Therefore, prevention of angiogenesis could lead to the prevention of metastasis of tumors and possibly contain the neoplastic growth at the primary site.

Knowledge of the role of angiogenesis in the maintenance and metastasis of tumors has led to a prognostic indicator for breast cancer. The amount of neovascularization found in the primary tumor was determined by counting the microvessel density in the area of the most intense neovascularization in invasive breast carcinoma. A high level of microvessel density was found to correlate with tumor recurrence. Control of angiogenesis by therapeutic means could possibly lead to cessation of the recurrence of the tumors.

Angiogenesis is also involved in normal physiological processes such as reproduction and wound healing. Angiogenesis is an important step in ovulation and also in implantation of the blastula after fertilization. Prevention of angiogenesis could be used to induce amenorrhea, to block ovulation or to prevent implantation by the blastula.

In wound healing, excessive repair or fibroplasia can be a detrimental side effect of surgical procedures and may be caused or exacerbated by angiogenesis. Adhesions are a frequent complication of surgery and lead to problems such as small bowel obstruction.

Accordingly, in one aspect, the present invention provides method to inhibit unwanted angiogenesis in a subject (including, but not limited to, a human or animal).

In another aspect, the present invention provides a method for the treatment for diseases mediated by angiogenesis.

In another aspect, the present invention provides a method for the treatment for macular degeneration.

In another aspect, the present invention provides a method for the treatment for all forms of proliferative vitreoretinopathy including those forms not associated with diabetes.

In another aspect, the present invention provides a method for the treatment for solid tumors.

In another aspect, the present invention provides a method for the treatment of blood-borne tumors, such as leukemia.

In another aspect, the present invention provides a method for the treatment of hemangioma.

In another aspect, the present invention provides a method for the treatment of retrolental fibroplasia.

In another aspect, the present invention provides a method for the treatment of psoriasis.

In another aspect, the present invention provides a method for the treatment of Kaposi's sarcoma.

In another aspect, the present invention provides a method for the treatment of Crohn's disease.

In another aspect, the present invention provides a method for the treatment of diabetic retinopathy.

Thus, in certain embodiments, the invention provides a method for preventing unwanted angiogenesis in a subject (including, but not limited to, a human or animal) comprising administering to a subject in need thereof a therapeutically effective amount of the compound of the invention in an amount effective to inhibit angiogenesis.

In certain other embodiments, the invention provides a method for treating an angiogenesis-dependent disease in a subject (including, but not limited to, a human or animal) comprising administering to a subject in need thereof a therapeutically effective amount of the compound of the invention in an amount effective to inhibit angiogenesis.

Diseases associated with corneal neovascularization that can be treated according to the present invention include but are not limited to, diabetic retinopathy, retinopathy of prematurity, corneal graft rejection, neovascular glaucoma and retrolental fibroplasia, epidemic keratoconjunctivitis, Vitamin A deficiency, contact lens overwear, atopic keratitis, superior limbic keratitis, pterygium keratitis sicca, sjogrens, acne rosacea, phylectenulosis, syphilis, Mycobacteria infections, lipid degeneration, chemical burns, bacterial ulcers, fungal ulcers, Herpes simplex infections, Herpes zoster infections, protozoan infections, Kaposi's sarcoma, Mooren's ulcer, Terrien's marginal degeneration, mariginal keratolysis, trauma, rheumatoid arthritis, systemic lupus, polyarteritis, Wegener's sarcoidosis, scleritis, Stevens-Johnson disease, pemphigoid, radial keratotomy, and corneal graph rejection.

Diseases associated with retinal/choroidal neovascularization that can be treated according to the present invention include, but are not limited to, diabetic retinopathy, macular degeneration, sickle cell anemia, sarcoid, syphilis, pseudoxanthoma elasticum, Paget's disease, vein occlusion, artery occlusion, carotid obstructive disease, chronic uveitis/vitritis, mycobacterial infections, Lyme's disease, systemic lupus erythematosis, retinopathy of prematurity, Eales' disease, Behcet's disease, infections causing a retinitis or choroiditis, presumed ocular histoplasmosis, Best's disease, myopia, optic pits, Stargardt's disease, pars planitis, chronic retinal detachment, hyperviscosity syndromes, toxoplasmosis, trauma and post-laser complications. Other diseases include, but are not limited to, diseases associated with rubeosis (neovasculariation of the angle) and diseases caused by the abnormal proliferation of fibrovascular or fibrous tissue including all forms of proliferative vitreoretinopathy, whether or not associated with diabetes.

Diseases associated with chronic inflammation can be treated by the compositions and methods of the present invention. Diseases with symptoms of chronic inflammation include inflammatory bowel diseases such as Crohn's disease and ulcerative colitis, psoriasis, sarcoidosis and rheumatoid arthritis. Angiogenesis is a key element that these chronic inflammatory diseases have in common. The chronic inflammation depends on continuous formation of capillary sprouts to maintain an influx of inflammatory cells. The influx and presence of the inflammatory cells produce granulomas and thus, maintains the chronic inflammatory state. Inhibition of angiogenesis by the compositions and methods of the present invention would prevent the formation of the granulomas and alleviate the disease.

The compositions and methods of the present invention can be used to treat patients with inflammatory bowel diseases such as Crohn's disease and ulcerative colitis. Both Crohn's disease and ulcerative colitis are characterized by chronic inflammation and angiogenesis at various sites in the gastrointestinal tract. Crohn's disease is characterized by chronic granulomatous inflammation throughout the gastrointestinal tract consisting of new capillary sprouts surrounded by a cylinder of inflammatory cells. Prevention of angiogenesis by the compositions and methods of the present invention inhibits the formation of the sprouts and prevents the formation of granulomas.

Crohn's disease occurs as a chronic transmural inflammatory disease that most commonly affects the distal ileum and colon but may also occur in any part of the gastrointestinal tract from the mouth to the anus and perianal area. Patients with Crohn's disease generally have chronic diarrhea associated with abdominal pain, fever, anorexia, weight loss and abdominal swelling. Ulcerative colitis is also a chronic, non-specific, inflammatory and ulcerative disease arising in the colonic mucosa and is characterized by the presence of bloody diarrhea.

The inflammatory bowel diseases also show extraintestinal manifestations such as skin lesions. Such lesions are characterized by inflammation and angiogenesis and can occur at many sites other than the gastrointestinal tract. The compositions and methods of the present invention are also capable of treating these lesions by preventing the angiogenesis, thus reducing the influx of inflammatory cells and the lesion formation.

Sarcoidosis is another chronic inflammatory disease that is characterized as a multisystem granulomatous disorder. The granulomas of this disease may form anywhere in the body and thus the symptoms depend on the site of the granulomas and whether the disease active. The granulomas are created by the angiogenic capillary sprouts providing a constant supply of inflammatory cells.

The compositions and methods of the present invention can also treat the chronic inflammatory conditions associated with psoriasis. Psoriasis, a skin disease, is another chronic and recurrent disease that is characterized by papules and plaques of various sizes. Prevention of the formation of the new blood vessels necessary to maintain the characteristic lesions leads to relief from the symptoms.

Another disease which can be treated according to the present invention is rheumatoid arthritis. Rheumatoid arthritis is a chronic inflammatory disease characterized by nonspecific inflammation of the peripheral joints. It is believed that the blood vessels in the synovial lining of the joints undergo angiogenesis. In addition to forming new vascular networks, the endothelial cells release factors and reactive oxygen species that lead to pannus growth and cartilage destruction. The factors involved in angiogenesis may actively contribute to, and help maintain, the chronically inflamed state of rheumatoid arthritis. Another disease that can be treated according to the present invention are hemangiomas, Osler-Weber-Rendu disease, or hereditary hemorrhagic telangiectasia, solid or blood borne tumors and acquired immune deficiency syndrome.

It will be appreciated that the compounds and compositions, according to the method of the present invention, may be administered using any amount and any route of administration effective for the treatment of cancer and/or disorders associated with metastasis and/or angiogenesis. Thus, the expression "effective amount" as used herein, refers to a sufficient amount of agent to inhibit the growth of tumor cells, or refers to a sufficient amount to reduce the effects of cancer.

The exact amount required will vary from subject to subject, depending on the species, age, and general condition of the subject, the severity of the diseases, the particular anticancer agent, its mode of administration, and the like.

The compounds of the invention are preferably formulated in dosage unit form for ease of administration and uniformity of dosage. The expression "dosage unit form" as used herein refers to a physically discrete unit of therapeutic agent appropriate for the patient to be treated. It will be understood, however, that the total daily usage of the compounds and compositions of the present invention will be decided by the attending physician within the scope of sound medical judgment. The specific therapeutically effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts (see, for example, Goodman and Gilman's, "The Pharmacological Basis of Therapeutics", Tenth Edition, A. Gilman, J. Hardman and L. Limbird, eds., McGraw-Hill Press, 155-173, 2001, which is incorporated herein by reference in its entirety).

Furthermore, after formulation with an appropriate pharmaceutically acceptable carrier, adjuvant or vehicle in a desired dosage, the pharmaceutical compositions of this invention can be administered to humans and other animals orally, rectally, parenterally, intracistemally, intravaginally, intraperitoneally, topically (as by powders, ointments, creams or drops), bucally, as an oral or nasal spray, or the like, depending on the severity of the infection being treated. In certain embodiments, compounds of the invention may be administered at dosage levels of about 0.001 mg/kg to about 50 mg/kg, of subject body weight per day, one or more times a day, to obtain the desired therapeutic effect. It will also be appreciated that dosages smaller than 0.001 mg/kg or greater than 50 mg/kg (for example 50-100 mg/kg) can be administered to a subject. In certain embodiments, compounds are administered orally or parenterally.

Treatment Kit

In other embodiments, the present invention relates to a kit for conveniently and effectively carrying out the methods in accordance with the present invention. In general, the pharmaceutical pack or kit comprises one or more containers filled with one or more of the ingredients of the pharmaceutical compositions of the invention. Such kits are especially suited for the delivery of solid oral forms such as tablets or capsules. Such a kit preferably includes a number of unit dosages, and may also include a card having the dosages oriented in the order of their intended use. If desired, a memory aid can be provided, for example in the form of numbers, letters, or other markings or with a calendar insert, designating the days in the treatment schedule in which the dosages can be administered. Alternatively, placebo dosages, or calcium dietary supplements, either in a form similar to or distinct from the dosages of the pharmaceutical compositions, can be included to provide a kit in which a dosage is taken every day. Optionally associated with such container(s) can be a notice in the form prescribed by a governmental agency regulating the manufacture, use or sale of pharmaceutical products, which notice reflects approval by the agency of manufacture, use or sale for human administration.

Equivalents

The representative examples that follow are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples which follow and the references to the scientific and patent literature cited herein. It should further be appreciated that the contents of those cited references are incorporated herein by reference to help illustrate the state of the art. Throughput this document, various publications are referred to, each of which is hereby incorporated by reference in its entirety in an effort to more fully describe the state of the art to which the invention pertains.

The following examples contain important additional information, exemplification and guidance that can be adapted to the practice of this invention in its various embodiments and the equivalents thereof.

EXEMPLIFICATION

The compounds of this invention and their preparation can be understood further by the examples that illustrate some of the processes by which these compounds are prepared or used. It will be appreciated, however, that these examples do not limit the invention. Variations of the invention, now known or further developed, are considered to fall within the scope of the present invention as described herein and as hereinafter claimed.

1) General Description of Synthetic Methods:

The practitioner has a a well-established literature of macrolide chemistry to draw upon, in combination with the information contained herein, for guidance on synthetic strategies, protecting groups, and other materials and methods useful for the synthesis of the compounds of this invention. For example, synthetic guidance may be found in International Application Nos.: PCT/US04/09380 and PCT/US04/09571, each filed Mar. 26, 2004; and U.S. Provisional Application Nos. 60/458,827, filed Mar. 28, 2003, and 60/496,165, filed Aug. 19, 2003. Each of the above listed applications are hereby incorporated by reference in its entirety.

The various references cited herein provide helpful background information on preparing compounds similar to the inventive compounds described herein or relevant intermediates, as well as information on formulation, uses, and administration of such compounds which may be of interest.

Moreover, the practitioner is directed to the specific guidance and examples provided in this document relating to various exemplary compounds and intermediates thereof.

The compounds of this invention and their preparation can be understood further by the examples that illustrate some of the processes by which these compounds are prepared or used. It will be appreciated, however, that these examples do not limit the invention. Variations of the invention, now known or further developed, are considered to fall within the scope of the present invention as described herein and as hereinafter claimed.

According to the present invention, any available techniques can be used to make or prepare the inventive compounds or compositions including them. For example, a variety of solution phase synthetic methods such as those discussed in detail below may be used. Alternatively or additionally, the inventive compounds may be prepared using any of a variety combinatorial techniques, parallel synthesis and/or solid phase synthetic methods known in the art.

It will be appreciated as described below, that a variety of inventive compounds can be synthesized according to the methods described herein. The starting materials and reagents used in preparing these compounds are either available from commercial suppliers such as Aldrich Chemical Company (Milwaukee, Wis.), Bachem (Torrance, Calif.), Sigma (St. Louis, Mo.), or are prepared by methods well known to a person of ordinary skill in the art following procedures described in such references as Fieser and Fieser 1991, "Reagents for Organic Synthesis", vols 1-17, John Wiley and Sons, New York, N.Y., 1991; Rodd 1989 "Chemistry of Carbon Compounds", vols. 1-5 and supps, Elsevier Science Publishers, 1989; "Organic Reactions", vols 1-40, John Wiley and Sons, New York, N.Y., 1991; March 2001, "Advanced Organic Chemistry", 5th ed. John Wiley and Sons, New York, N.Y.; and Larock 1990, "Comprehensive Organic Transformations: A Guide to Functional Group Preparations", $2^{nd}$ ed. VCH Publishers. These schemes are merely illustrative of some methods by which the compounds of this invention can be synthesized, and various modifications to these schemes can be made and will be suggested to a person of ordinary skill in the art having regard to this disclosure.

The starting materials, intermediates, and compounds of this invention may be isolated and purified using conventional techniques, including filtration, distillation, crystallization, chromatography, and the like. They may be characterized using conventional methods, including physical constants and spectral data.

Certain exemplary compounds of the invention are listed below:

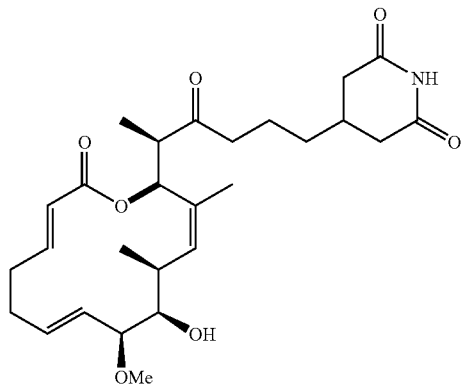

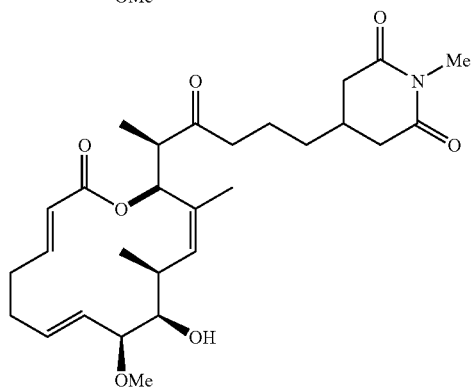

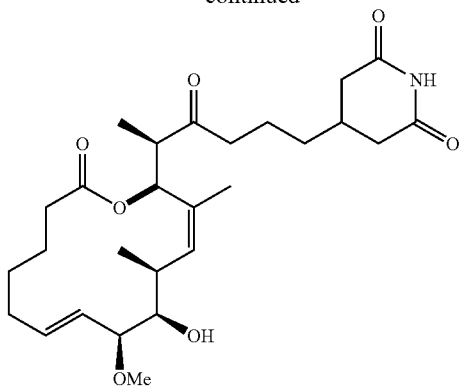

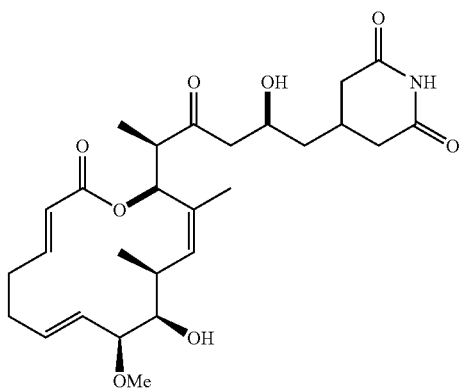

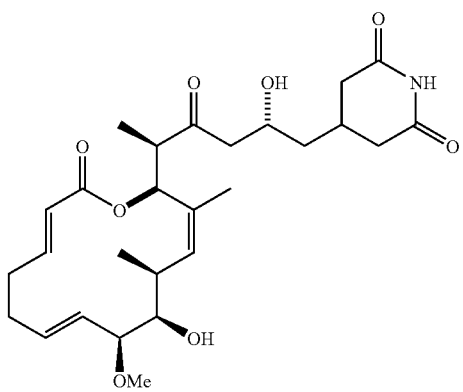

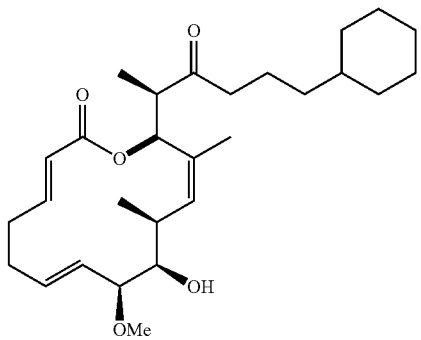

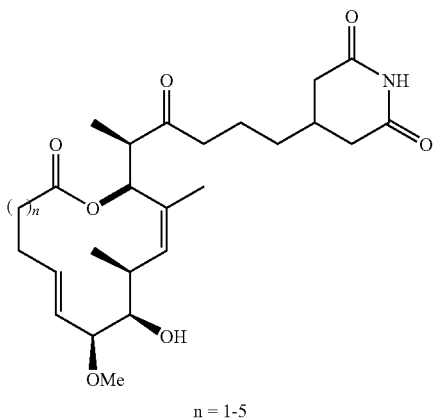

n = 1-5

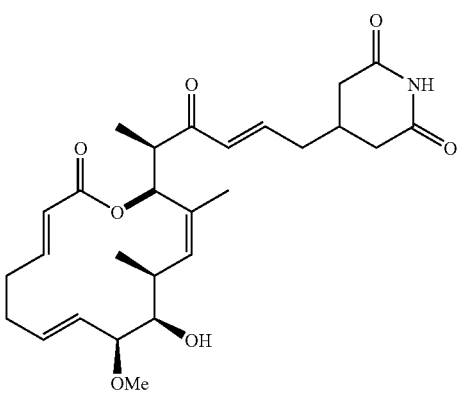

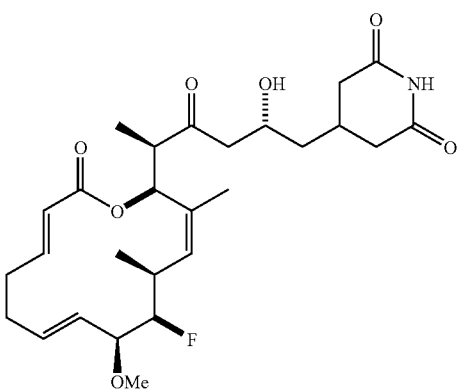

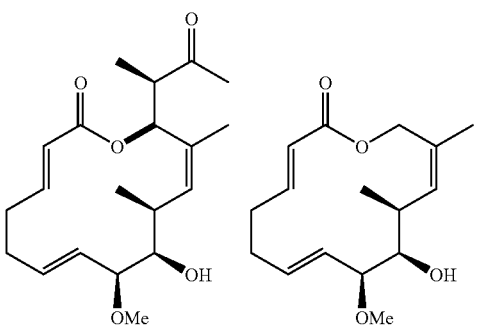

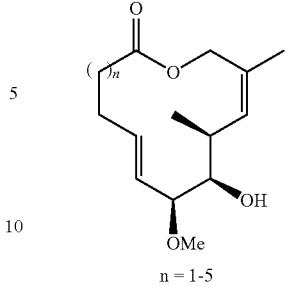

n = 1-5

As discussed herein, cancer chemotherapy traditionally relies on therapeutic agents with cytotoxic properties that inhibit tumor cell proliferation and cause cell death. Recently, the idea of targeting cell migration as an alternative strategy for the development of anti-cancer therapies has generated considerable interest.[1] Intense research efforts are currently directed to the exploration of cell shape change and movement and their underlying mechanisms.[2] Cell migration is involved in a number of physiological processes, including ovulation, embryonic development, tissue regeneration (wound healing), and inflammation. On the other hand, cell migration is also observed in pathological conditions such as tumor angiogenesis, cancer cell invasion, and metastasis.[3] It is believed that primary solid tumors depend on angiogenesis (formation of new blood vessels) to obtain the necessary oxygen and nutrient supplies for growth beyond a certain size (ca. 1-2 mm). The transition from a pre-angiogenic condition to tumor angiogenesis,[4] often referred to as the angiogenic switch, is followed by tumor growth, cancer cell invasion, and metastasis.[5] In principle, it could be possible to halt (or retard) this procession at different stages with the help of cell migration inhibitors. Since cell migration under ordinary physiological conditions in adults is rather infrequent, its repression might be accompanied by manageable toxicity.

A significant part of our general research program focuses on the development of novel, natural product-inspired anti-cancer agents. These efforts have led to the total chemical synthesis of a number of prominent anti-tumor natural products, such as the epothilones,[6] Taxol®,[7] and most recently, radicicol[8] and TMC-95A/B.[9] The recent entry of 12,13-desoxyepothilone B (dEpoB), first prepared by total chemical synthesis, into phase II clinical trials,[10] has been followed by the discovery of a new generation of highly potent epothilone analogs.[11] For the most part, our endeavors have converged on cytotoxic agents. The possibility of exploiting natural products as leads for the development of anti-angiogenic and anti-metastatic agents was prompted by the recent isolation and synthesis of compounds such as epoxyquinol A and B,[12] trachyspic acid,[13] azaspirene,[14] evodiamine,[15] motuporamines,[16] borrelidin,[17] and terpestacin.[18]

In particular, a series of independent reports by Imoto[19] and Kosan Bioscience researchers[20] on the discovery of the natural product migrastatin (1) enhanced our interest in this area (Scheme 16). It was reported that 1, isolated from a cultured broth of *Streptomyces*, has the potential of metastasis suppression through its ability to inhibit tumor cell migration Although the reported activity of migrastatin in a wound healing assay was rather modest ($IC_{50}$ value of 29 μM), we considered it as an attractive lead compound in the search for other, more potent agents. The structure of migrastatin (1), determined by X-ray crystal structure analysis, features a 14-membered macrolactone with a characteristic glutarimide-containing side chain. Embedded in the macrocycle are a trisubstituted (Z)-alkene and two disubstituted (E)-alkenes, as well as three contiguous stereocenters. The side chain projecting from the cyclic core is associated with stereogenic centers at C13 and C14.

Upon reviewing the literature in search of glutarimide-containing natural products, prominent examples such as cycloheximide (CM),[21] streptimidone,[22] and thalidomide (which has resurfaced recently as an anti-angiogenic agent despite its controversial history[23]) can be identified. Moreover, a number of structural homologs of migrastatin, namely lactimidomycin,[24] dorrigocin A and B,[20,25] isomigrastatin,[20] and NK30424A/B,[26] have been discovered (Scheme 16). In 1992, lactimidomycin was isolated from *Streptomyces amphibiosporus* and characterized by researchers at Bristol-Myers Squibb. This unique triene-containing 12-membered macrolactone antibiotic is highly cytotoxic in vitro against a number of tumor cell lines and displays in vivo anti-tumor activity in mice. In addition, lactimidomycin exhibits potent anti-fungal properties and acts as an inhibitor of DNA and protein synthesis. Two years later, the isolation of dorrigocin A and its allylic isomer dorrigocin B from *Streptomyces platensis* was described by researchers at Abbott Laboratories. The dorrigocins are linear polyketide carboxylic acids with a functional group arrangement closely related to migrastatin and isomigrastatin (see below), respectively. They were found to reverse the morphology of ras-transformed NIH/3T3 cells from a transformed phenotype to a normal one. Dorrigocin A was also reported to be the first natural product inhibitor of the carboxyl methyltransferase involved in Ras processing. In 2002, the dorrigocins were again isolated from *Streptomyces platensis* by researchers at Kosan Biosciences along with migrastatin and a new member of the family, isomigrastatin. Structurally, isomigrastatin can be described as being derived from migrastatin by an allylic transposition (C13→C11) and a concomitant double bond isomerization. Thus, isomigrastatin is a 12-membered macrolactone with an exocyclic trisubstituted (E)-alkene. The Kosan researchers have shown that the hydrolysis of isomigrastatin leads to dorrigocin B, whereas the hydrolysis of migrastatin produces a geometric isomer of dorrigocin A. The biological profile of isomigrastatin has not been reported to date. The latest members of the glutarimide-containing macrolide family are the natural products NK30424A and its stereoisomer NK30424B, isolated from *Streptomyces* sp. NA30424 by researchers at Nippon Kayaku. Furthermore, four related compounds, derived from oxidation of the thioether to the sulfoxide, were detected as minor constituents in the cultured broth and were titled as NK30424AS1-2 and NK30424BSI-2. The NK compounds are formally derived from isomigrastatin by conjugate addition of cysteine to the C2-C3 double bond and hydroxylation at C17. Interestingly, these NK congeners are reported to be very potent inhibitors of lipopolysaccharide-induced tumor necrosis factor-α (INF-α) promoter activity. To date, migrastatin is the only member of the natural product family described above in which the relative and absolute configurations have been determined. Possibly, total chemical synthesis might aid in deciphering the stereochemistry of other members of this series.

Scheme 16.
Structure of Migrastatin and Related Natural Products

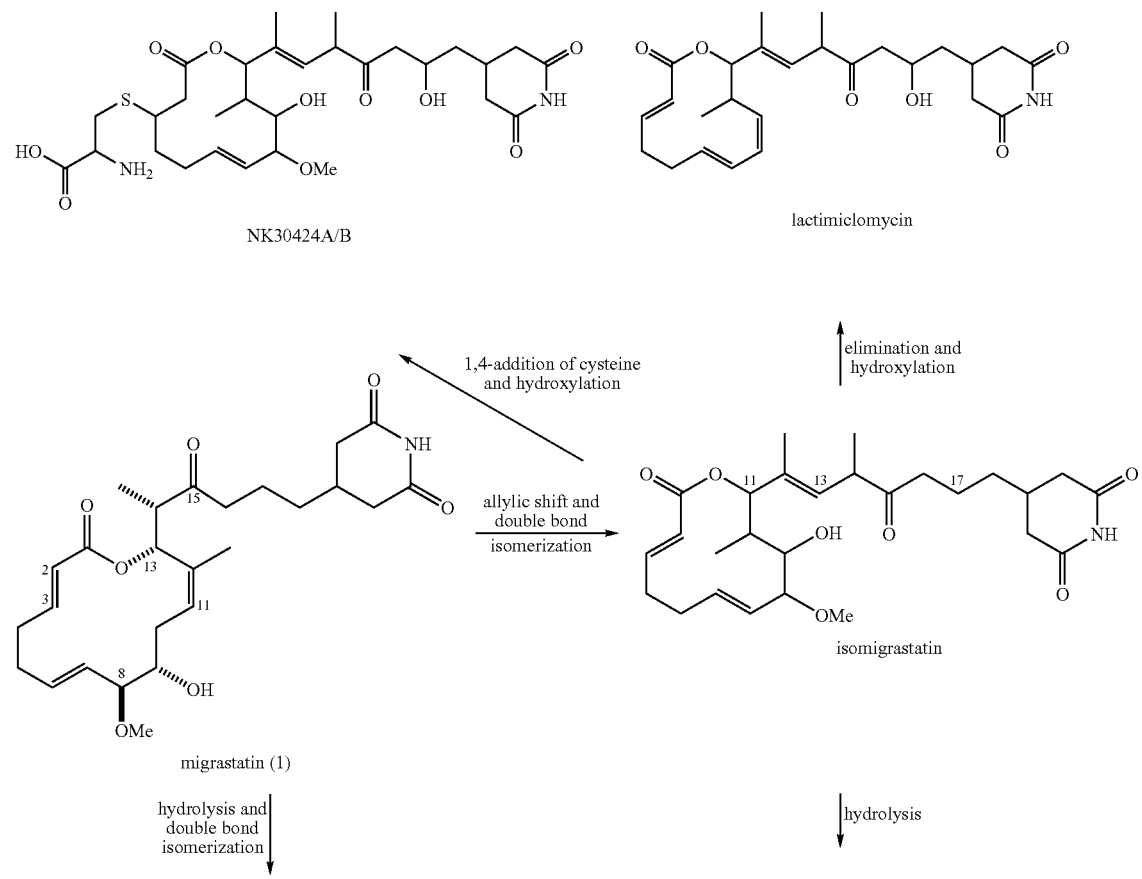

-continued

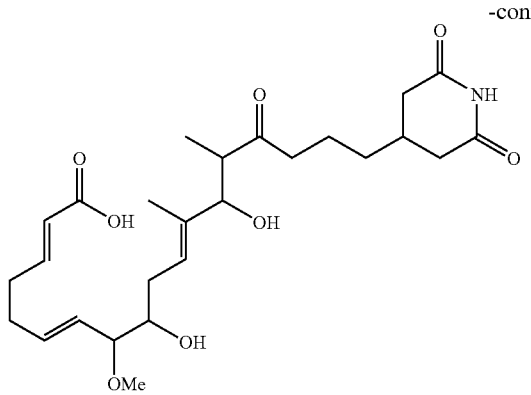

dorrigocin A

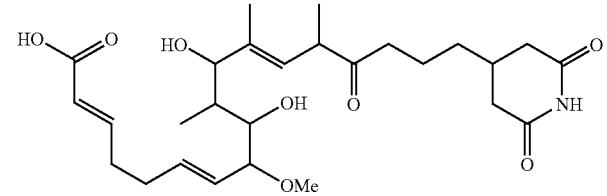

dorrigocin B

In one aspect, the present invention provides synthetic methods for preparing migrastatin and analogs thereof. The first asymmetric total synthesis of naturally occurring (+)-migrastatin (1) is described herein. Exemplary syntheses of Migrastatin analogs are also described herein. The total synthesis of 1 provides researchers (including Applicant) access to material for an independent evaluation of the biology of the natural product and with opportunities via standard medicinal chemistry for gaining access to a broad range of structural analogs. Moreover, the present invention provides synthetic methods allowing access to a variety of Migrastatin analogs and the exploration of structural types that could not, plausibly, be accessible by chemical modification of migrastatin itself. From a practical standpoint, in vitro screening of migrastatin derivatives (e.g., in cell migration assays) may well lead to informative structure-activity relationship (SAR) profiles, conceivably assisting in the emergence of compounds with improved biological profiles for progression to in vivo models. Preliminary SAR trends are provided herein. In addition, efforts directed at target identification are expected to yield some insight into the biological mode of action of migrastatin and its congeners and analogs.

As discussed above, in one aspect, the present invention provides methods for the preparation of Migrstatin and analogs thereof. Detailed below is a synthetic approach, which resulted in an efficient and flexible total synthesis of 1. Additional guidance may be found, for example, in Gaul, C. et al., *J. Am. Chem. Soc.* 2003, 125(20), 6042-6043; Njardarson, J. T. et al., *J. Am. Chem. Soc.* 2004, 126(4), 1038-1040; Gaul, C. et al., *J. Am. Chem. Soc:* 2004, 126(36), 11326-11337; and Shan, D. et al., *Proc. Natl. Acad. Sci. USA,* 2005, 102(10), 3772-3776; each of which is hereby incorporated by reference in its entirety. Migrstatin having known biological activity, it was expected that its analogs would exhibit similar activity. As discussed above, however, the present invention provides the ability to synthesize various migrastatin analogs with a variety of structural features; thereby allowing one to probe and evaluate Structure-Activity Relationships trends within this class of macrocyclic compounds. Preliminary SAR studies[28] have been reported. For example, guidance may be found in U.S. Provisional Application Nos. 60/458,827 filed Mar. 28, 2003 and 60/496,165 filed Aug. 19, 2003; each of which are incorporated herein by reference. In a preliminary study, a few migrastatin analogs which were evaluated in both tube formation and wound healing assay (See Example 52 and Tables 1 and 2). In addition to two analogs closely structurally related to migrastatin (i.e., N-Methyl-migrastatin and 2,3-Dihydromigrastatin (41)), the question of how the migrastatin C-13 side chain might impact activity was investigated (cf. Migrastatin-Core (45)). One advantage of this type of compounds lies in the simplicity of their structure; They are therefore easier to synthesize, less costly and more amenable to large scale preparation. Compound 45, along with the other two migrastatin analogs were thus subjected to the aforementioned assays. A chamber cell migration assay was also proposed that could be used to screen and identify migrastatin analogs exhibiting cell migration inhibitory activity (See Example 52 and Table 3). Preliminary results are summarized in Tables 1-3 below.

TABLE 1

Tube formation assay

| Substance | Minimum effect concentration |
|---|---|
| Migrastatin (1) | 100 μM |
| N-Methyl-migrastatin | 200 μM |
| 2,3-Dihydromigrastatin (41) | 50 μM |
| Migrastatin-Core (45) | 10 μM |

Tested concentrations: 200, 100, 50, 25, 10 μM

TABLE 2

Scratch Assay

| Substance | Minimum effect concentration |
|---|---|
| Migrastatin (1) | 100 μM |
| N-Methyl-migrastatin | 100 μM |
| 2,3-Dihydromigrastatin (41) | 25 μM |

Tested concentrations: 200, 100, 50, 25, 10 μM

TABLE 3

Chamber Assay

| Substance | $IC_{50}$ |
|---|---|
| Migrastatin (1) | 200 μM |

Tested concentrations: 200, 100, 50, 25, 10 μM

Based on the aforementioned preliminary biological data, and without wishing to be bound to any particular theory, we proposed that "truncated" migrastatin analogs (i.e., analogs lacking the side chain at C-13, or having a significantly shorter side chain at C-13) may exhibit improved therapeutic activity. For example, compounds such as those having the general structures depicted below were expected to show good activity as cell migration inhibitors and/or angiogenesis inhibitors:

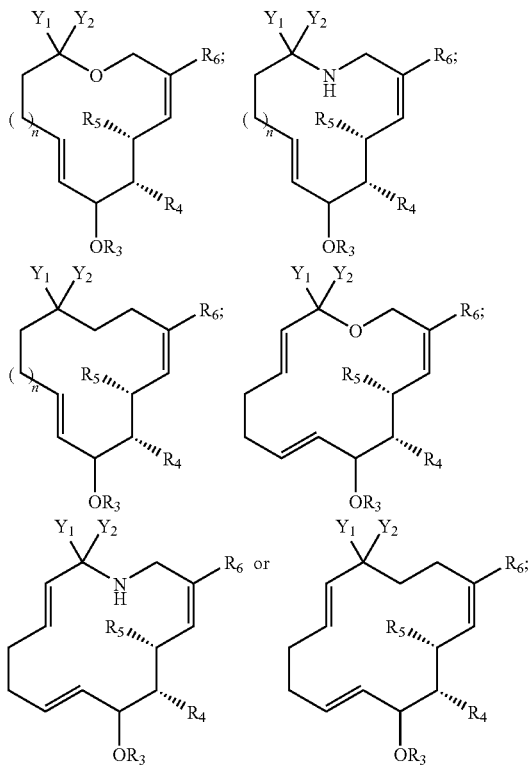

wherein n and $R_3$-$R_6$ are as defined in classes and subclasses herein; and $Y_1$ and $Y_2$ are independently hydrogen, an aliphatic, heteroaliphatic, alicyclic, heterocyclic, aryl or heteroaryl moiety; or —$WR^{Y1}$; wherein W is independently —O—, —S— or —$NR^{Y2}$—, wherein each occurrence of $R^{Y1}$ and $R^{Y2}$ is independently hydrogen, or an aliphatic, heteroaliphatic, alicyclic, heterocyclic, aryl or heteroaryl moiety; or $Y_1$ and $Y_2$ together with the carbon atom to which they are attached form a moiety having the structure:

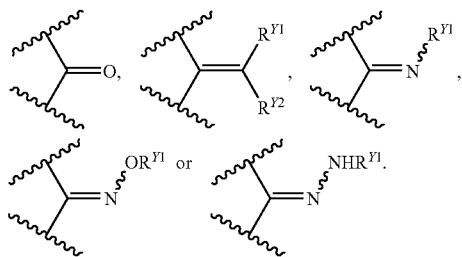

In order to evaluate this hypothesis further, additional analogs were synthesized and tested. In vitro and in vivo biological evaluations in a mouse breast cancer cell and mouse breast cancer model, respectively are detailed in WO 2004/087672 and WO 2004/087673. Specifically, compounds were tested in chamber cell migration, cell proliferation and wound healing assays. Cell migration inhibitory activity of compounds of the invention was evaluated with 4T1 mouse breast tumor cells in chamber cell migration and wound healing assays.

Compounds were also subjected to mouse stability studies. As expected, macrolactone-type compounds showed lesser stability in mouse plasma than their macrolactam or macroketone counterparts.

Finally, compounds showing very good in vitro activity (e.g. chamber 4T1 and HUVEC cell migration assay) were tested in vivo in a mouse breast cancer model.

As discussed above, these findings have been reported in WO 2004/087673. That International Application was directed to compositions and methods for the treatment of metastatic breast cancer at specific dosage ranges. The present application is based on the discovery that migrastatin derivatives possess highly potent cell migration inhibitory and anti-proliferative activity in selective cancerous cells, e.g., ovarian and colon cancers. Relevant biological data are discussed in more detail below (See, for example, Tables 4 & 5, and FIGS. 2-19).

Exemplary Synthetic Approach.

It was particularly desirable to devise a concise, flexible, and readily scaleable synthesis, since it would remain for synthesis to fuel an aggressive SAR elucidation program and to provide significant quantities of materials for in vivo studies. This is in keeping with the notion that total synthesis was viewed as a first milestone of the project, rather than as an end-point. In doing so, several structural features were considered and evaluated. For example, the (E)-configuration of the C2-C3 and C6-C7 double bonds, and the (Z)-configuration of the C11-C12 double bond of the trienic lactone are important features of the migrastatin core. Moreover, maintaining stereocontrol over the dispositions of the stereogenic centers at C8, C9, C10, and C13 was significant. In addition, the introduction of the side-chain projecting from C13 and the inclusion of the stereocenter at C14, which is not part of the ring structure, were equally important aspects of a successful synthesis of the migrastatin target, as were the incorporation of the C15 keto group as well as the δ-substituted glutarimide at C18.

In one embodiment, a synthetic approach that embraces these structural issues is presented in Scheme 17. As depicted in Scheme 17, a retrosynthetic analysis is based on components 2, 3, 4, 5, and 6. The (E)-geometric character of the C2-C3 double bond could be secured via recourse to the known compound 6. An important feature of this synthesis would be the use of aldehyde 2, bearing the methoxy-substituted stereogenic center, ultimately to be emplaced at C8. Another important building block would be diene 3. This type of synergistically activated, dibranched, bisoxygenated butadiene was part of our all-carbon Diels-Alder research in the mid 1970's.[29] Indeed, in the 1980's this type of diene was used in the context of our LACDAC chemistry to create dihydropyrans.[30] The aldehyde in this case would be the previously discussed 2. Appropriate disconnection of the pyran would expose the four carbon segment comprising C10 through C13. The two methyl-branching elements of 3 would appear at C10 and C12 in migrastatin following appropriate manipulations. At the outset, the precise nature of the R function in keto building block 4 awaited specification. A decisive criterion for various candidate structures that might be contemplated would be their amenability to linkage to the emerging C13 in the context of macrolactone formation, while enabling smooth incorporation of the δ-branched glutarimide. We note that the sum of fragments 2 and 6 contains two carbons in excess of those required for formation of the 14-membered macrolactone. Such a disconnection invited the prospect of establishing this lactone through a ring-closing metathesis (RCM) reaction with extrusion of the two seemingly extraneous carbon centers. A more detailed analysis of synthetic issues appears in the context of the next section, in which we describe the implementation of the broad plan.

Scheme 17.
Exemplary Strategy for the Assembly of Migrastatin

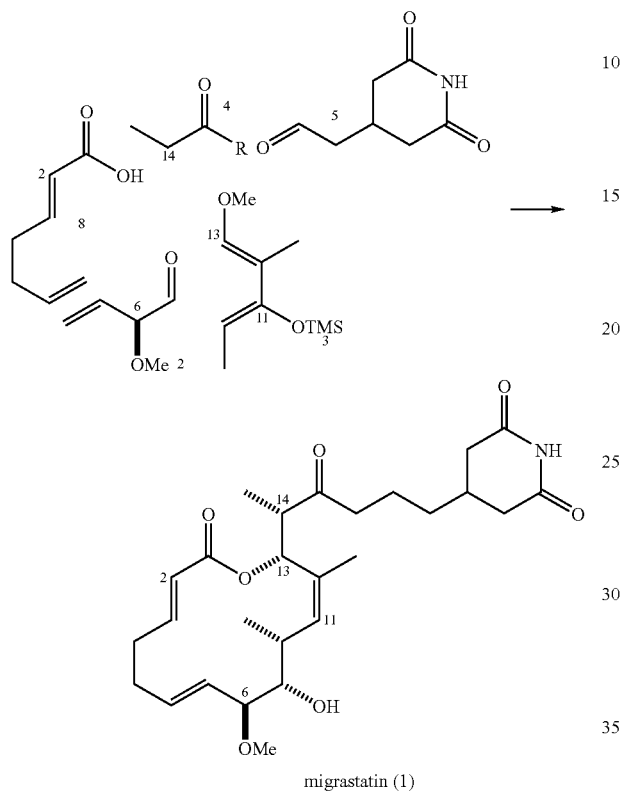

migrastatin (1)

Model Study.

It seemed prudent to assess, in the context of a model study, the feasibility of RCM to construct the 14-membered ring of migrastatin (Scheme 18).[31] In this connection, we would also address the stereoselectivity (geometry of the C6-C7 double bond) and chemoselectivity (undesired RCM-participation of the C2-C3 and C11-C12 double bonds) of the ring-closing reaction. Such questions were to be first posed in a study directed to the synthesis of the migrastatin core structure lacking the glutarimide-containing side chain. Since we were concerned about the stability, stereochemical integrity, and potential volatility of the previously unknown α-methoxy-α-vinyl aldehyde 2 (Scheme 17) contemplated for the LACDAC reaction, we began, in this testing phase, with the structurally less challenging heterodienophilic siloxy-aldehyde 8 (Scheme 18). This compound was prepared from commercially available (S)-3-benzyloxy-1,2-propanediol 7[32] in four steps. The sterically demanding TBDPS protecting group was selected with a view toward suppressing a possible β-chelation pathway relative to the desired α-chelation mode in the LACDAC sequence. Earlier research from Reetz[33] provided a suggestion that oxygen chelation effects in the control of diastereofacial reactions are suppressed in bulky silylether settings.

Indeed, as intended, reaction of aldehyde 8 and diene 3[34] under the influence of TiCl$_4$ yielded the α-chelation controlled product 9 (Scheme 18).[35] Treatment of dihydropyrone 9 with NaBH$_4$ and CeCl$_3$·7H$_2$O (Luche reduction)[36] led to the corresponding 1,2-reduced compound, which underwent a Ferrier rearrangement[37] in aqueous acidic THF to produce lactol 10, with the desired (Z)-olefin now in place. Reductive opening of lactol 10 with LiBH$_4$ afforded diol 11 in 55% overall yield from dihydropyrone 9. The primary hydroxyl group of 11 was selectively acylated with 2,6-heptadienoyl chloride 12[38] and, thereafter, the secondary hydroxyl group in the acylation product was protected as its MOM ether.

Scheme 18.
A Model Study: Synthesis of the Migrastatin Core 15$^a$

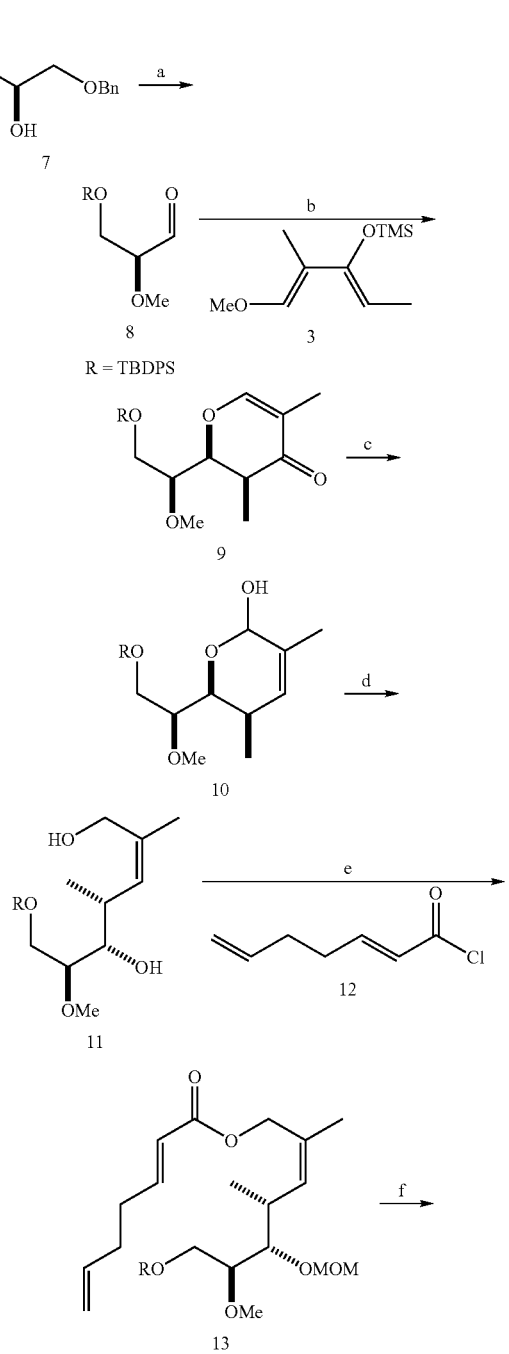

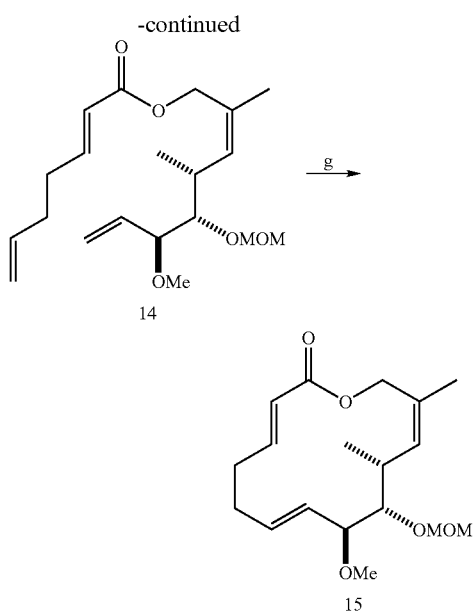

14

15

*a*Reagents and conditions:
(a) (i) TBDPSCl, imidazole, DMF, rt,
  (ii) MeI, NaH, THF, rt,
  (iii) H$_2$, Pd(OH)$_2$, EtOAc, rt,
  (iv) (COCl)$_2$, Et$_3$N, DMSO, CH$_2$Cl$_2$, -78° C. to rt, 66%;
(b) (i) TiCl$_4$, CH$_2$Cl$_2$, -78° C.,
  (ii) TFA, CH$_2$Cl$_2$, rt, 79%;
(c) (i) NaBH$_4$, CeCl$_3$•7H$_2$O, EtOH, 0° C.,
  (ii) CSA, H$_2$O, THf, reflux;
(d) LiBH$_4$, H$_2$O, THF, rt, 55% from 9;
(e) (i) DMAP, CH$_2$Cl$_2$, rt,
  (ii) MOMCl, Bu$_4$NI, i-Pr$_2$NEt, CH$_2$Cl$_2$, rt, 57%;
(f) (i) HF•pyridine, THF, rt,
  (ii) Dess-Martin periodinane, CH$_2$Cl$_2$, rt,
  (iii) Tebbe reagent, pyridine, THF, -78° C. to -10° C., 54%;
(g) Grubbs-II catalyst 16 (20 mol %), toluene (0.5 mM), reflux, 50%.

The RCM precursor 14 was reached from 13 through a three step sequence, consisting of deprotection, oxidation, and Tebbe olefination.[39] When tetraene 14 was subjected to the action of Grubbs catalyst 16[40] (see structures below) in refluxing toluene,[41] the 1-membered macrolactone 15 was generated as the desired (E)-congener in 50% yield. Competitive participation of the electron-poor double bond and the sterically hindered C11-C12 double bond in the metathesis step could not be detected. Interestingly, treatment of 14 with Grubbs-I catalyst 17 in refluxing CH$_2$Cl$_2$ led exclusively to the dimeric product derived from cross metathesis of the terminal double bond of the acyl moiety.

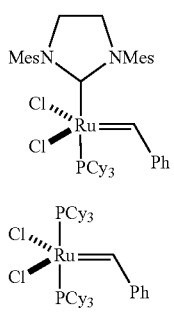

Grubbs-II (16)

Grubbs-I (17)

Synthesis of Intermediate 26.

The model study demonstrated the efficacy of the LAC-DAC sequence to construct the three stereocenters C8-C10 and the power of RCM to establish the macrocyclic system. Encouraged by these early results, we embarked on the total synthesis of migmstatin. Prior to facing the unresolved issues of building up the remaining stereocenters at C13 and C14 in the context of emplacement of the glutarimide moiety, we addressed an issue of process, asking the question whether α-methoxy-α-vinyl aldehyde 2 might indeed serve as a suitable heterodienophile in the reaction with diene 3 after all. Utilization of aldehyde 2 in the LACDAC reaction would allow us to streamline the synthesis in a most useful way by avoiding the chemistry needed to incorporate the C6-C7 double bond required for RCM.

Happily, we could gain an excellent entry into this type of aldehyde, starting from commercially available dimethyl 2,3-O-isopropylidene-L-tartrate 18 (Scheme 19). Toward this end, tartrate 18 was reduced by DIBALH to the corresponding dialdehyde, which was then reacted in situ with divinylzinc to afford carbinol 19 in a highly stereoselective fashion.[42] Dimethylation and cleavage of the acetonide protecting group with aqueous acid furnished 1,2-diol 20 in excellent yield.[43] The desired α-methoxy-α-vinyl aldehyde 2 emerged following cleavage of the glycol linkage of 20. Importantly, no attempts were undertaken to isolate 2 in neat form. Instead, a stock solution of the aldehyde as obtained from the glycol cleavage was directly used for the LACDAC sequence. We were rather encouraged to find that the α-chelation-controlled cyclocondensation of 2 with butadiene 3 occurred in very good yield, producing dihydropyrone 21 as the only detected diastereomer. Compound 21 not only possesses the three contiguous stereocenter of the macrolide, but it also serves as a template for the construction of the trisubstituted C11-C12 (Z)-alkene (Scheme 20). From a process standpoint, it is noteworthy that only two chromatographic purifications were needed to obtain pure 21, rendering the sequence amenable to scale-up.

Scheme 19.
Synthesis of Dihydropyrone 21 by a Cyclocondensation (LACDAC)*a*

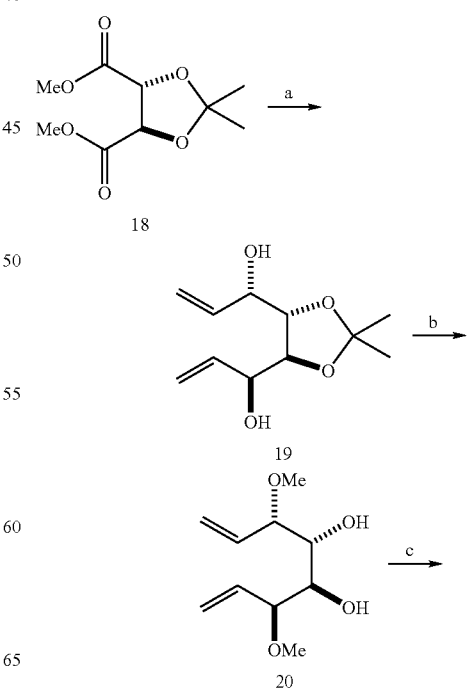

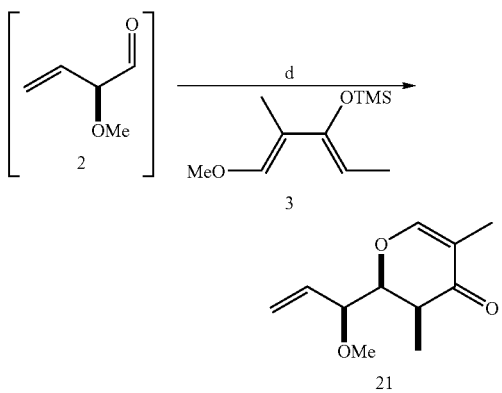

*Reagents and conditions:
(a) DIBALH, then ZnCl$_2$, H$_2$C=CHMgBr, toluene, -78° C. to rt, 75% (ds > 90%);
(b) (i) MeI, NaH, DMF, rt,
   (ii) 2 M HCl, MeOH, reflux, 80%;
(c) Pb(OAc)$_4$, Na$_2$CO$_3$, CH$_2$Cl$_2$, 0° C. to rt;
(d) (i) TiCl$_4$, CH$_2$Cl$_2$, -78° C.,
   (ii) TFA, CH$_2$Cl$_2$, rt, 87% from 20.

Transformation of dihydropyrone 21 into open-chain diol 25 was accomplished as described for our model study (Scheme 18) using a reduction-Ferrier rearrangement-reductive ring-opening protocol (Scheme 20). Initially, we followed the Luche procedure for the reduction of enones to effect the conversion of 21 to 22. Subsequently, we found that the addition of cerium salts was not needed in our case. In fact, all the reductants screened led exclusively to 1,2-reduction. In the end, LiBH$_4$ turned out to be the reducing agent of choice based on its associated ease of handling and workup. When alcohol 22 was subjected to catalytic amounts of camphorsulfonic acid (CSA) in refluxing aqueous THF, the desired Ferrier-rearranged product 23 was obtained, together with small amounts of dimeric acetal 24. It is appropriate to note that there are few examples of aqueous Ferrier rearrangements reported in the literature,[44] whereas variants that involve alcohol-based nucleophiles are widely encountered. Reductive opening of lactol 23 with LiBH$_4$ afforded diol 25 in 53% overall yield (from dihydropyrone 21). In investigating the preparative aspects of the sequence 21-25, we realized that larger amounts of 24 (ca. 15%) were isolated when the Ferrier rearrangement was conducted at higher concentrations (0.3M instead of 0.1M). Happily, we were able to obtain single crystals of dimer 24. X-Ray analysis led to a decisive structural verification,[45] revealing the relative configuration of the three contiguous stereocenters and the geometry of the double bond to be as predicted on the basis of our precedents. By extension, this X-ray analysis also confirms the structure of diol 25.

A next step in this synthesis of migrastatin involved differentiation of the two hydroxyl groups of 25. Previously, we had accomplished this sub-goal via a three step sequence, namely acetylation of the primary hydroxyl group, silylation of the secondary hydroxyl group, and subsequent removal of the acetate protecting group.[27] However, during scale-up efforts, we observed the formation of considerable amounts of diacetylated product. This obstacle complicated purification procedures and lowered the overall yield of the sequence. Fortunately, the problem could easily be solved by initial disilylation, followed by a mild and selective deprotection, producing allylic alcohol 26 in 80% yield (Scheme 20).

Scheme 20.
Synthesis of Intermediate 26$^a$

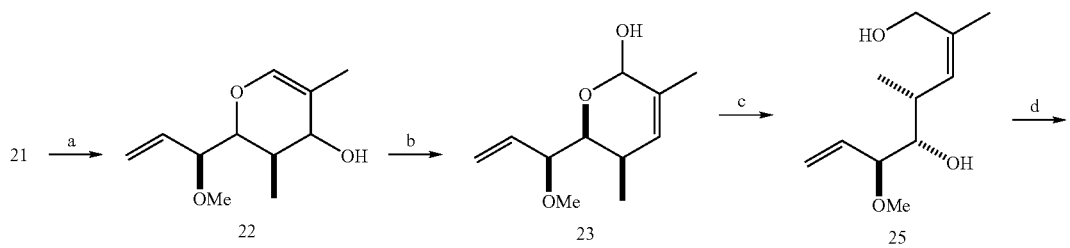

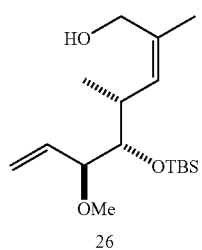

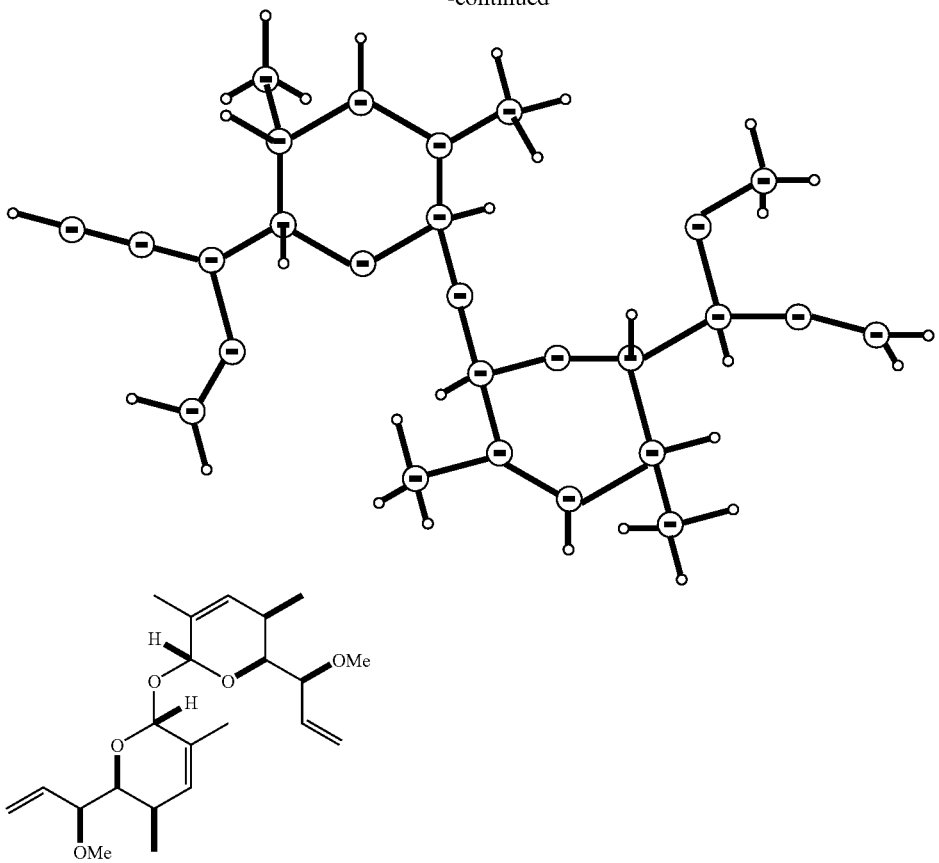

*Reagents and conditions:
(a) LiBH$_4$, MeOH, THF, -10° C.;
(b) CSA, H$_2$O, THF, reflux;
(c) LiBH$_4$, H$_2$O, THF, rt, 53% from 21;
(d) (i) TBSOTf, 2,6-lutidine, CH$_2$Cl$_2$, rt,
(ii) HOAc, H$_2$O, THF (3:1:1), rt, 80%.

Incorporation of the Glutarimide-Containing Side Chain.

A straightforward way to construct the two remaining stereocenters at C13 and C14 could, in principle, be accomplished by an anti-selective aldol reaction between an aldehyde derived from 26 and an appropriate propionyl fragment. Indeed, Dess-Martin oxidation[46] of 26 generated angelic-type aldehyde 27 (Scheme 21). Fortunately, 27 proved to be notably resistant to (Z)→(E)-double bond isomerization or vinylogous epimerization, and, accordingly, could serve as a potential substrate in the aldol construction. In our early studies, we explored Masamune's anti-aldol protocol, which utilizes a boron enolate of readily available norephedrine derivatives.[47] This aldol reaction indeed worked smoothly with aldehyde 27. Nonetheless, we were particularly drawn to a mild MgCl$_2$-catalyzed anti-aldol procedure that had recently been disclosed by Evans.[48] In practice, aldehyde 27 reacted with propionyl oxazolidinone 28 in the presence of MgCl$_2$, triethylamine, and TMSCl to afford, after treatment with TFA, the desired aldol adduct 29 in 67% yield as a single diastereomer. Noteworthy, the robust reaction conditions, which tolerate the use of reagent-grade ethyl acetate and high substrate concentrations, are attractive features for scale-up purposes. Since the next step of the total synthesis was the protection of the C13 hydroxyl group as a TES ether, we tried to accomplish the anti-aldol joining with TESCl instead of TMSCl. Unfortunately, the reaction was very slow under these conditions, and the yields were far from satisfactory. Hence, we had to protect the secondary hydroxyl group with TESCl in a separate step (29→30) (Scheme 21).

Having successfully merged three of our five components, we focused now on attaching glutarimide aldehyde 5 to the main fragment. A Horner-Wadsworth-Emmons (HWE) reaction between β-ketophosphonate 32 and aldehyde 5 appeared to be a plausible, attractive solution to this synthetic problem (Scheme 21). Toward this end, we investigated the direct addition of lithiated dimethyl methylphosphonate to imide 30 to access the desired phosphonate 32 in a single transformation. Unfortunately, this transformation met with no success, resulting in recovery of starting material.[49] Accordingly, the chiral auxiliary was removed reductively (30→31). Progress continued with a simple and reliable three step oxidation-addition-reoxidation protocol, cleanly affording phosphonate 32. Glutarimide aldehyde 5,[50] the fourth component in our synthetic plan, was then treated with phosphonate 32 using the Masamune-Roush variant of the HWE reaction.[51] Enone 33 was obtained as a single olefin isomer in excellent yield (Scheme 21). Fortunately, neither this reaction nor any of the subsequent trarsformations required protection of the glutarimide nitrogen. Conjugate reduction of enone 33 with the Stryker reagent[52] and cleavage of the TES protecting group occurred smoothly to give alcohol 34. At this stage, the path was clear for introduction of our last component, 2,6-heptadienoic acid 6.

Scheme 21.
Incorporation of the Side Chain by an
Anti-Aldol Reaction and a HWE coupling[a]

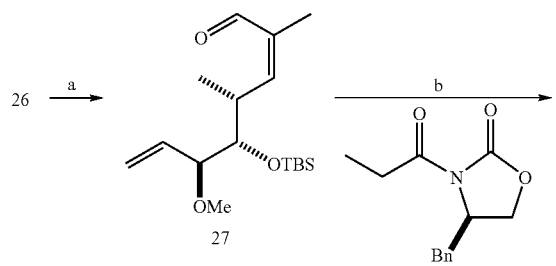

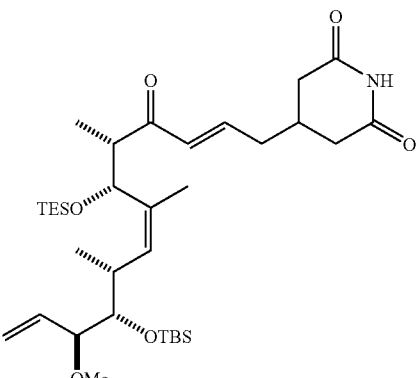

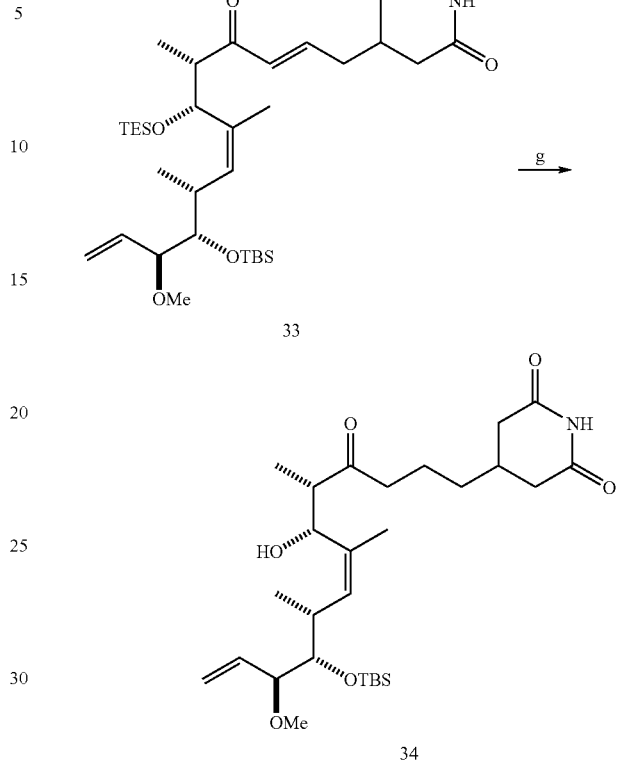

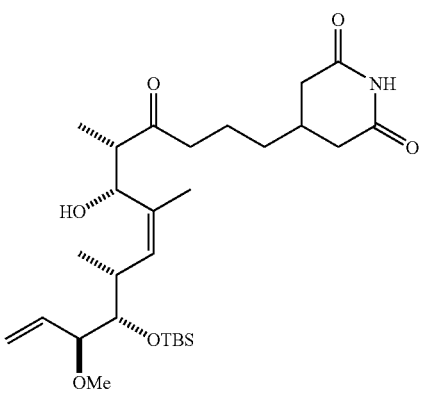

[a]Reagents and conditions:
(a) Dess-Martin periodinane, $CH_2Cl_2$, rt;
(b) (i) $MgCl_2$, $Et_3N$, TMSCl, EtOAc, rt,
 (ii) TFA, MeOH, rt, 67% from 26;
(c) TESCl, imidazole, $CH_2Cl_2$, rt;
(d) $LiBH_4$, MeOH, THF, rt, 83% from 29;
(e) (i) Dess-Martin periodinane, $CH_2Cl_2$, rt,
 (ii) dimethyl methylphosphonate, BuLi, THF, -78° C. to 0° C.,
 (iii) Dess-Martin periodinane, $CH_2Cl_2$, rt;
(f) LiCl, DBU, MeCN, rt, 57% from 31;
(g) (i) $[(Ph_3P)CuH]_6$, toluene, rt,
 (ii) HOAc, $H_2O$, THF (3:1:1), rt, 82%.

Completion of a Total Synthesis of Migrastatin.

In our planning stages, we presumed that acylation of secondary alcohol 34 with acid 6 would be straightforward. Unexpectedly, a number of acylation conditions had to be explored to accomplish the desired transformation effectively. Only after several trial attempts did we find that a modified Yamaguchi acylation protocol[53] (using pyridine instead of DMAP) provided satisfying yields of acylated product 35 (Scheme 22). Most other standard ester formation protocols (a: acid chloride+DMAP, pyridine, or AgCN, b: acid+EDC or DCC, c: acid+Mukaiyama reagent,[54] d: Keck coupling[55]) led to either decomposition of starting material or an inseparable product mixture of 35 and β,γ-unsaturated ester 36 (Scheme 22). The latter presumably arose from acylation of 34 with the vinylketene derived from 6 upon activation of the acyl group. Attempts to isomerize the C3-C4 double bond of 36 back into conjugation resulted in loss of the carboxylic acid fragment, apparently through a β-elimination pathway.

Scheme 22.
Acylation of Alcohol 34 by a Modified Yamaguchi Procedure[a]

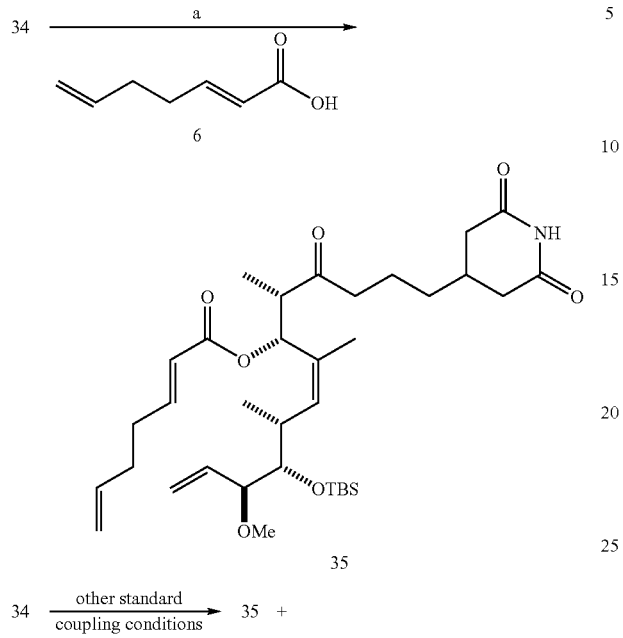

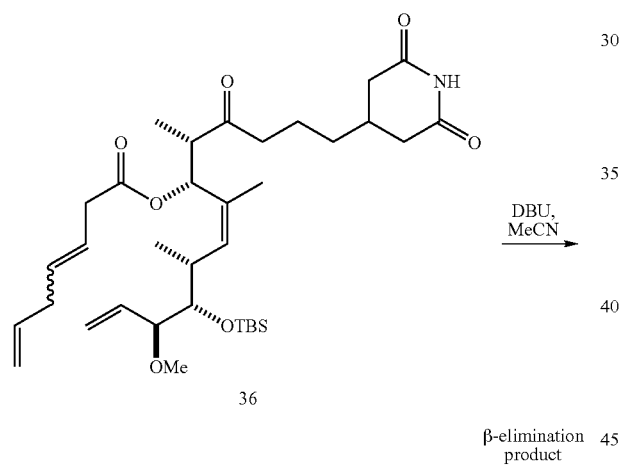

[a]Reagents and conditions:
(a) 2,4,6-trichlorobenzoyl chloride, i-Pr₂NEt, pyridine, toluene, rt, 67%.

Scheme 23.
RCM and Deprotection Leading to (+)-Migrastatin (1)[a]

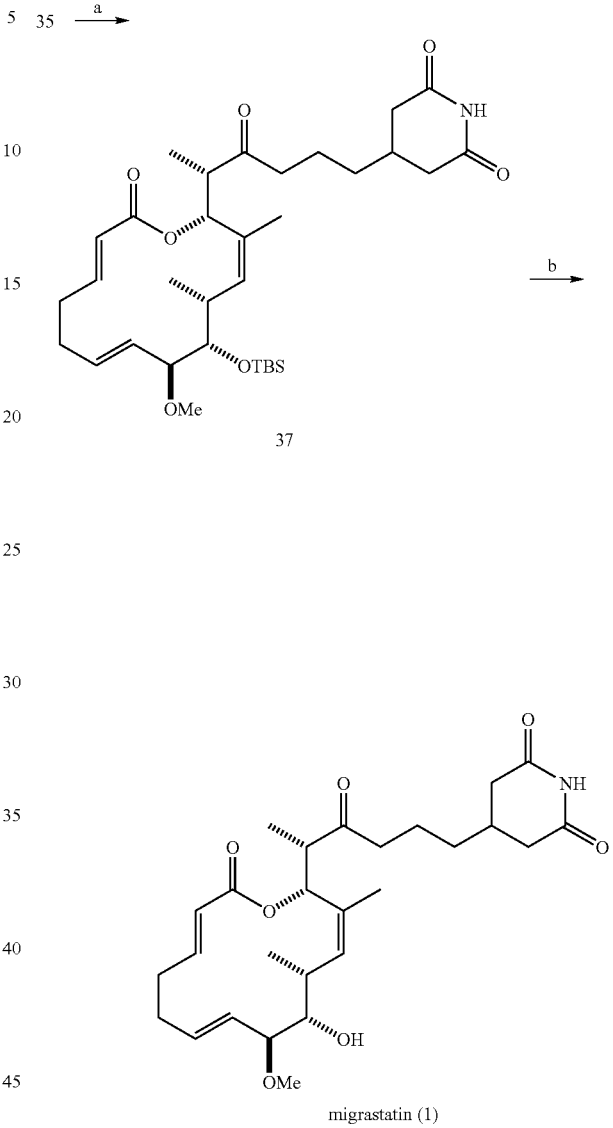

[a]Reagents and conditions:
(a) Grubbs-II catalyst 16 (20 mol %), toluene (0.5 mM), reflux, 69%;
(b) HF·pyridine, THF, rt, 85%.

With RCM precursor 35 now available, we were positioned to investigate the cyclization reaction (Scheme 23). In the event, the ring-closing metathesis conditions employed in our model system (Scheme 18) also sufficed nicely for the case at hand, delivering macrolactone 37 in a highly (E)-selective fashion in 69% yield. This corresponds to an increase in yield by almost 20% compared to our model studies! Finally, removal of the TBS protecting group by buffered hydrogen fluoride completed the total synthesis of (+)-migrastatin (1), whose physical data (NMR, MS, optical rotation) matched those of migrastatin isolated from natural sources.

Design, Chemical Synthesis, and Evaluation of Migrastatin Analogs.

Having achieved our initial objective, a total synthesis of migrastatin, we could take full advantage of our flexible multi-component synthesis for the subsequent preparation of a variety of analogs. As will be evident, our modular approach served as an excellent platform from which to quickly explore the SAR profile of migrastatin and assess the anti-metastatic potential of the migrastatin family.

In certain embodiments, our approach with respect to searching for, preparing, and evaluating migrastatin derivatives as to improved cell migration inhibition properties, comprised three distinct steps: design, chemical synthesis, and biological evaluation. In certain embodiments, the design of migrastatin analogs was aimed at probing the different regions of migrastatin for their contributions to biological activity. Certain regions of the molecule that we initially considered important and accessible by synthesis are highlighted in gray below. These regions were targeted for derivatization.

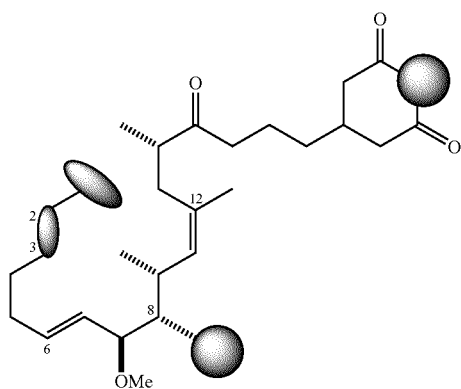 [SMILES: CCCCC/C=C/[C@H](OC)[C@@H](C)[C@H](C)/C=C(/C)C[C@H](C)C(=O)CCCC1CC(=O)CC(=O)C1]

In certain embodiments, the selection was driven by the following considerations: The glutarimide moiety is a characteristic functional feature of migrastatin, and might be indispensable for activity. The C2-C3 conjugated double bond is a potential site for deactivation by 1,4-addition of nucleophiles (e.g. thiols, confer the natural products NK30424A/B in Scheme 16), or on the contrary, could render migrastatin a suicide inhibitor by covalent bond formation with bionucleophiles present in the active site of an enzyme. The lactone functionality could possibly be a target of hydrolysis in living systems. As such, manipulation of the ester bond might enhance the in vivo stability of the molecule. Furthermore, the C6-C12 portion of migrastatin is highly functionalized, and thus, might have biological relevance. One simple way of exploring this region is through derivatization of the C9 hydroxyl group.

The chemical synthesis of migrastatin analogs was accomplished in an efficient manner by utilizing the concept of diverted total synthesis (DTS).[28] We put to advantage certain intermediates of the migrastatin synthesis, such as 26 and 34 (Schemes 20 and 21), as branching points to rapidly assemble a chemically diverse set of migrastatin derivatives. In keeping with the unique capabilities of diverted total synthesis, we focused on target structures that would not have been accessible through manipulations of the natural product itself or through biosynthetic pathways.

The biological evaluation of the compounds (in terms of their ability to inhibit cell migration) was accomplished in a Boyden chamber cell migration assay. In this assay, mouse breast tumor cells (4T1 cells) or endothelial cells (HUVECs) are seeded on the upper chamber of a transwell insert. Growth factor-containing serum is added to the lower chamber. After incubation for 6-8 hours in the presence of different concentrations of our analogs, cells that migrated from the upper chamber through the membrane to the lower compartment are counted. Additionally, some of the more potent compounds were tested for their effect on cell proliferation and metabolic stability in mouse plasma. The study helped provide a broad SAR picture with respect to migrastatin analogs.

In certain embodiments, synthetic studies towards the preparation of chemically diversified migrastatin analogs commenced with the synthesis of 2,3-dihydromigrastatin 41 and N-methylated 2,3-dihydromigrastatin 42. Secondary alcohol 34 (Scheme 21), an advanced intermediate involved in the exemplary migrastatin synthesis described herein, was acylated with 6-heptenoyl chloride 38 to deliver RCM precursor 39 (Scheme 24). As expected, acylation proceeded smoothly, without the use of the reaction conditions utilized for the acylation of 34 with 2,6-heptadienoic acid 6 (Scheme 22). Compound 39 was cyclized to macrolactone 40 by a very efficient (E)-selective RCM. Cleavage of the TBS ether with HF.pyridine yielded our first analog, 2,3-dihydromigrastatin 41. Alternatively, compound 41 was prepared directly from migrastatin by regioselective reduction using the Stryker reagent (Scheme 24). The yield of the direct transformation, however, was compromised by the formation of a side product that arose from an intramolecular aldol addition of the transient copper enolate to the C15 ketone. Methylation of the glutarimide nitrogen was accomplished by treatment of 41 with MeI and $Cs_2CO_3$ in acetone, delivering methylated 2,3-dihydromigrastatin 42 in excellent yield.

The first set of compounds—migrastatin, together with its analogs 41 and 42—was then evaluated in the chamber cell migration assay. The $IC_{50}$ value for fully synthetic migrastatin with 4T1 tumor cells was 29 μM (Table 4); this result was in excellent agreement with that reported by Imoto for migrastatin obtained from natural sources. Interestingly, reduction of the C2-C3 double bond and methylation of the glutarimide nitrogen were well tolerated with respect to maintenance of activity. Analogs 41 and 42 are actually slightly more potent than migrastatin itself, with $IC_{50}$ values of 10 μM and 7 μM, respectively (Table 4).

Scheme 24.
Preparation of Migrastatin Analogs 41 and 42[a]

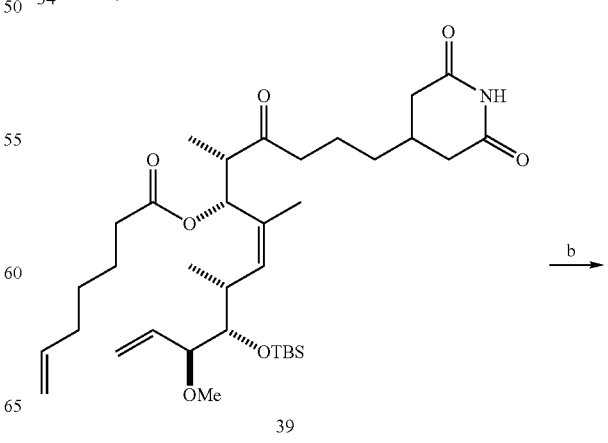

82% yield. The same trend was observed for the subsequent transformation, in which the ring closure was achieved in excellent (76%) yield for the saturated case (46→47). By contrast, the unsaturated core was delivered in lower (55%) yield (43→44). Finally, protecting group removal delivered macrolactones 45 and 48 without complications.

Scheme 25.
Synthesis of Migrastatin Core 45 and Macrolactone 48[a]

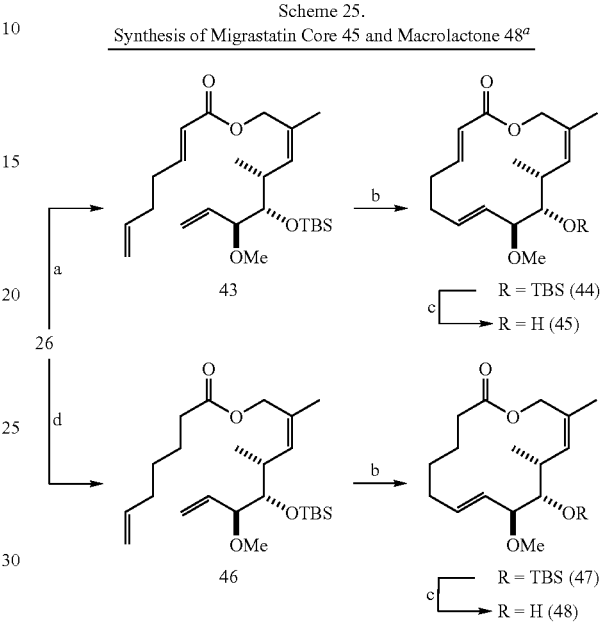

[a]Reagents and conditions:
(a) 2,6-heptadienoic acid 6, 2,4,6-trichlorobenzoyl chloride, i-Pr$_2$NEt, pyridine, toluene, rt, 48%;
(b) Grubbs-II catalyst 16 (20 mol %), toluene (0.5 mM), reflux, 55% (44), 76% (47);
(c) HF·pyridine, THF, rt, 66% (45), 94% (48); (d) 6-heptenoyl chloride 38, DMAP, CH$_2$Cl$_2$, rt, 82%.

In other embodiments, scale-up studies were carried out to establish the applicability of the exemplary synthesis described herein to the preparation of migrastatin and analogs thereof in sufficient quantities for biological evaluation in animal models. For example, variation of the RCM parameters for a potential large scale preparation of the macrocycles were evaluated. The original reaction conditions called for 20 mol % catalyst at 0.5 mM concentration, but as illustrated for the cyclization of 46 to 47 (Scheme 26), the RCM product could be obtained in just slightly reduced yield by conducting the reaction with 10 mol % catalyst at 5 mM concentration.

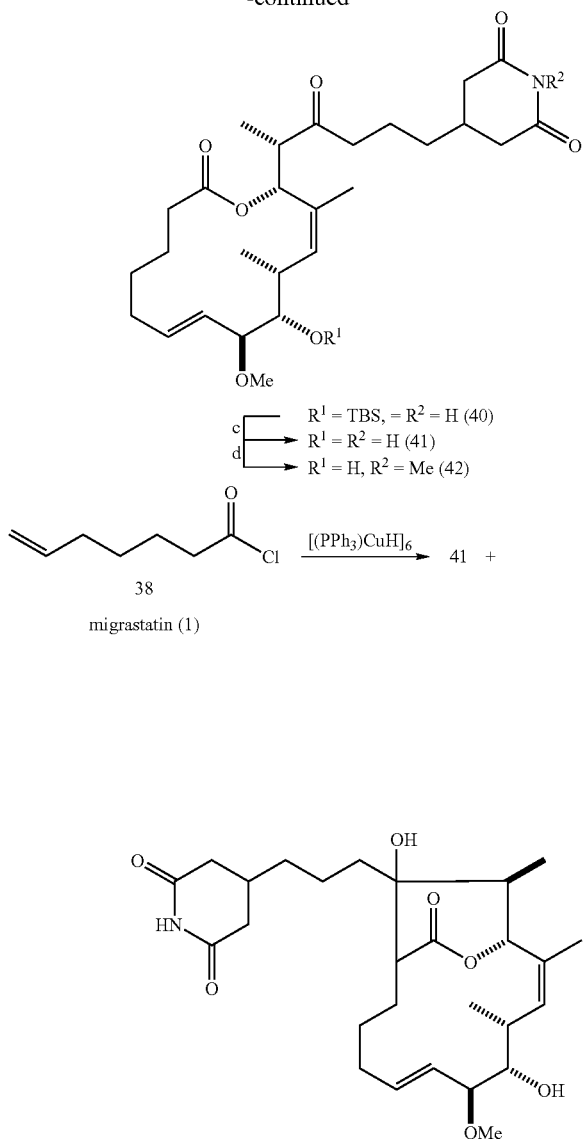

[a]Reagents and conditions:
(a) 6-heptenoyl chloride 38, DMAP, CH$_2$Cl$_2$, rt, 69%;
(b) Grubbs-II catalyst 16 (20 mol %), toluene (0.5 mM), reflux, 79%;
(c) HF·pyridine, THF, rt, 81%;
(d) MeI, Cs$_2$CO$_3$, acetone, 85%.

The small change in inhibitory activity upon alkylation of the glutarimide moiety encouraged us to undertake a more drastic structural modification of the migrastatin skeleton. Toward this end, analogs were synthesized lacking the entire glutarimide-containing side chain, namely migrastatin core 45 and the corresponding reduced version 48 (Scheme 25). Starting from advanced intermediate 26 (Scheme 20), derivatives 45 and 48 were quickly assembled via the already established acylation-RCM-deprotection sequence. While the reaction of 26 with 2,6-heptadienoic acid 6 produced acylated product 43 in only moderate (48%) yield, the acylation steps in the 'dihydro series' occurred smoothly, affording 46 in Scheme 26. Optimization of the RCM Conditions for Scale-Up Purposes

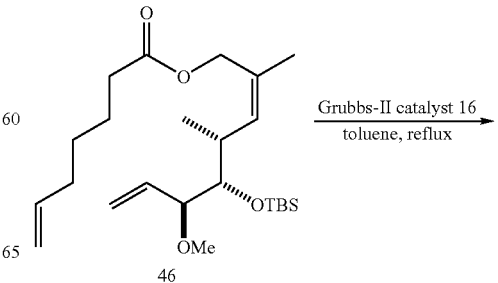

-continued

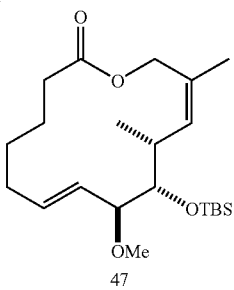

47

| conc. | cat. loading | yield |
|---|---|---|
| 0.5 mM | 20 mol % | 76% |
| 2 mM | 20 mol % | 67% |
| 5 mM | 10 mol % | 63% |

Upon examination of compounds 45 and 48 in the cell migration assay, we achieved, to our great surprise, a major breakthrough in potency (Table 4). The $IC_{50}$ values for migrastatin core 45 and macrolactone 48 were found to be 22 nM and 24 nM, respectively. This translates into an increase in activity by three orders of magnitude compared to migrastatin! This appears to lead to the conclusion that the migrastatin side chain may not be required for in vitro inhibition of tumor cell migration. However, it remains to be determined if migrastatin and core analogs 45 and 48 are indeed directed at the same cellular targets.

Another potential interesting site of derivatization of the migrastatin structure is the C6-C12 region with its two double bonds, three stereocenters, and two heteroatoms. An easy way of derivatizing this portion of the molecule was found to be the acylation or oxidation of the C9 hydroxyl group, producing macrolactones 49 and 50, respectively (Scheme 27). As shown in Table 4, the inhibitory activity of analogs 49 and 50 was reduced by roughly an order of magnitude, compared to macrolactone 48, indicating that the C9 position is sensitive toward modification.

Scheme 27.
Modification of Macrolactone 48 at the C9 position and Hydrolysis of 48[a]

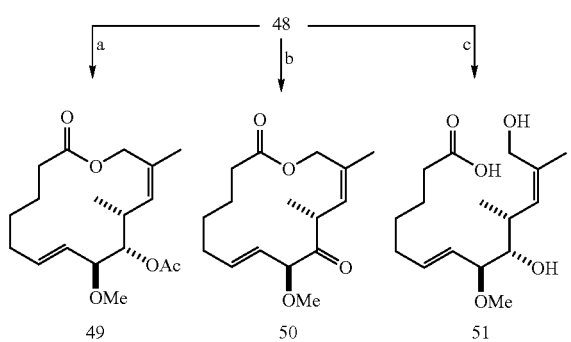

[a]Reagents and conditions:
(a) AcCl, DMAP, CH$_2$Cl$_2$, rt, 76%;
(b) Dess-Martin periodinane, CH$_2$Cl$_2$, rt, 72%;
(c) 0.5 M NaOH, MeOH, rt, 77%.

Starting from our lead compound migrastatin, we were able to reach simplified congeners/analogs with drastically improved inhibitory activities, in particular macrolactones 45 and 48. In anticipation of subsequent in vivo evaluation of these compounds and others, preliminary metabolic stability studies were carried out. Without wishing to be bound to any particular theory, based on our experiences from the epothilone program,[56] we propose that the ester bond of the macrolactones may be susceptible to ring opening by esterases in mouse (or human) plasma Such hydrolysis would presumably lead to a loss in compound activity. Accordingly, mouse blood plasma stability of migrastatin and novel analogs 41, 42, 45, and 48 was evaluated. As summarized in Table 5, migrastatin and side chain-containing derivatives 41 and 42 were completely inert toward lactone opening over the full test period (one hour). However, the most active compounds, macrolactones 45 and 48, were hydrolyzed rapidly (Table 5). These findings are not entirely surprising, considering that the ester bonds in 45 and 48 are sterically less congested relative to those in the other analogs. As a test of the 'deactivation hypothesis', the hydrolysis product of macrolactone 48 was prepared (Scheme 27) and tested for its activity against tumor cell migration. Surprisingly, compound 51 was not completely inactive in the chamber assay, but retained a good part of its activity ($IC_{50}$ value of 378 nM). Therefore, compound 48 might be effective in the projected in vivo models despite its sensitivity toward hydrolysis. Nevertheless, the data on the unsatisfactory metabolic stability of 45 and 48 influenced us, when we entered the second phase of our analog program. The aspiration of reaching migrastatin congeners and/or analogs with enhanced plasma stability and retained or improved activity (compared to 45 or 48) led to the diverted total synthesis of macrolactam 55, macroketone 60 (Scheme 28), and the sterically hindered macrolactones 65 and 68 (Scheme 29).

The synthesis of analogs 55, 60, 65, and 68 diverged from the original route to migrastatin at the stage of the advanced intermediate 26. For the preparation of lactam 55, alcohol 26 was subjected to Mitsunobu conditions with DPPA affording allylic azide 52 in 87% yield (Scheme 28).[57] To avoid double bond isomerization of the (Z)-allylic system, azide 52 was immediately reduced following the Staudinger protocol[57] and subsequently joined with 6-heptenoic acid under standard peptide coupling conditions. The resulting product, amide 53, was treated with RCM catalyst 16 under our established reaction conditions, delivering lactam 54 in 60% yield. The latter was then deprotected with HF.pyridine to afford lactam 55.

The preparation of ketone 60 required the conversion of alcohol 26 into allylic bromide 56, which was displaced by β-ketosulfone 57 (Scheme 28).[57] Subsequent reductive removal of the sulfone group yielded RCM precursor 58. The ring closure of 58 to the carbocycle was accomplished, again, very efficiently and selectively by RCM. The desired macroketone 60 was obtained following deprotection of 59.

Scheme 28.
Synthesis of Macrolactam 55 and Macroketone 60[a]

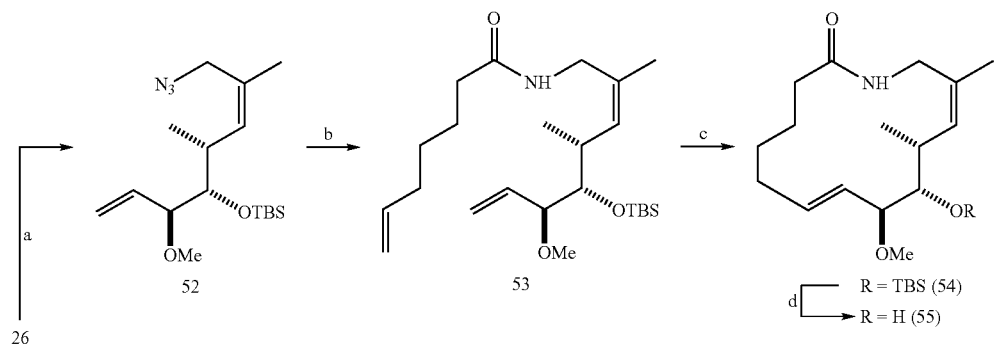

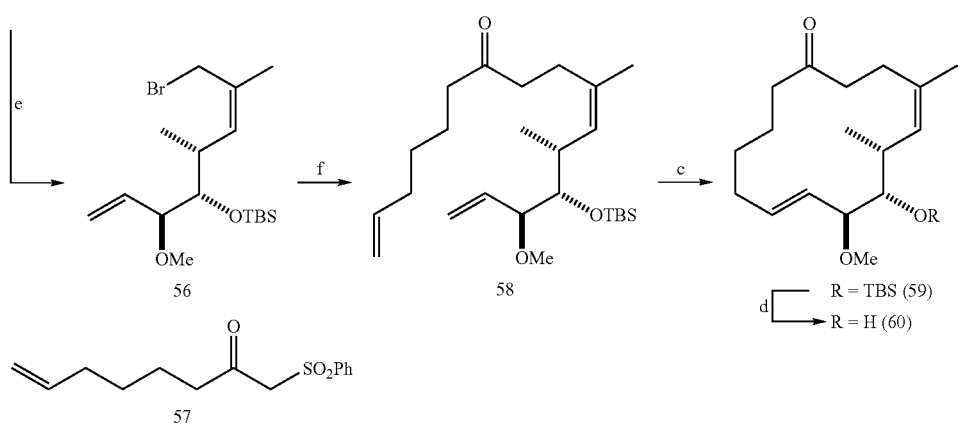

[a]Reagents and conditions:
(a) DPPA (diphenylphosphoryl azide), DBU, toluene, rt, 87%;
(b) (i) PPh₃, H₂O, THF, 70° C.,
   (ii) 6-heptenoic acid, EDC, i-Pr₂NEt, CH₂Cl₂, rt, 92%;
(c) Grubbs-II catalyst 16 (20 mol %), toluene (0.5 mM), reflux, 60% (54), 81% (59);
(d) HF·pyridine, THF, rt, 81% (55), 90% (60);
(e) CBr₄, solid supported PPh₃, CH₂Cl₂, rt;
(f) (i) β-ketosulfone 57, DBU, toluene, rt,
   (ii) Na/Hg, Na₂HPO₄, MeOH, rt, 61% from 26.

The synthesis of isopropyl macrolactones 65 and 68 also commenced from alcohol 26 (Scheme 29). Oxidation of 26 generated the corresponding (Z)-enal which was then treated with i-PrMgCl. When the nucleophilic addition was carried out in THF, an equimolar mixture of the desired addition products 61/62 (3:2 ratio) and the reduced product 26 was obtained. It is well documented in the literature that addition of isopropyl-Grignard reagents to hindered substrates competes with reduction through hydride delivery from the nucleophile.[58] Fortunately, the product ratio could be improved by changing the solvent from THF to Et$_2$O. The reduction pathway was almost completely suppressed by slow addition of i-PrMgCl to a solution of the aldehyde in Et$_2$O, while carefully maintaining the reaction temperature at −78° C. for several hours. Diastereomers 61 and 62 were derivatized as their (S)-MPA and (R)-MPA esters (MPA=α-methoxyphenylacetic acid) and analyzed by NMR, leading to the assignment of the newly created stereocenter:[59] Major isomer 61 has the 'unnatural' (S)-configuration and minor isomer 62 has the 'natural' (R)-configuration. In addition, the results of the NMR experiment were probed by a degradation study. We were able to transform compound 31 (Scheme 21), a synthetic intermediate of the total synthesis of migrastatin, into minor isomer 62, thereby delivering convincing proof for the correctness of the configurational assignment. The transformation was accomplished by converting alcohol 31 into its tosylate, reducing the tosylate with LiAlH$_4$,[60] and removing the TES protecting group. For the preparation of lactones 65 and 68, the addition products 61 and 62 were separated and independently acylated (Scheme 29). Intermediates 63 and 66 were then subjected to our RCM conditions, furnishing the macrocycles 64 and 67 in very good yield. Deprotection occurred smoothly and provided the diastereomeric isopropyl lactones 65 and 68.

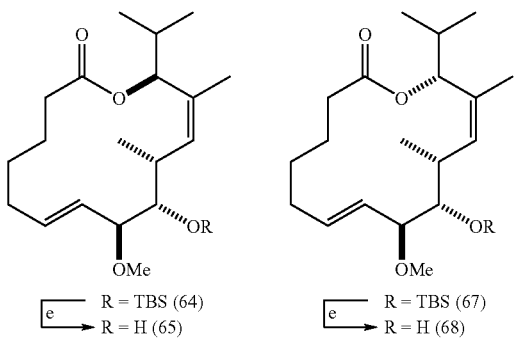

[a]Reagents and conditions:
(a) (i) Dess-Martin periodinane, CH$_2$Cl$_2$, rt,
  (ii) i-PrMgCl, Et$_2$O, -78° C., 86% (3:2-mixture of 61 and 62);
(b) (i) TsCl, pyridine, THF, rt,
  (ii) LiAlH$_4$, Et$_2$O, rt,
  (iii) HOAc, H$_2$O, THF (3:1:1), rt, yield not determined;
(c) 6-heptenoic acid, 2,4,6-trichlorobenzoyl chloride, i-Pr$_2$NEt, pyridine, toluene, rt, 75% (63), 70% (66);
(d) Grubbs-II catalyst 16 (20 mol %), toluene (0.5 mM), reflux;
(e) HF•pyridine, THF, rt, 65% (65 from 63), 66% (68 from 66).

Scheme 29.
Synthesis of the Diastereomeric Isopropyl Macrolactones 65 and 68[a]

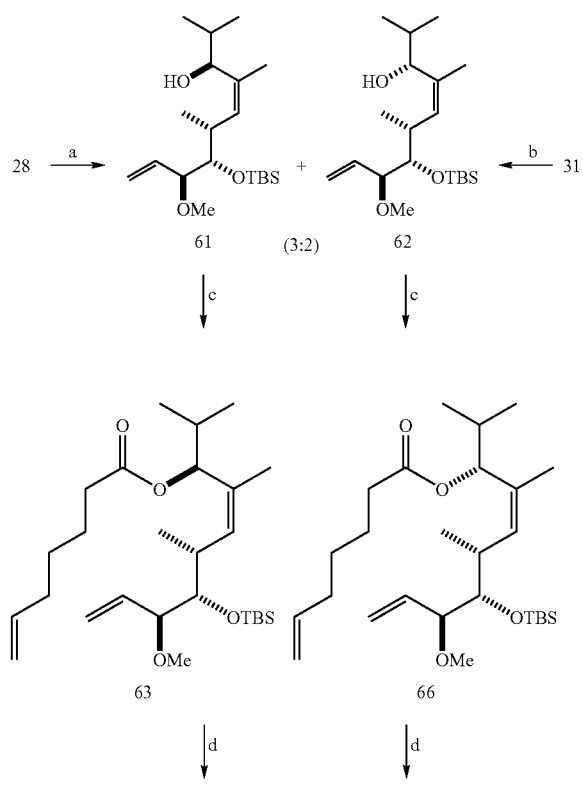

Indeed, lateral modification of the vulnerable ester bond of macrolactones 45 and 48 for more robust entities led to the desired effect of enhanced metabolic stability in all four cases: Macrolactam 55, macroketone 60, and isopropyl macrolactones 65 and 68 display no sign of degradation in our assay (Table 5). When tested for their ability to inhibit 4T1 cell migration, compounds 55 and 60 were found to be considerably more active than the natural product migrastatin (255 nM and 100 nM, respectively, Table 4), although some loss of potency relative to lactones 45 and 48 was recorded. Surprisingly, incorporation of an isopropyl group at C13 proved to be deleterious for biological function. Isopropyl macrolides 65 and 68 exhibited only very weak effects on tumor cell migration (Table 4).

As depicted in Scheme 30, our SAR studies were further diverted on the basis of macroketone 60. The ketone functionality proved to be an attractive handle for additional derivatization. We started our explorations by adding various nucleophiles to the carbonyl functionality accessing analogs 69-71. Simple NaBH$_4$ reduction of 60 afforded secondary alcohol 69 as a mixture of diastereomers, while addition of MeMgBr gave the corresponding tertiary carbinol mixture 70. Following a procedure by Olah,[61] nucleophilic addition of a trifluoromethyl group to 60 was accomplished using (trifluoromethyl)trimethylsilane (TMSCF$_3$) and catalytic amounts of Bu$_4$NF (TBAF). This treatment produced the TMS-protected alcohol intermediate which was transformed into 71 upon prolonged exposure to TBAF (compound 71 was isolated as a single diastereomer after chromatography). Traditional functionalities, such as in oxime 72, could also be easily incorporated starting from macroketone 60. As a part of our long term goal of elucidating the cellular target of migrastatin and our new migrastatin scaffolds, we condensed commercially available Biotin-dPEG$_4$™-hydrazide with ketone 60 furnishing the biotin-labeled acylhydrazone 73.

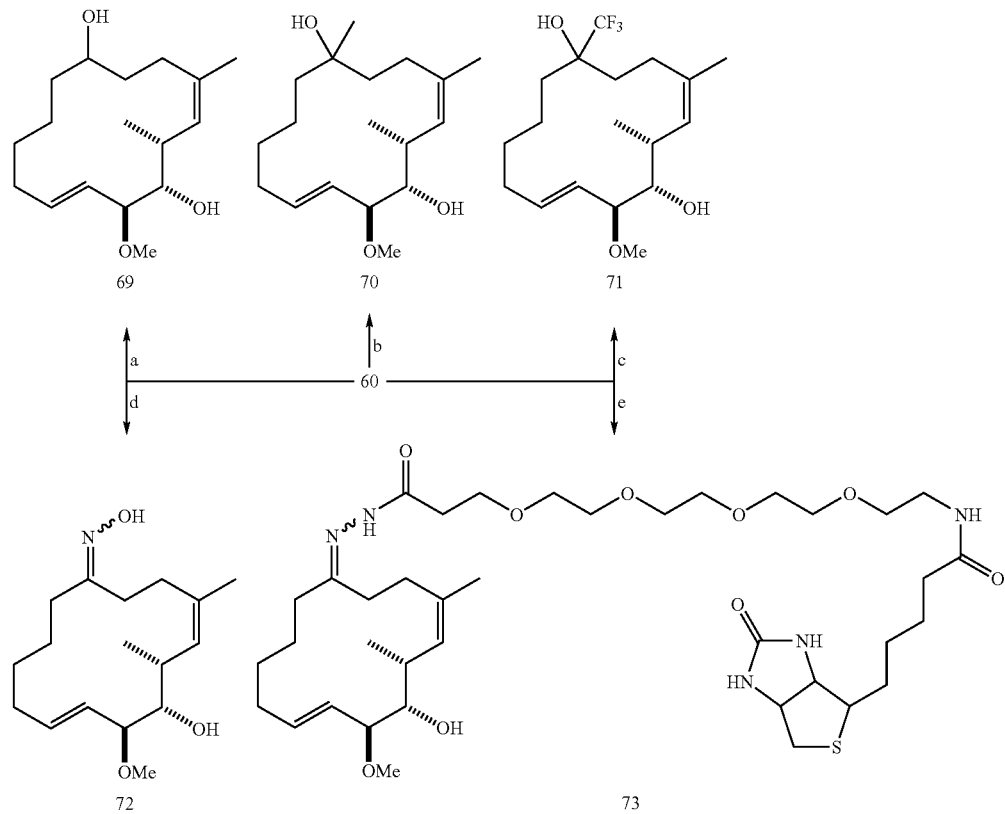

Scheme 30.
Derivatization of Macroketone 60$^a$ $^a$Reagents and conditions:
(a) NaBH$_4$, MeOH, rt, 95%;
(b) MeMgBr, THF, 0° C. to rt, 95%;
(c) TMSCF$_3$, TBAF, THF, 0° C. to rt, 80%;
(d) NH$_2$OH•HCl, pyridine, 45° C., 70%;
(e) Biotin-dPEG4-hydrazide, EtOH, 55° C., 75%.

Derivatives 69-73 were evaluated for their ability to inhibit tumor cell migration in a chamber assay with mouse breast tumor cells (See WO 2004/087672). It was reported that substitution of the ketone functionality for a more polar group, such as an alcohol or oxime function, seems to be detrimental to compound activity. Secondary alcohol 69, tertiary alcohol 70, and oxime 72 are rather weak migration inhibitors. It appears that incorporation of a trifluoromethyl group can compensate for the loss of activity caused by the hydroxyl group: Macrocyclic CF$_3$-alcohol 71 displays the same activity profile as macroketone 60. In addition, inhibitory potency is largely retained in biotinylated hydrazone 73. Therefore, system 73, although a mixture of geometric isomers, could qualify as a probe to assist in the target identification process.

The effect of migrastatin and cell migration inhibitors 48, 55, and 60 on mouse 4T1 cell proliferation has been previously examined. Specifically, it was reported that macrolactone 48, macrolactam 55, and macroketone 60 did not have any cytotoxic or anti-proliferative effects up to 20 μM, whereas migrastatin turned out to be a weak proliferation inhibitor (IC$_{50}$ value of 42 μM). Based on these initial results, it was proposed that cell proliferation inhibition is not a contributor to the effects observed in the chamber assays, and that the migrastatin analogs of the invention may be specific for cell migration inhibition (See, for example WO 2004/087672). Applicant now reports new data (human cells) demonstrating, among other things, that the compounds of the invention are potent cell proliferation inhibitors, in addition to inhibiting cell migration. Furthermore, it was discovered that compounds of the invention exhibit cell migration and cell proliferation inhibitory activity in selective human tumor cell lines.

Additional evaluation was conducted in a variety of human cancer cells and xenographs (See FIGS. 4-19). Specifically, six solid human tumor cell lines and four liquid cancer cell lines were investigated with respect to the inhibitory potential of the most potent compounds macrolactone (48), macroketone (55) and macrolactam (60). Unexpectedly, a very high selectivity between the various tumor cell lines was detected (Table 4 and FIG. 2). (+)-Migrastatin (1) did not respond well to any of the cell lines tested. As stated above, non-transformed human cells such as HUVEC appear to be largely more resistant to the compounds. In contrast, three of our tested cell lines (HT 29, Ovcar3 and RL) clearly demonstrate a very sensitive response in terms of migration inhibition, without interfering with cell proliferation. Surprisingly, the highly metastatic human breast cancer cell line MDA MB435 responded only slightly to 48, but not at all to 55 and 60.[65] None of the compounds responded to the human breast cancer cell line MCF-7. This was an unforeseen discovery, especially in light of the response observed for these compounds to the 4T1 mouse breast cancer cell line (previously reported in WO 2004/087672). These findings suggest a highly specific effect on selective cancerous cells, primarily ovarian (Ovcar3) and colon (HT 29) cancers, in comparison to non-transformed cells indicating a large window for possible therapeutic approaches. Based on these data, compound 48 appears to be of particular interest.

cies. Accordingly, there is provided a method for treating and/or preventing acsites in a subject in need thereof comprising administering an effective amount of a compound of formula I. In certain embodiments, the subject is a mammal. In certain exemplary embodiments, the subject is human.

As shown in the Examples herein, compounds of the invention have been shown to alter adhesion, which is one of the major pathways in metastasis inhibition, as opposed to cell migration.

In addition, compounds of the invention have unexpectedly been shown to inhibit cell proliferation. Therefore we suggest, that we can utilize the inventive compounds as cytotoxic agents (i.e., agents that inhibit cell division and are potentially useful in cancer chemotherapy).

In summary, compounds of the invention have been shown to have potent activity in human ovarian and colon cancer (in vivo and in vitro), as well as multiple myeloma Surprisingly, little response was observed in human breast cancer cells. Compounds of the invention have been shown to exert their activity, not only as cell migration inhibitors, but also by inhibiting cell proliferation and altering the adhesion process.

Furthermore, as demonstrated in Table 4, compounds of the invention can enhance cell migration (See for example,

TABLE 4

Chamber Cell Migration Assay for Various Human Cancer Cells.

| | HT 29 | HCT 116 | IGROV | Ovcar3 | RL | RPMI8226 | CAG | MDA MB435 |
|---|---|---|---|---|---|---|---|---|
| 48 | 13 ± 3 | 60 ± 12 | 76 ± 4 | 20 ± 2 | 38 ± 6 | 88 ± 5 | 89 ± 12 | 68 ± 7 |
| 55 | 106 ± 3 | 165 ± 18 | 101 ± 3 | 55 ± 10 | 75 ± 7 | 82 ± 7 | 96 ± 5 | 112 ± 6 |
| 60 | 95 ± 9 | 104 ± 2 | 91 ± 5 | 65 ± 13 | 85 ± 12 | 92 ± 7 | 94 ± 6 | 98 |

Note with respect to Table 4:
The number represents percent (%) of uninhibited cells as determined by a chamber cell migration assay. Concentrations of compounds employed: 10X $IC_{50}$: 48 (240 nM), 55 (1000 nM), 60 (2550 nM).

TABLE 5

Wound Healing Assay for Various Human Cancer Cells.

| | HT 29 | HCT 116 | IGROV | Ovcar3 | RL | RPMI8226 | CAG | MDA MB435 |
|---|---|---|---|---|---|---|---|---|
| 48 | + | + | + | + | n.d. | n.d. | n.d. | + |
| 55 | − | − | − | + | n.d. | n.d. | n.d. | − |
| 60 | − | − | − | + | n.d. | n.d. | n.d. | − |

Note with respect to Table 5:
The plus/minus sign refers to a successful (+) or unsuccessful (−) inhibition of cell migration as determined by a wound healing assay. n.d. = not done. Concentrations of compounds employed: 10X $IC_{50}$: 48 (240 nM), 55 (1000 nM), 60 (2550 nM).

The present invention demonstrates that migrastatin analogs are potent inhibitors of cell migration and cell proliferation in selected human cancer cells. For example, we identified ovarian, colon and multiple myeloma cancer cells as the most responsive. Surprisingly, the tested compounds exhibited little to no activity in the human breast cancer cells investigated (i.e., MDA MB435 and MCF-7). Accordingly, without wishing to be bound to any particular theory, there is provided a method for treating and/or preventing ovarian and/or colon cancer in a subject in need thereof comprising administering an effective amount of a compound of formula I. In certain embodiments, the method is for treating and/or preventing metastatic ovarian and/or colon cancer. In certain embodiments, the subject is a mammal. In certain exemplary embodiments, the subject is human.

Figure 9:
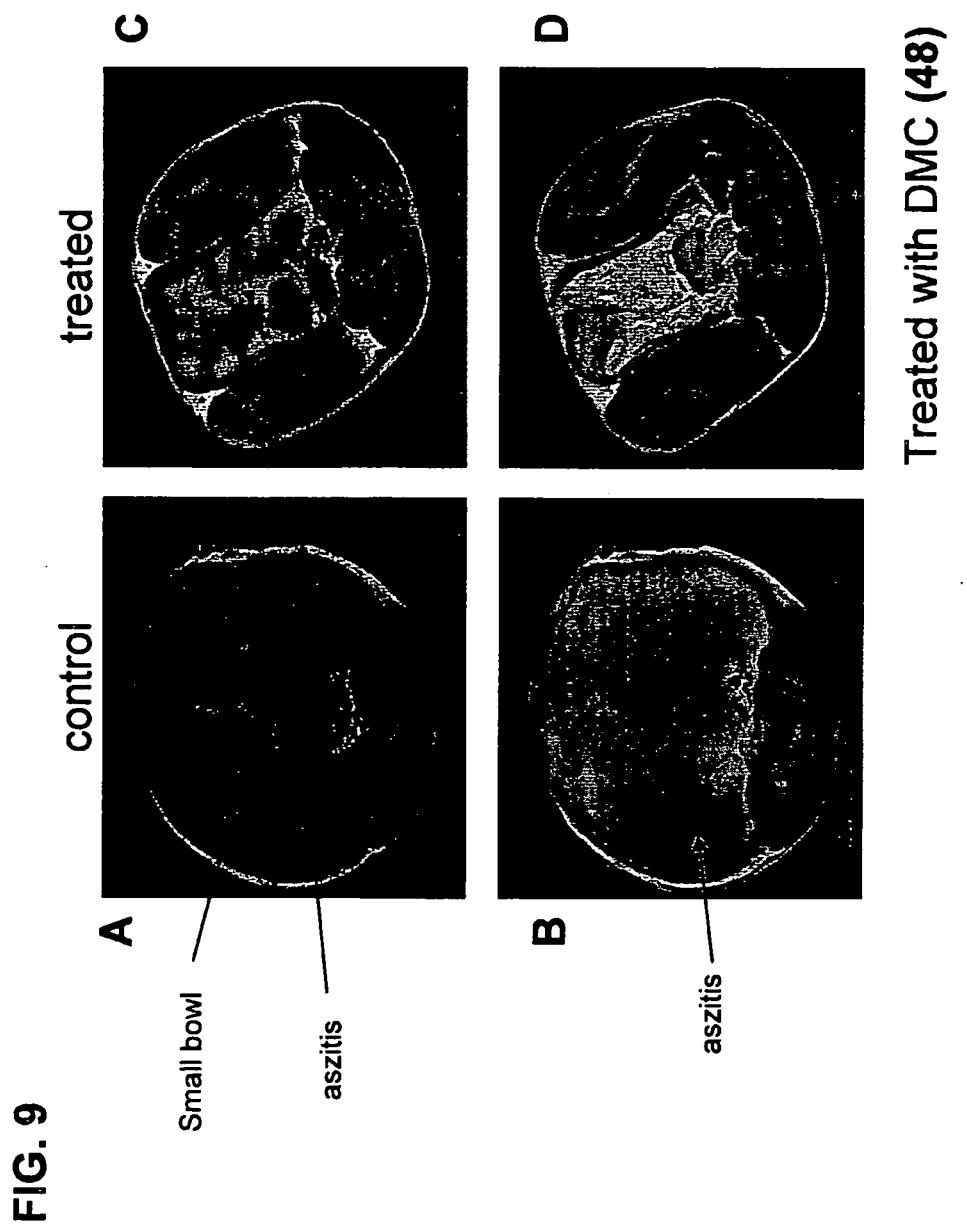
FIG. 9 depicts peritoneal tumor spread and ascitis development experiments in mice. Figures A-B: control mice. Figures C-D: mice treated with DMC (48). The experiment shows that 4 out of 4 control mice had ascitis, whereas 1 out of 4 treated mice had ascitis.
Figure 13:
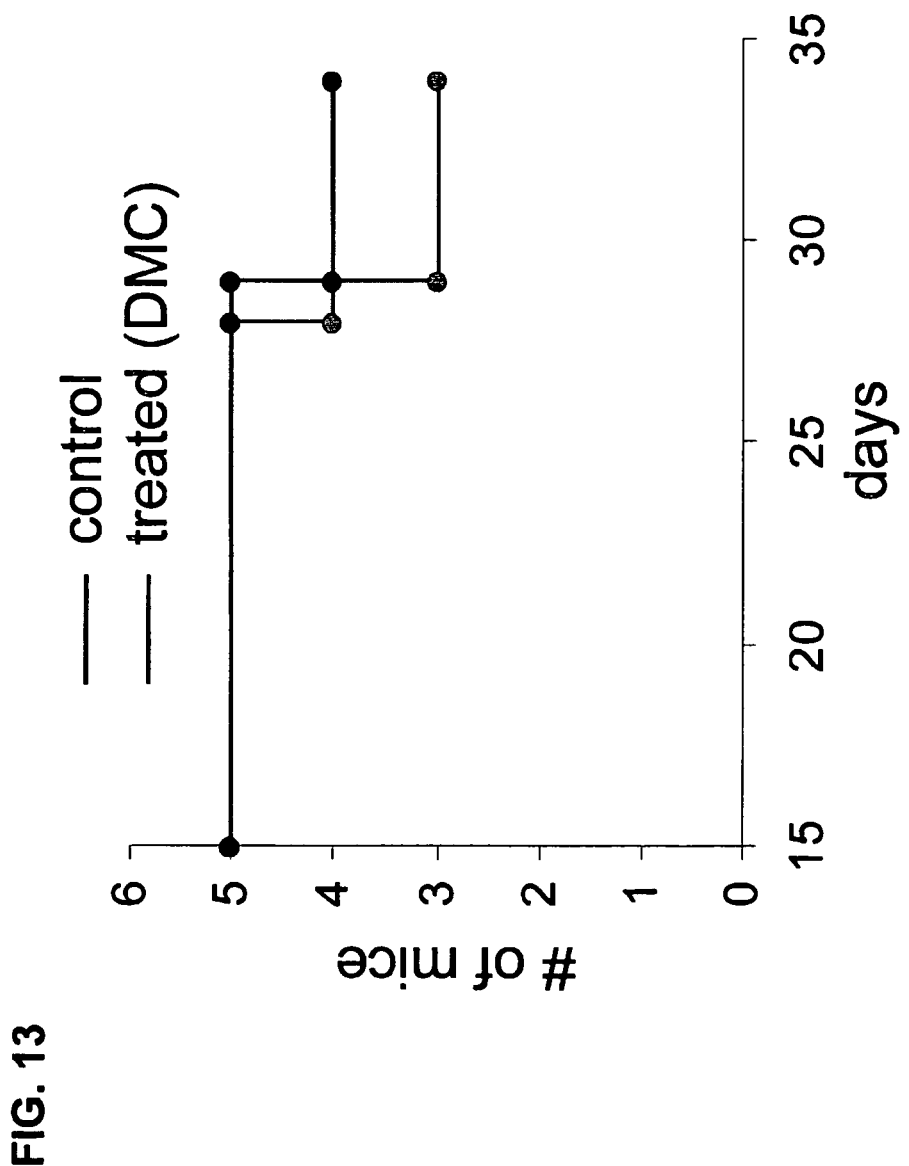
FIG. 13 depicts a survival-curve graph of mice treated with migrastatin analog (48) in an ovarian xenograph model.

As shown in Example 57 and FIG. 9, migrastatin analogs are useful for blocking ascites (excess fluid in the abdominal cavity), a condition often associated with various malignacompounds 55 and 66 which exhibit cell migration % in excess of 100). Without wishing to be bound to any particular theory, we propose that compounds of the invention are useful for facilitating wound healing. Accordingly, there is provided a method for treating a wound or facilitating wound healing in a subject in need thereof comprising administering an effective amount of a compound of formula I. In certain embodiments, the subject is a mammal. In certain exemplary embodiments, the subject is human.

The dosages as the same for human and mice given in mg/kg body weight. I suggest to include a very high dose with the implication of a possible chemotherapeutic drug. A low dose could become interesting for minimal residual disease treatment.

Dosage ranges suitable for administration to a subject (e.g., humans) suffering from a condition associated with ovarian, colon, ovarian, myeloma, and/or lymphoma tumor metastasis were defined based on the in vitro data of Tables 7 & 8 and in vivo data detailed in FIGS. 4-19. Methods for extrapolating effective dosages in mice and other animals, to humans are known in the art (See, for example, U.S. Pat. No. 4,938,949). For example, in certain embodiments, compounds of the invention (for example those useful for the treatment of colon and/or ovarian cancer) may be administered at dosage levels of about 0.01 mg/kg to about 300 mg/kg, from about 0.1 mg/kg to about 250 mg/kg, from about 1 mg/kg to about 200 mg/kg, from about 1 mg/kg to about 150 mg/kg, from about 1 mg/kg to about 100 mg/kg, from about 1 mg/kg to about 90 mg/kg, from about 1 mg/kg to about 80 mg/kg, from about 1 mg/kg to about 70 mg/kg, from about 1 mg/kg to about 60 mg/kg, from about 1 mg/kg to about 50 mg/kg, from about 1 mg/kg to about 40 mg/kg, from about 1 mg/kg to about 30 mg/kg, from about 1 mg/kg to about 20 mg/kg, from about 5 mg/kg to about 100 mg/kg, from about 5 mg/kg to about 90 mg/kg, from about 5 mg/kg to about 80 mg/kg, from about 5 mg/kg to about 70 mg/kg, from about 5 mg/kg to about 60 mg/kg, from about 5 mg/kg to about 50 mg/kg, from about 5 mg/kg to about 40 mg/kg, from about 5 mg/kg to about 30 mg/kg, from about 5 mg/kg to about 20 mg/kg, from about 10 mg/kg to about 100 mg/kg, from about 10 mg/kg to about 90 mg/kg, from about 10 mg/kg to about 80 mg/kg, from about 10 mg/kg to about 70 mg/kg, from about 10 mg/kg to about 60 mg/kg, from about 10 mg/kg to about 50 mg/kg, from about 10 mg/kg to about 40 mg/kg, from about 10 mg/kg to about 30 mg/kg, from about 10 mg/kg to about 20 mg/kg, from about 20 mg/kg to about 100 mg/kg, from about 20 mg/kg to about 90 mg/kg, from about 20 mg/kg to about 80 mg/kg, from about 20 mg/kg to about 70 mg/kg, from about 20 mg/kg to about 60 mg/kg, from about 20 mg/kg to about 50 mg/kg, from about 20 mg/kg to about 40 mg/kg, from about 20 mg/kg to about 30 mg/kg, of subject body weight per day, one or more times a day, to obtain the desired therapeutic effect. In certain embodiments, compounds may be administered at a dosage of about 1 mg/kg or greater, 5 mg/kg or greater±10 mg/kg or greater, 15 mg/kg or greater, 20 mg/kg or greater, 25 mg/kg or greater, 30 mg/kg or greater, 35 mg/kg or greater, 40 mg/kg or greater, 45 mg/kg or greater, 50 mg/kg or greater, 60 mg/kg or greater, 70 mg/kg or greater, of body weight. It will also be appreciated that dosages smaller than 0.01 mg/kg or greater than 70 mg/kg (for example 70-200 mg/kg) can be administered to a subject.

In certain embodiments, compounds may be used in chemotherapy (i.e., as cytotoxic drug) and may be administered at higher dosage. For example, compounds to be used in chemotherapy may be administered from about 100 mg/kg to about 300 mg/kg, from about 120 mg/kg to about 280 mg/kg, from about 140 mg/kg to about 260 mg/kg, from about 150 mg/kg to about 250 mg/kg, from about 160 mg/kg to about 240 mg/kg, of subject body weight per day, one or more times a day, to obtain the desired therapeutic effect.

In certain other embodiments, compounds may be used in supportive therapy (e.g., as an adjuvant to surgery or irradiation in a range of common types of tumour) and may be administered at lower dosage. For example, compounds to be used in supportive therapy may be administered from about 1 mg/kg to about 30 mg/kg, from about 1 mg/kg to about 25 mg/kg, from about 5 mg/kg to about 20 mg/kg, of subject body weight per day, one or more times a day, to obtain the desired therapeutic effect.

In certain other embodiments, compounds may be used for preventing and/or treating metastatic cancer (e.g., ovarian and/or colon cancer) and may be administered at an intermediate dosage. For example, compounds to be used in supportive therapy may be administered from about 1 mg/kg to about 80 mg/kg, from about 5 mg/kg to about 70 mg/kg, from about 10 mg/kg to about 70 mg/kg, from about 10 mg/kg to about 60 mg/kg, from about 20 mg/kg to about 70 mg/kg, from about 20 mg/kg to about 60 mg/kg, of subject body weight per day, one or more times a day, to obtain the desired therapeutic effect Without wishing to be bound to any particular theory, the following preliminary structure-activity relationship (SAR) trends appear to emerge: reduction of the 2,3-double bond of migrastatin results in no significant loss of activity. Similarly, alkylation of the glutarimide nitrogen does not appear to negatively impact activity. Complete removal of the C-13 side-chain (e.g., compounds 45, 48, 49, 50, 55, 60 and 71), thereby producing simple macrolactones, dramatically increases activity. This region appears to be relatively sensitive, as indicated by the following observations: replacing the sidechain with a small (isopropyl) mimic results in almost complete loss of activity. When the oxygen of the macrolactone is replaced with either a nitrogen or a carbon atom, the effect is much more subtle (activity decreases by about one order of magnitude). When the conjugated 2,3-olefin is reduced, activity does not appear to be negatively impacted. For compounds of formula (I) where $X_1$ is $CH_2$ and $Y_1$, $Y_2$ taken together with the carbon atom to which they are attached is C(=O) (i.e., macroketone), oxime formation, reduction or addition of small nucleophiles to the ketone moiety appears to be detrimental to activity while the addition of larger nucleophiles ($CF_3$) is tolerated. The activity of compounds of formula (I) where $R_4$ is C=O or OAc (e.g., compounds 49 and 50) is minimally affected (about one order of magnitude) as compared to the corresponding compounds where $R_4$ is OH (e.g., compounds 45 and 48).

General Reaction Procedures:

Unless mentioned specifically, reaction mixtures were stirred using a magnetically driven stirrer bar. Reactions involving air or moisture-sensitive reagents or intermediates were performed under argon or nitrogen atmosphere in glassware which had been heat gun or flame-dried under high vacuum. An inert atmosphere refers to either dry argon or dry nitrogen. Reactions were monitored either by thin layer chromatography, by proton nuclear magnetic resonance (NMR) or by high-pressure liquid chromatography (HPLC), of a suitably worked up sample of the reaction mixture.

Indicated reaction temperatures refer to those of the reaction bath, while room temperature (rt) is noted as 22° C. Preparative reactions were stirred magnetically. Tetrahydrofuran (THF), diethyl ether ($Et_2O$), methylene chloride ($CH_2Cl_2$), and toluene were obtained from a dry solvent system (activated alumina columns, positive pressure of argon). All other solvents were used as received in Sure/Seal bottles (Aldrich). Triethylamine ($Et_3N$), diisopropylethylamine (i-$Pr_2NEt$), pyridine, 2,6-lutidine, and chlorotrimethylsilane (TMSCl) were distilled from $CaH_2$ immediately prior to use. All other reagents were purchased from Aldrich at the highest commercial quality and used without further purification, with the exception of the Stryker reagent which was purchased from Fluka, the RCM catalysts 16 and 17 which were purchased from Strem, and biotin-$dPEG_4$-hydrazide which was purchased from Quanta Biodesign.

Listed below are abbreviations used for some common organic reagents referred to herein:

CSA: Camphorsulphonic acid
DBU: 1,8-Diazabicyclo[5.4.0]undec-7-ene
Dess-Martin: Dess-Martin periodinane
DIBAL-H: Diisobutyl aluminum hydride
DMAP: N,N-Dimethylaminopyridine
DMF: N,N-Dimethylformamide
TBSOTf: Tert-butyl-dimethylsilyl triflate
TESCl: Triethylsilyl chloride
TFA: Trifluoroacetic acid
TMSCl: Trimethylsilyl chloride
THF: Tetrahydrofuran General Work Up Procedures:

Unless mentioned specifically, reaction mixtures were cooled to room temperature or below then quenched, when necessary, with either water or a saturated aqueous solution of ammonium chloride. Desired products were extracted by partitioning between water and a suitable water-immiscible solvent (e.g. ethyl acetate, dichloromethane, diethyl ether). The desired product containing extracts were washed appropriately with water followed by a saturated solution of brine. On occasions where the product containing extract was deemed to contain residual oxidants, the extract was washed with a 10% solution of sodium sulphite in saturated aqueous sodium bicarbonate solution, prior to the aforementioned washing procedure. On occasions where the product containing extract was deemed to contain residual acids, the extract was washed with saturated aqueous sodium bicarbonate solution, prior to the aforementioned washing procedure (except in those cases where the desired product itself had acidic character). On occasions where the product containing extract was deemed to contain residual bases, the extract was washed with 10% aqueous citric acid solution, prior to the aforementioned washing procedure (except in those cases where the desired product itself had basic character). Post washing, the desired product containing extracts were dried over anhydrous magnesium sulphate, and then filtered. The crude products were then isolated by removal of solvent(s) by rotary evaporation under reduced pressure, at an appropriate temperature (generally less than 45° C.).

General Purification Procedures:

Unless mentioned specifically, chromatographic purification refers to flash column chromatography on silica, using a single solvent or mixed solvent as eluent. Suitably purified desired product containing elutes were combined and concentrated under reduced pressure at an appropriate temperature (generally less than 45° C.) to constant mass. Final compounds were dissolved in 50% aqueous acetonitrile, filtered and transferred to vials, then freeze-dried under high vacuum before submission for biological testing.

Analytical Equipment:

Optical rotations were measured on a JASCO DIP-370 digital polarimeter at rt. Concentration (c) in g/100 ml and solvent are given in parentheses. Infrared spectra were obtained on a Perkin-Elmer 1600 FT-IR spectrophotometer neat or as a film in $CHCl_3$ (NaCl plates). Absorption bands are noted in $cm^{-1}$. $^1H$- and $^{13}C$-NMR spectra were recorded on a Bruker AMX-400 or a Bruker DRX-500 spectrometer in $CDCl_3$. Chemical shifts (δ-values) are reported in ppm with residual undeuterated $CHCl_3$ as the internal standard (referenced to 7.26 ppm for $^1H$-NMR and 77.0 ppm for $^{13}C$-NMR). Coupling constants (J) (H,H) are given in Hz, spectral splitting patterns are designated as singulet (s), doublet (d), triplet (t), quadruplet (q), multiplet or more overlapping signals (m), apparent (app), broad signal (br). Low resolution mass spectra (ionspray, a variation of electrospray) were acquired on a Perkin-Elmer Sciex API 100 spectrometer. Samples were introduced by direct infusion. High resolution mass spectra (fast atom bombardment, FAB) were acquired on a Micromass 70-SE-4F spectrometer. Flash chromatography (FC) was performed with E. Merck silica gel (60, particle size 0.040-0.063 mm). Preparative thin layer chromatography (TLC) was performed with Whatman Partisil Plates (10×10 cm, 60 Å, 200 μm).

Example 1

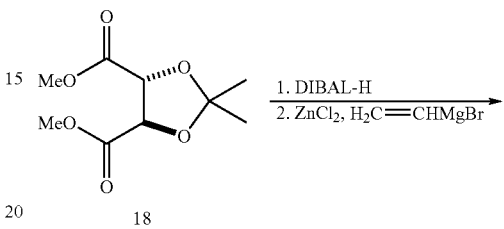

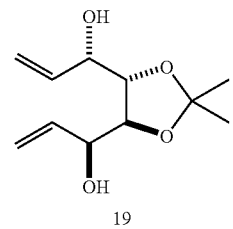

Vinyl Carbinol 19:

Compound 19 was prepared using a slightly modified literature procedure by Madsen. (See, Jorgensen, M.; Iversen, E. H.; Paulsen, A. L.; Madsen, R. *J. Org. Chem.* 2001, 66, 4630).

Preparation of the Divinylzinc Reagent: To Vinylmagnesium Bromide (294 mL, 294 mmol, 1.0M in THF) was added slowly a solution of anhydrous $ZnCl_2$ (20.0 g, 147 mmol, beads) in THF (100 mL) to yield a dark brown solution of divinylzinc in THF (with some precipitate).

Preparation of vinyl carbinol 19: To a solution of dimethyl 2,3-O-isopropylidene-L-tartrate 18 (8.58 g, 39.3 mmol) in toluene (100 mL) at −78° C. was added slowly DIBALH (90 mL, 90.0 mmol, 11.0M in toluene). The reaction mixture turned into a white slurry during the course of the addition. After stirring for 3 h (the reaction temperature has to be kept at −78° C. to prevent overreduction), the divinylzinc solution as prepared above was added to the reaction mixture via cannula over 45 min. After stirring for another 30 min, the reaction mixture was warmed to rt and stirred for 4 h. The reaction mixture was then carefully (!) treated with saturated aqueous $NH_4Cl$ solution and 20% aqueous Na/K-tartrate solution. The organic layer was separated and the aqueous layer was extracted with $Et_2O$ (3×). The combined organic layers were dried ($MgSO_4$) and concentrated under reduced pressure. Purification of the crude product by FC (hexane/EtOAc 4:1) afforded vinyl carbinol 19 (6.28 g, 75%, diastereoselectivity >90%) as a colorless oil. $^1H$-NMR (400 MHz, $CDCl_3$) δ 6.04-5.94 (m, 2H), 5.40 (d, J=17.3, 2H), 5.30 (d, J=10.5, 2H), 4.19-4.16 (m, 2H), 3.89-3.87 (m, 2H), 2.91 (br s, 2H), 1.42 (s, 6H).

Example 2

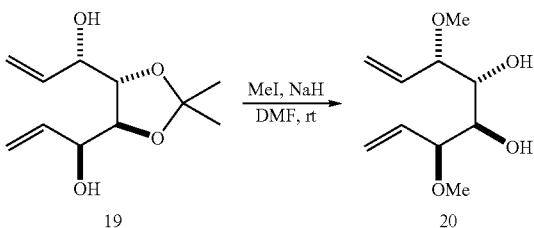

1,2-Diol 20:

The preparation of compound 20 has been reported before by Chang, (See, Lee, W. W.; Chang, S. *Tetrahedron: Asymmetry* 1999, 10, 4473) but experimental details have not been provided.

To a solution of vinyl carbinol 19 (6.28 g, 29.2 mmol) in DMF (100 mL) at 0° C. was added NaH (2.58 g, 64.5 mmol, 60% dispersion in mineral oil) and, 5 min later, MeI (4.38 mL, 70.3 mmol). The reaction mixture was warmed to rt, stirred for 45 min, and then treated with 2M $NH_4OH$. The organic layer was separated and the aqueous layer was extracted with $Et_2O$ (3×). The combined organic layers were dried ($MgSO_4$) and concentrated under reduced pressure. The crude product was dissolved in MeOH (150 mL) and 2M HCl (50 mL) and heated to reflux for 2 h. The reaction mixture was cooled to rt, treated with saturated aqueous $Na_2CO_3$ solution and diluted with $Et_2O$. The organic layer was separated and the aqueous layer was extracted with $Et_2O$ (3×). The combined organic layers were dried ($MgSO_4$) and concentrated under reduced pressure. Purification of the crude product by FC (hexane/EtOAc 2:1) afforded 1,2-diol 20 (4.72 g, 80%) as a colorless oil. $[\alpha]_D$ +31.00 (c 1.77, $CHCl_3$); IR (neat) 3454, 3078, 2982, 2936, 2824, 1643, 1420, 1192, 1102, 992; $^1$H-NMR (500 MHz, $CDCl_3$) δ 5.77-5.71 (m, 2H), 5.36-5.32 (m, 4H), 3.81 (app t, J=6.3, 2H), 3.76 (d, J=5.5, 2H), 3.32 (s, 6H), 2.96 (br s, 2H); $^{13}$C-NMR (125 MHz, $CDCl_3$) δ 135.08, 119.27, 86.65, 71.23, 57.15; MS (ESI) 225 [M+Na$^+$]; HRMS (FAB) calcd. for $C_{10}H_{18}O_4Na$ [M+Na$^+$] 225.1103. found 225.1079.

Example 3

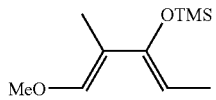

Butadiene 3:

Compound 3 was prepared using modified literature procedures (See, Danishefsky, S. J. et al.; J. *J. Am. Chem. Soc.* 1979, 101, 7001).

To a suspension of NaH (4.40 g, 110 mmol, 60% dispersion in mineral oil) in toluene (90 mL) and MeOH (0.1 mL) at 0° C. was added a mixture of 3-pentanone (10.6 mL, 105 mmol) and methyl formate (8.00 mL, 130 mmol) over 1 hr. The reaction mixture was warmed to rt, stirred for another 3 h, and then diluted with $Et_2O$. The suspension was filtered and the precipitate was washed with $Et_2O$. The resulting crude sodium salt of 1-hydroxy-2-methyl-1-penten-3-one was dissolved in DMSO (100 mL) and $Me_2SO_4$ (9.16 mL, 97.0 mmol) was added at rt. After stirring for 30 min, the reaction mixture was treated with 2M $NH_4OH$ and diluted with $Et_2O$. The organic layer was separated, washed with $H_2O$ and saturated aqueous NaCl solution, dried ($MgSO_4$), and concentrated under reduced pressure to afford 1-methoxy-2-methyl-1-penten-3-one (8.27 g, 74%). To a solution of 1-methoxy-2-methyl-1-penten-3-one (2.60 g, 20.3 mmol) in $Et_2O$ (12.0 mL) was added $Et_3N$ (7.08 mL, 50.8 mmol) and TMSOTf (3.68 mL, 20.3 mL) at 0° C. The reaction mixture was warmed to rt, stirred for another 3 h, and then poured onto a saturated aqueous $NaHCO_3$ solution. The organic layer was separated, washed with saturated aqueous NaCl solution, dried ($MgSO_4$), and concentrated under reduced pressure to afford butadiene 3 (3.66 g, 90%). $^1$H-NMR (400 MHz, $CDCl_3$) δ 6.35 (s, 1H), 4.75 (q, J=6.9, 1H), 3.63 (s, 3H), 1.66 (s, 3H), 1.62 (d, J=6.9, 3H), 0.22 (s, 9H).

Example 4

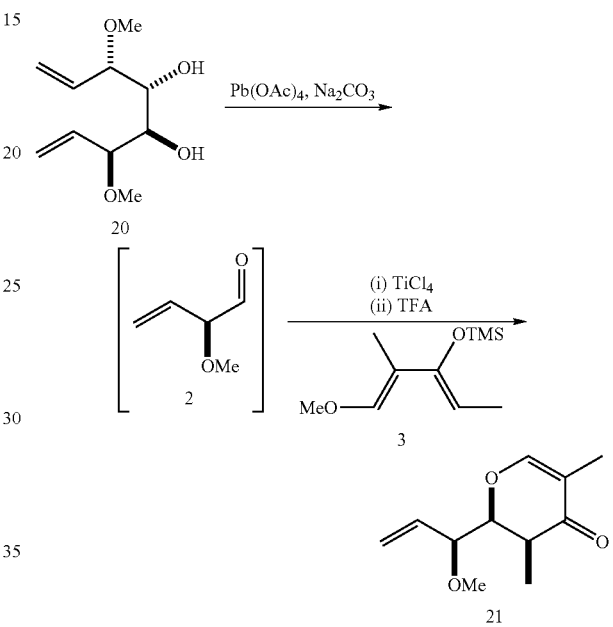

Dihydropyrone 21:

To a solution of diol 20 (2.55 g, 12.6 mmol) in $CH_2Cl_2$ (130 mL) at 0° C. was added $Na_2CO_3$ (1.40 g, 13.2 mmol) and $Pb(OAc)_4$ (5.87 g, 13.2 mmol). The reaction mixture was warmed to rt, stirred for 25 min, and then treated with ethylene glycol (300 μL). After stirring for another 5 min, the reaction mixture was filtered through a Celite pad. The filtrate was washed with saturated aqueous $NaHCO_3$ solution and saturated aqueous NaCl solution and dried ($MgSO_4$). The obtained solution of α-methoxy-α-vinyl aldehyde 2 in $CH_2Cl_2$ was cooled to −78° C., and then $TiCl_4$ (2.77 mL, 25.2 mmol) and butadiene 3 (6.06 g, 30.3 mmol) were added. After stirring for 20 min, the reaction mixture was treated with MeOH (5 min), followed by the addition of saturated aqueous $NaHCO_3$ solution and 20% aqueous Na/K-tartrate solution. The organic layer was separated and the aqueous layer was extracted with $CH_2Cl_2$ (3×). The combined organic layers were dried ($MgSO_4$) and concentrated under reduced pressure. The crude product was dissolved in $CH_2Cl_2$ (130 mL) and TFA (13 mL) and stirred for 1 hr. Toluene (50 mL) was added and the reaction mixture was concentrated under reduced pressure. Purification of the crude product by FC (hexane/EtOAc 20:1→10:1→7:1) afforded dihydropyrone 21 (4.31 g, 87%) as a colorless oil. $[\alpha]_D$ +77.1° (c 2.00, $CHCl_3$); IR (neat) 2980, 2938, 2883, 2827, 1785, 1671, 1622, 1602, 1460, 1387, 1305, 1214, 1176, 1085, 1010; $^1$H-NMR (500 MHz, $CDCl_3$) δ 7.36 (s, 1H), 5.63-5.54 (m, 1H), 5.48-5.43 (m, 2H), 4.25 (dd, J=8.6, 2.9, 1H), 3.88 (app t, J=8.5, 1H), 3.37 (s, 3H), 2.44 (dq, J=7.2, 2.9, 1H), 1.68 (s, 3H), 1.07 (d, J=7.2, 3H); $^{13}$C-NMR (125 MHz, CDCl$_3$) δ 198.99, 160.75, 131.79, 122.06, 112.51, 82.69, 81.99, 56.37, 40.62, 10.42, 9.96; MS (ESI) 219 [M+Na$^+$]; HRMS (FAB) calcd. for C$_{11}$H$_{16}$O$_3$Na [M+Na$^+$] 219.0997. found 219.0991.

Example 5

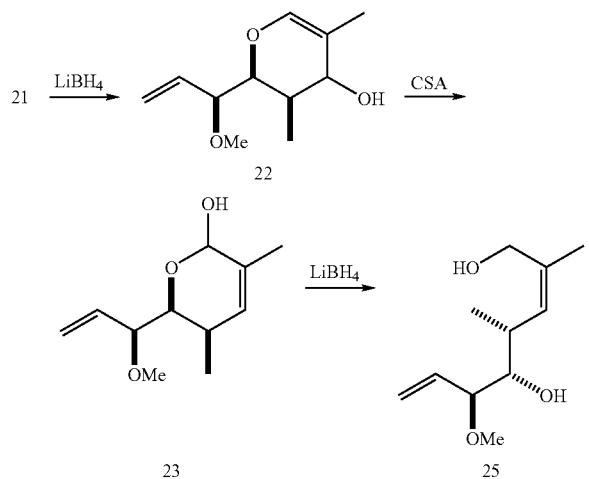

Diol 25:

To a solution of dihydropyrone 21 (4.30 g, 21.9 mmol) in THF (50 mL) at −10° C. was added MeOH (977 μL, 24.1 mmol) and LiBH$_4$ (12.1 mL, 24.1 mmol, 2M in THF). After stirring for 10 min, the reaction mixture was carefully treated with 0.2M HCl (25 mL) and stirring was continued for another 20 min. Then the organic layer was separated and the aqueous layer was extracted with EtOAc (4×). The combined organic layers were dried (MgSO$_4$) and concentrated under reduced pressure. The crude alcohol 22 was dissolved in THF (280 mL) and H$_2$O (28 mL), and champhorsulfonic acid (1.02 g, 4.38 mmol) was added. After refluxing for 2 h, the reaction mixture was treated with saturated aqueous NaHCO$_3$ solution. The organic layer was separated and the aqueous layer was extracted with EtOAc (3×). The combined organic layers were dried (MgSO$_4$) and concentrated under reduced pressure. The crude lactol 23 was dissolved in THF (60 mL) and H$_2$O (15 mL), and LiBH$_4$ (12.1 mL, 24.1 mmol, 2M in THF) was added at rt. After stirring for 15 min, the reaction mixture was treated with 0.2M HCl (35 mL) and stirring was continued for another 20 min. Then the organic layer was separated and the aqueous layer was extracted with EtOAc (3×). The combined organic layers were dried (MgSO$_4$) and concentrated under reduced pressure. Purification of the crude product by FC (hexane/EtOAc 4:1→2:1→1:1) afforded diol 25 (2.34 g, 53%) as a colorless oil. [α]$_D$ +40.0° (c 1.00, CHCl$_3$); IR (CHCl$_3$) 3621, 3565, 3444, 3012, 2934, 2868, 1449, 1393, 1238, 1083; $^1$H-NMR (500 MHz, CDCl$_3$) δ 55.74-5.67 (m, 1H), 5.33-5.25 (m, 2H), 5.16 (d, J=10.2, 1H), 4.12 (d, J=11.9, 1H), 3.95 (d, J=11.9, 1H), 3.48 (dd, J=8.1, 5.4, 1H), 3.26 (app t, J=5.5, 1H), 3.23 (s, 3H), 2.74-2.68 (m, 1H), 2.57 (br s, 2H), 1.79 (d, J=1.4, 3H), 0.98 (d, J=6.9, 3H); $^{13}$C-NMR (125 MHz, CDCl$_3$) δ 135.32, 135.20, 130.41, 119.51, 83.42, 77.44, 61.51, 55.93, 34.80, 21.89, 16.85; MS (ESI) 223 [M+Na$^+$]; HRMS (FAB) calcd. for C$_{11}$H$_{20}$O$_3$Na [M+Na$^+$] 223.1310. found 223.1301.

Example 6

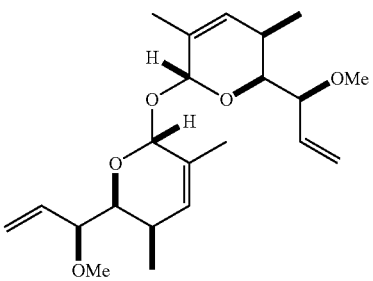

Dimeric Acetal 24:

The Ferrier rearrangement described above was carried out at a concentration of 0.07M. When the Ferrier rearrangement was conducted at a concentration of 0.30M, the formation of a side product, which corresponds to dimeric acetal 24, was observed. Compound 24 was isolated after FC (hexane/EtOAc 20:1→10:1) in 15-20% yield as a white crystalline solid. M.p. 83-85° C.; [α]$_D$ −161.3° (c 1.00, CHCl$_3$); IR (CHCl$_3$) 3003, 2910, 2816, 1446, 1382, 1317, 1211, 1088, 965; $^1$H-NMR (500 MHz, CDCl$_3$) δ 5.67-5.59 (m, 4H), 5.39-5.28 (m, 6H), 3.93 (dd, J=8.4, 2.9, 21), 3.57 (app t, J=8.2, 2H), 3.32 (s, 6H), 1.94-1.91 (m, 2H), 1.74 (s, 6H), 0.91 (d, J=6.8, 6H); $^{13}$C-NMR (125 MHz, CDCl$_3$) δ 134.66, 132.01, 129.40, 119.11, 93.37, 83.15, 72.19, 56.79, 30.44, 18.81, 12.78; MS (ESI) 401 [M+Na$^+$]; HRMS (FAB) calcd. for C$_{22}$H$_{35}$O$_5$ [M+H$^+$] 379.2485. found 379.2486.

Example 7

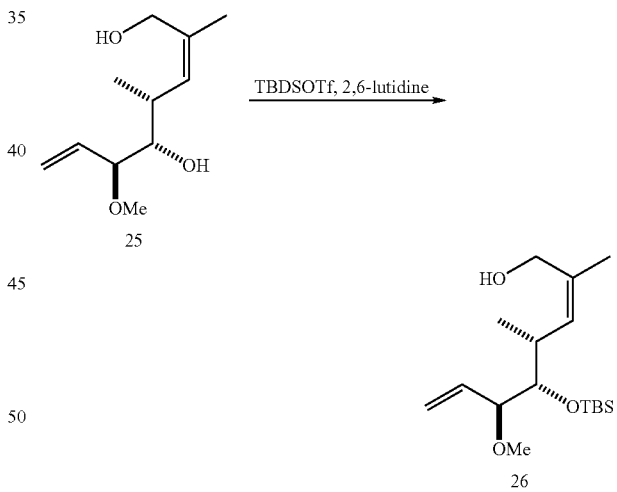

Monoprotected Diol 26:

To a solution of diol 25 (364 mg, 1.82 mmol) in CH$_2$Cl$_2$ (8 mL) at rt was added 2,6-lutidine (530 μL, 4.55 mmol) and TBSOTf (961 μL, 4.19 mmol). After stirring for 20 min, the reaction mixture was treated with saturated aqueous NaHCO$_3$ solution. The organic layer was separated and the aqueous layer was extracted with CH$_2$Cl$_2$ (3×). The combined organic layers were dried (MgSO$_4$) and concentrated under reduced pressure. Purification of the crude product by FC (hexane/EtOAc 30:1) afforded the corresponding diprotected diol (731 mg, 94%) as a colorless oil. [α]$_D$ +0.1° (c 1.00, CHCl$_3$); IR (CHCl$_3$) 2929, 2856, 1472, 1253, 1076; $^1$H-NMR (500 MHz, CDCl$_3$) δ 5.67-5.60 (m, 1H), 5.29-5.21 (m, 3H), 4.14

(d, J=11.8, 1H), 4.04 (d, J=11.8, 1H), 3.43 (dd, J=7.2, 2.9, 1H), 3.37 (app t, J=7.5, 1H), 3.21 (s, 3H), 2.60-2.56 (m, 1H), 1.72 (d, J=0.9, 3H), 0.91-0.89 (m, 21H), 0.05-0.04 (m, 12H); $^{13}$C-NMR (125 MHz, CDCl$_3$) δ 135.44, 133.27, 131.41, 118.43, 86.20, 78.68, 61.91, 56.17, 33.85, 26.17, 25.93, 20.99, 18.56, 18.36, 14.13, −3.82, −4.80, −5.29; MS (ESI) 451 [M+Na$^+$]; HRMS (FAB) calcd. for C$_{23}$H$_{45}$O$_3$Si$_2$Na [M+Na$^+$] 451.3040. found 451.3054.

A solution of the diprotected diol (731 mg, 1.71 mmol) in HOAc (9 mL), THF (3 mL), and H$_2$O (3 mL) was stirred at rt for 8 h. The reaction mixture was neutralized with solid Na$_2$CO$_3$ and diluted with H$_2$O and Et$_2$O. The organic layer was separated and the aqueous layer was extracted with Et$_2$O (3×). The combined organic layers were dried (MgSO$_4$) and concentrated under reduced pressure. Purification of the crude product by FC (hexane/EtOAc 10:1 & 5:1) afforded monoprotected diol 26 (456 mg, 85%) as a colorless oil. [α]$_D$ +3.80 (c 1.85, CHCl$_3$); IR (neat) 3352, 2957, 2930, 2857, 1472, 1462, 1250, 1127, 1081, 1028; $^1$H-NMR (500 MHz, CDCl$_3$), δ 5.73-5.66 (m, 1H), 5.30-5.24 (m, 3H), 4.12 (dd, J=11.8, 4.9, 1H), 4.00 (dd, J=11.8, 6.5, 1H), 3.48-3.43 (m, 2H), 3.22 (s, 3H), 2.69-2.61 (m, 1H), 1.78 (d, J=1.1, 3H), 1.68 (br t, 1H), 0.90-0.89 (m, 12H), 0.06 (s, 3H), 0.04 (s, 3H); $^{13}$C-NMR (125 MHz, CDCl$_3$) δ 135.15, 133.05, 118.54, 85.89, 78.28, 61.76, 56.12, 34.23, 26.11, 25.64, 21.53, 18.49, 15.32, −3.88, −4.70; MS (ESI) 337 [M+Na$^+$]; HRMS (FAB) calcd. for C$_{17}$H$_{34}$O$_3$SiNa [M+Na$^+$] 337.2175. found 337.2162.

Example 8

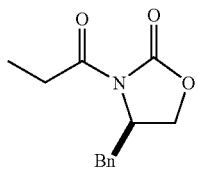

28

Propionyl Oxazolidinone 28:

Compound 28 was prepared by reaction of (R)-(+)-4-benzyl-2-oxazolidinone with BuLi and propionyl chloride in THF according to standard literature procedures (See, Evans, D. A. *Aldrichimica Acta* 1982, 15, 23).

Example 9

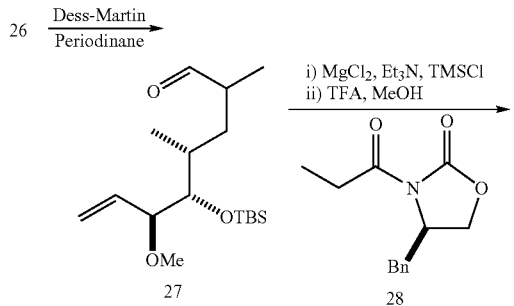

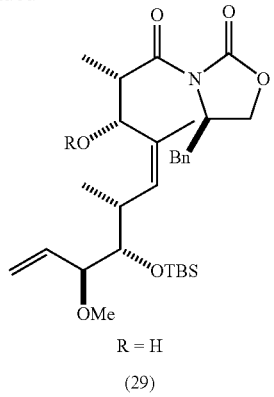

R = H
(29)

Aldol Product 29:

To a solution of alcohol 26 (189 mg, 0.601 mmol) in CH$_2$Cl$_2$ (4 mL) at rt was added Dess-Martin periodinane (280 mg, 0.661 mmol). After stirring for 50 min, the reaction mixture was treated with saturated aqueous Na$_2$S$_2$O$_3$ solution and saturated aqueous NaHCO$_3$ solution. The organic layer was separated and the aqueous layer was extracted with CH$_2$Cl$_2$ (3×). The combined organic layers were dried (MgSO$_4$) and concentrated under reduced pressure to yield crude aldehyde 27. IR (neat) 2958, 2936, 2891, 2858, 1674, 1467, 1378, 1249, 1126, 1093, 1031; $^1$H-NMR (500 MHz, CDCl$_3$) δ 10.06 (s, 1H), 6.51 (dd, J=10.7, 1.5, 1H), 5.63 (ddd, J=17.4, 10.5, 7.9, 1H), 5.32-5.25 (m, 21), 3.56 (dd, J=6.6, 3.8, 1H), 3.45 (app t, J=7.3, 1H), 3.42-3.35 (m, 1H), 3.20 (s, 3H), 1.75 (s, 31), 1.03 (d, J=6.6, 3H), 0.91 (s, 9H), 0.07 (s, 3H), 0.02 (s, 3H); $^{13}$C-NMR (125 MHz, CDCl$_3$) δ 191.36, 153.37, 134.76, 133.96, 119.12, 85.73, 78.03, 56.21, 33.15, 26.05, 18.44, 16.37, 14.73, −3.84, −4.85.

The crude aldehyde 27 was dissolved in EtOAc (2 mL) and added to neat propionyl oxazolidinone 28 (210 mg, 0.902 mmol). The reaction mixture was then treated at rt with anhydrous MgCl$_2$ (57 mg, 0.601 mmol), Et$_3$N (210 μL, 1.50 mmol), and TMSCl (153 μL, 1.20 mmol). After stirring for 36 h, the reaction mixture was filtered through a silica plug (Et$_2$O) and the filtrate was concentrated under reduced pressure. The residual oil was dissolved in MeOH (3 mL), treated with TFA (1 drop) and stirred for 10 min. Toluene (3 mL) was added and the reaction mixture was concentrated under reduced pressure. Purification of the crude product by FC (hexane/CH$_2$Cl$_2$ 1:1→CH$_2$Cl$_2$) afforded aldol product 29 (219 mg, 67%) as a colorless oil. [α]$_D$ −16.1° (c 1.77, CHCl$_3$); IR (neat) 3505, 2920, 2856, 1782, 1699, 1453, 1384, 1258, 1208, 1125, 1079, 1020; $^1$H-NMR (500 MHz, CDCl$_3$) δ 7.35-7.26 (m, 5H), 5.64 (ddd, J=17.6, 10.3, 7.6, 1H), 5.56 (d, J=10.2, 1H), 5.37 (dd, J=10.4, 1.8, 1H), 5.30 (dd, J=17.4, 1.8, 1H), 4.73-4.69 (m, 2H), 4.22-4.16 (m, 2H), 4.14-4.08 (m, 1H), 3.46 (dd, J=8.0, 1.8, 1H), 3.39 (app t, J=8.0, 1H), 3.36 (dd, J=14.1, 3.8, 1H), 3.21 (s, 3H), 2.81 (dd, J=13.6, 9.6, 1H), 2.75-2.68 (m, 1H), 2.39 (br s, 1H), 1.75 (s, 3H), 1.02 (d, J=7.0, 3H), 0.92 (s, 9H), 0.91 (d, J=6.0, 3H), 0.07 (s, 3H), 0.04 (s, 3H); $^{13}$C-NMR (125 MHz, CDCl$_3$) δ 176.48, 153.94, 135.68, 135.35, 134.76, 131.41, 129.52, 128.94, 127.29, 119.26, 86.43, 78.16, 72.78, 66.06, 56.01, 55.76, 41.09, 37.74, 33.44, 26.16, 18.60, 17.16, 14.48, 13.60, −3.74, −4.86; MS (ESI) 546 [M+H$^+$]; HRMS (FAB) calcd. for C$_{30}$H$_{48}$NO$_6$Si [M+H$^+$] 546.3251. found 546.3251.

Example 10

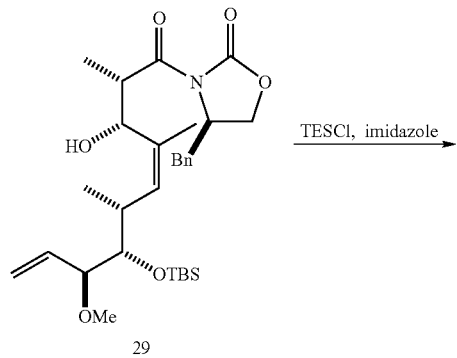

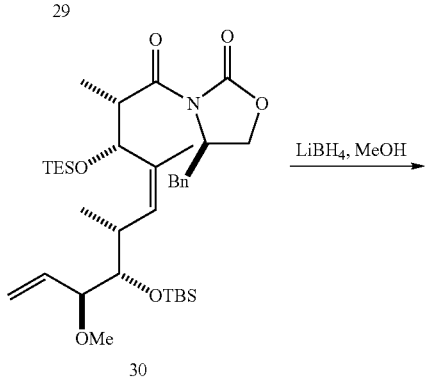

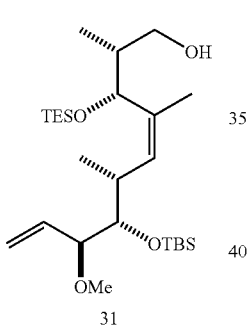

Primary Alcohol 31:

To a solution of aldol product 29 (215 mg, 0.394) in CH$_2$Cl$_2$ (5 mL) at rt was added imidazole (107 mg, 1.58 mmol) and TESCl (198 μL, 1.18 mmol). After stirring for 12 h, the reaction mixture was treated with H$_2$O and diluted with CH$_2$Cl$_2$. The organic layer was separated and the aqueous layer was extracted with CH$_2$Cl$_2$ (3×). The combined organic layers were dried (MgSO$_4$) and concentrated under reduced pressure to afford the TES-protected aldol product 30. The crude product 30 was dissolved in THF (5 mL), and MeOH (64 μL, 0.394 mmol) and LiBH$_4$ (35 mg, 1.58 mmol) were added at rt. After stirring for 1 h, the reaction mixture was treated with 0.5M NaOH. The organic layer was separated and the aqueous layer was extracted with Et$_2$O (3×). The combined organic layers were dried (MgSO$_4$) and concentrated under reduced pressure. Purification of the crude product by FC (hexane/EtOAc 10:1) afforded primary alcohol 31 (159 mg, 83%) as a colorless oil. [α]$_D$ +10.9° (c 2.38, CHCl$_3$); IR (neat) 3460, 2970, 2930, 2880, 1460, 1380, 1250, 1130, 1060, 1020; $^1$H-NMR (500 MHz, CDCl$_3$) δ 5.60-5.53 (m, 1H), 5.35-5.26 (m, 3l), 4.31 (d, J=9.1, 1H), 3.68-3.58 (m, 2H), 3.42-3.34 (m, 2H), 3.20 (s, 3l), 3.13 (app d, J=7.0, 1H), 2.65-2.59 (m, 1H), 1.94-1.88 (m, 1H), 1.67 (d, J=1.2, 3H), 0.94 (t, J=8.0, 9H), 0.93-0.91 (m, 12H), 0.70 (d, J=7.1, 3H), 0.58 (q, J=8.0, 6H), 0.04 (s, 3H), 0.00 (s, 3H); $^{13}$C-NMR (125 MHz, CDCl$_3$) δ 135.10, 133.66, 133.46, 118.84, 86.46, 78.30, 76.58, 68.33, 56.08, 38.87, 33.24, 26.13, 18.58, 17.70, 14.25, 12.64, 6.75, 4.74, −3.85, −4.89; MS (ESI) 509 [M+Na$^+$]; HRMS (FAB) calcd. for C$_{26}$H$_{54}$O$_4$Si$_2$Na [M+Na$^+$] 509.3458. found 509.3468.

Example 11

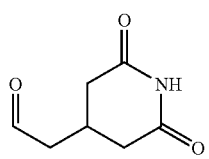

Glutarimide Aldehyde 5:

Compound 5 was synthesized according to a literature procedure (See, Egawa, Y. et al.; *Chem. Pharm. Bull.* 1963, 11, 589).

Example 12

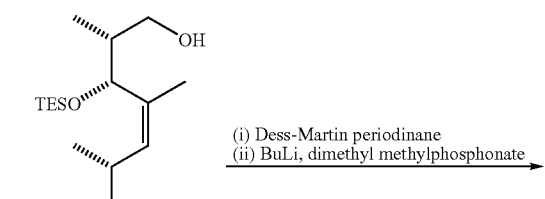

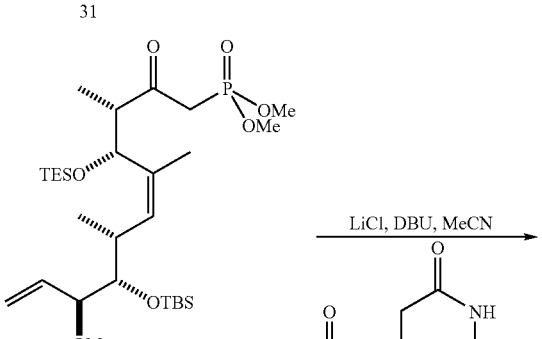

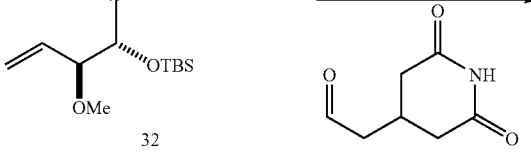

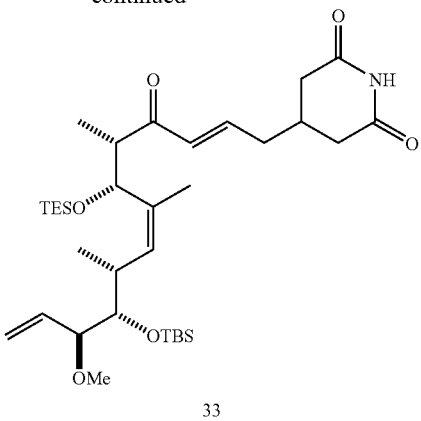

33

Enone 33:

To a solution of primary alcohol 31 (142 mg, 0.292 mmol) in CH$_2$Cl$_2$ (5 mL) at rt was added Dess-Martin periodinane (136 mg, 0.321 mmol). After stirring for 45 min, the reaction mixture was treated with saturated aqueous Na$_2$S$_2$O$_3$ solution and saturated aqueous NaHCO$_3$ solution. The organic layer was separated and the aqueous layer was extracted with CH$_2$Cl$_2$ (3×). The combined organic layers were dried (MgSO$_4$) and concentrated under reduced pressure. In a separate flask, dimethyl methylphosphonate (316 µL, 2.92 mmol) in THF (2 mL) at −78° C. was treated with BuLi (1.64 mL, 2.62 mmol, 1.6M in hexane). After stirring for 20 min, the crude aldehyde obtained from the Dess-Martin oxidation was dissolved in THF (1 mL) and added to the reaction mixture. The reaction mixture was warmed to 0° C., stirred for 15 min, and then treated with saturated aqueous NH$_4$Cl solution. The organic layer was separated and the aqueous layer was extracted with EtOAc (4×). The combined organic layers were dried (MgSO$_4$) and concentrated under reduced pressure. The crude product was dissolved in CH$_2$Cl$_2$ (5 mL), and Dess-Martin periodinane (136 mg, 0.321 mmol) was added at rt. After stirring for 20 min, the reaction mixture was treated with saturated aqueous Na$_2$S$_2$O$_3$ solution and saturated aqueous NaHCO$_3$ solution. The organic layer was separated and the aqueous layer was extracted with CH$_2$Cl$_2$ (1×) and EtOAc (3×). The combined organic layers were dried (MgSO$_4$) and concentrated under reduced pressure. The crude phosphonate 32 was put under high vacuum for 1 hr. To a solution of the crude product 32 in MeCN (5 mL) at rt was added anhydrous LiCl (25 mg, 0.583 mmol) and DBU (87 µL, 0.583 mmol). After stirring for 10 min, a solution of glutarimide aldehyde 5 (136 mg, 0.875 mmol) in MeCN (1 mL) was added. After stirring for 1 h, the reaction mixture was treated with saturated aqueous NH$_4$Cl solution and diluted with EtOAc. The organic layer was separated and the aqueous layer was extracted with EtOAc (3×). The combined organic layers were dried (MgSO$_4$) and concentrated under reduced pressure. Purification of the crude product by FC (hexane/EtOAc 4:1-2:1) afforded enone 33 (105 mg, 57%) as a colorless oil. [α]$_D$ +4.4° (c 1.69, CHCl$_3$); IR (neat) 2955, 2931, 2877, 2855, 1722, 1698, 1628, 1461, 1377, 1288, 1254, 1128, 1066, 1035; $^1$H-NMR (500 MHz, CDCl$_3$) δ 7.91 (br s, 1H), 6.71-6.67 (m, 1H), 6.26 (d, J=15.9, 1H), 5.65 (ddd, J=17.4, 10.4, 8.4, 1H), 5.41-5.36 (m, 2H), 5.29 (dd, J=17.4, 1.6, 1H), 4.62 (d, J=9.3, 1H), 3.43 (app d, J=7.2, 1H), 3.38-3.33 (m, 1H), 3.21 (s, 3H), 3.09-2.99 (m, 1H), 2.75-2.66 (m, 3H), 2.36-2.28 (m, 5H), 1.66 (s, 3H), 0.91 (s, 9H), 0.87-0.82 (m, 15H), 0.46 (q, J=7.9, 6H), 0.05 (s, 3H), −0.01 (s, 3H); $^{13}$C-NMR (125 MHz, CDCl$_3$) δ 202.98, 171.17, 140.21, 134.99, 134.43, 134.09, 132.47, 119.18, 86.57, 78.53, 72.86, 55.97, 47.67, 37.47, 37.43, 37.27, 33.22, 29.82, 29.69, 26.13, 18.59, 14.18, 12.53, 6.76, 4.71, −3.83, −4.91; MS (ESI) 636 [M+H$^+$]; HRMS (FAB) calcd. for C$_{34}$H$_{62}$NO$_6$Si$_2$ [M+H$^+$] 636.4116. found 636.4116.

Example 13

Secondary Alcohol 34:

To a solution of enone 33 (101 mg, 0.159 mmol) in toluene (4.5 mL) at rt was added the Stryker reagent (156 mg, 0.079 mmol, dark red solid if quality is good). After stirring for 3.5 h, hexane (3 mL) was added, and the reaction mixture was exposed to air, stirred for 20 min, and concentrated under reduced pressure. Purification of the crude product by FC hexane/EtOAc 6:1-2:1) afforded the corresponding saturated ketone as a colorless oil. [α]$_D$ +7.7° (c 3.00, CHCl$_3$); IR (neat) 3217, 2954, 2932, 2877, 1713, 1459, 1377, 1253, 1126, 1061, 1035, 1006; $^1$H-NMR (500 MHz, CDCl$_3$) δ 8.05 (br s, 1H), 5.63 (ddd, J=17.0, 10.0, 8.2, 1H), 5.40-5.36 (m, 2H), 5.28 (dd, J=17.0, 1.8, 1H), 4.55 (d, J=9.4, 1H), 3.41 (dd, J=8.2, 1.2, 1H), 3.35 (app t, J=8.2, 1H), 3.19 (s, 3H), 2.82-2.64 (m, 4H), 2.60-2.41 (m, 2H), 2.29-2.23 (m, 2H), 2.18-2.10 (m, 1H), 1.62 (d, J=1.2, 3H), 1.61-1.53 (m, 2H), 1.43-1.34 (m, 2H), 0.92-0.90 (m, 12H), 0.86 (t, J=7.8, 9H), 0.77 (d, J=7.0, 3H), 0.46 (q, J=7.8, 6H), 0.03 (s, 3H), −0.02 (s, 3H); $^{13}$C-NMR (125 MHz, CDCl$_3$) δ 213.45, 172.06, 134.91, 134.57, 132.25, 119.24, 86.58, 78.52, 72.90, 55.94, 49.29, 44.53, 37.75, 34.32, 33.18, 30.44, 26.11, 19.97, 18.57, 17.16, 13.90, 12.46, 6.75, 4.71, −3.85, −4.93; MS (ESI) 638 [M+H$^+$]; HRMS (FAB) calcd. for C$_{34}$H$_{64}$NO$_6$Si$_2$ [M+H$^+$] 638.4272. found 638.4273.

A solution of the saturated ketone in HOAc (3 mL), THF (1 mL), and H$_2$O (1 mL) was stirred at rt for 2 h. The reaction mixture was neutralized with solid Na$_2$CO$_3$ and diluted with H$_2$O and EtOAc. The organic layer was separated and the aqueous layer was extracted with EtOAc (3×). The combined organic layers were dried (MgSO$_4$) and concentrated under reduced pressure. Purification of the crude product by FC hexane/EtOAc 4:1-1:1) afforded secondary alcohol 34 (68 mg, 82%) as a white foam. [α]$_D$ +1.0° (c 1.00, CHCl$_3$); IR (CHCl$_3$) 3601, 3366, 3035, 2931, 2861, 1708, 1455, 1378, 1249, 1120, 1026; $^1$H-NMR (500 MHz, CDCl$_3$) δ 8.22 (br s, 1H), 5.63-5.56 (m, 1H), 5.48 (d, J=9.3, 1H), 5.33 (dd, J=10.3, 1.5, 1H), 5.27 (dd, J=17.2, 1.5, 1H), 4.60 (d, J=9.8, 1H), 3.42-3.35 (m, 2H), 3.18 (s, 3H), 2.79-2.63 (m, 4H), 2.58-2.54 (m, 2H), 2.29-2.23 (m, 2H), 2.18-2.10 (m, 1H), 1.95 (br s, 1H), 1.67 (d, J=1.0, 3H), 1.66-1.59 (m, 2H), 1.42-1.37 (m, 2H), 0.91 (s, 9H), 0.89 (d, J=6.6, 3H), 0.87 (d, J=7.1, 3H), 0.05 (s, 3H), 0.01 (s, 3H); $^{13}$C-NMR (125 MHz, CDCl$_3$) δ 214.01, 172.21, 135.51, 134.72, 131.56, 119.19, 86.30, 78.26, 71.69, 55.98, 48.87, 42.70, 37.73, 37.70, 34.08, 33.26, 30.32, 26.11, 20.07, 18.55, 17.35, 13.87, 13.63, −3.79, −4.90; MS (ESI) 546 [M+Na$^+$]; HRMS (FAB) calcd. for C$_{29}$H$_{49}$NO$_6$SiNa [M+Na$^+$] 546.3227. found 546.3227.

Example 14

2,6-Heptadienoic Acid 6:

Compound 6 can be prepared by γ-alkylation of crotonic acid with allyl bromide (See, Katzenellenbogen, J. A. et al.; *J. Chem. Soc., Perkin Trans.* 1 1998, 2721). However, it was found that the procedure described below is more convenient for larger scale preparations of 2,6-heptadienoic acid 6.

To a solution of oxalyl chloride (3.36 mL, 39.2 mmol) in CH$_2$Cl$_2$ (100 mL) at −78° C. was added DMSO (5.56 mL, 78.3 mmol). After stirring for 5 min, 4-penten-1-ol (2.00 mL, 19.6 mmol) was added, and after another 15 min Et$_3$N (13.6 mL, 97.9 mmol) was added. The reaction mixture was warmed to rt and then treated with 0.1M HCl. The organic layer was separated, washed with saturated aqueous NaCl solution, dried (MgSO$_4$), and treated with Ph$_3$PCHCO$_2$t-Bu (7.38 g, 19.6 mmol) at rt. The reaction mixture was stirred for 5 h and then treated with saturated aqueous NH$_4$Cl solution and diluted with CH$_2$Cl$_2$. The organic layer was separated and the aqueous layer was extracted with CH$_2$Cl$_2$ (3×). The combined organic layers were dried (MgSO$_4$) and concentrated under reduced pressure. The crude product was filtered through a silica plug (CH$_2$Cl$_2$/pentane 1:1) to give t-butyl (E)-2,6-heptadienoate. To a solution of this ester in CH$_2$Cl$_2$ (40 mL) was added TFA (5 mL) at rt. After stirring for 12 h, the reaction mixture was concentrated under reduced pressure. Purification of the crude product by FC (hexane/EtOAc 15:1→5:1) afforded 2,6-heptadienoic acid 6 (1.67 g, 68%) as a colorless oil. $^1$H-NMR (400 MHz, CDCl$_3$) δ 7.12-7.05 (m, 1H), 5.88-5.76 (m, 2H), 5.08-5.02 (m, 2H), 2.37-2.32 (m, 2H), 2.26-2.21 (m, 2H).

Example 15

Formation of the Mixed Anhydride:

To a solution of 2,6-heptadienoic acid 6 (68 mg, 0.535 mmol) in toluene (1 mL) at rt was added 2,4,6-trichlorobenzoyl chloride (84 µL, 0.535 mmol) and i-Pr$_2$NEt (89 µL, 0.508 mmol). The reaction mixture was stirred for 3 h and then used as it is as a stock solution (0.54M) for the subsequent acylation reactions.

Example 16

Unsaturated Ester 35:

To a solution of alcohol 34 (41 mg, 0.078 mmol) in toluene (0.1 mL) at rt was added pyridine (25 µL, 0.313 mmol) and the mixed anhydride (See above for the preparation of a stock solution of the mixed anhydride in toluene) (460 µL, 0.235 mmol, 0.54M in toluene). After stirring for 24 h, the reaction mixture was directly loaded onto a silica column and purified by FC (hexane/EtOAc 10:1→4:1→2:1) to afford unsaturated ester 35 (33 mg, 67%) as a colorless oil. [α]$_D$ −29.0° (c 1.00, CHCl$_3$); IR (neat) 3214, 3081, 2930, 2856, 1722, 1452, 1377, 1256, 1126, 1028; $^1$H-NMR (500 MHz, CDCl$_3$) δ 7.87 (br s, 1H), 6.89 (app dt, J=15.5, 6.8, 1H), 5.81-5.62 (m, 4H), 5.61 (dd, J=10.3, 1.2, 1H), 5.38 (dd, J=10.3, 1.8, 1H), 5.32 (dd, J=17.3, 1.4, 1H), 5.03-4.98 (m, 2H), 3.43-3.39 (m, 2H), 3.21 (s, 3H), 3.00-2.85 (m, 2H), 2.72-2.68 (m, 2H), 2.56-2.44 (m, 2H), 2.30-2.24 (m, 4H), 2.23-2.08 (m, 3H), 1.62 (s, 3H), 1.61-1.58 (m, 2H), 1.36-1.32 (m, 2H), 0.94 (app t, J=7.2, 6H), 0.90 (s, 9H), 0.06 (s, 3H), 0.00 (s, 3H); $^{13}$C-NMR (125 MHz, CDCl$_3$) δ 211.20, 171.83, 164.68, 148.92, 137.72, 136.96, 134.57, 127.00, 121.15, 119.23, 115.60, 86.28, 78.39, 73.79, 56.03, 47.39, 41.45, 37.72, 34.16, 33.84, 31.97, 31.46, 30.40, 26.21, 26.13, 20.10, 18.59, 17.70, 13.72, 12.66, −3.76, −4.94; MS (ESI) 654 [M+Na$^+$]; HRMS (FAB) calcd. for C$_{35}$H$_{57}$NO$_7$SiNa [M+Na$^+$] 654.3826. found 654.3835.

Example 17

TBS-Migrastatin 37:

To a solution of unsaturated ester 35 (29 mg, 0.046 mmol) in refluxing toluene (100 mL) was added Grubbs-II catalyst 16 (8 mg, 0.0092 mmol). After stirring for 15 min, the reaction mixture was cooled to rt and filtered through a silica plug (hexane/EtOAc 1:3). Purification of the crude product by FC (hexane/EtOAc 5:1→2:1→1:1) afforded TBS-migrastatin 37 (19 mg, 69%) as a white solid. [α]$_D$ +13.7° (c 0.50, CHCl$_3$); $^1$H-NMR (500 MHz, CDCl$_3$) δ 7.77 (br s, 1H), 6.54-6.48 (m, 1H), 5.59 (d, J=15.7, 1H), 5.56 (d, J=10.7, 1H), 5.51-5.45 (m, 1H), 5.22 (dd, J=15.4, 4.6, 1H), 5.08 (d, J=9.5, 1H), 3.39 (dd, J=8.1, 4.6, 1H), 3.19 (s, 3H), 3.03 (app d, J=7.8, 1H), 2.98-2.92 (m, 1H), 2.91-2.85 (m, 1H), 2.73-2.68 (m, 2H), 2.50 (app t, J=6.9, 2H), 2.44-2.40 (m, 2H), 2.29-2.09 (m, 5H), 1.81 (d, J=1.1, 3H), 1.64-1.57 (m, 2H), 1.37-1.31 (m, 2H), 1.11 (d, J=7.2, 3H), 0.92-0.90 (m, 12H), 0.04 (s, 3H), −0.01 (s, 3H); $^{13}$C-NMR (125 MHz, CDCl$_3$) δ 210.81, 171.82, 163.80, 150.36, 133.94, 130.17, 129.49, 128.78, 121.88, 83.37, 79.25, 76.82, 56.68, 51.15, 40.24, 37.70, 37.68, 34.17, 33.47, 31.15, 30.36, 30.27, 26.29, 20.12, 18.63, 13.61, 13.30, −3.61, −4.95; MS (ESI) 626 [M+Na$^+$]; HRMS (FAB) calcd. for C$_{33}$H$_{53}$NO$_7$SiNa [M+Na$^+$] 626.3489. found 626.3489.

Example 18

Migrastatin 1:

To a solution of TBS-migrastatin 37 (19 mg, 0.032 mmol) in THF (1.5 mL) at rt was added HF.pyridine (0.25 mL). After stirring for 15 h, the reaction mixture was carefully treated with MeOTMS (3 mL) and concentrated under reduced pressure. Purification of the crude product by FC (hexane/EtOAc 2:1→1:1→1:2) afforded migrastatin 1 (13 mg, 85%) as a white solid. [α]$_D$ +12.6° (c 0.50, MeOH); $^1$H-NMR (500 MHz, CDCl$_3$) δ 7.82 (br s, 1H), 6.49 (ddd, J=15.7, 10.5, 3.7, 1H), 5.64 (d, J=10.7, 1.2, 1H), 5.58 (dd, J=15.7, 1.2, 1H), 5.54-5.48 (m, 1H), 5.24 (dd, J=15.5, 4.7, 1H), 5.08 (d, J=10.0, 1H), 3.47 (dd; J=8.7, 4.7, 1H), 3.30 (s, 3H), 3.03 (dd, J=8.7, 1.7, 1H), 2.99-2.87 (m, 2H), 2.80 (br s, 1H), 2.73-2.68 (m, 2H), 2.50 (app t, J=6.9, 2H), 2.44-2.39 (m, 2H), 2.28-2.17 (m, 4H), 2.16-2.08 (m, 1H), 1.86 (d, J=1.2, 3H), 1.69-1.55 (m, 2H), 1.41-1.30 (m, 2H), 1.12 (d, J=7.2, 3H), 0.96 (d, J=6.9, 3H); $^{13}$C-NMR (125 MHz, CDCl$_3$) δ 210.88, 171.78, 163.86, 150.01, 132.99, 131.17, 130.46, 127.87, 122.08, 82.39, 77.92, 76.92, 56.93, 51.18, 39.88, 37.68, 37.66, 34.12, 31.93, 31.08, 30.34, 30.09, 25.99, 20.09, 13.39; MS (ESI) 512 [M+Na$^+$]; HRMS (FAB) calcd. for C$_{27}$H$_{39}$NO$_7$Na [M+Na$^+$] 512.2624. found 512.2604.

Example 19

6-Heptenoyl Chloride 38:

To a solution of 6-heptenoic acid (251 µL, 1.85 mmol) in CH$_2$Cl$_2$ (5 mL) at rt was added oxalyl chloride (476 µL, 5.55 mmol) and DMF (1 drop). After stirring for 1 hr, the reaction mixture was concentrated under reduced pressure and put under high vacuum for 15 min. The residual yellow oil was dissolved in CH$_2$Cl$_2$ (3 mL) and used as a stock solution (0.62M) for the subsequent acylation reactions.

Example 20

Ester 39:

To a solution of alcohol 34 (37 mg, 0.070 mmol) in CH$_2$Cl$_2$ (2 mL) at rt was added DMAP (17 mg, 0.139 mmol) and 6-heptenoyl chloride (See above for the preparation of a stock solution of 6-heptenoyl chloride 38 in CH$_2$Cl$_2$) 38 (202 µL, 0.125 mmol, 0.62M in CH$_2$Cl$_2$). After stirring for 2 h, the reaction mixture was treated with 0.1M HCl and diluted with CH$_2$Cl$_2$. The organic layer was separated and the aqueous layer was extracted with CH$_2$Cl$_2$ (3×). The combined organic layers were dried (MgSO$_4$) and concentrated under reduced pressure. Purification of the crude product by FC (hexane/EtOAc 10:1→4:1→2:1) afforded ester 39 (31 mg, 69%) as a colorless oil. $^1$H-NMR (500 MHz, CDCl$_3$) δ 8.22 (br s, 1H), 5.79-5.72 (m, 1H), 5.67-5.61 (m, 2H), 5.55 (d, J=10.3, 1H), 5.36 (dd, J=10.3, 1.3, 1H), 5.30 (d, J=17.1, 1H), 5.00-4.92 (m, 2H), 3.40-3.37 (m, 2H), 3.20 (s, 3H), 2.93-2.85 (m, 2H), 2.71 (dd, J=17.0, 4.0, 2H), 2.55-2.42 (m, 2H), 2.29-2.21 (m, 2H), 2.19-2.11 (m, 3H), 2.09-2.00 (m, 2H), 1.60 (s, 3H), 1.59-1.51 (m, 5H), 1.47-1.42 (m, 1H), 1.38-1.32 (m, 2H), 0.92-0.90 (m, 15H), 0.05 (s, 3H), −0.01 (s, 3H); $^{13}$C-NMR (125 MHz, CDCl$_3$) δ 211.06, 172.07, 171.68, 138.28, 137.75, 134.48, 126.86, 119.24, 114.73, 86.25, 78.39, 73.62, 56.01, 47.13, 41.67, 37.70, 34.18, 34.08, 33.78, 33.28, 30.41, 28.21, 28.18, 26.11, 24.38, 20.12, 18.56, 17.61, 13.73, 12.64, −3.78, −4.97; MS (ESI) 656 [M+Na$^+$]; HRMS (FAB) calcd. for C$_{35}$H$_{59}$NO$_7$SiNa [M+Na$^+$] 656.3959. found 656.3956.

Example 21

TBS-2,3-Dihydromigrastatin 40:

To a solution of ester 39 (31 mg, 0.048 mmol) in refluxing toluene (100 mL) was added Grubbs-II catalyst 16 (8 mg, 0.0094 mmol). After stirring for 15 min, the reaction mixture was cooled to rt and filtered through a silica plug (hexane/EtOAc 1:3). Purification of the crude product by FC (hexane/EtOAc 5:1-2:1-1:1) afforded TBS-2,3-dihydromigrastatin 40 (23 mg, 79%) as a colorless oil. $^1$H-NMR (500 MHz, CDCl$_3$) δ 7.90 (br s, 1H), 5.65-5.57 (m, 2H), 5.35 (dd, J=15.7, 5.1, 1H), 5.20 (d, J=9.2, 1H), 3.43-3.40 (m, 1H), 3.23-3.20 (m, 1H), 3.21 (s, 3H), 3.03-2.98 (m, 1H), 2.95-2.91 (m, 1H), 2.73-2.69 (m, 2H), 2.59-2.43 (m, 2H), 2.33-2.22 (m, 4H), 2.17-2.07 (m, 3H), 1.75 (d, J=0.9, 3H), 1.61-1.55 (m, 5H), 1.40-1.35 (m, 3H), 1.07 (d, J=7.2, 3H), 0.94 (d, J=6.8, 3H), 0.91 (s, 9H), 0.07 (s, 3H), 0.03 (s, 3H); $^{13}$C-NMR (125 MHz, CDCl$_3$) 1 210.63, 171.84, 171.80, 134.70, 131.22, 129.51, 128.39, 82.98, 79.10, 76.46, 56.49, 51.24, 40.62, 37.74, 37.69, 34.18, 33.35, 33.18, 31.11, 30.37, 26.29, 25.76, 25.16, 22.80, 20.18, 18.71, 13.66, 13.12, −3.56, −4.97; MS (ESI) 628 [M+Na$^+$]; HRMS (FAB) calcd. for C$_{33}$H$_{55}$NO$_7$Na [M+Na$^+$] 628.3646. found 628.3644.

Example 22

2,3-Dihydromigrastatin 41:

To a solution of TBS-2,3-dihydromigrastatin 40 (23 mg, 0.038 mmol) in THF (1.5 mL) at rt was added HF.pyridine (0.3 mL). After stirring for 15 h, the reaction mixture was carefully treated with MeOTMS (4 mL) and concentrated under reduced pressure. Purification of the crude product by FC (hexane/EtOAc 2:1→1:1→1:2) afforded 2,3-dihydromigrastatin 41 (15 mg, 81%) as a white foam. $^1$H-NMR (500 MHz, CDCl$_3$) δ 7.97 (br s, 1H), 5.68-5.60 (m, 2H), 5.34 (dd, J=15.6, 5.6, 1H), 5.19 (d, J=9.7, 1H), 3.49-3.46 (m, 1H), 3.33 (s, 3H), 3.22 (app d, J=9.1, 1H), 3.07-3.00 (m, 1H), 2.98-2.91 (m, 1H), 2.72 (dd, J=17.1, 2.3, 2H), 2.59-2.50 (m, 1H), 2.49-2.40 (m, 1H), 2.30-2.04 (m, 7H), 1.79 (d, J=1.3, 3H), 1.63-1.56 (m, 4H), 1.55-1.48 (m, 1H), 1.42-1.35 (m, 3H), 1.09 (d, J=7.2, 3H), 0.99 (d, J=6.9, 3H); $^{13}$C-NMR (125 MHz, CDCl$_3$) δ 210.64, 171.88, 171.73, 133.95, 132.35, 130.27, 128.05, 81.92, 77.42, 76.45, 56.70, 51.38, 40.37, 37.73, 37.68, 34.15, 32.50, 31.72, 30.45, 30.35, 25.94, 24.80, 22.33, 20.16, 13.22, 13.20; MS (ESI) 514 [M+Na$^+$]; HRMS (FAB) calcd. for C$_{27}$H$_{41}$NO$_7$Na [M+Na$^+$] 514.2781. found 514.2768.

Example 23

N-Methyl-2,3-Dihydromigrastatin 42:

To a solution of 2,3-dihydromigrastatin 41 (4 mg, 0.0081 mmol) in acetone (0.4 mL) at rt was added MeI (excess) and Cs$_2$CO$_3$ (excess). After stirring for 4 h, the reaction mixture was concentrated under reduced pressure to a volume of ca. 0.2 mL. Purification of the residual solution by preparative TLC (hexane/EtOAc 1:2) afforded N-methyl-2,3-dihydromigrastatin 42 (3.5 mg, 85%) as a colorless oil. $^1$H-NMR (500 MHz, CDCl$_3$) δ 5.68-5.61 (m, 2H), 5.34 (dd, J=15.6, 5.6, 1H), 5.19 (d, J=9.6, 1H), 3.49-3.46 (m, 1H), 3.33 (s, 3H), 3.22 (app d, J=9.1, 1H), 3.14 (s, 3H), 3.07-3.01 (m, 1H), 2.95-2.89 (m, 1H), 2.82-2.78 (m, 2H), 2.58-2.50 (m, 1H), 2.49-2.42 (m, 1H), 2.33-2.27 (m, 2H), 2.25-2.04 (m, 5H), 1.79 (d, J=1.3, 3H), 1.65-1.52 (m, 5H), 1.47-1.42 (m, 1H), 1.37-1.31 (m, 2H), 1.09 (d, J=7.2, 3H), 0.99 (d, J=6.9, 3H); $^{13}$C-NMR (125 MHz, CDCl$_3$) δ 210.67, 172.20, 171.72, 133.93, 132.35, 130.33, 128.06, 81.92, 77.45, 76.47, 56.72, 51.38, 40.44, 38.75, 38.71, 34.27, 32.51, 31.73, 30.47, 29.34, 26.36, 25.94, 24.81, 22.33, 20.09, 13.23; MS (ESI) 528 [M+Na$^+$]; HRMS (FAB) calcd. for C$_{28}$H$_{43}$NO$_7$Na [M+Na$^+$] 528.2937. found 528.2939.

Example 24

Unsaturated Ester 43:

To a solution of alcohol 26 (109 mg, 0.346 mmol) in toluene (1 mL) at rt was added pyridine (84 µL, 1.04 mmol) and the mixed anhydride (See above for the preparation of a stock solution of the mixed anhydride in toluene) (1 mL, 0.535 mmol, 0.54M in toluene). After stirring for 12 h, the reaction mixture was filtered through a silica plug (hexane/EtOAc 30:1). Purification of the crude product by FC (pentane/CH$_2$Cl$_2$ 3:1→2:1) afforded unsaturated ester 43 (70 mg, 48%) as a colorless oil. [α]$_D$ +2.6° (c 1.00, CHCl$_3$); IR (CHCl$_3$) 2934, 2882, 2851, 1705, 1653, 1470, 1381, 1246, 1126, 1079, 1026; $^1$H-NMR (500 MHz, CDCl$_3$) δ 6.99-6.93 (m, 1H), 5.86-5.76 (m, 2H), 5.66-5.59 (m, 1H), 5.44 (d, J=9.5, 1H), 5.29-5.22 (m, 2H), 5.07-4.99 (m, 2H), 4.61 (d, J=12.1, 1H), 4.57 (d, J=12.1, 1H), 3.47 (dd, J=7.2, 2.9, 1H), 3.37 (app t, J=7.7, 1H), 3.19 (s, 3H), 2.63-2.59 (m, 1H), 2.33-2.28 (m, 2H), 2.24-2.19 (m, 2H), 1.73 (d, J=1.3, 3H), 0.91 (d, J=6.6, 3H), 0.90 (s, 9H), 0.05 (s, 3H), 0.02 (s, 3H); $^{13}$C-NMR (125 MHz, CDCl$_3$) δ 166.57, 148.47, 137.05, 135.58, 135.10, 128.21, 121.52, 118.79, 115.53, 86.26, 78.37, 63.07, 56.06, 34.26, 32.02, 31.48, 26.15, 21.49, 18.54, 13.96, −3.80, −4.85; MS (ESI) 445 [M+Na$^+$]; HRMS (FAB) calcd. for C$_{24}$H$_{43}$O$_4$Si [M+H$^+$] 423.2931. found 423.2929.

Example 25

TBS-Migrastatin Core 44:

To a solution of unsaturated ester 43 (35 mg, 0.083 mmol) in refluxing toluene (125 mL) was added Grubbs-II catalyst 16 (14 mg, 0.017 mmol). After stirring for 15 min, the reaction mixture was cooled to rt and filtered through a silica plug (hexane/EtOAc 4:1). Purification of the crude product by FC (hexane/EtOAc 20:1) afforded TBS-migrastatin core 44 (18 mg, 55%) as a colorless oil. $^1$H-NMR (500 MHz, CDCl$_3$) δ 6.85-6.79 (m, 1H), 5.74 (d, J=15.9, 1H), 5.56-5.50 (m, 2H), 5.12 (dd, J=15.5, 8.7, 1H), 4.68 (d, J=15.8, 1H), 4.62 (d, J=15.8, 1H), 3.44 (dd, J=8.3, 1.4, 1H), 3.33-3.30 (m, 1H), 3.17 (s, 3H), 3.03-2.97 (m, 1H), 2.47-2.36 (m, 2H), 2.31-2.24 (m, 1H), 2.21-2.14 (m, 1H), 1.64 (s, 3H), 0.92 (s, 9H), 0.83 (d, J=6.8, 3H), 0.07 (s, 3H), 0.06 (s, 3H); $^{13}$C-NMR (125 MHz, CDCl$_3$) δ 165.37, 149.91, 131.98, 130.48, 126.58, 121.83, 117.57, 85.82, 77.49, 65.56, 55.83, 33.11, 32.46, 30.01, 26.27, 22.17, 18.71, 12.90, −3.57, −5.02; MS (ESI) 417 [M+Na$^+$]; HRMS (FAB) calcd. for C$_{22}$H$_{38}$O$_4$SiNa [M+Na$^+$] 417.2437. found 417.2456.

Example 26

Migrastatin Core 45:

To a solution of TBS-migrastatin core 44 (18 mg, 0.0457 mmol) in THF (1.5 mL) at rt was added HF.pyridine (0.3 mL). After stirring for 14 h, the reaction mixture was carefully treated with MeOTMS (4 mL) and concentrated under reduced pressure. Purification of the crude product by FC (hexane/EtOAc 10:1→5:1) afforded migrastatin core 45 (8.5 mg, 66%) as a colorless oil. $[\alpha]_D$ +106.0° (c 0.50, CHCl$_3$); IR (CHCl$_3$) 3567, 2933, 2881, 1716, 1602, 1448, 1393, 1255, 1107, 1052; $^1$H-NMR (500 MHz, CDCl$_3$) δ 6.81-6.75 (m, 1H), 5.73 (d, J=15.9, 1H), 5.62-5.55 (m, 2H), 5.14 (dd, J=15.2, 6.8, 1H), 4.72 (d, J=15.6, 1H), 4.63 (d, J=15.6, 1H), 3.42-3.38 (m, 2H), 3.28 (s, 3H), 3.03-2.97 (m, 1H), 2.69 (br s, 1H), 2.47-2.38 (m, 2H), 2.32-2.18 (m, 2H), 1.68 (s, 3H), 0.88 (d, J=6.9, 3H); $^{13}$C-NMR (125 MHz, CDCl$_3$) δ 165.36, 149.52, 133.85, 129.79, 129.51, 127.50, 122.15, 84.62, 76.09, 65.40, 56.25, 32.20, 31.34, 29.99, 22.27, 12.66; MS (ESI) 303 [M+Na$^+$]; HRMS (FAB) calcd. for C$_{16}$H$_{24}$O$_4$Na [M+Na$^+$] 303.1571. found 303.1572.

Example 27

Ester 46:

To a solution of alcohol 26 (275 mg, 0.874 mmol) in CH$_2$Cl$_2$ (3 mL) at rt was added DMAP (214 mg, 1.75 mmol) and 6-heptenoyl chloride (See above for the preparation of a stock solution of 6-heptenoyl chloride 38 in CH$_2$Cl$_2$) 38 (2.5 mL, 1.57 mmol, 0.62M in CH$_2$Cl$_2$). After stirring for 20 min, the reaction mixture was treated with 0.1M HCl and diluted with CH$_2$Cl$_2$. The organic layer was separated and the aqueous layer was extracted with CH$_2$Cl$_2$ (3×). The combined organic layers were dried (MgSO$_4$) and concentrated under reduced pressure. Purification of the crude product by FC (hexane/EtOAc 30:1) afforded ester 46 (302 mg, 82%) as a colorless oil. $[\alpha]_D$ +3.0° (c 0.50, CHCl$_3$); IR (CHCl$_3$) 2980, 2933, 2863, 1722, 1458, 1382, 1252, 1112, 1024; $^1$H-NMR (500 MHz, CDCl$_3$) δ 5.83-5.75 (m, 1H), 5.66-5.59 (m, 1H), 5.43 (d, J=9.5, 1H), 5.30-5.23 (m, 2H), 5.03-4.94 (m, 2H), 4.56 (d, J=12.0, 1H), 4.51 (d, J=12.0, 1H), 3.46 (dd, J=7.2, 2.9, 1H), 3.37 (app t, J=7.7, 1H), 3.20 (s, 3H), 2.61-2.57 (m, 1H), 2.32 (app t, J=7.5, 2H), 2.06 (app q, J=7.2, 2H), 1.74 (d, J=1.2, 3H), 1.68-1.62 (m, 2H), 1.45-1.39 (m, 2H), 0.91 (s, 9H), 0.90 (d, J=6.5, 3H), 0.05 (s, 3H), 0.02 (s, 3H); $^{13}$C-NMR (125 MHz, CDCl$_3$) δ 173.65, 138.40, 135.59, 135.10, 128.12, 118.77, 114.67, 86.24, 78.36, 63.11, 56.07, 34.24, 34.17, 33.35, 28.35, 26.15, 24.46, 21.45, 18.54, 13.98, −3.80, −4.85; MS (ESI) 447 [M+Na$^+$]; HRMS (FAB) calcd. for C$_{24}$H$_{44}$O$_4$SiNa [M+Na$^+$] 447.2906. found 447.2893.

Example 28

TBS-Macrolactone 47:

To a solution of ester 46 (95 mg, 0.224 mmol) in refluxing toluene (450 mL) was added Grubbs-II catalyst 16 (38 mg, 0.045 mmol). After stirring for 15 min, the reaction mixture was cooled to rt and filtered through a silica plug (hexane/EtOAc 5:1). Purification of the crude product by FC (hexane/EtOAc 30:1) afforded TBS-macrolactone 47 (67 mg, 76%) as a colorless oil. $^1$H-NMR (500 MHz, CDCl$_3$) δ 5.71-5.65 (m, 1H), 5.56 (d, J=10.0, 1H), 5.28 (dd, J=15.7, 8.0, 1H), 4.52 (d, J=13.9, 1H), 4.35 (d, J=13.9, 1H), 3.46 (dd, J=7.7, 2.6, 1H), 3.39 (app t, J=7.8, 1H), 3.20 (s, 3H), 2.85-2.82 (m, 1H), 2.42-2.36 (m, 1H), 2.26-2.20 (m, 1H), 2.18-2.14 (m, 1H), 2.11-2.06 (m, 1H), 1.77-1.72 (m, 1H), 1.71 (d, J=1.1, 3H), 1.62-1.50 (m, 2H), 1.46-1.40 (m, 1H), 0.91 (s, 9H), 0.88 (d, J=6.8, 3H), 0.07 (s, 3H), 0.05 (s, 3H); $^{13}$C-NMR (125 MHz, CDCl$_3$) δ 173.74, 134.81, 133.62, 128.75, 126.14, 85.42, 77.78, 65.01, 55.97, 34.31, 34.01, 29.37, 27.34, 26.16, 23.36, 23.09, 18.58, 13.86, −3.78, −4.96; MS (ESI) 419 [M+Na$^+$]; HRMS (FAB) calcd. for C$_{22}$H$_{40}$O$_4$SiNa [M+Na$^+$] 419.2594., found 419.2601.

Example 29

Macrolactone 48:

To a solution of TBS-macrolactone 47 (179 mg, 0.452 mmol) in THF (6 mL) at rt was added HF.pyridine (in the beginning: 0.6 mL, after a total of 15 h: an additional 0.6 mL, after a total of 25 h: an additional 0.3 mL). After stirring for a total of 40 h, the reaction mixture was carefully treated with MeOTMS (12 mL) and concentrated under reduced pressure. Purification of the crude product by FC (hexane/EtOAc 10:1→5:1) afforded macrolactone 48 (120 mg, 94%) as a white crystalline solid. $[\alpha]_D$ +115.3° (c 1.00, CHCl$_3$); IR (CHCl$_3$) 3567, 3016, 2933, 2858, 1724, 1450, 1387, 1317, 1258, 1145, 1115, 979; $^1$H-NMR (500 MHz, CDCl$_3$) δ 5.74-5.67 (m, 2H), 5.23 (dd, J=15.7, 7.7, 1H), 4.54 (d, J=13.1, 1H), 4.29 (d, J=13.1, 1H), 3.46-3.39 (m, 2H), 3.30 (s, 3H), 2.82-2.77 (m, 1H), 2.44-2.39 (m, 1H), 2.26-2.15 (m, 2H), 2.03-1.97 (m, 1H), 1.74 (d, J=0.9, 3H), 1.74-1.70 (m, 1H), 1.60-1.52 (m, 2H), 1.36-1.32 (m, 1H), 0.93 (d, J=6.9, 3H); $^{13}$C-NMR (125 MHz, CDCl$_3$) δ 173.69, 135.19, 134.39, 129.02, 127.14, 83.82, 75.91, 64.76, 56.34, 34.23, 32.06, 29.88, 27.20, 23.40, 23.27, 12.81; MS (ESI) 305 [M+Na$^+$]; HRMS (FAB) calcd. for C$_{16}$H$_{26}$O$_4$Na [M+Na$^+$] 305.1719. found 305.1729.

Example 30

Acetylated Macrolactone 49:

To a solution of macrolactone 48 (4.5 mg, 0.016 mmol) in CH$_2$Cl$_2$ (0.75 mL) at rt was added DMAP (6 mg, 0.048 mmol) and AcCl (3.5 μL, 0.048 mmol). After stirring for 24 h, the reaction mixture was concentrated under reduced pressure to a volume of ca. 0.2 mL. Purification of the residual solution by preparative TLC (hexane/EtOAc 2:1) afforded the acetylated macrolactone 49 (4 mg, 76%) as a colorless oil. $^1$H-NMR (500 MHz, CDCl$_3$) δ 5.78-5.72 (m, 1H), 5.37 (dd, J=15.7, 8.2, 1H), 5.28 (d, J=10.0, 1H), 4.89 (dd, J=8.0, 3.6, 1H), 4.56 (d, J=13.2, 1H), 4.32 (d, J=13.2, 1H), 3.57 (app t, J=8.1, 1H), 3.23 (s, 3H), 3.02-2.97 (m, 1H), 2.46-2.41 (m, 1H), 2.25-2.19 (m, 2H), 2.11 (s, 3H), 2.10-2.05 (m, 1H), 1.81-1.75 (m, 1H), 1.71 (d, J=0.9, 3H), 1.61-1.53 (m, 2H), 1.43-1.39 (m, 1H), 0.95 (d, J=6.9, 3H); $^{13}$C-NMR (125 MHz, CDCl$_3$) δ 173.61, 170.82, 135.23, 132.14, 127.76, 82.63, 76.83, 64.69, 56.46, 34.30, 32.10, 29.58, 27.02, 23.39, 23.04, 21.10, 14.85; MS (ESI) 347 [M+Na$^+$]; HRMS (FAB) calcd. for C$_{18}$H$_{28}$O$_5$Na [M+Na$^+$] 347.1834. found 347.1848.

Example 31

Oxidized Macrolactone 50:

To a solution of macrolactone 48 (7 mg, 0.025 mmol) in CH$_2$Cl$_2$ (1.5 mL) at rt was added Dess-Martin periodinane (12 mg, 0.027 mmol). After stirring for 4 h, the reaction mixture was concentrated under reduced pressure to a volume of ca. 0.2 mL. Purification of the residual solution by preparative TLC (hexane/EtOAc 1:1) afforded oxidized macrolactone 50 (5 mg, 72%) as a colorless oil. $^1$H-NMR (500 MHz, CDCl$_3$) δ 5.92-5.86 (m, 1H), 5.73 (d, J=9.9, 1H), 5.34 (dd, J=15.5, 8.0, 1H), 4.54 (d, J=11.6, 1H), 4.37 (d, J=8.0, 1H), 4.31 (d, J=11.6, 1H), 3.71-3.65 (m, 1H), 3.32 (s, 3H), 2.41-

2.36 (m, 1H), 2.27-2.21 (m, 1H), 2.20-2.16 (m, 1H), 2.06-1.99 (m, 1H), 1.81 (s, 31), 1.68-1.60 (m, 2H), 1.58-1.51 (m, 1H), 1.41-1.33 (m, 1H), 1.19 (d, J=7.1, 3H); $^{13}$C-NMR (125 MHz, CDCl$_3$) δ 207.91, 173.74, 138.30, 130.64, 130.42, 124.64, 86.15, 62.75, 56.65, 41.61, 34.04, 30.35, 26.64, 23.40, 23.18, 18.89; MS (ESI) 303 [M+Na$^+$]; HRMS (FAB) calcd. for C$_{16}$H$_{24}$O$_4$Na [M+Na$^+$] 303.1572. found 303.1588.

Example 32

Hydrolyzed Core 51:

To a solution of macrolactone 48 (5 mg, 0.018 mmol) in MeOH (1.5 mL) at rt was added 0.5M NaOH (0.3 mL). After stirring for 2 h, the reaction mixture was concentrated under reduced pressure to a volume of ca 0.5 mL, diluted with CH$_2$Cl$_2$, and acidified with 1M HCl (2 mL). The organic layer was separated, dried (MgSO$_4$), and concentrated under reduced pressure to afford hydrolyzed core 51 (4 mg, 77%) as a colorless oil. $^1$H-NMR (500 MHz, CDCl$_3$) δ 5.75-5.70 (m, 1H), 5.34 (dd, J=15.5, 8.7, 1H), 5.23 (d, J=10.1, 1H), 4.15 (d, J=11.8, 1H), 3.97 (d, J=11.8, 1H), 3.47-3.44 (m, 1H), 3.29-3.26 (m, 1H), 3.23 (s, 3H), 2.74-2.69 (m, 1H), 2.36 (app t, J=7.4, 2H), 2.14 (app q, J=7.1, 2H), 1.82 (d, J=1.2, 3H), 1.69-1.63 (m, 2H), 1.51-1.45 (m, 2H), 0.99 (d, J=6.7, 3H); $^{13}$C-NMR (125 MHz, CDCl$_3$) δ 177.87, 136.20, 134.96, 130.90, 127.34, 83.24, 77.55, 61.56, 55.65, 34.56, 33.59, 31.81, 28.38, 24.13, 22.00, 16.39; MS (ESI) 323 [M+Na$^+$]; HRMS (FAB) calcd. for C$_{16}$H$_{28}$O$_5$Na [M+Na$^+$] 323.1834. found 323.1840.

Example 33

Allylic Azide 52:

To a solution of alcohol 26 (300 mg, 0.954 mmol) in toluene (3 mL) at rt was added DBU (214 µL, 1.43 mmol) and diphenylphosphoryl azide (308 µL, 1.43 mmol). After stirring for 5 h, the reaction mixture was treated with saturated aqueous NH$_4$Cl solution and diluted with Et$_2$O. The organic layer was separated and the aqueous layer was extracted with Et$_2$O (3×). The combined organic layers were dried (MgSO$_4$) and concentrated under reduced pressure. Purification of the crude product by FC (hexane/EtOAc 30:1) afforded allylic azide 52 (281 mg, 87%) as a colorless oil. Compound 52 should be used immediately for the subsequent steps to avoid double bond isomerization. $^1$H-NMR (500 MHz, CDCl$_3$) δ 5.68-5.60 (m, 1H), 5.52 (d, J=10.0, 1H), 5.32-5.25 (m, 2H), 3.81 (d, J=13.0, 1H), 3.66 (d, J=13.0, 1H), 3.45 (dd, J=7.1, 3.0, 1H), 3.39 (app t, J=7.5, 1H), 3.21 (s, 3H), 2.56-2.52 (m, 1H), 1.77 (d, J=1.2, 3H), 0.93-0.90 (m, 12H), 0.06 (s, 3H0, 0.04 (s,3H); $^{13}$C-NMR (125 MHz, CDCl$_3$) δ 135.97, 135.19, 127.27, 118.81, 86.04, 78.39, 56.13, 51.46, 34.40, 26.14, 22.21, 18.53, 14.43, -3.80, 4.77; MS (ESI) 362 [M+Na$^+$]; HRMS (FAB) calcd. for C$_{17}$H$_{33}$N$_3$O$_2$SiNa [M+Na$^+$] 362.2240. found 362.2239.

Example 34

Amide 53:

To a solution of azide 52 (184 mg, 0.542 mmol) in THF (5 mL) at 70° C. was added PPh$_3$ (249 mg, 0.949 mmol) and H$_2$O (49 µL, 2.71 mmol). After stirring for 4 h, the reaction mixture was dried (MgSO$_4$) and concentrated under reduced pressure. The residue was dissolved in CH$_2$Cl$_2$ (5 mL) and treated with i-Pr$_2$NEt (378 µL, 2.17 mmol), 6-heptenoic acid (147 µL, 1.08 mmol), and EDC (207 mg, 1.08 mmol). After stirring for 30 min, the reaction mixture was concentrated under reduced pressure to a volume of ca. 1 mL. Purification of the residual solution by FC(CH$_2$Cl$_2$→CH$_2$Cl$_2$/Et$_2$O 10:1) afforded amide 53 (211 mg, 92%) as a colorless oil. $^1$H-NMR (500 MHz, CDCl$_3$) δ 5.83-5.74 (m, 1H), 5.70-5.64 (m, 1H), 5.41 (br s, 1H), 5.32-5.23 (m, 3H), 5.01-4.93 (m, 2H), 3.86 (dd, J=14.1, 5.6, 1H), 3.79 (dd, J=14.1, 5.5, 1H), 3.47-3.37 (m, 2H), 3.21 (s, 3H), 2.61-2.56 (m, 1H), 2.19-2.15 (m, 2H), 2.08-2.04 (m, 2H), 1.68 (d, J=1.3, 3H), 1.67-1.59 (m, 2H), 1.45-1.38 (m, 2H), 0.91-0.89 (m, 12H), 0.06 (s, 3H), 0.02 (s, 3H); $^{13}$C-NMR (125 MHz, CDCl$_3$) δ 172.79, 138.44, 135.10, 133.94, 129.82, 118.66, 114.66, 86.01, 78.22, 56.11, 39.84, 36.65, 34.26, 33.44, 28.52, 26.11, 25.25, 21.93, 18.50, 14.76, -3.83, -4.77; MS (ESI) 446 [M+Na$^+$]; HRMS (FAB) calcd. for C$_{24}$H$_{45}$NO$_3$SiNa [M+Na$^+$] 446.3066. found 446.3065.

Example 35

TBS-Macrolactam 54:

To a solution of amide 53 (105 mg, 0.248 mmol) in refluxing toluene (350 mL) was added Grubbs-H catalyst 16 (42 mg, 0.050 mmol). After stirring for 15 min, the reaction mixture was cooled to rt and filtered through a silica plug (hexane/EtOAc 1:2). Purification of the crude product by FC (hexane/EtOAc 2:1) afforded TBS-macrolactam 54 (59 mg, 60%) as a colorless oil. $^1$H-NMR (500 MHz, CDCl$_3$) δ 5.81-5.75 (m, 1H), 5.46 (d, J=9.9, 1H), 5.36 (dd, J=15.9, 6.0, 1H), 5.30 (br s, 1H), 3.77 (dd, J=13.9, 3.5, 1H), 3.66 (dd, J=13.9, 5.4, 1H), 3.48-3.44 (m, 2H), 3.21 (s, 3H), 2.63-2.58 (m, 1H), 2.21-2.08 (m, 3H), 2.05-1.98 (m, 1H), 1.73 (d, J=1.1, 3H), 1.65-1.49 (m, 3H), 1.39-1.32 (m, 1H), 0.92-0.90 (m, 12H), 0.07 (s, 3H), 0.05 (s, 3H); $^{13}$C-NMR (125 MHz, CDCl$_3$) δ 173.26, 134.11, 133.90, 129.03, 128.54, 84.80, 77.46, 56.29, 41.41, 36.01, 34.48, 29.59, 27.45, 26.11, 24.68, 24.32, 18.56, 14.77, -3.92, -4.93; MS (ESI) 418 [M+Na$^+$]; HRMS (FAB) calcd. for C$_{22}$H$_{41}$NO$_3$SiNa [M+Na$^+$] 418.2753. found 418.2752.

Example 36

Macrolactam 55:

To a solution of TBS-macrolactam 54 (91 mg, 0.230 mmol) in THF (3 mL) at rt was added HF.pyridine (in the beginning: 0.4 mL, after a total of 18 h: an additional 0.15 mL). After stirring for a total of 21 h, the reaction mixture was carefully treated with MeOTMS (5 mL) and concentrated under reduced pressure. Purification of the crude product by FC (hexane/EtOAc 1:1→1:2) afforded macrolactam 55 (52 mg, 81%) as a colorless oil. [α]$_D$ +101.3° (c 1.00, CHCl$_3$); IR (CHCl$_3$) 3566, 3444, 3021, 2936, 2828, 1658, 1504, 1478, 1398, 1229, 1088, 979; $^1$H-NMR (500 MHz, CDCl$_3$) δ 5.79-5.73 (m, 1H), 5.66 (d, J=10.2, 1H), 5.24 (dd, J=15.8, 7.5, 1H), 5.12 (br s, 1H), 3.91 (dd, J=13.7, 4.1, 1H), 3.50-3.46 (m, 2H), 3.34-3.30 (m, 1H), 3.31 (s, 3H), 2.89 (br s, 1H), 2.56-2.52 (m, 1H), 2.32-2.25 (m, 2H), 2.16-2.11 (m, 1H), 1.96-1.89 (m, 1H), 1.77 (d, J=1.1, 3H), 1.73-1.51 (m, 3H), 1.37-1.32 (m, 1H), 0.94 (d, J=6.9, 3H); $^{13}$C-NMR (125 MHz, CDCl$_3$) δ 173.36, 135.52, 133.77, 129.89, 128.73, 83.21, 76.38, 56.45, 41.40, 35.95, 32.27, 29.86, 27.00, 24.82, 24.42, 13.03; MS (ESI) 304 [M+Na$^+$]; HRMS (FAB) calcd. for C$_{16}$H$_{27}$NO$_3$Na [M+Na$^+$] 304.1888. found 304.1889.

Example 37

Allylic Bromide 56:

To a solution of alcohol 26 (325 mg, 1.03 mmol) in CH$_2$Cl$_2$ (10 mL) at rt was added solid supported PPh$_3$ (excess until reaction complete) and CBr$_4$ (478 mg, 1.44 mmol). After stirring for 15 min, the reaction mixture was filtered through a cotton plug and concentrated under reduced pressure to yield the allylic bromide 56. $^1$H-NMR (500 MHz, CDCl$_3$) δ 5.67 (ddd, J=17.2, 10.3, 8.3, 1H), 5.41 (dd, J=10.0, 0.9, 1H), 5.31 (dd, J=10.3, 2.0, 1H), 5.27 (dt, J=17.2, 1.0, 1H), 3.94 (s, 2H), 3.55 (dd, J=7.2, 3.0, 1H), 3.39 (app t, J=7.4, 1H), 3.21 (s, 3H), 2.63-2.56 (m, 1H), 1.81 (d, J=0.9, 3H), 0.93 (d, J=6.4, 3H), 0.91 (s, 9H), 0.06 (s, 3H), 0.03 (s, 3H); $^{13}$C-NMR (125 MHz, CDCl$_3$) δ 136.35, 135.20, 129.64, 118.82, 86.09, 77.57, 56.15, 34.68, 32.34, 26.13, 21.91, 18.50, 13.54, −3.83, −4.82.

Example 38

β-Ketosulfone 57:

To a solution of methyl phenyl sulfone (1.43 g, 9.14 mmol) in THF (15 mL) at −15° C. was added BuLi (6.28 mL, 10.0 mmol, 1.6M in hexane). After stirring for 30 min, the reaction mixture was cooled to −78° C. and ethyl 6-heptenoate (802 μL, 4.57 mmol) was added. The reaction mixture was warmed to rt and then treated with saturated aqueous NH$_4$Cl solution. The organic layer was separated and the aqueous layer was extracted with EtOAc (3×). The combined organic layers were dried (MgSO$_4$) and concentrated under reduced pressure. Purification of the crude product by FC (hexane/EtOAc 5:1) afforded β-ketosulfone 57 (1.12 g, 92%) as a white solid. $^1$H-NMR (500 MHz, CDCl$_3$) δ 7.88-7.86 (m, 2H), 7.68-7.65 (m, 1H), 7.58-7.54 (m, 2H), 5.79-5.71 (m, 1H), 5.00-4.92 (m, 2H), 4.14 (s, 2H), 2.70-2.67 (m, 2H), 2.05-2.00 (m, 2H), 1.58-1.52 (m, 2H), 1.38-1.32 (m, 2H); $^{13}$C-NMR (125 MHz, CDCl$_3$) δ 197.99, 138.14, 134.19, 129.25, 129.06, 128.17, 114.73, 66.70, 44.12, 33.26, 27.85, 22.42; MS (ESI) 289 [M+Na$^+$]; HRMS (FAB) calcd. for C$_{14}$H$_{18}$O$_3$SNa [M+Na$^+$] 289.0874. found 289.0882.

Example 39

Ketone 58:

To a solution of β-ketosulfone 57 (685 mg, 2.57 mmol) in toluene (5 mL) at rt was added DBU (385 μL, 2.57 mmol). After stirring for 50 min, a solution of crude allylic bromide 56 in toluene (5 mL) was added and the reaction mixture was stirred for another 45 min. The reaction mixture was concentrated under reduced pressure to a volume of ca. 1 mL and the residual solution was filtered through a silica plug (hexane/EtOAc 7:1). To a solution of crude allylated sulfone in MeOH (10 mL) at rt was added Na$_2$HPO$_4$ (366 mg, 2.57 mmol) and 10% Na/Hg (474 mg, ca. 2.06 mmol). After stirring for 3 h, the reaction mixture was filtered through a cotton plug and H$_2$O was added to the filtrate. The organic layer was separated and the aqueous layer was extracted with CH$_2$Cl$_2$ (3×). The combined organic layers were dried (MgSO$_4$) and concentrated under reduced pressure. Purification of the crude product by FC (hexane/EtOAc 30:1) afforded ketone 58 (258 mg, 61%) as a colorless oil. $^1$H-NMR (500 MHz, CDCl$_3$) δ 5.82-5.75 (m, 1H), 5.67-5.60 (m, 1H), 5.29-5.18 (m, 3H), 5.02-4.93 (m, 2H), 3.41 (dd, J=7.2, 2.8, 1H), 3.37 (app t, J=7.6, 1H), 3.20 (s, 3H), 2.52-2.47 (m, 1H), 2.44-2.38 (m, 4H), 2.28-2.18 (m, 2H), 2.06 (app q, J=7.1, 2H), 1.64 (d, J=1.2, 3H), 1.62-1.56 (m, 2H), 1.41-1.35 (m, 2H), 0.90 (s, 9H), 0.87 (d, J=6.7, 3H), 0.05 (s, 3H), 0.01 (s, 3H); $^{13}$C-NMR (125 MHz, CDCl$_3$) δ 210.57, 138.45, 135.30, 131.81, 131.30, 118.53, 114.64, 86.27, 78.61, 56.10, 42.64, 41.23, 34.05, 33.50, 28.46, 26.16, 26.12, 23.27, 23.11, 18.55, 14.05, −3.79, −4.79; MS (ESI) 445 [M+Na$^+$]; HRMS (FAB) calcd. for C$_{25}$H$_{46}$O$_3$SiNa [M+Na$^+$] 445.3114. found 445.3095.

Example 40

TBS-Macroketone 59:

To a solution of ketone 58 (258 mg, 0.610 mmol) in refluxing toluene (1200 mL) was added Grubbs-II catalyst 16 (104 mg, 0.122 mmol). After stirring for 15 min, the reaction mixture was cooled to rt and filtered through a silica plug (hexane/EtOAc 2:1). Purification of the crude product by FC (hexane/EtOAc 20:1) afforded TBS-macroketone 59 (194 mg, 81%) as a colorless oil. $^1$H-NMR (500 MHz, CDCl$_3$) δ 5.67-5.61 (m, 1H), 5.32 (dd, J=15.7, 6.7, 1H), 5.26 (dd, J=9.8, 0.9, 1H), 3.41-3.36 (m, 2H), 3.21 (s, 3H), 2.55-2.49 (m, 1H), 2.46-2.41 (m, 1H), 2.39-2.33 (m, 1H), 2.32-2.18 (m, 5H), 2.14-2.10 (m, 1H), 1.68-1.63 (m, 1H), 1.67 (d, J=1.3, 3H), 1.62-1.53 (m, 2H), 1.51-1.46 (m, 1H), 0.90 (s, 9H), 0.89 (d, J=6.8, 3H), 0.05 (s, 3H), 0.00 (s, 3H); $^{13}$C-NMR (125 MHz, CDCl$_3$) δ 211.96, 133.10, 131.91, 131.68, 129.87, 84.77, 79.32, 56.24, 41.44, 40.91, 34.32, 30.25, 28.74, 26.84, 26.15, 23.15, 22.85, 18.60, 12.78, −3.85, −5.03; MS (ESI) 417 [M+Na$^+$]; HRMS (FAB) calcd. for C$_{23}$H$_{42}$O$_3$SiNa [M+Na$^+$] 417.2801. found 417.2819.

Example 41

Macroketone 60:

To a solution of TBS-macroketone 59 (194 mg, 0.492 mmol) in THF (15 mL) at rt was added HF.pyridine (3.5 mL). After stirring for 15 h, the reaction mixture was carefully treated with MeOTMS (25 mL) and concentrated under reduced pressure. Purification of the crude product by FC (hexane/EtOAc 10:1→14:1) afforded macroketone 60 (124 mg, 90%) as a colorless oil. [α]$_D$ +77.6° (c 0.50, CHCl$_3$); IR (neat) 3566, 3022, 3015, 2975, 2937, 2879, 1700, 1448, 1384, 1237, 1109, 1085, 979; $^1$H-NMR (500 MHz, CDCl$_3$) δ 5.72 (ddd, J=15.0, 8.5, 6.0, 1H), 5.37 (dd, J=10.0, 0.9, 1H), 5.31 (dd, J=15.6, 7.8, 1H), 3.47 (app t, J=8.5, 1H), 3.36 (dd, J=9.2, 1.2, 1H), 3.31 (s, 3H), 2.78 (br s, 1H), 2.51-2.45 (m, 2H), 2.37-2.32 (m, 2H), 2.26-2.16 (m, 5H), 1.69 (d, J=1.3, 3H), 1.68-1.59 (m, 2H), 1.55-1.50 (m, 2H), 0.95 (d, J=6.8, 3H); $^{13}$C-NMR (125 MHz, CDCl$_3$) a 212.10, 135.23, 132.91, 130.26, 129.22, 83.69, 77.62, 56.45, 42.08, 40.67, 32.57, 30.33, 28.57, 27.01, 23.22, 23.14, 12.61; MS (ESI) 303 [M+Na$^+$]; HRMS (FAB) calcd. for C$_{17}$H$_{28}$O$_3$Na [M+Na$^+$] 303.1936. found 303.1938.

Example 42

Secondary Alcohols 61 and 62:

To a solution of alcohol 26 (360 mg, 1.15 mmol) in CH$_2$Cl$_2$ (5 mL) at rt was added Dess-Martin periodinane (970 mg, 2.29 mmol). After stirring for 1 h, the reaction mixture was treated with saturated aqueous Na$_2$S$_2$O$_3$ solution and saturated aqueous NaHCO$_3$ solution. The organic layer was separated and the aqueous layer was extracted with CH$_2$Cl$_2$ (3×). The combined organic layers were dried (Na$_2$SO$_4$) and concentrated under reduced pressure to afford the corresponding aldehyde 27. Crude product 27 was dissolved in Et$_2$O (12 mL) and i-PrMgCl (2.90 mL, 5.80 mmol, 2M in THF) was added at −78° C. After stirring for 5 h, the reaction mixture was treated with saturated aqueous NH$_4$Cl solution. The organic layer was separated and the aqueous layer was extracted with EtOAc (3×). The combined organic layers were dried (MgSO$_4$) and concentrated under reduced pressure. Purification of the crude product by FC (toluene/EtOAc 19:1) afforded (S)-secondary alcohol 61 (186 mg, 50%) and (R)-secondary alcohol 62 (134 mg, 36%) as colorless oils.

(S)-Secondary Alcohol 61:

IR (neat) 3476, 2956, 2929, 2884, 2857, 1471, 1462, 1378, 1251, 1127, 1096, 1080, 1032, 1006; $^1$H-NMR (500 MHz, CDCl$_3$) δ 5.78-5.68 (m, 1H), 5.31-5.23 (m, 3H), 3.98 (d, J=9.8, 1H), 3.51-3.48 (m, 2H), 3.24 (s, 3H), 2.73-2.68 (m, 1H), 1.78-1.69 (m, 1H), 1.66 (s, 3H), 1.60 (br s, 1H), 1.03 (d, J=6.4, 3H), 0.91 (s, 9H), 0.89 (d, J=6.0, 3H), 0.73 (d, J=6.9, 3H), 0.07 (s, 3H), 0.05 (s, 3H); $^{13}$C-NMR (125 MHz, CDCl$_3$) δ 135.37, 134.58, 133.16, 118.24, 85.74, 77.85, 75.73, 56.23, 33.64, 30.96, 26.13, 19.51, 18.93, 18.48, 17.56, 15.66, −3.86, −4.57; MS (ESI) 379 [M+Na$^+$]; HRMS (FAB) calcd. for C$_{20}$H$_{40}$O$_3$SiNa [M+Na$^+$] 379.2644. found 379.2663.

(R)-Secondary Alcohol 62:

IR (neat) 3378, 2955, 2931, 2919, 2872, 1466, 1455, 1378, 1249, 1119, 1096, 1079, 1026; $^1$H-NMR (500 MHz, CDCl$_3$) δ 5.59 (ddd, J=17.3, 10.3, 8.2, 1H), 5.40 (dd, J=10.3, 1.4, 1H), 5.31 (dd, J=10.2, 1.5, 1H), 5.27 (dd, J=17.3, 1.4, 1H, 3.97 (d, J=9.2, 1H, 3.43 (dd, J=7.4, 2.2, 1H), 3.37 (app t, J=8.1, 1H), 3.21 (s, 3H), 2.67-2.62 (m, 1H), 1.80-1.73 (m, 1H), 1.67 (d, J=1.5, 3H), 1.37 (br s, 1H), 1.04 (d, J=6.5, 3H), 0.91 (s, 9H), 0.90 (d, J=6.6, 3H), 0.76 (d, J=6.6, 3H), 0.05 (s, 3H), 0.02 (s, 3H); $^{13}$C-NMR (125 MHz, CDCl$_3$) δ 135.02, 134.13, 133.88, 118.86, 86.39, 78.35, 75.92, 56.06, 33.16, 31.52, 26.15, 19.52, 19.34, 18.59, 17.68, 13.74, −3.80, −4.84; MS (ESI) 379 [M+Na$^+$]; HRMS (FAB) calcd. for C$_{20}$H$_{40}$O$_3$SiNa [M+Na$^+$] 379.2644. found 379.2643.

Example 43

(S)-Isopropyl Ester 63:

To a solution of alcohol 61 (55 mg, 0.154 mmol) in toluene (0.4 mL) at rt was added pyridine (62 μL, 0.772 mmol) and the mixed anhydride of 6-heptenoic acid (The preparation of the mixed anhydride of 6-heptenoic acid and 2,4,6-trichlorobenzoyl chloride was performed exactly as for the mixed anhydride of 2,6-heptadienoic acid and 2,4,6-trichlorobenzoyl chloride (see above)) and 2,4,6-trichlorobenzoyl chloride (1.5 mL, 0.75 mmol, 0.50M in toluene). After stirring 15 h, the reaction mixture was directly loaded onto a silica column and purified by FC (toluene) to afford (S)-isopropyl ester 63 (54 mg, 75%) as a colorless oil. IR (neat) 2928, 2830, 1732, 1470, 1378, 1247, 1125, 1096, 1032; $^1$H-NMR (500 MHz, CDCl$_3$) δ 5.81-5.76 (m, 2H), 5.41 (d, J=10.4, 1H), 5.31 (dd, J=10.3, 2.0, 1H) 5.24 (app d, J=17.2, 1H), 5.17 (app d, J=9.9, 1H), 5.00 (app d, J=17.1, 1H), 4.94 (d, J=5.8, 1H), 3.59 (dd, J=8.0, 1.8, 1H), 3.32 (app t, J=8.4, 1H), 3.20 (s, 3H), 2.73-2.68 (m, 1H), 2.28 (app t, J=7.5, 2H), 2.08-2.04 (m, 2H), 1.91-1.88 (m, 1H), 1.66-1.59 (m, 3H), 1.61 (s, 3H), 1.44-1.41 (m, 1H), 0.91 (d, J=8.3, 3H), 0.90 (s, 9H), 0.84 (d, J=6.7, 3H), 0.77 (d, J=6.9, 3H), 0.04 (s, 3H), −0.02 (s, 3H); $^{13}$C-NMR (125 MHz, CDCl$_3$) δ 172.48, 138.46, 135.43, 135.32, 129.62, 118.71, 114.62, 86.92, 78.07, 77.52, 77.34, 55.83, 34.42, 33.39, 33.27, 29.71, 28.38, 26.22, 24.66, 19.22, 18.53, 18.36, 12.69, −3.80, −4.96; MS (ESI) 489 [M+Na$^+$]; HRMS (FAB) calcd. for C$_{27}$H$_{50}$O$_4$SiNa [M+Na$^+$] 489.3376. found 489.3362.

Example 44

(R)-Isopropyl Ester 66:

Preparation performed exactly as for (S)-isopropyl ester 63, affording (R)-isopropyl ester 66 in 70% yield. IR (neat) 2956, 2928, 2856, 1732, 1469, 1462, 1370, 1249, 1129, 1032; $^1$H-NMR (500 MHz, CDCl$_3$) δ 5.81-5.74 (m, 1H), 5.61 (ddd, J=17.6, 10.6, 7.6, 1H), 5.45 (d, J=9.4, 1H), 5.33 (dd, J=10.4, 1.9, 1H), 5.29 (dd, J=17.0, 1.9, 1H), 5.15 (app d, J=9.8, 1H), 4.99 (dd, J=17.0, 1.9, 1H), 4.95-4.93 (m, 1H), 3.40-3.38 (m, 2H), 3.21 (s, 3H), 2.82-2.76 (m, 1H), 2.29 (app t, J=7.5, 2H), 2.08-2.03 (m, 2H), 1.97-1.90 (m, 2H), 1.64-1.61 (m, 1H), 1.61 (d, J=1.3, 3H), 1.43-1.36 (m, 2H), 0.92 (d, J=6.6, 3H), 0.91 (s, 9H), 0.89 (d, J=6.6, 3H), 0.79 (d, J=6.0, 3H), 0.05 (s, 3H), 0.01 (s, 3H); $^{13}$C-NMR (125 MHz, CDCl$_3$) δ 172.82, 138.47, 135.59, 134.68, 129.61, 118.97, 114.63, 86.41, 78.32, 77.72, 56.06, 34.42, 33.65, 33.38, 29.71, 28.35, 26.18, 24.58, 19.38, 18.96, 18.61, 18.19, 12.89, −3.76, −4.91; MS (ESI) 489 [M+Na$^+$]; HRMS (FAB) calcd. for C$_{27}$H$_{50}$O$_4$SiNa [M+Na$^+$] 489.3376. found 489.3363.

Example 45

(S)-Isopropyl Macrolactone 65:

To a solution of (S)-isopropyl ester 63 (25 mg, 0.053 mmol) in refluxing toluene (100 mL) was added Grubbs-II catalyst 16 (9 mg, 0.0107 mmol). After stirring for 15 min, the reaction mixture was cooled to rt and filtered through a silica plug (hexane/EtOAc 1:3). After evaporation of the solvent, crude product 64 was dissolved in THF (3 mL) and treated with HF.pyridine (0.75 mL) at rt. After stirring for 40 h, the reaction mixture was carefully treated with MeOTMS (6 mL) and concentrated under:reduced pressure. Purification of the crude product by FC(CH$_2$Cl$_2$/EtOAc 9:1) afforded (S)-isopropyl macrolactone 65 (12 mg, 65%) as a colorless oil. [α]$_D$ +25.1° (c 0.32, CHCl$_3$); IR (neat) 3479, 2967, 2926, 2876, 1724, 1448, 1373, 1257, 1237, 1091; $^1$H-NMR (500 MHz, CDCl$_3$) δ 5.70 (ddd, J=15.4, 8.5, 5.3, 1H), 5.33 (dd, J=10.0, 0.9, 1H), 5.30 (d, J=7.0, 1H), 5.19-5.13 (m, 1H), 3.40-3.30 (m, 2H), 3.28 (s, 3H), 2.99-2.95 (m, 1H), 2.76 (br s, 1H), 2.36-2.24 (m, 2H), 2.20-2.08 (m, 2H), 1.99 (app dt, J=7.0, 6.9, 1H), 1.69 (d, J=1.3, 3H), 1.62-1.52 (m, 4H), 0.94 (d, J=7.0, 3H), 0.91 (d, J=6.6, 3H), 0.86 (d, J=6.9, 3H); $^{13}$C-NMR (125 MHz, CDCl$_3$) δ 172.9,7, 135.94, 133.83, 130.09, 127.75, 86.47, 78.70, 55.98, 33.99, 32.80, 30.38, 29.82, 27.34, 22.57, 21.38, 19.09, 18.05, 15.20; MS (ESI) 347 [M+Na$^+$]; HRMS (FAB) calcd. for C$_{19}$H$_{32}$O$_4$Na [M+Na$^+$] 347.2198. found 347.2187.

Example 46

(R)-Isopropyl Macrolactone 68:

Preparation performed exactly as for (S)-isopropyl macrolactone 65, affording (R)-isopropyl macrolactone 68 in 66% yield. [α]$_D$ +21.3° (c 0.09, CHCl$_3$); IR (neat) 3499, 2967, 2926, 2866, 1729, 1453, 1383, 1257, 1111; $^1$H-NMR (500 MHz, CDCl$_3$) δ 5.65 (app dt, J=15.5, 7.5, 1H), 5.58 (dd, J=10.7, 1.3, 1H), 5.35 (dd, J=15.5, 6.0, 1H), 4.87 (d, J=7.6, 1H), 3.49 (dd, J=9.1, 6.0, 1H), 3.34 (s, 3H), 3.27 (br d, J=8.8, 1H), 3.13-3.07 (m, 1H), 2.86 (br s, 1H), 2.34-2.15 (m, 4H), 2.06-1.99 (m, 1H), 1.76 (d, J=1.6, 3H), 1.75-1.58 (m, 3H), 1.47-1.41 (m, 1H), 0.98 (d, J=7.0, 3H), 0.93 (d, J=6.7, 3H), 0.92 (d, J=6.7, 3H); $^{13}$C-NMR (125 MHz, CDCl$_3$) δ 172.50, 132.45, 132.08, 131.58, 128.26, 82.45, 80.74, 77.44, 56.67, 33.00, 32.66, 31.76, 30.56, 25.57, 24.91, 22.44, 19.02, 18.96, 13.20; MS (ESI) 347 [M+Na$^+$]; HRMS (FAB) calcd. for C$_{19}$H$_{32}$O$_4$Na [M+Na$^+$] 347.2198. found 347.2196.

Example 47

Macrocyclic Secondary Alcohol 69 (Diastereomeric Mixture):

To a solution of macroketone 60 (4 mg, 0.014 mmol) in MeOH (0.3 mL) at rt was added NaBH$_4$ (2 mg, 0.042 mmol). After stirring for 5 min, the reaction mixture was carefully treated with 1M HCl (1 mL) and stirring was continued for another 20 min. Then the reaction mixture was diluted with EtOAc, the organic layer was separated, and the aqueous layer was extracted with EtOAc (4×). The combined organic layers were dried (MgSO$_4$) and concentrated under reduced pressure to afford a diastereomeric mixture of macrocyclic secondary alcohol 69 (4 mg, 95%) as a colorless oil. IR (neat) 3405, 2931, 2922, 2856, 1446, 1380, 1106, 1090; $^1$H-NMR (500 MHz, CDCl$_3$) δ 5.66-5.59 (m, 2H), 5.32 (app t, J=8.4, 2H), 5.27-5.19 (m, 2H), 3.83-3.72 (m, 2H), 3.49 (s, 1H), 3.46-3.40 (m, 2H), 3.36 (app t, J=10.0, 1H), 3.30 (s, 6H), 2.74 (br s, 2H), 2.59-2.46 (m, 2H), 2.31-2.26 (m, 2H), 2.19-2.06 (m, 2H), 2.02-1.90 (m, 2H), 1.83-1.72 (m, 4H), 1.70 (s, 6H), 1.68-1.13 (m, 12H), 0.94 (app t, J=6.3, 6H); $^{13}$C-NMR (125 MHz, CDCl$_3$) δ 136.43, 136.22, 134.53, 134.21, 129.52, 129.40, 129.28, 129.19, 84.38, 84.14, 77.51, 77.42, 71.17, 70.66, 56.28, 56.22, 33.36, 33.30, 32.87, 32.50, 32.21, 32.16, 30.47, 30.34, 26.93, 26.91, 26.83, 25.50, 23.46, 23.37, 21.90, 19.67, 12.58, 12.44; MS (ESI) 305 [M+Na$^+$]; HRMS (FAB) calcd. for C$_{17}$H$_{30}$O$_3$Na [M+Na$^+$] 305.2093. found 305.2103.

Example 48

Macrocyclic Tertiary Alcohol 70 (Diastereomeric Mixture):

To a solution of macroketone 60 (5.5 mg, 0.020 mmol) in THF (0.4 mL) at 0° C. was added MeMgBr (66 μL, 0.200 mmol, 3M in Et$_2$O). After stirring for 5 min, the reaction mixture was treated with saturated aqueous NH$_4$Cl solution and diluted with EtOAc. The organic layer was separated and the aqueous layer was extracted with EtOAc (4×). The combined organic layers were dried (MgSO$_4$) and concentrated under reduced pressure to afford a diastereomeric mixture of macrocyclic tertiary alcohol 70 (6.0 mg, 95%) as a colorless oil. IR (neat) 3434, 2933, 2856, 1460, 1448, 1117, 1083; $^1$H-NMR (500 MHz, CDCl$_3$) δ 5.66-5.60 (m, 2H), 5.34-5.31 (m, 2H), 5.24-5.17 (m, 2H), 3.46-3.32 (m, 6H), 3.30 (s, 6H), 2.80-2.70 (m, 2H), 2.61-2.51 (m, 2H), 2.30-2.26 (m, 2H), 2.17 (br s, 1H), 2.14-2.01 (m, 2H), 1.95-1.82 (m, 2H), 1.77-1.60 (m, 2H), 1.70 (s, 6H), 1.58-1.36 (m, 8H), 1.34-1.14 (m, 5H), 1.20 (s, 6H), 1.02 (app t, J=7.2, 2H), 0.94-0.92 (m, 6H); $^{13}$C-NMR (125 MHz, CDCl$_3$) δ 136.55, 136.44, 134.45, 134.35, 129.44, 129.32, 84.34, 84.24, 72.90, 72.80, 56.27, 56.23, 38.71, 38.60, 38.48, 38.43, 32.10, 32.09, 30.92, 30.56, 29.69, 29.32, 29.24, 27.41, 27.37, 26.79, 24.27, 23.34, 23.33, 21.91, 21.14, 12.64, 12.57; MS (ESI) 319 [M+Na$^+$]; HRMS (FAB) calcd. for C$_{18}$H$_{32}$O$_3$Na [M+Na$^+$] 319.2249. found 319.2264.

Example 49

Macrocyclic CF$_3$-Alcohol 71 (Major):

To a solution of macroketone 60 (10 mg, 0.036 mmol) and TMSCF$_3$ (27 μL, 0.180 mmol) in THF (0.6 mL) at rt was added a catalytic amount of TBAF. After stirring for 1 h, the reaction mixture was treated with excess TBAF and stirred for another 5 h. The reaction mixture was concentrated under reduced pressure. Purification of the crude product by FC (hexane/EtOAc 3:1) afforded a diastereomeric mixture of alcohol 71 (10 mg, 80%) as a colorless oil. Further purification by FC (hexane/EtOAc 7:1→3:1) provided the major isomer 71 in pure form as a colorless oil. IR (neat) 3409, 2963, 2931, 2922, 1457, 1244, 1150, 1112; $^1$H-NMR (500 MHz, CDCl$_3$) δ 5.64 (ddd, J=17.2, 9.4, 5.1, 1H), 5.34 (d, J=10.7, 1H), 5.19 (dd, J=17.2, 8.2, 1H), 3.43 (app t, J=9.0, 1H), 3.36 (app d, J=9.5, 1H), 3.30 (s, 3H), 2.87 (br s, 1H), 2.56-2.47 (m, 1H), 2.31-2.26 (m, 1H), 2.11-2.03 (m, 1H), 2.00-1.84 (m, 2H), 1.71-1.68 (m, 2H), 1.69 (s, 3H), 1.69-1.38 (m, 4H), 1.30-1.22 (m, 2H), 0.99 (app t, J=7.3, 1H), 0.93 (d, J=7.0, 3H); $^{13}$C-NMR (125 MHz, CDCl$_3$) δ 136.38, 133.31, 129.78, 129.45, 83.77, 56.33, 32.00, 31.02, 30.41, 29.72, 26.99, 25.09, 23.93, 23.27, 20.20, 19.63, 12.74; MS (ESI) 373 [M+Na$^+$]; HRMS (FAB) calcd. for C$_{18}$H$_{29}$F$_3$O$_3$Na [M+Na$^+$] 373.1966. found 373.1971.

Example 50

Macrooxime 72 (Diastereomeric Mixture):

A solution of macroketone 60 (5 mg, 0.018 mmol) and NH$_2$OH.HCl (12 mg, 0.178 mmol) in pyridine (0.3 mL) was heated to 45° C. for 3 h. The reaction mixture was concentrated under reduced pressure and the crude product was purified by FC (hexane/EtOAc 1:1) to afford a diastereomeric mixture of macrooxime 72 (4 mg, 70%) as a colorless oil. IR (neat) 3326, 2930, 1447, 1109, 1086, 981; $^1$H-NMR (500 MHz, CDCl$_3$) δ 5.72-5.64 (m, 2H), 5.37 (d, J=9.1, 2H), 5.31-5.25 (m, 2H), 3.50-3.45 (m, 2H), 3.38-3.35 (m, 2H), 3.32 (s, 6H), 2.82 (br s, 2H), 2.62-2.57 (m, 2H), 2.43-2.36 (m, 2H), 2.29-2.04 (m, 14H), 1.76 (d, J=1.6, 3H), 1.71 (d, J=1.8, 3H), 1.56-1.48 (m, 6H), 1.27-1.24 (m, 2H), 0.97 (d, J=6.8, 3H), 0.96 (d, J=6.8, 3H); $^{13}$C-NMR (125 MHz, CDCl$_3$) δ 161.91, 161.66, 135.46, 135.30, 134.03, 133.76, 129.76, 129.64, 129.29, 129.19, 83.93, 83.89, 77.65, 77.48, 56.42, 33.66, 32.57, 32.51, 32.42, 30.62, 30.41, 30.29, 28.22, 27.01, 26.94, 26.70, 26.64, 24.42, 23.51, 23.13, 12.67; MS (ESI) 318 [M+Na$^+$]; HRMS (FAB) calcd. for C$_{17}$H$_{29}$NO$_3$Na [M+Na$^+$] 318.2045. found 318.2049.

Example 51

Biotinylated Macrohydrazone 73 (Diastereomeric Mixture):

A solution of macroketone 60 (6 mg, 0.021 mmol) and biotin-dPEG$_4$-hydrazide (13 mg, 0.026 mmol) in EtOH (0.3 mL) was heated to 55° C. for 1 h. The reaction mixture was concentrated under reduced pressure and the crude product was purified by FC(CH$_2$Cl$_2$/MeOH. 4:1) to afford a diastereomeric mixture of biotinylated macrohydrazone 73 (12 mg, 75%) as a colorless oil. IR (neat) 3291, 2930, 2872, 2703, 1691, 1680, 1668, 1540, 1459, 1261, 1104; $^1$H-NMR (500 MHz, CDCl$_3$) δ 9.56 (s, 0.4H), 9.50 (s, 0.4H), 9.23 (s, 0.6H), 9.10 (s, 0.6H), 6.77-6.73 (m, 2H), 6.58 (s, 0.6H), 6.50 (s, 6H), 6.12 (s, 0.4H), 6.08 (s, 0.4H), 5.70-5.63 (m, 2H), 5.42-5.34 (m, 2H), 5.32-5.25 (m, 2H), 5.18 (s, 0.8H), 5.04 (s, 1.2H), 4.50-4.47 (m, 2H), 4.37-4.32 (m, 2H), 3.83-3.79 (m, 4H), 3.68-3.55 (m, 32H), 3.48-3.41 (m, 6H), 3.39-3.28 (m, 8H), 3.16-3.14 (m, 2H), 2.97-2.89 (m, 5H), 2.82 (s, 0.6H), 2.78 (s, 0.4H), 2.74-2.70 (m, 2H), 2.64-2.56 (m, 4H), 2.30-2.22 (m, 10H), 2.20-2.02 (m, 4H), 2.17 (s, 3H), 1.77 (s, 3H), 1.75-1.64 (m, 12H), 1.25-1.24 (m, 2H), 0.95 (d, J=7.0, 3.6H), 0.92 (d, J=6.6, 2.4H); $^{13}$C-NMR (125 MHz, CDCl$_3$) δ 173.95, 173.74, 173.33, 173.22, 163.73, 163.67, 163.49, 160.94, 160.65, 156.08, 155.65, 135.39, 135.02, 134.78, 133.92, 133.65, 132.80, 132.62, 130.73, 130.61, 129.71, 129.56, 129.39, 128.99, 128.92, 83.99, 83.83, 83.79, 83.70, 77.64, 77.53, 77.46, 77.41, 70.42, 70.38, 70.14, 70.04, 69.92, 61.77, 61.73, 60.08, 56.46, 56.40, 40.61, 40.54, 39.13, 39.10, 36.29, 35.86, 35.77, 33.17, 32.68, 32.44, 30.92, 30.67, 30.46, 30.36, 29.68, 28.07, 27.41, 26.88, 26.58, 25.51, 25.45, 24.59, 23.63, 23.49, 23.26, 12.71, 12.66; MS (ESI) 768 [M+H$^+$]; HRMS (FAB) calcd. for C$_{38}$H$_{66}$N$_5$O$_9$S [M+H$^+$] 768.4581. found 768.4581.

Example 52

Preliminary Biological Data:

1. Tube Formation Assay (Table 1)

A protocol was designed based on the instructions from the provider (BD Bioscience, San Jose, Calif.). Briefly, wells of a 48 well culture dish were covert with 150 μL matrigel and the matrigel was gelatinized for 30 min at 37° C. A 80-90% confluent HUVEC (BD Bioscience, San Jose, Calif.) culture was trypsin treated, the detached cells were collected by centrifugation and resuspended in EGM-2 media (BD Bioscience, San Jose, Calif.). Cell concentration was adjusted to 100.000 cells/mL. 400 μL of the cell suspension were filled in the matrigel coated wells, and a solution of the inhibitor was added to the intended final concentration. The plates were incubated at 37° C. with 5% $CO_2$ for 16-18 h. Media was removed, and the matrigel surface was washed twice with 500 μL PBS before cells were labeled with 250 μL 8 μM Calcein AM (Pierce, Rockford, Ill.) in PBS for 30 min at 37° C. After two additional washing steps (500 μL PBS) cells were visualized under an inverted microscope. Fluorescence was excited at 488 nm and recorded at 538 nm. The minimum effect concentration was defined as the minimal inhibitor concentration that caused a definite disturbance of the complexity of the formed tube network.

2. Wound Healing Assay (Table 2)

The wound healing assay was performed based on the method described by Nakae et al. (Nakae et al., *J. Antibiotics* (2000), 53, 1130-1136). Briefly, adherent cells were grown in a suitable media to confluence (e.g. KYSE-520 cells in RPMI-1640 with 10% FBS). Cells were starved for 24 h in serum free media A scratch (ca. 0.5 mm) was applied and the cell layer was washed twice with PBS after removal of the media. Fresh, serum free media with the test compound at the desired concentration was added and the cells were incubated for 28 to 30 h at 37° C., 5% $CO_2$. The scratch size was compared to that observed for cells exposed to 100 μM Migrastatin. Test compounds associated with a scratch size equal to or larger than that observed for cells exposed to 100 μM Migrastatin were deemed to have cell migration inhibitory activity at least equal to Migrastatin.

3. Chamber Cell Migration Assay (Table 3)

Cells were grown in an appropriate media to 70 to 80% confluence and incubated in serum and growth factor free media for 24 h. Cells were detached by trypsin treatment, collected by centrifugation and resuspended in serum free media to a final concentration of 150,000 cells/mL. 400 μL of the cell suspension were loaded into a fibronectin coated insert for 24 well multidishes. 750 μL fully supplemented media were applied to the compartment under the insert. To both chambers the inhibitor was added at the intended concentration and the plates were incubated for 36 h at 37° C., 5% $CO_2$. The media from both chambers was aspirated, the lower section was filled with 300 μL CyQuant assay solution (Molecular Probes, Eugene, Oreg.), and incubated at room temperature for 5 min. The resulting CyQuant assay solution was transferred to the cavities of a 96 well microtiter plate and the fluorescence signal was recorded in an appropriate reader. The CyQuant dye forms a highly fluorescent complex with DNA, thus the fluorescence signal is proportional to the number of cells that migrated through the membrane in the presence of the test compound ($N^{inh}$) A positive control (i.e., without a test compound in the growth media) was carried out according to the procedure described above, except that no test compound was added. The positive control fluorescent reading correlates with the number of cells that migrate through the membrane in the absence of inhibitor ($N^+$). A negative control (i.e., without a test compound and without attractants (e.g., growth factors, serum) in the growth media) was carried out according to the procedure described above, except that no test compound and attractants were added. The negative control fluorescent reading correlates with the number of cells that migrate through the membrane through nondirected processes ($N^-$). The anti-migratory effect of a test compound is determined by the ratio ($N^{inh}-N^-$)/($N^+-N^-$).

Cell Culture with Respect to Examples 53-55:

The human ovarian cancer cell lines Ovcar3 and IGROV were grown in M5 media. The colon cell lines HT 29 and HCT 116 were cultivated in DMEM containing 10% FCS in a humidified environment at 37° C. Myeloma cell lines CAG (obtained from The Myeloma Institute for Research and Therapy, University of Arkansas) and RPMI8226 as well as lymphoma cell line RL were maintained at RPMI1640 medium containing 10% FCS. All cell lines were acquired from the ATCC if not otherwise stated.

Example 53

Cell Migration Assays (See Table 4).

Cell migrations were assayed with 8 μm of microporous 6.5-mm transwell plates (Corning). 200 μl of $2 \times 10^5$ cells in serum-free RPMI1640 medium containing 0.5% BSA were added to the upper chamber and 600 μl of medium with 10% fetal bovine serum was added to the lower chamber. Transwells were incubated for 6 hours at 37° C. for liquid tumor cells (RL, RPMI8226 and CAG) and for 12 hours for solid tumors (HT29, HCT 116, IGROV and Ovcar3) with following concentrations of chemical compounds in both upper and lower chambers (2,3-dihydro-migrastatin core (48): 240 nM, migrastatin lactam (55): 2,550 nM, migrastatin ketone (60): 1,000 nM). Cells migrated to the lower wells were collected and counted for liquid tumors, solid tumors were processed as previously described.[28] Data shown are representative of at least three experiments.

Example 54

Figure 2:
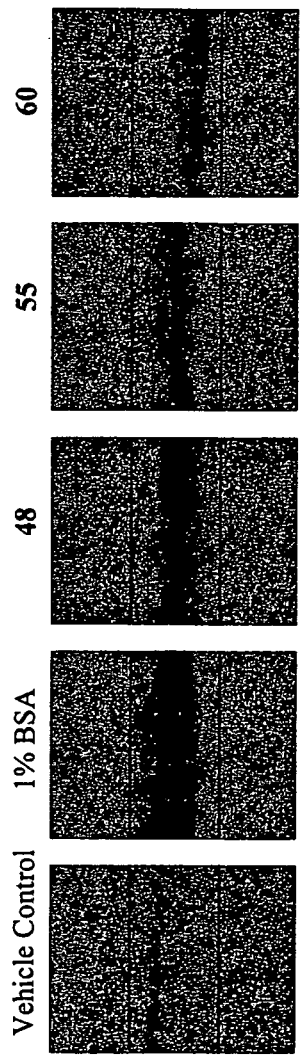
FIG. 2 depicts Wound Healing Cell Migration Assay Results for Ovarian Cancer Cell Line Ovcar3. Concentrations of compounds employed were as follows: 10×IC$_{50}$: 48 (240 nM), 55 (1000 nM), 60 (2550 nM).

Scratch Assay (See Table 5 and FIG. 2).

The tumor cells were seeded into 24-multiwell plates (Becton-Dickinson) and cultivated until the cells formed a confluent monolayer. Wounds were set by horizontally scratching the monolayer with a sterile pipette tip. The cells were thereafter washed twice with Phosphate Buffered Saline (PBS) to remove detached cells. Growth media was then added containing different concentrations of the chemical compound and incubated at 37° C. (2,3-dihydro-migrtstatin core (48): 240 and 2,400 nM, migrastatin lactam (55): 2,550 and 25,500 nM, migrastatin ketone (60): 1,000 and 10,000 nM). The cells were photographed at the beginning of the experiment and after 24 and 48 h to assess the progression of cell migration into the wound.

Example 55

Figure 3:
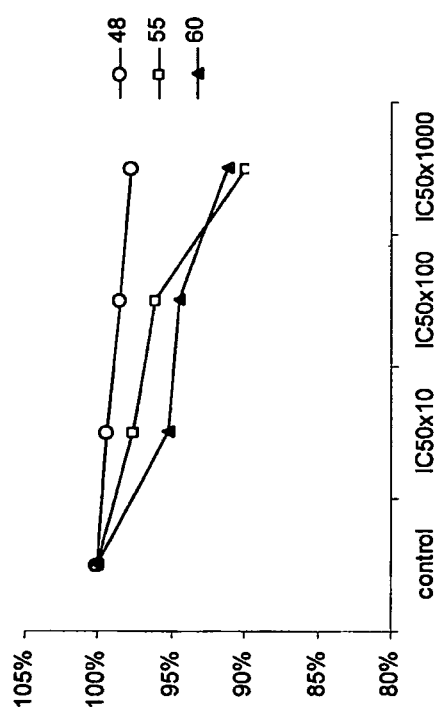
FIG. 3 depicts effects of migrastatin analogs on CAG cell proliferation. IC$_{50}$: DMC (48)=24 nM, macroketone (55)=100 nM and macrolactam (60)=255 nM.

CAG Cell Proliferation Assay (See FIG. 3).

$5 \times 10^3$ CAG cells were plated into wells of 96 multi-well plates (Becton-Dickinson) using RPMI with 10% FCS (Sigma) as growth media in the presence or absence of chemical compounds and then incubated at 37° C. for 72 hours. In the last 20 hours, sodium 3'-[1-(phenylamino-carbonyl)-3,4-tetrazolium]-bis(4-methoxy-6-nitro) benzene sulfonic acid hydrate (XTT) was added and optical absorbance at 490 nm were measured. As reference wavelength 650 nm was used. The number of living cells, thus the total metabolic activity, directly correlates to the amount of orange formazan formed. The result was expressed as percentage of the control.

Example 56

Figure 4:
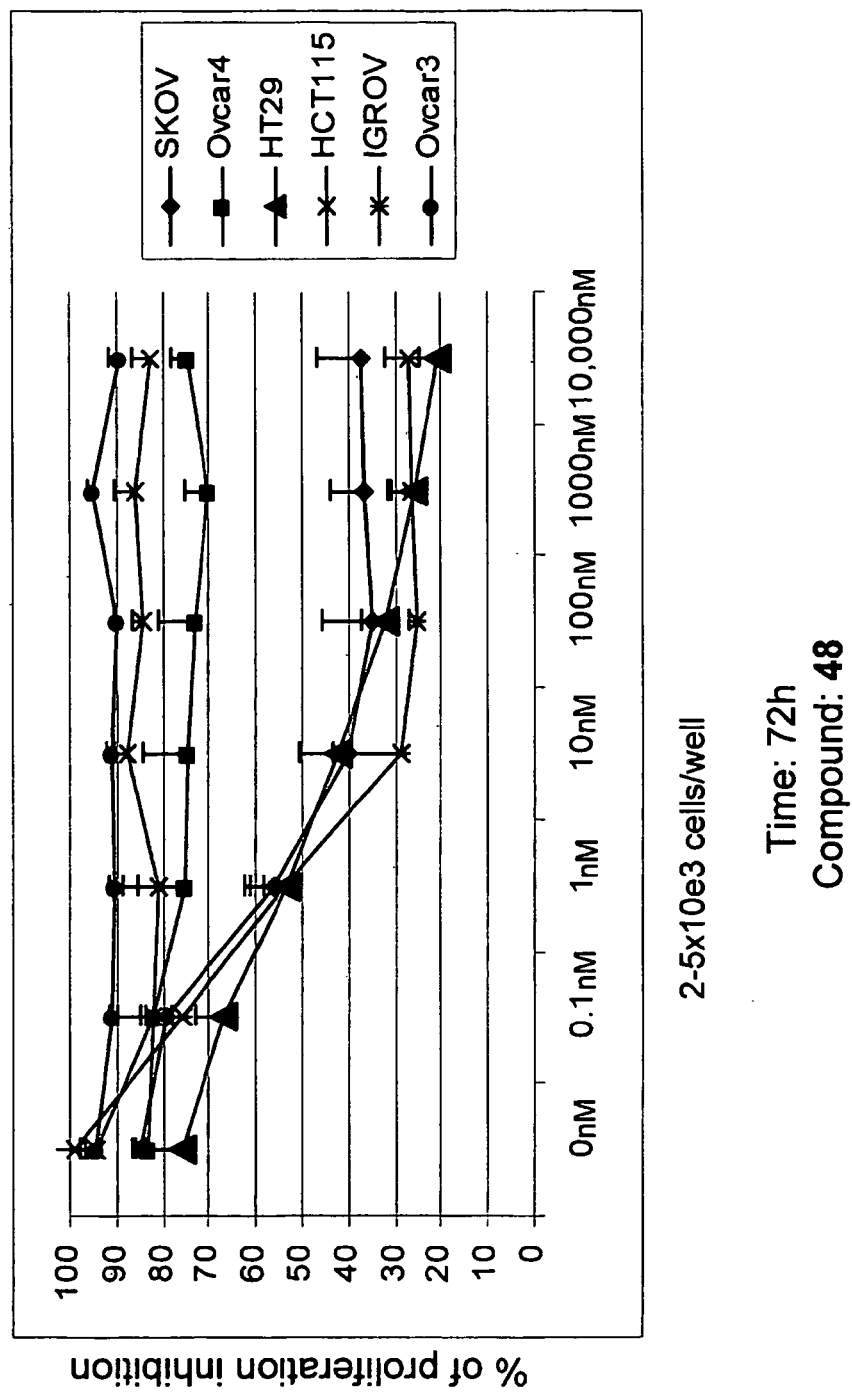
FIG. 4 depicts effects of migrastatin analog (48) on proliferation of a variety of human cells lines (XTT-Assay).
Figure 6:
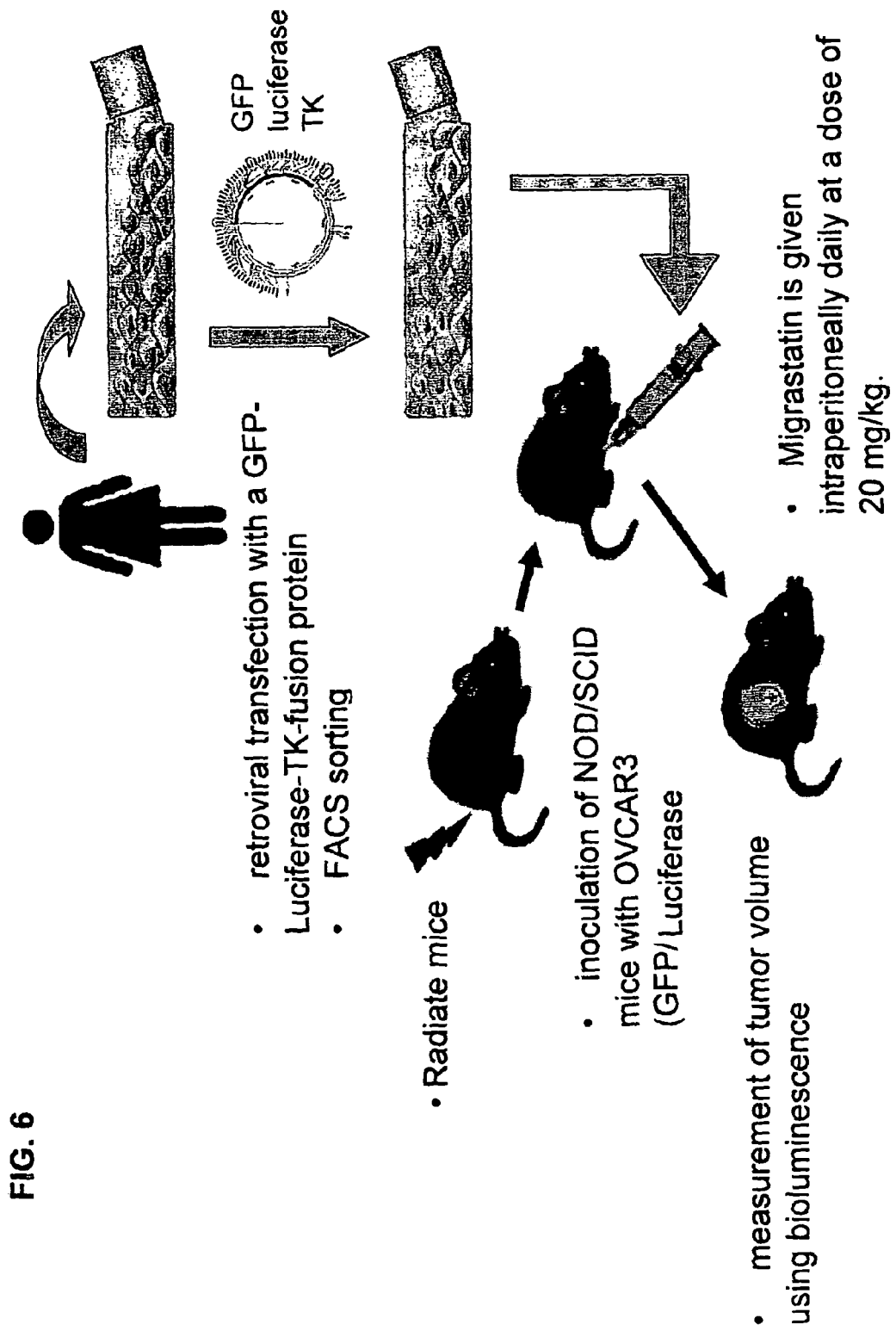
FIG. 6 outlines an exemplary diagram for conducting an Ovcar3 (GFP-Luciferase-TK) xenograph experiment.

Cell Proliferation and Viability Assay for Adherent Cells (FIG. 4).

Cell proliferation and viability measurement were assessed by a colorimetric assay using sodium 39-(phenylaminocarbonyl)-3,4-tetrazolium-bis(4-methoxy-6-nitro) benzene sulfonic acid hydrate (XTT, Sigma, St. Louis, Mo.), and phenazine methosulphate (PMS, Sigma, St. Louis, Mo.). Cells from indicated lines were plated at 5~10×10×103/well in 96 well plates in the presence of different concentration of compounds for 52 hrs. Then 50 µL of XTT/PMS mixture was added to each well and incubated for an additional 20 hrs at 37° C. Plate absorbance was measured directly at optical density of 490 nm (reference wavelength at 650 nm) in an ELISA reader (Thermo Max Microplate Reader, Molecular Devices, CA). The data was expressed as the mean of readings obtained in wells with treatment with subtraction of the reading with vehicle control. The total metabolic activity, which correspond to the number of living cells directly correlate to the amount of orange formazan formed in a cell. The result is expressed as percentage of the control.

Results

The effect of DMC (48) on proliferation could be divided into two groups. One half showed an inhibition of proliferation (SKOV, HT29 and IGROV), without any morphological sign of apoptosis or cell death (negative tryptan blue stain) and a second group of uninfluenced tumor cells (HCT116, Ovcar3 and Ovcar4).

Example 57

In Vivo Metastatic Models

Figure 8:
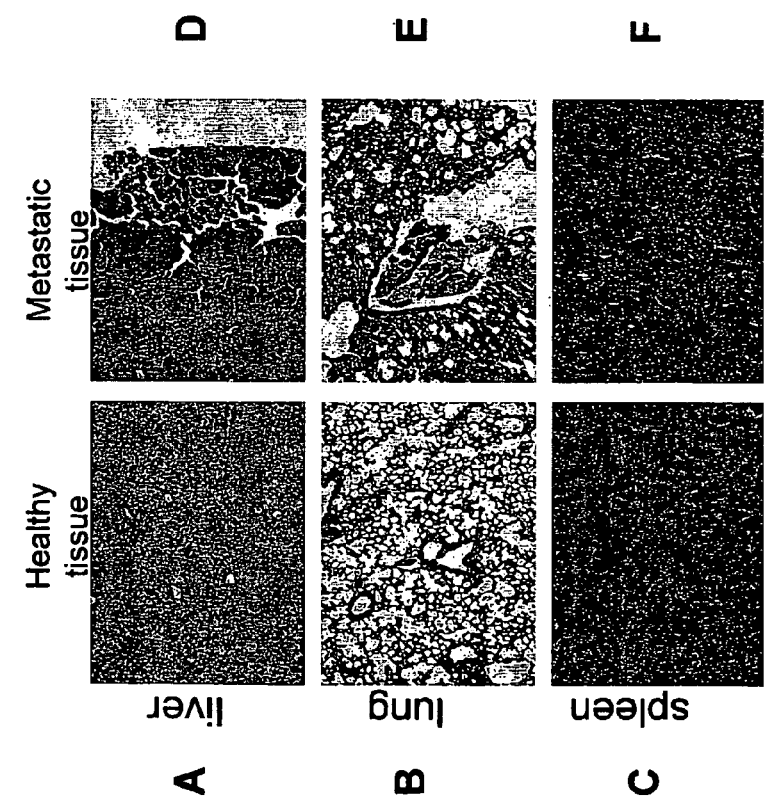
FIG. 8 depicts histological sections of mouse liver, lung and spleen, demonstrating the infiltration of Ovcar3 ovarian cancer cells into the tissue. Figures A-C: healthy mice. Figures D-F: intraperitoneally injected ovarian metastatic mice.

The human ovarian tumor cell line OVCAR3 was transduced with a triple fusion gene HSV-TK/eGFP/FLuc, expressing thymidine kinase, enhanced green fluorescence protein and firefly luciferase. Whole animal imaging by luciferase bioluminescence (FIGS. 7A & B), allowed identification and quantification of disseminated tumor. We quantified the tumor burden in each organ, by sacrificing the mouse shortly after luciferin injecting and imaging of the dissected organs (lung, liver and spleen) (FIG. 8). In all instances tumor engraftment was initiated with $1$-$5 \times 10^7$ cells and the recipients received 3 Gy irradiation 10 days before tumor engraftment. These tumor cells generated bulky omental metastases with diffuse microscopic peritoneal carcinomatosis causing ascites (FIG. 9), significant pleural effusion with diffuse macroscopic peritoneal carcinomatosis and liver, lung and paraaortic metastases.

Migrastatin was administrated daily by intraperitoneal injection. Treatment was initiated once primary tumor was well established. Animals were imaged at weekly intervals to monitor tumor growth and location of metastases (imaging sensitivity 200-500 cells). No significant body weight loss was observed with all Migrastatin derivatives (FIGS. 10-12).

Results

In the first set of mice (5 control and 5 treated mice) an inhibition of ascitis was achieved through the daily injection of 40 mg/kg DMC (48) i.p. in 3 out of 4 mice at the endpoint of the experiment, were as all control mice developed ascites (FIG. 9). Also an increase of survival could be observed with the DMC (48) treated mice with a reduction of the total tumor mass.

Figure 14:
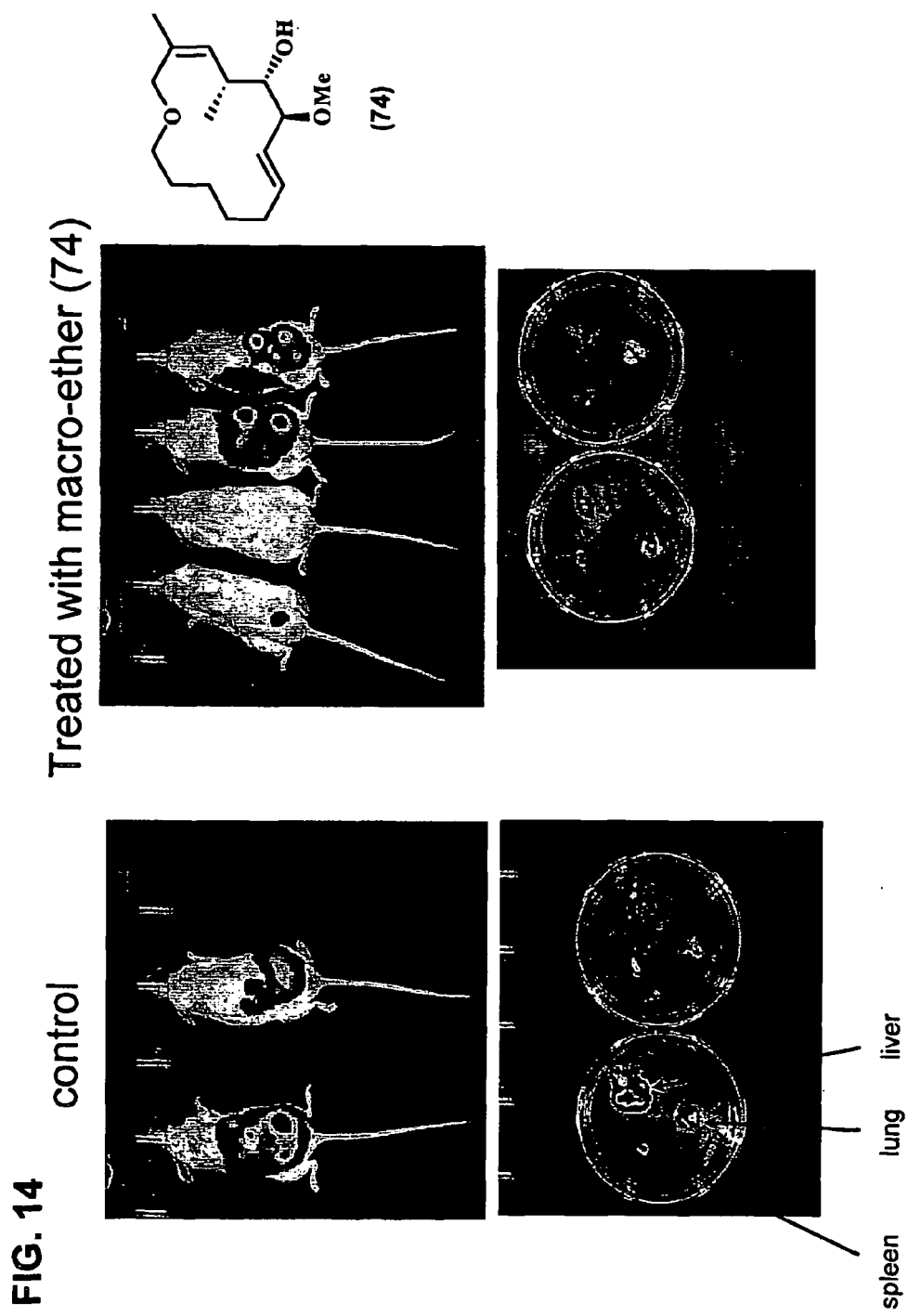
FIG. 14 depicts effects of migmstatin analog (74) in an ovarian in vivo xenograph experiment.
Figure 16:
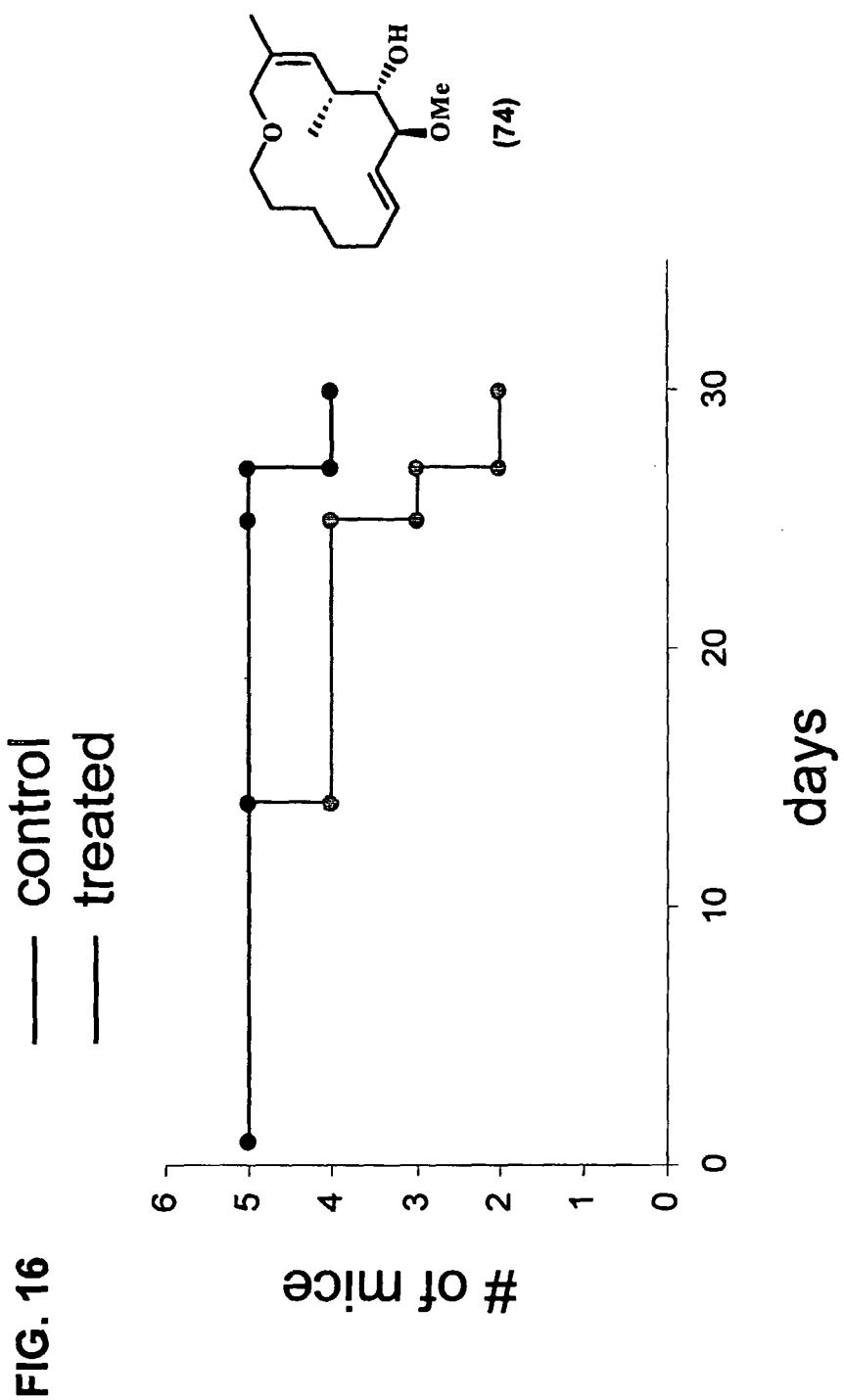
FIG. 16 depicts a survival-curve graph of mice treated with migrastatin analog (74) in an ovarian xenograph model.

A second set of treated mice with Migrastatin ether (74) at 40 mg/kg three times a week showed a reduction of tumor mass of 50% with a reduction of metastasis of over 80% for liver and highly significant reduction in lung and spleen. In this cohort the survival was considerably prolonged with no observed side effects such as weight loss (FIGS. 14-16).

Figure 19:
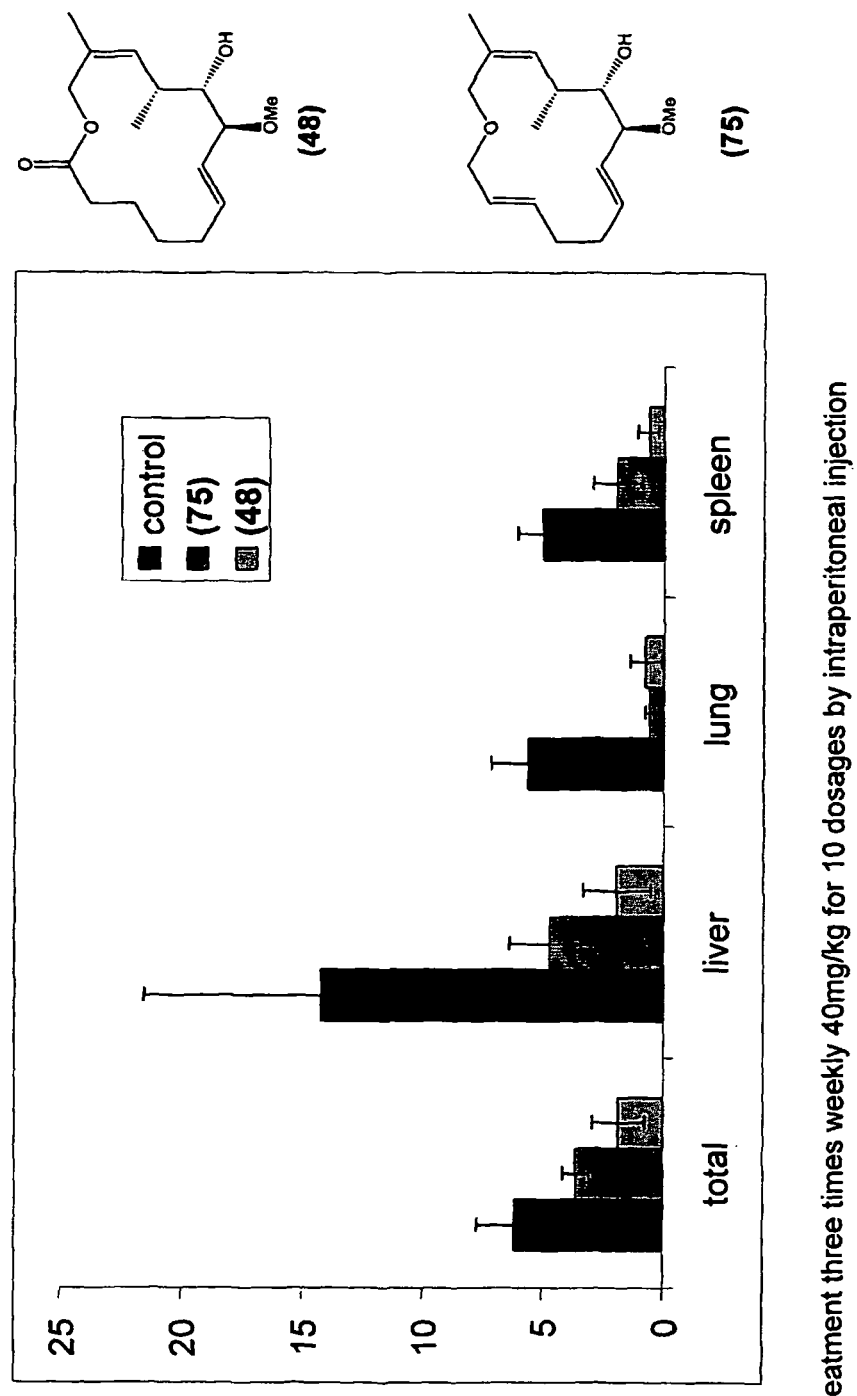
FIG. 19 depicts metastasis inhibition experiments for migrastatin analogs (48) and (75) in an ovarian xenograph model.

A third set of treated mice with Migrastatin ether (75) and Migrastatin analog (48) at 40 mg/kg three times a week for 10 treatments showed a reduction of tumor mass of 60% and over 50%, respectively; with a reduction of metastasis of over 50% and 80%, respectively for liver and highly significant reduction in lung and spleen (FIG. 19).

Example 58

Microarray Analysis of DMC (48) Treated Cells after 6 h and 18 h of Treatment

Figure 18:
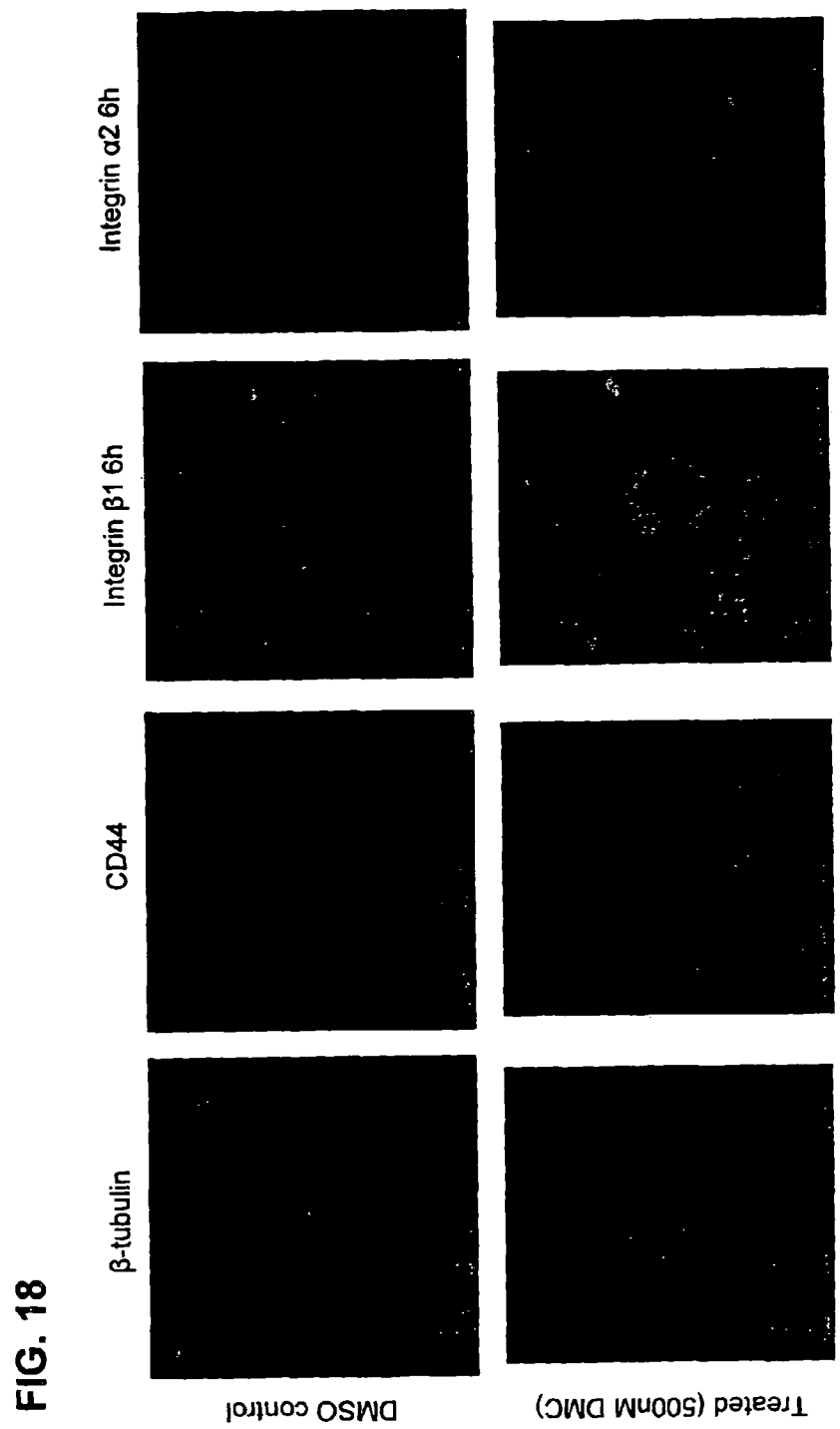
FIG. 18 depicts immunofluorescent staining experiments with human ovarian cancer cells Ovcar3 treated with 500 nM migrastatin analog (48).

For the microarray comparison (Affymetrix chip -AU133 plus) human ovarian cancer cells (Ovcar3) and human colon cancer cells (HT29) were treated with 500 nM DMC (48) for 6 h and 18 h or left untreated. A large panel of up and down regulated genes were detected including a broad array of motility, cell shape and chemotaxis genes (FIG. 17). In addition the micro array analysis of HT-29 colon cancer cells demonstrated an upregulation of E-cadherin in both 6 h and 18 h. Upregulated microarray genes were confirmed through immunfluoreszent microscopy (Integrin α2 and CD44). Other tested cytoskeletal markers as β-tubulin did not show any modulations after 6 h or 24 h (FIG. 18).

Example 59

Immunofluorescence Staining

Ovcar3 cells in exponential growth phase were seeded into 24 well plates at $2 \times 10^4$/ml in the presence of 500 nM of DMC (48). After 18 h cells were harvested and washed with PBS, and fixed with 95% methanol, 5% acetic acid solution for 20 min at −20° C. At the time of staining, cells were pre-blocked at room temperature in PBS with 3% BSA and 0.2% Na-azide. After washing, the cells were then incubated with indicated monoclonal antibody (FIG. 18), diluted 1:200 in 1.5% blocking serum, at 37° C. Cells were washed again and incubated with anti-mouse-Alexa red secondary antibody in the dark at 37° C. Cells were then counter-stained with 4,6-diamidino-2-phenylindole (DAPI) at 0.2 µg/ml PBS.

REFERENCES

1. Fenteany, G.; Zhu, S. *Curr. Top. Med. Chem.* 2003, 3, 593.
2. Lauffenburger, D. A.; Horwitz, A. F. *Cell* 1996, 84, 359.
3. Carmeliet, P. *Nat. Med.* 2003, 9, 653.
4. For research efforts toward anti-angiogenic agents, consult: (a) Brower, V. *Nat. Biotechnol.* 1999, 17, 963; (b) Klohs, W. D.; Hamby, J. M. *Curr. Opin Biotechnol.* 1999, 10, 544; (c) Deplanque, G; Harris, A. L. *Eur. J. Cancer* 2000, 36, 1713; (d) Scappaticci, F. A. *J. Clin. Oncol.* 2002, 20, 3906; (e) Cristofanilli, M.; Chamsangavej, C.; Hortobagyi, G. N. *Nat. Rev. Drug Discovery* 2002, 1, 415; (f) Kerbel, R.; Folkman, *J. Nat. Rev. Cancer* 2003, 2, 727.
5. Woodhouse, E. C.; Chuaqui, R. F.; Liotta, L. A. *Cancer* 1997, 80 (S8), 1529.
6. For comprehensive reviews, see: (a) Harris, C. R.; Danishefsky, S. J. *J. Org. Chem.* 1999, 64, 8434; (b) Stachel, S. J.; Biswas, K.; Danishefsky, S. J. *Curr. Pharm. Des.* 2001, 7, 1277.
7. Danishefsky, S. J.; Masters, J. J.; Young, W. B.; Link, J. T.; Snyder, L. B.; Magee, T. V.; Jung, D. K.; Isaacs, R. C. A.;

Bornmann, W. G.; Alaimo, C. A.; Coburn, C. A.; DiGrandi, M. J. *J. Am. Chem. Soc.* 1996, 118, 2843.
8. For the synthesis and biological evaluation of radicicol and cyclopropyl-radicicol, see: (a) Garbaccio, R. M.; Stachel, S. J.; Baeschlin, D. K.; Danishefsky, S. J. *J. Am. Chem. Soc.* 2001, 123, 10903; (b) Yamamoto, K.; Garbaccio, R. M.; Stachel, S. J.; Solit, D. B.; Chiosis, G.; Rosen, N.; Danishefsky, S. *J. Angew. Chem. Int. Ed.* 2003, 42, 1280; (c) Yang, Z. Q.; Danishefsky, S. J. *J. Am. Chem. Soc.* 2003, 125, 9602.
9. For the synthesis and evaluation of TMC-95A/B, see: (a) Lin, S.; Danishefsky, S. J. *Angew. Chem. Int. Ed.* 2001, 40, 512; (b) Yang, Z. Q.; Kwok, B. H.; Lin, S.; Koldobskiy, M. A.; Crews, C. M.; Danishefsky, S. J. *Chembiochem* 2003, 6, 508.
10. For more information about clinical trials of dEpoB, visit: www.kosan.com
11. For the synthesis and biological evaluation of recent epothilone analogs, see: (a) Rivkin, A.; Yoshimura, F.; Gabarda, A. E.; Chou, T. C.; Dong, H.; Tong, W. P.; Danishefsky, S. J. *J. Am. Chem. Soc.* 2003, 125, 2899; (b) Yoshimura, F.; Rivkin, A.; Gabarda, A. E.; Chou, T. C.; Dong, H.; Sukenick, G.; Morel, F. F.; Taylor, R. E.; Danishefsky, S. J. *Angew. Chem. Int. Ed.* 2003, 42, 2518.
12. For the isolation of epoxyquinol A and B, see: (a) Kakeya, H.; Onose, R.; Koshino, H.; Yoshida, A.; Kobayashi, K.; Kageyama, S. I.; Osada, H. *J. Am. Chem. Soc.* 2002, 124, 3496; (b) Kakeya, H.; Onose, R.; Yoshida, A.; Koshino, H.; Osada, H. *J. Antibiot.* 2002, 55, 829. For the synthesis of epoxyquinol A and B, see: (a) Shoji, M.; Yamaguchi, J.; Kakeya, H.; Osada, H.; Hayashi, Y. *Angew. Chem. Int. Ed* 2002, 41, 3192; (b) Chaornin, L.; Bardhan, S.; Pace, E. A.; Liang, M. C.; Gilmore, T. D.; Porco Jr., J. A. *Org. Lett.* 2002, 4, 3267; (c) Mehta, G.; Islam, K. *Tetrahedron Lett.* 2003, 44, 3569.
13. For the isolation of trachyspic acid, see: (a) Shiozawa, H.; Takahashi, M.; Takatsu, T.; Kinoshita, T.; Tanzawa, K.; Hosoya, T.; Furuya, K.; Furihata, K.; Seto, H. *J. Antibiot.* 1995, 48, 357. For the synthesis of trachyspic acid, see: (b) Hirai, K.; Ooi, H.; Esumi, T.; Iwabuchi, Y.; Hatakeyama, S. *Org. Lett.* 2003, 5, 857.
14. For the isolation of azaspirene, see: Asami, Y.; Kakeya, H.; Onose, R.; Yoshida, A.; Matsuzaki, H.; Osada, H. *Org. Lett.* 2002, 4, 2845. For the synthesis of azaspirene, see: Hayashi, Y.; Shoji, M.; Yamaguchi, J.; Sato, K.; Yamaguchi, S.; Mukaiyama, T.; Sakai, K.; Asami, Y.; Kakeya, H.; Osada, H. *J. Am. Chem. Soc.* 2002, 124, 12078.
15. A screening approach revealed evodiamine as a potent anti-invasive and anti-metastatic agent: Ogasawara, M.; Matsubara, T.; Suzuki, H. *Biol. Pharm. Bull.* 2001, 24, 720; Ogasawara, M.; Matsubara, T.; Suzuki, H. *Biol. Pharm. Bull.* 2001, 24, 917; Ogasawara, M.; Matsunaga, T.; Takahashi, S.; Saiki, I.; Suzuki, H. *Biol. Pharm. Bull* 2002, 25, 1491.
16. For the isolation, synthesis, and discussion of the anti-angiogenic properties of the motuporamines, see: Williams, D. E.; Lassota, P.; Andersen, R. J. *J. Org. Chem.* 1998, 63, 4838; Roskelley, C. D.; Williams, D. E.; McHardy, L. M.; Leong, K. G.; Troussard, A.; Karsan, A.; Andersen, R. J.; Dedhar, S.; Roberge, M. *Cancer Res.* 2001, 61, 6788; Williams, D. E.; Craig, K. S.; Patrick, B.; McHardy, L. M.; van Soest, R.; Roberge, M.; Andersen, R. J. *J. Org. Chem.* 2002, 67, 245.
17. For the discovery of the anti-angiogenic properties of borrelidin, see: Wakabayashi, T.; Kageyama, R.; Naruse, N.; Tsukahara, N.; Funahashi, Y.; Kitoh, K.; Watanabe, Y. *J. Antibiot.* 1997, 50, 671. For the synthesis of borrelidin, see: Duffey, M. O.; LeTiran, A.; Morken, J. P. *J. Am. Chem. Soc.* 2003, 125, 1458.
18. For the discovery of the anti-angiogenic properties of terpestacin, see: Jung, H. J.; Lee, H. B.; Kim, C. J.; Rho, J. R.; Shin, J.; Kwon, H. J. *J. Antibiot* 2003, 56, 492. For the synthesis of terpestacin, see: Tatsuta, K.; Masuda, N. *J. Antibiot.* 1998, 51, 602; Myers, A. G.; Siu, M.; Ren, F. *J. Am. Chem. Soc.* 2002, 124, 4230; Chan, J.; Jamison, T. F. *J. Am. Chem. Soc.* 2003, 125, 11514.
19. Nakae, K.; Yoshimoto, Y.; Sawa, T.; Homma, Y.; Hamada, M.; Takeuchi, T.; Imoto, M. *J. Antibiot.* 2000, 53, 1130; Nakae, K.; Yoshimoto, Y.; Ueda, M.; Sawa, T.; Takahashi, Y.; Naganawa, H.; Takeuchi, T.; Imoto, M. *J. Antibiot.* 2000, 53, 1228; Takemoto, Y.; Nakae, K.; Kawatani, M.; Takahashi, Y.; Naganawa, H.; Imoto, M. *J. Antibiot.* 2001, 54, 1104; Nakamura, H.; Takahashi, Y.; Naganawa, H.; Nakae, K.; Imoto, M.; Shiro, M.; Matsumura, K.; Watanabe, H.; Kitahara, T. *J. Antibiot.* 2002, 55, 442.
20. Woo, E. J.; Starks, C. M.; Carney, J. R.; Arslanian, R.; Cadapan, L.; Zavala, S.; Licari, P. *J. Antibiot.* 2002, 55, 141.
21. Cycloheximide (CHX) is a glutarimide antibiotic that inhibits protein synthesis. CHX is widely used for studies of cell death and is commercially available as Ready Made solution by Sigma. For a more recent leading article, see: Mattson, M. P.; Furukawa, K. *Apoptosis* 1997, 2, 257.
22. For a recent synthesis of streptimidone, a glutarimide antibiotic, see: Kondo, H.; Oritani, T.; Kiyota, H. *Eur. J. Org. Chem.* 2000, 3459.
23. For the original discovery of the anti-angiogenic properties of thalidomide, see: D'Amato, R. J.; Loughnan, M. S.; Flynn, E.; Folkman, J. *Proc. Natl. Acad. Sci.* 1994, 91, 4082. For recent discussions of the use of thalidomide in anti-cancer therapy, see: Thomas, D. A.; Kantaijian, H. M. *Curr. Opin. Oncol.* 2000, 12, 635; Raje, N.; Anderson, K. C. *Curr. Opin. Oncol.* 2002, 14, 635; Dredge, K; Dalgleish, A. G.; Marriott, J. B. *Anti-Cancer Drugs* 2003, 14, 331; Capitosti, S. M; Hansen, T. P.; Brown, M. L. *Bioorg. Med. Chem.* 2004, 12, 327.
24. Sugawara, K.; Nishiyama, Y.; Toda, S.; Komiyama, N.; Hatori, M.; Moriyama, T.; Sawada, Y.; Kamei, H.; Konishi, M.; Oki, T. *J. Antibiot.* 1992, 45, 1433.
25. Karwowski, J. P.; Jackson, M.; Sunga, G.; Sheldon, P.; Poddig, J. B.; Kohl, W. L.; Adam, S. *J. Antibiot.* 1994, 47, 862; Hochlowski, J. E.; Whittern, D. N.; Hill, P.; McAlpine, J. B. *J. Antibiot.* 1994, 47, 870; Kadam, S.; McAlpine, J. B. *J. Antibiot.* 1994, 47, 875.
26. Takayasu, Y.; Tsuchiya, K.; Aoyama, T.; Sukenaga, Y. *J. Antibiot.* 2001, 54, 1111; Takayasu, Y.; Tsuchiya, K.; Sukenaga, Y. *J. Antibiot* 2002, 55, 337.
27. Gaul, C.; Njardarson, J. T.; Danishefsky, S. J. *J. Am. Chem. Soc.* 2003, 125, 6042.
28. Njardarson, J. T.; Gaul, C.; Shan, D.; Huang, X. Y.; Danishefsky, S. J. *J. Am. Chem. Soc.* 2004, 126, 1038.
29. Danishefsky, S. J.; Kitahara, T. *J. Am. Chem. Soc.* 1974, 96, 7807.
30. Danishefsky, S. J. *Aldrichimica Acta* 1986, 19, 59; Danishefsky, S. J. *Chemtracts* 1989, 2, 273.
31. Gaul, C.; Danishefsky, S. J. *Tetrahedron Lett.* 2002, 43, 9039.
32. (S)-3-benzyloxy-1,2-propanediol 7 is commercially available (Fluka, Aldrich), but only at a high cost. Compound 7 can be easily prepared from inexpensive starting materials: Xiang, G.; McLaughlin, L. W. *Tetrahedron* 1998, 54, 375; Kitaori, K.; Furukawa, Y.; Yoshimoto, H.; Otera, J. *Tetrahedron* 1999, 55, 14381.

33. Reetz, M. T.; Kessler, K. *J. Org. Chem.* 1985, 50, 5434.
34. Danishefsky, S. J.; Yan, C. F.; Singh, R. K.; Gammill, R. B.; McCurry Jr., P. M.; Fritsch, N.; Clardy, J. *J. Am. Chem. Soc.* 1979, 101, 7001.
35. For chelation-controlled cyclocondensations of α-alkoxy aldehydes with synergistically activated dienes, see: Danishefsky, S. J.; Pearson, W. H.; Harvey, D. F.; Maring, C. J.; Springer, J. P. *J. Am. Chem. Soc.* 1985, 107, 1256.
36. Luche, J. L.; Gemal, A. L. *J. Am. Chem. Soc.* 1979, 101, 5848.
37. Ferrier, R. J. *J. Chem. Soc.* 1964, 5443.
38. Katzenellenbogen, J. A.; Crumrine, A. L. *J. Am. Chem. Soc.* 1976, 98, 4925; Ahmrar, M.; Duyck, C.; Fleming I. *J. Chem. Soc., Perkin Trans.* 1 1998, 2721.
39. Tebbe, F. N.; Parshall, G. W.; Reddy, G. S. *J. Am. Chem. Soc.* 1978, 100, 3611.
40. For initial reports of Grubbs-II catalyst 16, see: Scholl, M.; Trnka, T. M.; Morgan, J. P.; Grubbs, R. H *Tetrahedron Lett.* 1999, 40, 2247; Scholl, M.; Ding, S.; Lee, C. W.; Grubbs, R. H. *Org. Lett.* 1999, 1, 953.
41. For the first report of these new, optimized RCM conditions, see: Yamamoto, K.; Biswas, K.; Gaul, C.; Danishefsky, S. J. *Tetrahedron Lett.* 2003, 44, 3297. The same reaction conditions were also applied to the first total synthesis of epothilone 490: Biswas, K.; Lin, H.; Njardarson, J. T.; Chappell, M. D.; Chou, T. C.; Guan, Y.; Tong, W. P.; He, L.; Horwitz, S. B.; Danishefsky, S. J. *J. Am. Chem. Soc.* 2002, 124, 9825.
42. Jorgensen, M.; Iversen, E. H.; Paulsen, A. L.; Madsen, R. *J. Org. Chem.* 2001, 66, 4630.
43. Lee, W. W.; Chang, S. *Tetrahedron: Asymmetry* 1999, 10, 4473.
44. Danishefsky, S. J.; Kato, N.; Askin, D.; Kerwin Jr., J. F. *J. Am. Chem. Soc.* 1982, 104, 360; Eng, H. M.; Myles, D. C. *Tetrahedron Lett.* 1999, 40, 2279.
45. Crystallographic data (excluding structural data) for compound 24 have been deposited with the Cambridge Crystallographic Data Centre (CCDC) as Deposition No. CCDC 230121.
46. Dess, D. B.; Martin, J. C. *J. Am. Chem. Soc.* 1991, 113, 7277.
47. Abiko, A.; Liu, J. F.; Masamune, S. *J. Am. Chem. Soc.* 1997, 119, 2586.
48. Evans, D. A.; Tedrow, J. S.; Shaw, J. T.; Downey, C. W. *J. Am. Chem. Soc.* 2002, 124, 392.
49. For examples of the direct addition of lithiated dimethyl methylphosphonate to esters, see for example: Edmonds, M. K.; Abell, A. D. *J. Org. Chem.* 2001, 66, 3747; Smith III, A. B.; Frohn, M. *Org. Lett.* 2001, 3, 3979.
50. Egawa, Y.; Suzuki, M.; Okuda, T. *Chem. Pharm. Bull.* 1963, 11, 589.
51. Blanchette, M. A.; Choy, W.; Davis, J. T.; Essenfeld, A. M.; Masamune, S.; Roush, W. R.; Sakai, T. *Tetrahedron Lett.* 1984, 25, 2183.
52. Mahoney, W. S.; Brestensky, D. M.; Stryker, J. M. *J. Am. Chem. Soc.* 1988, 110, 291. The Stryker reagent provided by Aldrich performed poorly in the conjugate reduction. The reagent provided by Fluka or prepared by us led to superior results.
53. Inanaga, J.; Hirata, K.; Saeki, H.; Katsuki, T.; Yamaguchi, M. *Bull. Chem. Soc. Jpn.* 1979, 52, 1989. For a recent example, see: Song, F.; Fidanze, S.; Benowitz, A. B.; Kishi, Y. *Org. Lett.* 2002, 4, 647.
54. Mukaiyama, T., Usui, M.; Shimada, E.; Saigo, K. *Chem. Lett.* 1975, 1045; Mukaiyama, T. *Angew. Chem. Int. Ed.* 1979, 18, 707.
55. Boden, E. P.; Keck, G. E. *J. Org. Chem.* 1985, 50, 2394.
56. Stachel, S. J.; Lee, C. B.; Spassova, M.; Chappell, M. D.; Bornmann, W. G.; Danishefsky, S. J. *J. Org. Chem.* 2001, 66, 4369 (includes an example for the Mitsunobu-Staudinger sequence).
57. Chun, J.; Li, G.; Byun, H. S.; Bittman, R. *J. Org. Chem.* 2002, 67, 2600.
58. For a recent example, see: Dixon, D. J.; Krause, L.; Ley, S. V. *J. Chem. Soc., Perkin Trans.* 1, 2001, 2516.
59. Trost, B. M.; Bunt, R. C.; Pulley, S. R. *J. Org. Chem.* 1994, 59, 4202; Seco, J. M.; Latypov, S. K.; Quinoa, E.; Riguera, R. *Tetrahedron* 1997, 53, 8541; Seco, J. M.; Quinoa, E.; Riguera, R. *Tetrahedron: Asymmetry* 2000, 11, 2781.
60. Li, D. R.; Xia, W. J.; Shi, L.; Tu, Y. Q. *Synthesis* 2004, 41.
61. Prakash, G. K. S.; Krishnarnurti, R.; Olah, G. A. *J. Am. Chem. Soc.* 1989, 111, 393.
62. Miller, F. R, Miller, B. E., and Heppner, G. H. 1983. Characterization of metastatic heterogeneity among subpopulations of a single mouse mammary tumor: heterogeneity in phenotypic stability. Invasion Metastasis 33: 22-31.
63. Pulaski, B. A., and Ostrand-Rosenberg, S. 1998. Reduction of established spontaneous mammary carcinoma metastases following immunotherapy with major histocompatibility complex class II and B7.1 cell-based tumor vaccines. Cancer Res 58: 1486-1493.
64. Aslakson, C. J., and Miller, F. R. 1992. Selective events in the metastatic process defined by analysis of the sequential dissemination of subpopulations of a mouse mammary tumor. Cancer Research 52: 1399-1405.
65. MCF-7, another human breast cancer cell line, did not respond at all.

We claim:
1. A method for treating ovarian cancer in a subject comprising administering to a subject in need thereof a therapeutically effective amount of a compound having the structure:

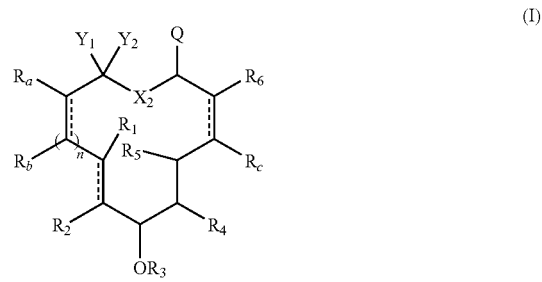

(I)

or pharmaceutically acceptable salt thereof;
wherein $R_1$ and $R_2$ are each hydrogen;
$R_3$ is hydrogen or methyl;
$R_4$ is —OH, OAc, $NH_2$, or F, or $R_4$ taken together with the carbon atom to which it is attached forms a moiety having the structure:

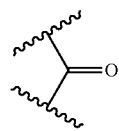

$R_5$ is hydrogen or methyl;
$R_6$ is hydrogen or methyl;
$R_a$ and $R_b$ are hydrogen;

$R_c$ is hydrogen;
n is 3;
$X_1$ is O, $NR^{X1}$ or $CR^{X1}R^{X2}$; wherein $R^{X1}$ and $R^{X2}$ are hydrogen;
Q is hydrogen; and
$Y_1$ and $Y_2$ are hydrogen, or $Y_1$ and $Y_2$ together with the carbon atom to which they are attached form a moiety having the structure:

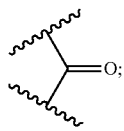

wherein the compound is administered at a dosage from about 1 mg/kg to about 70 mg/kg, or wherein the compound is administered at a dosage of about 70 mg/kg or greater; and wherein the compound is present in an amount effective to inhibit ovarian tumor metastasis.

2. A method for treating colon cancer in a subject comprising administering to a subject in need thereof a therapeutically effective amount of a compound having the structure:

(I)

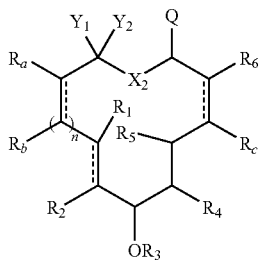

or pharmaceutically acceptable salt thereof;
wherein $R_1$ and $R_2$ are each hydrogen;
$R_3$ is hydrogen or methyl;
$R_4$ is —OH, OAc, $NH_2$, or F, or $R_4$ taken together with the carbon atom to which it is attached forms a moiety having the structure:

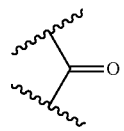 [SMILES: *C(*)=O]

$R_5$ is hydrogen or methyl;
$R_6$ is hydrogen or methyl;
$R_a$ and $R_b$ are hydrogen;
$R_c$ is hydrogen;
n is 3;
$X_1$ is O;
Q is hydrogen; and
$Y_1$ and $Y_2$ are hydrogen, or $Y_1$ and $Y_2$ together with the carbon atom to which they are attached form a moiety having the structure

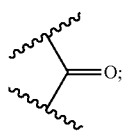 [SMILES: *C(*)=O]

wherein the compound is administered at a dosage from about 1 mg/kg to about 70 mg/kg, or wherein the compound is administered at a dosage of about 70 mg/kg or greater; and wherein the compound is present in an amount effective to inhibit colon tumor metastasis.

3. A method for treating colon or ovarian cancer in a subject comprising administering to a subject in need thereof a therapeutically effective amount of a pharmaceutical composition comprising:

a pharmaceutically acceptable carrier, adjuvant or vehicle; and a therapeutically effective amount of a compound having the structure:

(I)

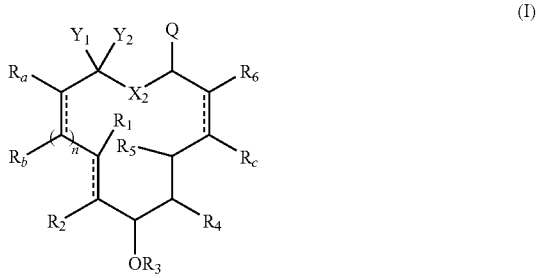

or pharmaceutically acceptable salt thereof;
wherein $R_1$ and $R_2$ are hydrogen;
$R_3$ is hydrogen or methyl;
$R_4$ is —OH, OAc, $NH_2$, or F, or $R_4$ taken together with the carbon atom to which it is attached forms a moiety having the structure:

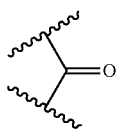

$R_5$ is hydrogen or methyl;
$R_6$ is hydrogen or methyl;
$R_a$ and $R_b$ are hydrogen;
$R_c$ is hydrogen;
n is 3;
$X_1$ is O;
Q is hydrogen; and
$Y_1$ and $Y_2$ are hydrogen, or $Y_1$ and $Y_2$ together with the carbon atom to which they are attached form a moiety having the structure:

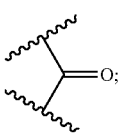

whereby the composition is formulated for administration to a subject at a dosage between about 1 mg/kg to about 70 mg/kg, or wherein the composition is formulated for administration to a subject at a dosage of about 70 mg/kg or greater.

4. The method of claim 3, wherein the dosage is between about 20 mg/kg to about 60 mg/kg of body weight.

5. The method of claim 3, wherein the dosage is between about 5 mg/kg to about 20 mg/kg of body weight.

6. The method of claim 3, wherein the dosage is between about 150 mg/kg to about 250 mg/kg of body weight.

7. The method of claim 1, wherein the compound is:

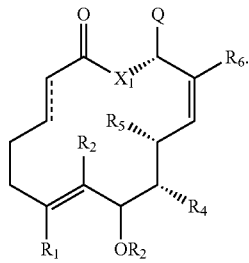

8. The method of claim 1, wherein in the compound, $R_5$ and $R_6$ are each methyl.

9. The method of claim 1, wherein in the compound, $R_3$ is methyl.

10. The method of claim 1, wherein in the compound, $R_4$ is OH, $NH_2$ or F.

11. The method of claim 1, wherein the compound has the structure:

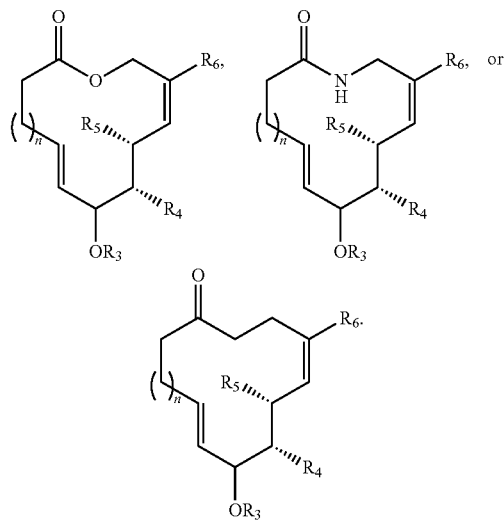

12. The method of claim 1, wherein the compound has the structure:

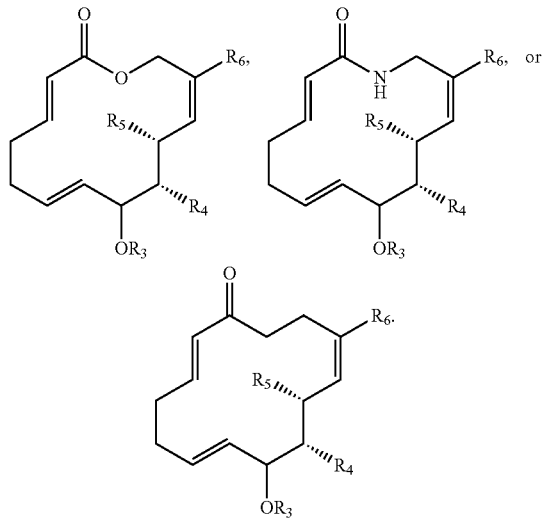

13. The method of claim 11, wherein in the compound, $R_3$ is methyl.

14. The method of claim 11, wherein in the compound, the stereocenter

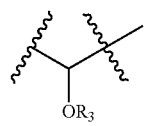

has the following stereochemistry

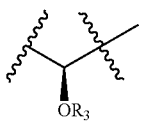

15. The method of claim 11, wherein in the compound, the stereocenter

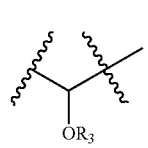

has the following stereochemistry

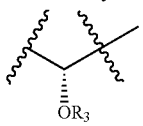

16. The method of claim 1, wherein the compound has one of the structures:

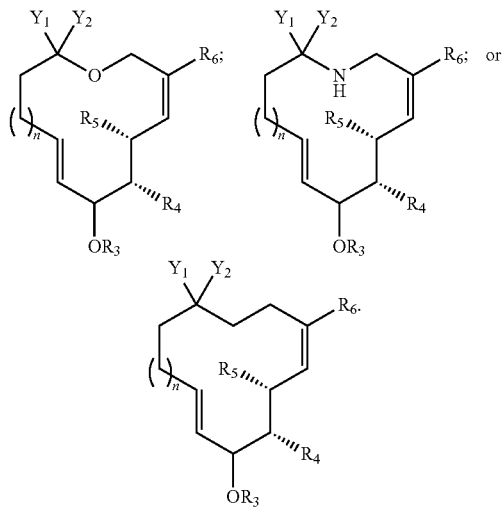

17. The method of claim 1, wherein the compound has one of the structures:

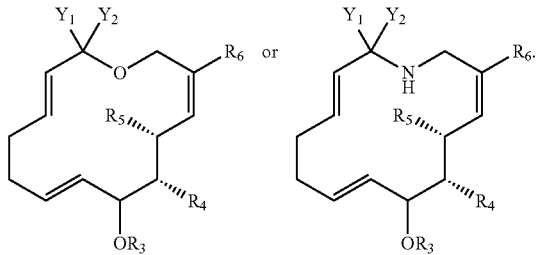

18. The method of claim 16 wherein the compound has the structure:

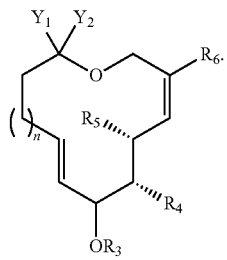

19. The method of claim 17 wherein the compound has the structure:

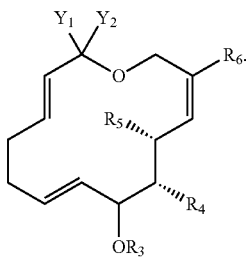

20. The method of claim 18, wherein $R_5$ and $R_6$ are each methyl.

21. The method of claim 18, wherein $R_3$ is methyl.

22. The method of claim 1, wherein the compound has one of the following structures:

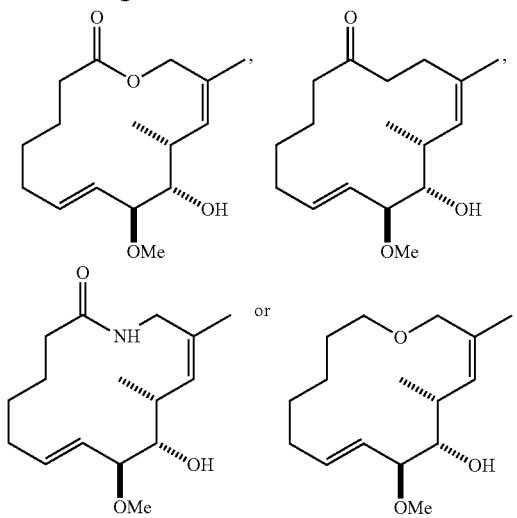

23. The method of claim 2, wherein the compound is present in an amount effective to inhibit metastasis of colon tumor cells.

24. The method of claim 1, wherein the compound is present in an amount effective to inhibit metastasis of ovarian tumor cells.

25. The method of claim 1, further comprising a cytotoxic agent.

26. The method of claim 25, wherein the cytotoxic agent is an anticancer agent.

27. The method of claim 1, further comprising a palliative agent.

28. The method of claim 22, wherein the composition is administered at a dosage between about 20 mg/kg to about 60 mg/kg of body weight.

29. The method of claim 22, further comprising administering a cytotoxic agent.

30. The method of claim 29, wherein the cytotoxic agent is an anticancer agent.

31. The method of claim 22, further comprising administering a palliative agent.

32. The method of claim 1, wherein the subject is a mammal.

33. The method of claim 32, wherein the subject is a human.

34. A compound of formula:

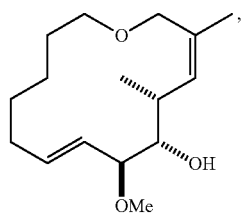 [SMILES: CO[C@H]1/C=C/CCCCCOC/C(C)=C\[C@@H](C)[C@@H]1O]

or a pharmaceutically acceptable salt thereof.

35. The method of claim 2, wherein the compound is present in an amount effective to inhibit migration of tumor cells from a primary colon tumor site to a secondary metastasis site.

36. The method of claim 1, wherein the compound is present in an amount effective to inhibit migration of tumor cells from a primary ovarian tumor site to a secondary metastasis site.

37. The method of claim 2, wherein the compound has the structure:

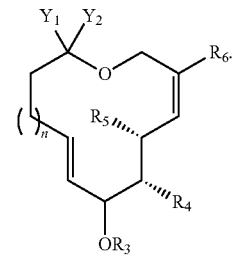

38. The method of claim 2, wherein the compound has the structure:

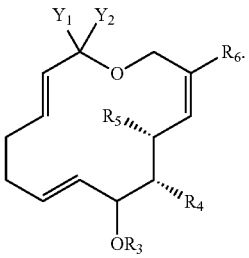

39. The method of claim 2, wherein the compound has one of the following structures:

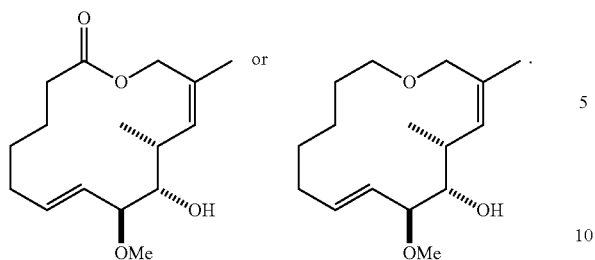

UNITED STATES PATENT AND TRADEMARK OFFICE
CERTIFICATE OF CORRECTION

PATENT NO. : 8,957,056 B2  
APPLICATION NO. : 11/597678  
DATED : February 17, 2015  
INVENTOR(S) : Samuel J Danishefsky et al.

Page 1 of 1

It is certified that error appears in the above-identified patent and that said Letters Patent is hereby corrected as shown below:

In the specification

In column 1, beginning at line 16 and ending at line 21, please delete:

"The invention was supported in part by Grant No. 08748 from the National Cancer Institute, Grant AI-16943 from the National Institutes of Health and by Postdoctoral Fellowships for Christoph Gaul (Deutscher Akademischer Austauschdienst, DAAD) and Jon Tryggvi Njardarson (General Motors Cancer Research Program). The U.S. govermnent may have certain rights in this invention."

and insert:

--This invention was made with government support under grant numbers AI016943 and CA103823 awarded by National Institutes of Health. The government has certain rights in the invention.--

Signed and Sealed this  
Twenty-eighth Day of June, 2016

Michelle K. Lee  
*Director of the United States Patent and Trademark Office*